(12) United States Patent
Gunic et al.

(10) Patent No.: US 8,344,012 B2
(45) Date of Patent: *Jan. 1, 2013

(54) COMPOUNDS, COMPOSITIONS AND METHODS OF USING SAME FOR MODULATING URIC ACID LEVELS

(75) Inventors: Esmir Gunic, San Diego, CA (US); Jean-Luc Girardet, San Diego, CA (US); David A. Paisner, Encinitas, CA (US)

(73) Assignee: Ardea Biosciences, Inc., San Diego, CA (US)

( * ) Notice: Subject to any disclaimer, the term of this patent is extended or adjusted under 35 U.S.C. 154(b) by 421 days.

This patent is subject to a terminal disclaimer.

(21) Appl. No.: 12/554,737

(22) Filed: Sep. 4, 2009

(65) Prior Publication Data

US 2010/0056542 A1 Mar. 4, 2010

Related U.S. Application Data

(60) Provisional application No. 61/094,388, filed on Sep. 4, 2008, provisional application No. 61/180,110, filed on May 20, 2009.

(51) Int. Cl.
*A61K 31/4164* (2006.01)
*C07D 233/54* (2006.01)

(52) U.S. Cl. .......... 514/398; 548/316.4; 548/324.1; 514/385; 514/396

(58) Field of Classification Search .......... 548/262.2, 548/263.2, 263.8, 316.4, 324.1; 514/383, 514/384, 385, 398
See application file for complete search history.

(56) References Cited

U.S. PATENT DOCUMENTS

| | | | |
|---|---|---|---|
| 4,198,513 A | 4/1980 | Baldwin et al. | |
| 5,939,462 A | 8/1999 | Connell et al. | |
| 7,368,467 B2 * | 5/2008 | Zelle et al. | 514/397 |
| 7,435,752 B2 | 10/2008 | Girardet et al. | |
| 7,683,087 B2 * | 3/2010 | Girardet et al. | 514/384 |
| 8,003,681 B2 | 8/2011 | Girardet et al. | |
| 8,084,483 B2 | 12/2011 | Quart et al. | |
| 8,193,234 B2 * | 6/2012 | Gunic et al. | 514/398 |
| 2006/0135556 A1 | 6/2006 | Girardet et al. | |
| 2008/0176850 A1 | 7/2008 | Girardet et al. | |
| 2009/0197825 A1 | 8/2009 | Quart | |
| 2010/0056464 A1 | 3/2010 | Gunic | |
| 2010/0056465 A1 | 3/2010 | Gunic | |
| 2010/0056593 A1 | 3/2010 | Gunic | |
| 2012/0122780 A1 | 5/2012 | De La Rosa et al. | |

FOREIGN PATENT DOCUMENTS

| | | |
|---|---|---|
| CA | 2761335 | 11/2010 |
| DE | 2147794 A1 | 3/1972 |
| WO | WO-2004-030611 | 4/2004 |
| WO | WO-2004-050643 | 6/2004 |
| WO | WO-2006-026356 A2 | 3/2006 |
| WO | WO-2007-050087 A1 | 5/2007 |
| WO | WO-2007-140002 A2 | 12/2007 |
| WO | WO-2008-057246 | 5/2008 |
| WO | WO-2009-070740 A2 | 6/2009 |

OTHER PUBLICATIONS

Du et al (2007): STN International HCAPLUS database, (Columbus, Ohio), Accession No. 2007:1396499.*
Girardet et al (2006): STN International HCAPLUS database, (Columbus, Ohio), Accession No. 2006:212865.*
Tantawy et al (1988): STN International HCAPLUS database, (Columbus, Ohio), Accession No. 1989:407302.*
Kruse et al (1990): STN International HCAPLUS database, (Columbus, Ohio), Accession No. 1990:35859.*
Gravestock et al (1999): STN International HCAPLUS database, (Columbus, Ohio), Accession No. 1999:795810.*
Aslanian et al (2006): STN International HCAPLUS database, (Columbus, Ohio), Accession No. 2006:740597.*
Verhoest et al (2006): STN International HCAPLUS database, (Columbus, Ohio), Accession No. 2006:680977.*
Zelle et al (2005): STN International HCAPLUS database, (Columbus, Ohio), Accession No. 2005:1006001.*
Anzai et al., :The Multivalent PDZ Domain—containing Protein PDZK1 Regulates Transport Activity of Renal Urate-Anion Exchanger URAT1 via Its C Terminus, J. Biol. Chem. 279:45942-45950 (2004).
Bundgaard, "Design and Application of Prodrugs," in Textbook of Drug Design and Development, Krosgaard-Larsen and Bundgaard, ed. 1991, Chapter 5, pp. 113-191 (1991).
Enomoto et al., "Molecular identification of a renal urate-anion exchanger that regulates blood urate levels," Nature 417:447-452 (2002).
Fleisher et al , "Improved oral drug delivery: solubility limitations overcome by the use of prodrugs," Advanced Drug Delivery Reviews 19:115 (1996).
Furniss et al., eds., Vogel's Encyclopedia of Practical Organic Chemistry, 5th Supp., Longman Scientific and Technical Ltd., Essex, 1991, pp. 809-816.
Heller, A., "Electrical Wiring of Redox Enzymes," Acc, Chem. Res. 23:128-134 (1990).
Saulnier et al., "An Efficient Method for the Synthesis of Guandino Prodrugs," Bioorg. Med. Chem. Ltrs. 4(16):1985-1990 (1994).
Zhang, Z. et al., "A Novel Nonnucleoside Analogue That Inhibits Human Immunodeficiency Virus Type I Isolates Resistant to Current Nonnucleoside Reverse Transcriptase Inhibitors," Antimicrobial Agents and Chemotherapy 51(2):429-437 (2007).
PCT/US08/84988 Search Report dated Jun. 23, 2009.
U.S. Appl. No. 12/554,719, filed Sep. 4, 2009.
U.S. Appl. No. 12/553,863, filed Sep. 3, 2009.
U.S. Appl. No. 12/553,844, filed Sep. 3, 2009.
De La Rosa et al., "Tri-substituted traizoles as potent non-nucleoside inhibitors of the HIV-1 reverse transcriptase," Bioorg. Med. Chem. Ltr. 16:4444-4449 (2006).
PCT/US09/055947 Search Report and Written Opinion dated Apr. 28, 2010.
PCT/US09/055948 Search Report and Written Opinion dated Apr. 29, 2010.

* cited by examiner

*Primary Examiner* — Golam M M Shameem
(74) *Attorney, Agent, or Firm* — Wilson, Sonsini, Goodrich & Rosati

(57) ABSTRACT

Described herein are compounds useful in the modulation of blood uric acid levels, formulations containing them and methods of making and using them. In some embodiments, the compounds described herein are used in the treatment or prevention of disorders related to aberrant levels of uric acid.

13 Claims, 4 Drawing Sheets

Graph of mean plasma concentration of 2-(5-Bromo-1-(4-cyanonaphthalen-1-yl)-1H-imidazol-2-ylthio)acetic acid (eg 1) at various time points (0.25, 0.5, 1, 3, 6, 12 and 24hr) post dosing, as released by *in vivo* metabolism of compounds 3, 8 and 9, after PO dosing to male rats (3mg/kg)

Graph of mean plasma concentrations of example 3 and example 1 (2-(5-Bromo-1-(4-cyanonaphthalen-1-yl)-1H-imidazol-2-ylthio)acetic acid), at various time points (0.25, 0.5, 1, 3, 6, 12 and 24hr) post PO dosing to male rats (3mg/kg).

Graph of mean plasma concentrations of example 8 and example 1 (2-(5-Bromo-1-(4-cyanonaphthalen-1-yl)-1H-imidazol-2-ylthio)acetic acid), at various time points (0.25, 0.5, 1, 3, 6, 12 and 24hr) post PO dosing to male rats (3mg/kg).

Graph of mean plasma concentrations of example 9 and example 1 (2-(5-Bromo-1-(4-cyanonaphthalen-1-yl)-1H-imidazol-2-ylthio)acetic acid), at various time points (0.25, 0.5, 1, 3, 6, 12 and 24hr) post PO dosing to male rats (3mg/kg).

COMPOUNDS, COMPOSITIONS AND METHODS OF USING SAME FOR MODULATING URIC ACID LEVELS

CROSS-REFERENCE

This application claims the benefit of U.S. Provisional Application No. 61/094,388, filed Sep. 4, 2008, and U.S. Provisional Application No. 61/180,110, filed May 20, 2009, both of which are incorporated herein by reference in their entirety.

BACKGROUND OF THE INVENTION

Aberrant uric acid levels are related to several disorders including, but not limited to, gout, gouty arthritis, inflammatory arthritis, kidney disease, nephrolithiasis (kidney stones), joint inflammation, deposition of urate crystals in joints, urolithiasis (formation of calculus in the urinary tract), deposition of urate crystals in renal parenchyma, Lesch-Nyhan syndrome, and Kelley-Seegmiller syndrome.

SUMMARY OF THE INVENTION

Disclosed herein, in certain embodiments, is a compound of formula (I):

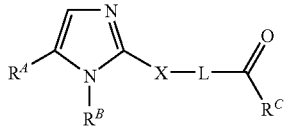

wherein:
X is O or S;
L is $-(CR^xR^{x'})_x-(CR^yR^{y'})_y-(CR^zR^{z'})_z-$; wherein x is 0 or 1; y is 0 or 1; z is 0 or 1; $R^x$, $R^{x'}$, $R^y$, $R^{y'}$, $R^z$ and $R^{z'}$ are each independently H, F, Cl, Br, I or optionally substituted $C_{1-3}$ alkyl; or $R^x$ and $R^{x'}$, or $R^y$ and $R^{y'}$, or $R^z$ and $R^{z'}$, or $R^x$ and $R^y$, or $R^y$ and $R^z$, or $R^x$ and $R^z$ together with the carbon atoms to which they are attached, form an optionally substituted, aromatic or non-aromatic, 3-7 membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S;
$R^A$ is H, Cl, Br, I, $NH_2$, methyl, ethyl, n-propyl, i-propyl, optionally substituted methyl, optionally substituted ethyl, optionally substituted n-propyl, optionally substituted i-propyl, $CF_3$, $CHF_2$ or $CH_2F$;
$R^B$ is

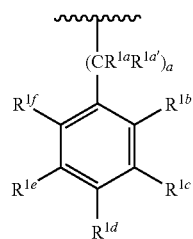

wherein a is 0, 1 or 2; $R^{1a}$ is H or optionally substituted $C_{1-3}$ alkyl; $R^{1a'}$ is H or optionally substituted $C_{1-3}$ alkyl; or $R^{1a}$ and $R^{1a'}$ together with the carbon atom to which they are attached form an optionally substituted 3-, 4-, 5- or 6-membered ring, optionally comprising 1 or 2 heteroatoms selected from O, N and S; $R^{1b}$, $R^{1c}$, $R^{1d}$, $R^{1e}$ and $R^{1f}$ are each independently H, F, Cl, Br, I, $CF_3$, CN, alkyl, cycloalkyl, cyclopropylmethyl, $NH_2$, NHR', NR'R'', OH, OR', SH, SR', C(O)R', $CO_2H$, COOR', $CONH_2$, CONHR', CONR'R''$SO_3H$, $S(O)_2R'$, $S(O)_2NH_2$, $S(O)_2NHR'$, $S(O)_2NR'R''$ aryl, heterocyclyl or heteroaryl; or $R^{1b}$ and $R^{1c}$, or $R^{1c}$ and $R^{1d}$, or $R^{1d}$ and $R^{1e}$, or $R^{1e}$ and $R^{1f}$ together with the two carbon atoms to which they are attached, form an optionally substituted, aromatic or non-aromatic, 5-, 6- or 7-membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S; and wherein the optional substituents are each independently H, F, Cl, Br, I, $CF_3$, CN, alkyl, cycloalkyl, cyclopropylmethyl, $NH_2$, NHR', NR'R'', OH, OR', SH, SR', C(O)R', $CO_2H$, COOR', $CONH_2$, CONHR', CONR'R'', $SO_3H$, $S(O)_2R'$, $S(O)_2NH_2$, $S(O)_2NHR'$, $S(O)_2NR'R''$, aryl, heterocyclyl or heteroaryl; wherein R' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; R'' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or R' and R'' together with the nitrogen atom to which they are attached form an optionally substituted, saturated or unsaturated 4-, 5- or 6-membered heterocyclic ring;
$R^C$ is an amino acid, a dipeptide, a tripeptide, a tetrapeptide, a polypeptide, a lipid, a phospholipid, a glycoside, a nucleoside, a nucleotide, an oligonucleotide, polyethylene glycol, $OR^{2a}$, $SR^{3a}$, $NR^{4a}R^{4b}$, or a combination thereof, wherein; $R^{2a}$ is substituted $C_1$-$C_4$ alkyl, optionally substituted $C_5$-$C_{10}$ alkyl, optionally substituted heteroalkyl, optionally substituted cycloalkyl, optionally substituted heterocycloalkyl, optionally substituted aryl or optionally substituted heteroaryl; or $R^{2a}$ is a pharmaceutically acceptable cation; or $R^{2a}$ is $-[C(R^{5a})(R^{5b})]_m R^{5c}$; $R^{3a}$ is hydrogen, optionally substituted $C_1$-$C_{10}$ alkyl, optionally substituted heteroalkyl, optionally substituted cycloalkyl, optionally substituted heterocycloalkyl, optionally substituted aryl, optionally substituted heteroaryl; or $R^{3a}$ is $-[C(R^{5a})(R^{5b})]_n R^{5c}$; $R^{4a}$ is hydrogen, optionally substituted alkyl, optionally substituted heteroalkyl, optionally substituted cycloalkyl or optionally substituted heterocycloalkyl; and $R^{4b}$ is hydrogen, optionally substituted alkyl, optionally substituted heteroalkyl, optionally substituted cycloalkyl or optionally substituted heterocycloalkyl; or $R^{4b}$ is $-[C(R^{5a})(R^{5b})]_n R^{5c}$, wherein $R^{5a}$ and $R^{5b}$ are each independently hydrogen, halogen, cyano, nitro, an amino acid, a dipeptide, a tripeptide, a tetrapeptide, a polypeptide, a lipid, a phospholipid, a glycoside, a nucleoside, a nucleotide, an oligonucleotide, polyethylene glycol, -L-OH, -L-SH, -L-$NH_2$, substituted -L-$C_1$-$C_3$ alkyl, optionally substituted -L-$C_4$-$C_9$ alkyl, optionally substituted L-$C_2$-$C_5$ alkenyl, optionally substituted L-$C_2$-$C_5$ alkynyl, optionally substituted L-$C_2$-$C_5$ heteroalkyl, optionally substituted -L-$C_3$-$C_7$ cycloalkyl, optionally substituted L-C$_3$-C$_7$ cycloalkenyl, optionally substituted -L-C$_3$-C$_7$ heterocycloalkyl, optionally substituted -L-C$_1$-C$_4$ haloalkyl, optionally substituted -L-C$_1$-C$_4$ alkoxy, optionally substituted -L-C$_1$-C$_4$ alkylamine, optionally substituted -L-di-(C$_1$-C$_4$)alkylamine, optionally substituted -L-C$_5$-C$_7$ aryl, optionally substituted -L-C$_5$-C$_7$ heteroaryl,

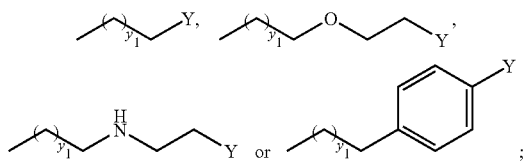

R$^{5c}$ is hydrogen, halogen, cyano, nitro, an amino acid, a dipeptide, a tripeptide, a tetrapeptide, a polypeptide, a lipid, a phospholipid, a glycoside, a nucleoside, a nucleotide, an oligonucleotide, polyethylene glycol, -L-OH, -L-SH, -L-NH$_2$, substituted -L-C$_1$-C$_3$ alkyl, optionally substituted -L-C$_4$-C$_9$ alkyl, optionally substituted L-C$_2$-C$_5$ alkenyl, optionally substituted L-C$_2$-C$_5$ alkynyl, optionally substituted L-C$_2$-C$_5$ heteroalkyl, optionally substituted -L-C$_3$-C$_7$ cycloalkyl, optionally substituted L-C$_3$-C$_7$ cycloalkenyl, optionally substituted -L-C$_3$-C$_7$ heterocycloalkyl, optionally substituted -L-C$_1$-C$_4$ haloalkyl, optionally substituted -L-C$_1$-C$_4$ alkoxy, optionally substituted -L-C$_1$-C$_4$alkylamine, optionally substituted -L-di (C$_1$-C$_4$)alkylamine, optionally substituted -L-C$_5$-C$_7$ aryl, optionally substituted -L-C$_5$-C$_7$ heteroaryl,

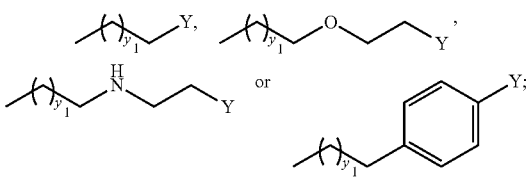

wherein L is a bond, —C(O)—, —S(O), or —S(O)$_2$; $y_1$ is 0, 1, 2 or 3; Y is OH, OMe, COOH, SO$_3$H, OSO$_3$H, OS(O)$_2$NH$_2$, P(O)(OH)$_2$, OP(O)(OH)$_2$, OP(O)(OH)(O—C$_{1-4}$ alkyl) or NY$^2$Y$^3$Y$^4$; wherein Y$^2$ and Y$^3$ are each independently hydrogen or methyl; or Y$^2$ and Y$^3$ are taken together with the nitrogen to which they are attached form a five or six membered ring that optionally contains an oxygen atom or a second nitrogen atom; and Y$^4$ is an electron pair or an oxygen atom; m is 1, 2, 3, 4; n is 0, 1, 2, 3, 4, 5, 6, 7, 8, 9 or 10.

In some embodiments, X is O. In some embodiments, X is S. In some embodiments, x is 1, y is 0 and z is 0. In some embodiments, X is S, x is 1, y is 0 and z is 0. In some embodiments, R$^x$ and R$^{x'}$ are H, F or methyl. In some embodiments, R$^x$ and R$^{x'}$ are both H. In some embodiments, R$^x$ and R$^{x'}$ are both F. In some embodiments, R$^x$ and R$^{x'}$ are both methyl. In some embodiments, x is 1, y is 0, z is 0, R$^x$ is H and R$^{x'}$ is H. In some embodiments, x is 1, y is 0, z is 0, R$^x$ is F and R$^{x'}$ is F. In some embodiments, x is 1, y is 0, z is 0, R$^x$ is methyl and R$^{x'}$ is methyl. In some embodiments, X is S, x is 1, y is 0, z is 0 and R$^x$ and R$^{x'}$ are either both H or both F. In some embodiments, R$^x$ and R$^{x'}$, or R$^y$ and R$^{y'}$, or R$^z$ and R$^{z'}$, or R$^x$ and R$^y$, or R$^y$ and R$^z$, or R$^x$ and R$^z$ together with the carbon atoms to which they are attached, form an optionally substituted, aromatic or non-aromatic, 3-7 membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S. In some embodiments, R$^x$ and R$^{x'}$, or R$^y$ and R$^{y'}$, or R$^z$ and R$^{z'}$, or R$^x$ and R$^y$, or R$^y$ and R$^z$, or R$^x$ and R$^z$ together with the carbon atoms to which they are attached, form an optionally substituted, aromatic or non-aromatic, 3-7 membered ring. In some embodiments, R$^x$ and R$^{x'}$ together with the carbon atoms to which they are attached, form an optionally substituted, aromatic or non-aromatic, 3-7 membered ring. In some embodiments, R$^x$ and R$^y$ together with the carbon atoms to which they are attached, form an optionally substituted, aromatic or non-aromatic, 3-7 membered ring. In some embodiments, R$^A$ is H. In some embodiments, R$^A$ is Br. In some embodiments, a is 0. In some embodiments, R$^{1b}$, R$^{1c}$, R$^{1d}$, R$^{1e}$ and R$^{1f}$ are each independently H, F, Cl, Br, I, CF$_3$, CN, alkyl, cycloalkyl, cyclopropylmethyl, NH$_2$, NHR', NR'R'', OH, OR', SH, SR', C(O)R', CO$_2$H, COOR', CONH$_2$, CONHR', CONR'R''SO$_3$H, S(O)$_2$R', S(O)$_2$NH$_2$, S(O)$_2$NHR', S(O)$_2$NR'R'' aryl, heterocyclyl or heteroaryl. In some embodiments, R$^{1b}$ and R$^{1c}$, or R$^{1c}$ and R$^{1d}$, or R$^{1d}$ and R$^{1e}$, or R$^{1e}$ and R$^{1f}$ together with the two carbon atoms to which they are attached, form an optionally substituted, aromatic or non-aromatic, 5-, 6- or 7-membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S. In some embodiments, R$^{1b}$ and R$^{1c}$ together with the two carbon atoms to which they are attached, form an optionally substituted, aromatic or non-aromatic, 5-, 6- or 7-membered ring. In some embodiments, R$^{1b}$ and R$^{1c}$ together with the two carbon atoms to which they are attached, form an optionally substituted, aromatic 5-, 6- or 7-membered ring. In some embodiments, R$^{1b}$ and R$^{1c}$ together with the two carbon atoms to which they are attached, form an optionally substituted, aromatic 6-membered ring.

In some embodiments, R$^B$ is

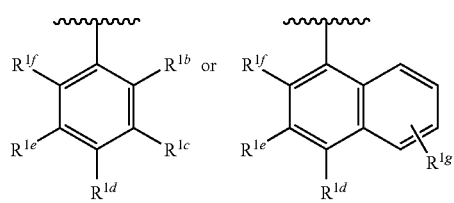

wherein R$^{1g}$ is H, F, Cl, Br, I, CF$_3$, CN, alkyl, cycloalkyl, cyclopropylmethyl, NH$_2$, NHR', NR'R'', OH, OR', SH, SR', C(O)R', CO$_2$H, COOR', CONH$_2$, CONHR', CONR'R'', SO$_3$H, S(O)$_2$R', S(O)$_2$NH$_2$, S(O)$_s$NHR', S(O)$_2$NR'R'', aryl, heterocyclyl or heteroaryl; wherein R' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; R'' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or R' and R'' together with the nitrogen atom to which they are attached form an optionally substituted, saturated or unsaturated 4-, 5- or 6-membered heterocyclic ring.

In some embodiments, $R^B$ is

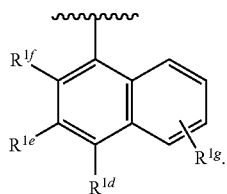

In some embodiments, $R^{1e}$, $R^{1f}$ and $R^{1g}$ are H. In some embodiments, $R^{1d}$ is CN, alkyl or cycloalkyl. In some embodiments, $R^{1e}$, $R^{1f}$ and $R^{1g}$ are H and $R^{1d}$ is CN, alkyl or cycloalkyl. In some embodiments, $R^{1e}$, $R^{1f}$ and $R^{1g}$ are H and $R^{1d}$ is CN or
cyclopropyl. In some embodiments, $R^B$ is

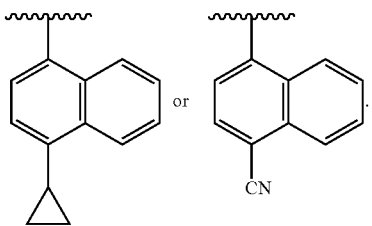

In some embodiments, X is S, x is 1, y is 0, z is 0 and $R^x$ and $R^{x'}$ are either both H or both F. In some embodiments, $R^C$ is an amino acid, a dipeptide, a tripeptide. In some embodiments, $R^C$ is an amino acid or a dipeptide. In some embodiments, $R^C$ is glycine, alanine or valine. In some embodiments, $R^C$ is a dipeptide comprising glycine, alanine or valine.

Disclosed herein, in certain embodiments, is a compound of Formula (I-A):

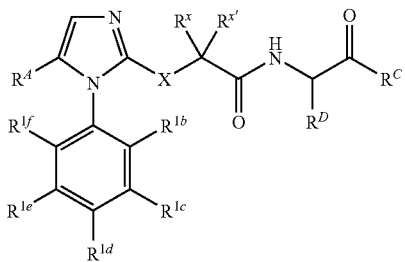

wherein:
X is O or S;
$R^A$ is H, Cl, Br, I, $NH_2$, methyl, ethyl, n-propyl, i-propyl, optionally substituted methyl, optionally substituted ethyl, optionally substituted n-propyl, optionally substituted i-propyl, $CF_3$, $CHF_2$ or $CH_2F$;
$R^{1b}$, $R^{1c}$, $R^{1d}$, $R^{1e}$ and $R^{1f}$ are each independently H, F, Cl, Br, I, $CF_3$, CN, alkyl, cycloalkyl, cyclopropylmethyl, $NH_2$, NHR', NR'R", OH, OR', SH, SR', C(O)R', $CO_2H$, COOR', $CONH_2$, CONHR', CONR'R"$SO_3H$, $S(O)_2R'$, $S(O)_2NH_2$, $S(O)_2NHR'$, $S(O)_2NR'R"$ aryl, heterocyclyl or heteroaryl; or $R^{1b}$ and $R^{1c}$, or $R^{1c}$ and $R^{1d}$, or $R^{1d}$ and $R^{1e}$, or $R^{1e}$ and $R^{1f}$ together with the two carbon atoms to which they are attached, form an optionally substituted, aromatic or non-aromatic, 5-, 6- or 7-membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S; and wherein the optional substituents are each independently H, F, Cl, Br, I, $CF_3$, CN, alkyl, cycloalkyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl or heteroaryl;
wherein
R' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;
R" is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or
R' and R" together with the nitrogen atom to which they are attached form an optionally substituted, saturated or unsaturated 4-, 5- or 6-membered heterocyclic ring;
$R^C$ is an amino acid, a dipeptide, a tripeptide, a tetrapeptide, a polypeptide, a lipid, a phospholipid, a glycoside, a nucleoside, a nucleotide, an oligonucleotide, polyethylene glycol, $OR^{2a}$, $SR^{3a}$, $NR^{4a}R^{4b}$, or a combination thereof, wherein;
$R^{2a}$ is substituted hydrogen, optionally substituted $C_1$-$C_{10}$ alkyl, optionally substituted heteroalkyl, optionally substituted cycloalkyl, optionally substituted heterocycloalkyl, optionally substituted aryl or optionally substituted heteroaryl; or $R^{2a}$ is a pharmaceutically acceptable cation; or $R^{2a}$ is $-[C(R^{5a})(R^{5b})]_m R^{5c}$;
$R^{3a}$ is hydrogen, optionally substituted $C_1$-$C_{10}$ alkyl, optionally substituted heteroalkyl, optionally substituted cycloalkyl, optionally substituted heterocycloalkyl, optionally substituted aryl, optionally substituted heteroaryl; or $R^{3a}$ is $-[C(R^{5a})(R^{5b})]_n R^{5c}$;
$R^{4a}$ is hydrogen, optionally substituted alkyl, optionally substituted heteroalkyl, optionally substituted cycloalkyl or optionally substituted heterocycloalkyl; and
$R^{4b}$ is hydrogen, optionally substituted alkyl, optionally substituted heteroalkyl, optionally substituted cycloalkyl or optionally substituted heterocycloalkyl; or $R^{4b}$ is $-[C(R^{5a})(R^{5b})]_n R^{5c}$, wherein
$R^{5a}$ and $R^{5b}$ are each independently hydrogen, halogen, cyano, nitro, an amino acid, a dipeptide, a tripeptide, a tetrapeptide, a polypeptide, a lipid, a phospholipid, a glycoside, a nucleoside, a nucleotide, an oligonucleotide, polyethylene glycol, -L-OH, -L-SH, -L-$NH_2$, substituted -L-$C_1$-$C_3$ alkyl, optionally substituted -L-$C_4$-$C_9$ alkyl, optionally substituted L-$C_2$-$C_5$ alkenyl, optionally substituted L-$C_2$-$C_5$ alkynyl, optionally substituted L-$C_2$-$C_5$ heteroalkyl, optionally substituted -L-$C_3$-$C_7$ cycloalkyl, optionally substituted L-$C_3$-$C_7$ cycloalkenyl, optionally substituted -L-$C_3$-$C_7$ heterocycloalkyl, optionally substituted -L-$C_1$-$C_4$ haloalkyl, optionally substituted -L-$C_1$-$C_4$ alkoxy, optionally substituted -L-$C_1$-$C_4$ alkylamine, optionally substituted -L-di-($C_1$-$C_4$)alkylamine, optionally substituted -L-$C_5$-$C_7$ aryl, optionally substituted -L-$C_5$-$C_7$ heteroaryl,

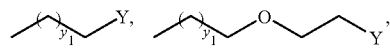

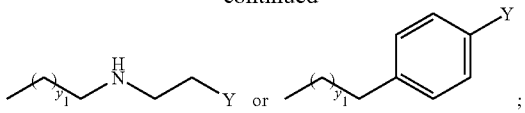

$R^{5c}$ is hydrogen, halogen, cyano, nitro, an amino acid, a dipeptide, a tripeptide, a tetrapeptide, a polypeptide, a lipid, a phospholipid, a glycoside, a nucleoside, a nucleotide, an oligonucleotide, polyethylene glycol, -L-OH, -L-SH, -L-NH$_2$, substituted -L-C$_1$-C$_3$ alkyl, optionally substituted -L-C$_4$-C$_9$ alkyl, optionally substituted L-C$_2$-C$_5$ alkenyl, optionally substituted L-C$_2$-C$_5$ alkynyl, optionally substituted L-C$_2$-C$_5$ heteroalkyl, optionally substituted -L-C$_3$-C$_7$ cycloalkyl, optionally substituted L-C$_3$-C$_7$ cycloalkenyl, optionally substituted -L-C$_3$-C$_7$ heterocycloalkyl, optionally substituted -L-C$_1$-C$_4$ haloalkyl, optionally substituted -L-C$_1$-C$_4$ alkoxy, optionally substituted -L-C$_1$-C$_4$alkylamine, optionally substituted -L-di(C$_1$-C$_4$)alkylamine, optionally substituted -L-C$_5$-C$_7$ aryl, optionally substituted -L-C$_5$-C$_7$ heteroaryl,

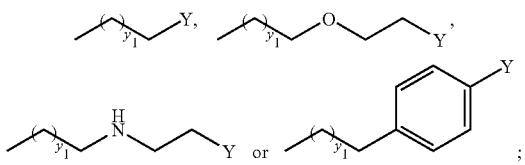

wherein
L is a bond, —C(O)—, —S(O), or —S(O)$_2$;
$y_1$ is 0, 1, 2 or 3;
Y is OH, OMe, COOH, SO$_3$H, OSO$_3$H, OS(O)$_2$NH$_2$, P(O)(OH)$_2$, OP(O)(OH)$_2$, OP(O)(OH)(O—C$_{1-4}$ alkyl) or NY$^2$Y$^3$Y$^4$; wherein Y$^2$ and Y$^3$ are each independently hydrogen or methyl; or Y$^2$ and Y$^3$ are taken together with the nitrogen to which they are attached form a five or six membered ring that optionally contains an oxygen atom or a second nitrogen atom; and Y$^4$ is an electron pair or an oxygen atom;
m is 1, 2, 3, 4;
n is 0, 1, 2, 3, 4, 5, 6, 7, 8, 9 or 10; and
$R^D$ is a natural or unnatural amino acid residue.

Disclosed herein, in certain embodiments, is a method for inhibiting a URAT-1 transporter, comprising contacting the URAT-1 transporter with a compound disclosed herein, or a metabolite, pharmaceutically acceptable salt, solvate, polymorph, ester, tautomer or prodrug thereof.

Disclosed herein, in certain embodiments, is a method for decreasing uric acid levels in one or more tissues or organs of a subject in need of decreased uric acid levels, comprising administering to the subject a uric acid level decreasing amount of a compound disclosed herein or a metabolite, pharmaceutically acceptable salt, solvate, polymorph, ester, tautomer or prodrug thereof. In some embodiments, the subject in need of decreased uric acid levels has a disorder characterized by an abnormally high content of uric acid in one or more tissues or organs of the subject. In some embodiments, the disorder is characterized by overproduction of uric acid, low excretion of uric acid, tumor lysis, a blood disorder or a combination thereof. In some embodiments, the blood disorder is polycythemia or myeloid metaplasia. In some embodiments, the subject in need of decreased uric acid levels is suffering from gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis. In some embodiments, the tissue or organ is blood. In some embodiments, the blood uric acid level is decreased by at least about 1 mg/dL. In some embodiments, the blood uric acid level is decreased by at least about 2 mg/dL. In some embodiments, the uric acid levels are decreased by at least about 10% in one or more tissues or organs of the subject. In some embodiments, the uric acid levels are decreased by at least about 25% in one or more tissues or organs of the subject. In some embodiments, the uric acid levels are decreased by at least about 50% in one or more tissues or organs of the subject.

Disclosed herein, in certain embodiments, is a method for decreasing uric acid levels in one or more tissues or organs of a subject comprising administering to the subject a uric acid level decreasing amount of a compound disclosed herein or a metabolite, pharmaceutically acceptable salt, solvate, polymorph, ester, tautomer or prodrug thereof, wherein the reduction in uric acid levels results in a reduction in hypertension or cardiovascular events.

Disclosed herein, in certain embodiments, is a method for reducing uric acid production, increasing uric acid excretion or both in a subject, comprising administering to the subject a compound disclosed herein or a metabolite, pharmaceutically acceptable salt, solvate, polymorph, ester, tautomer or prodrug thereof.

Disclosed herein, in certain embodiments, is a method of treating a subject suffering from a condition characterized by abnormal tissue or organ levels of uric acid comprising administering to the subject an effective amount of a compound disclosed herein or a metabolite, pharmaceutically acceptable salt, solvate, polymorph, ester, tautomer or prodrug thereof. In some embodiments, the condition is characterized by low tissue levels of uric acid. In some embodiments, the condition is characterized by high tissue levels of uric acid. In some embodiments, the condition is selected from gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis. In some embodiments, the condition is gout. In some embodiments, the condition is joint inflammation. In some embodiments, the joint inflammation is caused by deposits of uric acid crystals in the joint. In some embodiments, the uric acid crystals are deposited in the joint fluid (synovial fluid) or joint lining (synovial lining) In some embodiments, the method further comprises administering an agent effective for the treatment of the condition. In some embodiments, the agent is effective in reducing tissue levels of uric acid. In some embodiments, the agent is a nonsteroidal anti-inflammatory drugs (NSAIDs), colchicine, a corticosteroid, adrenocorticotropic hormone (ACTH), probenecid, sulfinpyrazone or allopurinol. In some embodiments, the agent is allopurinol.

Disclosed herein, in certain embodiments, is a method for treating or preventing hyperuricemia in a subject comprising administering to the subject an effective amount of a compound disclosed herein or a metabolite, pharmaceutically acceptable salt, solvate, polymorph, ester, tautomer or prodrug thereof.

Disclosed herein, in certain embodiments, is a method for preventing a condition characterized by abnormal tissue levels of uric acid in a subject at increased risk of developing the condition, comprising administering to the subject an effective amount of a compound disclosed herein or a metabolite, pharmaceutically acceptable salt, solvate, polymorph, ester, tautomer or prodrug thereof. In some embodiments, the condition is selected from gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis.

Disclosed herein, in certain embodiments, is a method for treating gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosisin a subject comprising administering to the subject an effective amount of a compound disclosed herein or a metabolite, pharmaceutically acceptable salt, solvate, polymorph, ester, tautomer or prodrug thereof.

Disclosed herein, in certain embodiments, is a method for treating gout in a subject comprising administering to the subject an effective amount of a compound disclosed herein or a metabolite, pharmaceutically acceptable salt, solvate, polymorph, ester, tautomer or prodrug thereof. In some embodiments, the method further comprises administering an agent effective for the treatment of the gout. In some embodiments, the agent is allopurinol.

Disclosed herein, in certain embodiments, is a method for preventing the formation or reducing the size of tophi/tophus in a subject, comprising administering to the subject an effective amount of a compound disclosed herein or a metabolite, pharmaceutically acceptable salt, solvate, polymorph, ester, tautomer or prodrug thereof.

Disclosed herein, in certain embodiments, is a method for treating hypoxanthine-guanine phosphoribosyltransferase (HPRT) deficiency in a subject comprising administering to the subject a compound disclosed herein or a metabolite, pharmaceutically acceptable salt, solvate, polymorph, ester, tautomer or prodrug thereof.

Disclosed herein, in certain embodiments, is a pharmaceutical composition comprising: a compound disclosed herein or a metabolite, pharmaceutically acceptable salt, solvate, polymorph, ester, tautomer or prodrug thereof; allopurinol; and optionally one or more pharmaceutically acceptable carriers.

Disclosed herein, in certain embodiments, is a pharmaceutical composition comprising: a compound disclosed herein or a metabolite, pharmaceutically acceptable salt, solvate, polymorph, ester, tautomer or prodrug thereof; at least one agent selected from the group consisting of a nonsteroidal anti-inflammatory drug (NSAID), Ibuprofen, Naproxen, Colchicine, Probenecid and Sulfinpyrazone; and optionally one or more pharmaceutically acceptable carriers.

Disclosed herein, in certain embodiments, is a pharmaceutical composition useful in the treatment of edema and hypertension which also maintains uric acid levels at pretreatment levels or causes a decrease in uric acid levels comprising: at least one antihypertensive agent; a uric acid level maintaining or lowering amount of a compound of the formula (I) or a metabolite, pharmaceutically acceptable salt, solvate, polymorph, ester, tautomer or prodrug thereof; and optionally one or more pharmaceutically acceptable carriers.

Disclosed herein, in certain embodiments, is a pharmaceutical composition useful in the treatment of cancer which also maintains uric acid levels at pretreatment levels or causes a decrease in uric acid levels comprising: at least one anticancer agent; a uric acid level maintaining or lowering amount of a compound disclosed herein or a metabolite, pharmaceutically acceptable salt, solvate, polymorph, ester, tautomer or prodrug thereof; and optionally one or more pharmaceutically acceptable carriers.

Disclosed herein, in certain embodiments, is a pharmaceutical composition useful for reducing the side effects of chemotherapy in a cancer patient, comprising: a uric acid level maintaining or lowering amount of a compound disclosed herein or a metabolite, pharmaceutically acceptable salt, solvate, polymorph, ester, tautomer or prodrug thereof; and optionally one or more pharmaceutically acceptable carriers.

This invention provides for compounds of formula (II), or a metabolite, pharmaceutically acceptable salt, solvate, polymorph, ester, tautomer or prodrug thereof:

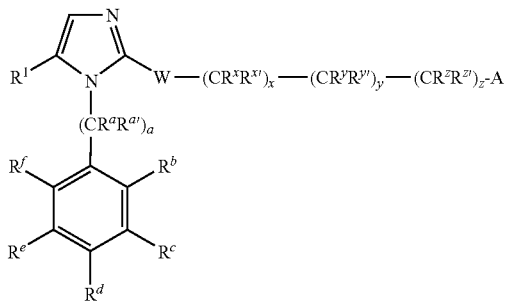

(II)

wherein:
W is O, S, S(O), S(O)$_2$, NH, N(optionally substituted alkyl), CH$_2$, CH$_2$O, CH$_2$S or CH$_2$NH;

R$^1$ is H, F, Cl, Br, I, CH$_2$F, CF$_2$H, CF$_3$, CN, OH, NO$_2$, NH$_2$, NH(alkyl) or N(alkyl)(alkyl), SO$_2$CH$_3$, SO$_2$NH$_2$, SO$_2$NHCH$_3$, CO$_2$-alkyl, optionally substituted alkyl, optionally substituted alkenyl, optionally substituted alkoxy, optionally substituted S-alkyl, optionally substituted cycloalkyl, optionally substituted heterocycle, optionally substituted aryl or optionally substituted heteroaryl;

a is 0, 1 or 2;
R$^a$ is H or optionally substituted C$_{1-3}$ alkyl;
R$^{a'}$ is H or optionally substituted C$_{1-3}$ alkyl; or
R$^a$ and R$^{a'}$ together with the carbon atom to which they are attached form an optionally substituted, 3-, 4-, 5- or 6-membered ring, optionally comprising 1 or 2 heteroatoms selected from O, N and S;

R$^b$, R$^c$, R$^d$, R$^e$ and R$^f$ are each independently H, F, Cl, Br, I, CF$_3$, CN, alkyl, cycloalkyl, cyclopropylmethyl, NH$_2$, NHR', NR'R'', OH, OR', SH, SR', C(O)R', CO$_2$H, COOR', CONH$_2$, CONHR', CONR'R'', SO$_3$H, S(O)$_2$R', S(O)$_2$NH$_2$, S(O)$_2$NHR', S(O)$_2$NR'R'', aryl, heterocyclyl or heteroaryl;

wherein
R' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;

R'' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or R' and R'' together with the nitrogen atom to which they are attached form an optionally substituted, saturated or unsaturated 4-, 5- or 6-membered heterocyclic ring; or $R^b$ and $R^c$, or $R^c$ and $R^d$, or $R^d$ and $R^e$, or $R^e$ and $R^f$ together with the two carbon atoms to which they are attached, form an optionally substituted, aromatic or non-aromatic, 5-, 6- or 7-membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S; and wherein the optional substituents are each independently F, Cl, Br, I, $CF_3$, CN, alkyl, cycloalkyl, cyclopropylmethyl, $NH_2$, NHR', NR'R", OH, OR', SH, SR', C(O) R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl or heteroaryl;

x is 0 or 1;
y is 0 or 1;
z is 0 or 1;
$R^x$, $R^{x'}$, $R^y$, $R^{y'}$, $R^z$ and $R^{z'}$ are each independently H, F, Cl, Br, or optionally substituted $C_{1-3}$ alkyl; or
$R^x$ and $R^{x'}$, or $R^y$ and $R^{y'}$, or $R^z$ and $R^{z'}$, or $R^x$ and $R^y$, or $R^y$ and $R^z$, or $R^x$ and $R^z$ together with the carbon atoms to which they are attached, form an optionally substituted, aromatic or non-aromatic, 3-7 membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S;
A is H, C(O)O—$B^1$ or C(O)NH—$B^2$; wherein
$B^1$ is H, optionally substituted $C_{1-6}$ alkyl or a pharmaceutically acceptable cation;
$B^2$ is H or optionally substituted $C_{1-6}$ alkyl; and wherein all alkyl, alkylene, cycloalkyl, heterocyclyl, aryl and heteroaryl moieties may be optionally further substituted.

In some embodiments, the invention provides for compounds of formula (II).

In further or additional embodiments, the invention provides for pharmaceutically acceptable salts of compounds of formula (II). In further or additional embodiments, the invention provides for pharmaceutically acceptable solvates of compounds of formula (II). In further or additional embodiments, the invention provides for pharmaceutically acceptable polymorphs of compounds of formula (II). In further or additional embodiments, the invention provides for pharmaceutically acceptable esters of compounds of formula (II). In further or additional embodiments, the invention provides for pharmaceutically acceptable tautomers of compounds of formula (II). In further or additional embodiments, the invention provides for pharmaceutically acceptable prodrugs of compounds of formula (II).

In some embodiments W is $CH_2$, $CH_2O$, $CH_2S$ or $CH_2NH$. In further or additional embodiments, W is $CH_2$. In further or additional embodiments, W is $CH_2O$. In further or additional embodiments, W is $CH_2S$. In further or additional embodiments, W is $CH_2NH$. In other embodiments W is O, S, S(O), $S(O)_2$, NH, N(optionally substituted alkyl). In further or additional embodiments, W is O, S or NH. In further or additional embodiments, W is S, S(O), $S(O)_2$. In further or additional embodiments, W is O. In further or additional embodiments, W is S. In further or additional embodiments, W is NH.

In some embodiments, $R^1$ is H, F, Cl, Br, I, $CH_2F$, $CF_2H$, $CF_3$, CN, OH, $NO_2$, $NH_2$, NH(alkyl) or N(alkyl)(alkyl), $SO_2CH_3$, $SO_2NH_2$, $SO_2NHCH_3$ or $CO_2$-alkyl. In further or additional embodiments, $R^1$ is H. In further or additional embodiments, $R^1$ is Cl or Br. In further or additional embodiments, $R^1$ is Br. In further or additional embodiments, $R^1$ is $CH_2F$, $CF_2H$ or $CF_3$. In further or additional embodiments, $R^1$ is CN, OH or $NO_2$. In further or additional embodiments, $R^1$ is $NH_2$, NH(alkyl) or N(alkyl)(alkyl). In further or additional embodiments, $R^1$ is $SO_2CH_3$, $SO_2NH_2$ or $SO_2NHCH_3$. In further or additional embodiments, $R^1$ is COOH or $CO_2$-alkyl. In further or additional embodiments, $R^1$ is optionally substituted alkyl or alkenyl. In further or additional embodiments, $R^1$ is optionally substituted alkyl. In further or additional embodiments, $R^1$ is optionally substituted alkoxy or optionally substituted S-alkyl. In further or additional embodiments, $R^1$ is optionally substituted cycloalkyl. In further or additional embodiments, $R^1$ is optionally substituted heterocycle. In further or additional embodiments, $R^1$ is optionally substituted aryl. In further or additional embodiments, $R^1$ is optionally substituted phenyl. In further or additional embodiments, $R^1$ is optionally substituted naphthyl. In further or additional embodiments, $R^1$ is optionally substituted heteroaryl. In further or additional embodiments, $R^1$ is substituted alkyl or alkenyl. In further or additional embodiments, $R^1$ is substituted alkyl. In further or additional embodiments, $R^1$ is substituted alkoxy or substituted S-alkyl. In further or additional embodiments, $R^1$ is substituted cycloalkyl. In further or additional embodiments, $R^1$ is substituted heterocycle. In further or additional embodiments, $R^1$ is substituted aryl. In further or additional embodiments, $R^1$ is substituted phenyl. In further or additional embodiments, $R^1$ is substituted naphthyl. In further or additional embodiments, $R^1$ is substituted heteroaryl. In further or additional embodiments, $R^1$ is H, F, Cl, Br, I, $CH_2F$, $CF_2H$, $CF_3$, $NH_2$, optionally substituted alkyl, optionally substituted aryl or optionally substituted heteroaryl. In further or additional embodiments, $R^1$ is H, F, Cl, Br, I, $CH_2F$, $CF_2H$, $CF_3$, $NH_2$, optionally substituted alkyl, optionally substituted aryl or optionally substituted heteroaryl. In further or additional embodiments, $R^1$ is H, F, Cl, Br, $CH_2F$, $CF_2H$, $CF_3$, $NH_2$, $CH_3$, optionally substituted phenyl or optionally substituted heteroaryl. In further or additional embodiments, $R^1$ is optionally substituted phenyl or optionally substituted heteroaryl. In further or additional embodiments, $R^1$ is

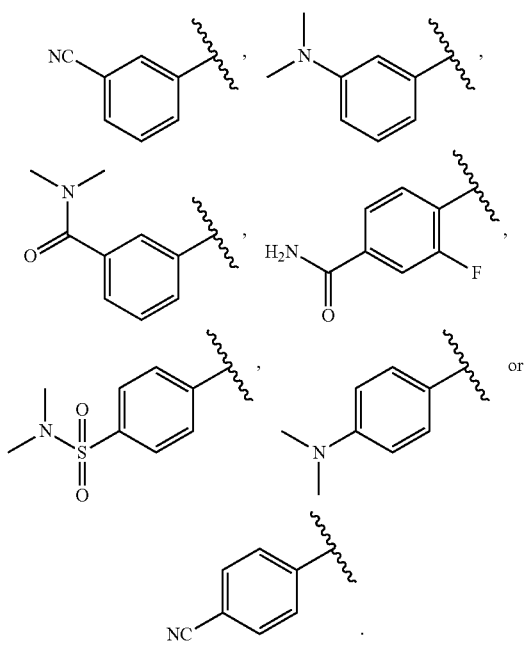

In further or additional embodiments, $R^1$ is optionally substituted pyridyl, optionally substituted pyrimindinyl, optionally substituted thiazolyl, optionally substituted furanyl, optionally substituted thiophenyl, optionally substituted pyrazolyl, optionally substituted oxazolyl, optionally substituted isoxazolyl, optionally substituted indolyl, optionally substituted iosindolyl, optionally substituted pyrazinyl, optionally substituted benzofuranyl, optionally substituted benzothiophenyl, optionally substituted indazolyl, optionally substituted benzthiazolyl, optionally substituted purinyl, optionally substituted quinolinyl or optionally substituted benzisoxazolyl. In further or additional embodiments, $R^1$ is

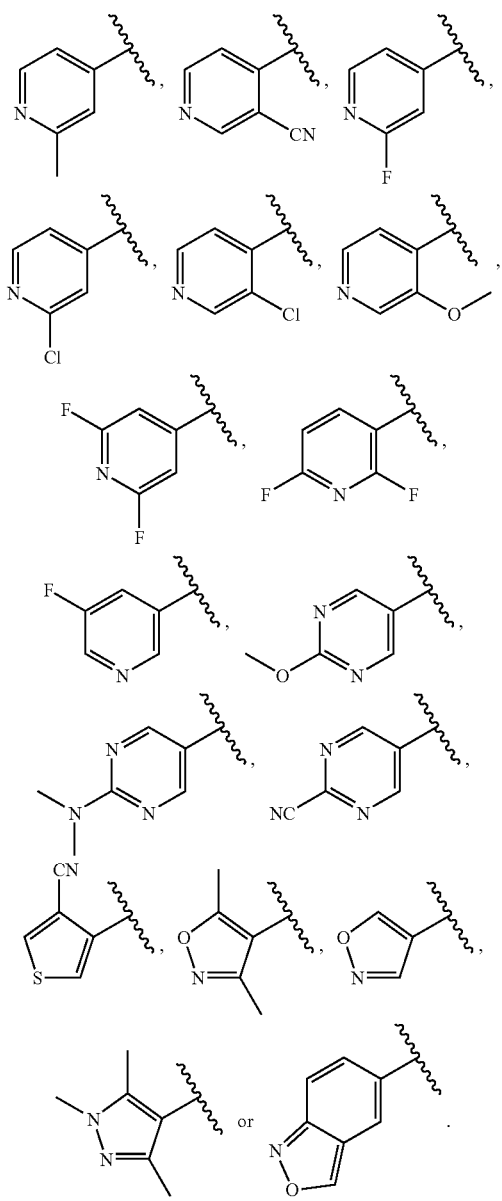

In some embodiments, W is S and $R^1$ is H, F, Cl, Br, $CH_2F$, $CF_2H$, $CF_3$, $NH_2$, optionally substituted phenyl or optionally substituted heteroaryl. In further or additional embodiments, W is O; and $R^1$ is H, F, Cl, Br, $CH_2F$, $CF_2H$, $CF_3$, $NH_2$, optionally substituted phenyl or optionally substituted heteroaryl. In further or additional embodiments, W is S; and $R^1$ is Br.

In some embodiments, a is 0. In further or additional embodiments, a is 1. In further or additional embodiments, a is 2. In further or additional embodiments, a is 0 or 1. In further or additional embodiments, a is 1, $R^a$ is H and $R^{a'}$ is H.

In further or additional embodiments, $R^a$ and $R^{a'}$ together with the carbon atom to which they are attached form an optionally substituted, 3-, 4-, 5- or 6-membered ring, optionally comprising 1 or 2 heteroatoms selected from O, N and S. In further or additional embodiments, $R^a$ and $R^{a'}$ together with the carbon atom to which they are attached form an optionally substituted 3-, 4-, 5- or 6-membered ring. In further or additional embodiments, $R^a$ and $R^{a'}$ together with the carbon atom to which they are attached form an optionally substituted 3-membered ring. In further or additional embodiments, $R^a$ and $R^{a'}$ together with the carbon atom to which they are attached form a substituted 3-membered ring. In further or additional embodiments, $R^a$ and $R^{a'}$ together with the carbon atom to which they are attached form an unsubstituted 3-membered ring. In further or additional embodiments, $R^a$ and $R^{a'}$ together with the carbon atom to which they are attached form an optionally substituted 4-membered ring. In further or additional embodiments, $R^a$ and $R^{a'}$ together with the carbon atom to which they are attached form a substituted 4-membered ring. In further or additional embodiments, $R^a$ and $R^{a'}$ together with the carbon atom to which they are attached form an unsubstituted 4-membered ring. In further or additional embodiments, $R^a$ and $R^{a'}$ together with the carbon atom to which they are attached form an optionally substituted 5-membered ring. In further or additional embodiments, $R^a$ and $R^{a'}$ together with the carbon atom to which they are attached form a substituted 5-membered ring. In further or additional embodiments, $R^a$ and $R^{a'}$ together with the carbon atom to which they are attached form an unsubstituted 5-membered ring. In further or additional embodiments, $R^a$ and $R^{a'}$ together with the carbon atom to which they are attached form an optionally substituted 6-membered ring. In further or additional embodiments, $R^a$ and $R^{a'}$ together with the carbon atom to which they are attached form a substituted 6-membered ring. In further or additional embodiments, $R^a$ and $R^{a'}$ together with the carbon atom to which they are attached form an unsubstituted 6-membered ring. In further or additional embodiments, $R^a$ and $R^{a'}$ together with the carbon atom to which they are attached form an optionally substituted 3-, 4-, 5- or 6-membered ring, comprising 1 heteroatom selected from O, N and S. In further or additional embodiments, $R^a$ and $R^{a'}$ together with the carbon atom to which they are attached form an optionally substituted 3-, 4-, 5- or 6-membered ring, comprising 1 oxygen atom. In further or additional embodiments, $R^a$ and $R^{a'}$ together with the carbon atom to which they are attached form an optionally substituted 3-, 4-, 5- or 6-membered ring, comprising 1 nitrogen atom. In further or additional embodiments, $R^a$ and $R^{a'}$ together with the carbon atom to which they are attached form an optionally substituted 3-, 4-, 5- or 6-membered ring, comprising 1 sulfur atom. In further or additional embodiments, $R^a$ and $R^{a'}$ together with the carbon atom to which they are attached form an optionally substituted 3-, 4-, 5- or 6-membered ring, comprising 2 heteroatoms selected from O, N and S.

In some embodiments, W is S, $R^1$ is H, F, Cl, Br, $CH_2F$, $CF_2H$, $CF_3$, $NH_2$, optionally substituted phenyl or optionally substituted heteroaryl and a is 0. In some embodiments, W is O, $R^1$ is H, F, Cl, Br, $CH_2F$, $CF_2H$, $CF_3$, $NH_2$, optionally substituted phenyl or optionally substituted heteroaryl and a is 0. In further or additional embodiments, W is S, $R^1$ is H, F, Cl, Br, $CH_2F$, $CF_2H$, $CF_3$, $NH_2$, optionally substituted phenyl or optionally substituted heteroaryl and a is 1. In further or additional embodiments, W is S, $R^1$ is H, F, Cl, Br, $CH_2F$, $CF_2H$, $CF_3$, $NH_2$, optionally substituted phenyl or optionally substituted heteroaryl, a is 1, $R^a$ is H and $R^{a'}$ is H.

In some embodiments, A is H. In some embodiments, A is $C(O)O$—$B^1$. In further or additional embodiments, A is $C(O)OH$. In further or additional embodiments, A is $C(O)O$— optionally substituted $C_{1-6}$ alkyl. In further or additional embodiments, A is $C(O)O$— optionally substituted $C_{1-3}$ alkyl. In further or additional embodiments, A is $C(O)O$— optionally substituted $C_{1-2}$ alkyl. In further or additional embodiments, A is $C(O)O$— substituted $C_{1-2}$ alkyl. In further or additional embodiments, A is $C(O)O$—$C_{1-2}$ alkyl. In further or additional embodiments, A is a carboxylate anion, associated with a pharmaceutically acceptable cation. In some embodiments, A is $C(O)NH$—$B^2$. In further or additional embodiments, A is $C(O)NH_2$. In further or additional embodiments, A is $C(O)NH$— optionally substituted $C_{1-6}$ alkyl. In further or additional embodiments, A is $C(O)NH$— optionally substituted $C_{1-3}$ alkyl. In further or additional embodiments, A is $C(O)NH$— optionally substituted $C_{1-2}$ alkyl. In further or additional embodiments, A is $C(O)NH$— substituted $C_{1-2}$ alkyl. In further or additional embodiments, A is $C(O)NH$—$C_{1-2}$ alkyl.

In some embodiments, x is 0. In further or additional embodiments, x is 1. In further or additional embodiments, y is 0. In further or additional embodiments, y is 1. In further or additional embodiments, z is 0. In further or additional embodiments, z is 1. In some embodiments, x is 0, y is 0 and z is 0. In some embodiments, x is 1, y is 0 and z is 0. In some embodiments, x is 1, y is 1 and z is 0. In some embodiments, x is 1, y is 1 and z is 1.

In further or additional embodiments, z is 0 and A is $C(O)O$—$B^1$. In further or additional embodiments, z is 0, A is $C(O)O$—$B^1$ and $B^1$ is H or optionally substituted $C_{1-6}$ alkyl. In further or additional embodiments, y is 0, z is 0 and A is $C(O)O$—$B^1$. In further or additional embodiments, y is 0, z is 0, A is $C(O)O$—$B^1$ and $B^1$ is H or optionally substituted $C_{1-6}$ alkyl. In further or additional embodiments, x is 1 and $R^x$ is not H. In further or additional embodiments, A is $C(O)O$—$B^1$, x is 1 and $R^x$ is not H. In further or additional embodiments, x is 1 and $R^x$ and $R^{x'}$ are not H. In further or additional embodiments, A is $C(O)O$—$B^1$, x is 1 and $R^x$ and $R^{x'}$ are not H. In further or additional embodiments, x is 1 and $R^x$ is optionally substituted $C_{1-3}$ alkyl. In further or additional embodiments, A is $C(O)O$—$B^1$, x is 1 and $R^x$ is optionally substituted $C_{1-3}$ alkyl. In further or additional embodiments, x is 1 and $R^x$ and $R^{x'}$ are optionally substituted $C_{1-3}$ alkyl. In further or additional embodiments, A is $C(O)O$—$B^1$, x is 1 and $R^x$ and $R^{x'}$ are optionally substituted $C_{1-3}$ alkyl. In further or additional embodiments, x is 1 and $R^x$ is methyl. In further or additional embodiments, A is $C(O)O$—$B^1$, x is 1 and $R^x$ is methyl. In further or additional embodiments, x is 1 and $R^x$ and $R^{x'}$ are methyl. In further or additional embodiments, A is $C(O)O$—$B^1$, x is 1 and $R^x$ and $R^{x'}$ are methyl.

In some embodiments, z is 0 and A is H. In further or additional embodiments, y is 0, z is 0 and A is H. In further or additional embodiments, $R^x$ is not H. In further or additional embodiments, $R^x$ and $R^{x'}$ are not H.

In further or additional embodiments, $R^x$ is optionally substituted $C_{1-3}$ alkyl. In further or additional embodiments, $R^x$ and $R^{x'}$ are optionally substituted $C_{1-3}$ alkyl. In further or additional embodiments, y is 0, z is 0, A is H and $R^x$ is not H. In further or additional embodiments, y is 0, z is 0, A is H and $R^x$ and $R^{x'}$ are not H. In further or additional embodiments, y is 0, z is 0, A is H and $R^x$ is optionally substituted $C_{1-3}$ alkyl. In further or additional embodiments, y is 0, z is 0, A is H and $R^x$ and $R^{x'}$ are optionally substituted $C_{1-3}$ alkyl. In some embodiments, $R^x$, $R^{x'}$, $R^y$, $R^{y'}$, $R^z$ and $R^{z'}$ are each independently H. In further or additional embodiments, at least one of $R^x$, $R^{x'}$, $R^y$, $R^{y'}$, $R^z$ and $R^{z'}$ is not H. In further or additional embodiments, at least two of $R^x$, $R^{x'}$, $R^y$, $R^{y'}$, $R^z$ and $R^{z'}$ are not H. In further or additional embodiments, at least one of $R^x$, $R^{x'}$, $R^y$, $R^{y'}$, $R^z$ and $R^{z'}$ is optionally substituted $C_{1-3}$ alkyl. In further or additional embodiments, at least one of $R^x$, $R^{x'}$, $R^y$, $R^{y'}$, $R^z$ and $R^{z'}$ is substituted $C_{1-3}$ alkyl. In further or additional embodiments, at least one of $R^x$, $R^{x'}$, $R^y$, $R^{y'}$, $R^z$ and $R^{z'}$ is $C_{1-3}$ alkyl. In further or additional embodiments, at least one of $R^x$, $R^{x'}$, $R^y$, $R^{y'}$, $R^z$ and $R^{z'}$ is optionally substituted methyl. In further or additional embodiments, at least one of $R^x$, $R^{x'}$, $R^y$, $R^{y'}$, $R^z$ and $R^{z'}$ is substituted methyl. In further or additional embodiments, at least one of $R^x$, $R^{x'}$, $R^y$, $R^{y'}$, $R^z$ and $R^{z'}$ is methyl. In further or additional embodiments, at least one of $R^x$, $R^{x'}$, $R^y$, $R^{y'}$, $R^z$ and $R^{z'}$ is optionally substituted ethyl. In further or additional embodiments, at least one of $R^x$, $R^{x'}$, $R^y$, $R^{y'}$, $R^z$ and $R^{z'}$ is substituted ethyl. In further or additional embodiments, at least one of $R^x$, $R^{x'}$, $R^y$, $R^{y'}$, $R^z$ and $R^{z'}$ is ethyl. In further or additional embodiments, $R^x$ is optionally substituted $C_{1-3}$ alkyl. In further or additional embodiments, $R^x$ is substituted $C_{1-3}$ alkyl. In further or additional embodiments, $R^x$ is $C_{1-3}$ alkyl. In further or additional embodiments, $R^x$ is optionally substituted methyl. In further or additional embodiments, $R^x$ is substituted methyl. In further or additional embodiments, $R^x$ is methyl. In further or additional embodiments, $R^x$ is optionally substituted ethyl. In further or additional embodiments, $R^x$ is substituted ethyl. In further or additional embodiments, $R^x$ is ethyl. In further or additional embodiments, $R^x$ and $R^{x'}$ are optionally substituted $C_{1-3}$ alkyl. In further or additional embodiments, $R^x$ and $R^{x'}$ are substituted $C_{1-3}$ alkyl. In further or additional embodiments, $R^x$ and $R^{x'}$ are $C_{1-3}$ alkyl. In some embodiments, x, y, and z are each 1 and $R^x$, $R^{x'}$, $R^y$, $R^{y'}$, $R^z$ and $R^{z'}$ are each H.

In some embodiments, $R^x$ and $R^{x'}$, or $R^y$ and $R^{y'}$, or $R^z$ and $R^{z'}$, or $R^x$ and $R^y$, or $R^y$ and $R^z$, or $R^x$ and $R^z$ together with the carbon atoms to which they are attached, form an optionally substituted, aromatic or non-aromatic, 3-7 membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S. In further or additional embodiments, $R^x$ and $R^{x'}$ together with the carbon atoms to which they are attached, form an optionally substituted, aromatic or non-aromatic, 3-7 membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S. In further or additional embodiments, $R^y$ and $R^{y'}$ together with the carbon atoms to which they are attached, form an optionally substituted, aromatic or non-aromatic, 3-7 membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S. In further or additional embodiments, $R^z$ and $R^{z'}$ together with the carbon atoms to which they are attached, form an optionally substituted, aromatic or non-aromatic, 3-7 membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S. In further or additional embodiments, $R^x$ and $R^y$ together with the carbon atoms to which they are attached, form an optionally substituted, aromatic or non-aromatic, 3-7 membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S. In further or additional embodiments, $R^y$ and $R^z$ together with the carbon atoms to which they are attached, form an optionally substituted, aromatic or non-aromatic, 3-7 membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S. In further or additional embodiments, $R^x$ and $R^z$ together with the carbon atoms to which they are attached, form an optionally substituted, aromatic or non-aromatic, 3-7 membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S.

In some embodiments, $R^x$ and $R^{x'}$, or $R^y$ and $R^{y'}$, or $R^z$ and $R^{z'}$, or $R^x$ and $R^y$, or $R^y$ and $R^z$, or $R^x$ and $R^z$ together with the carbon atoms to which they are attached, form an optionally substituted, aromatic or non-aromatic, 3-7 membered ring, optionally comprising 1 or 2 heteroatoms selected from O, N and S. In further or additional embodiments, the ring is a 3-membered ring. In further or additional embodiments, the ring is a 4-membered ring. In further or additional embodiments, the ring is a 5-membered ring. In further or additional embodiments, the ring is a 6-membered ring. In further or additional embodiments, the ring is a 7-membered ring. In further or additional embodiments, the ring does not comprise any heteroatoms. In further or additional embodiments, the ring comprises 1 heteroatom. In further or additional embodiments, the ring comprises 1 oxygen atom. In further or additional embodiments, the ring comprises 1 sulfur atom. In further or additional embodiments, the ring comprises 1 nitrogen atom. In further or additional embodiments, the ring comprises 2 heteroatoms. In further or additional embodiments, the ring is unsubstituted. In further or additional embodiments, the ring comprises at least one substituent. In further or additional embodiments, the ring comprises at least two substituents. In further or additional embodiments, the ring comprises at least three substituents. In further or additional embodiments, the ring is non-aromatic. In further or additional embodiments, the ring is aromatic.

In further or additional embodiments, $R^x$ and $R^{x'}$ together with the carbon atoms to which they are attached, form an optionally substituted, non-aromatic 3-6 membered ring. In further or additional embodiments, $R^x$ and $R^{x'}$ together with the carbon atoms to which they are attached, form an optionally substituted, non-aromatic 3 membered ring. In further or additional embodiments, $R^x$ and $R^{x'}$ together with the carbon atoms to which they are attached, form an optionally substituted, non-aromatic 4 membered ring. In further or additional embodiments, $R^x$ and $R^{x'}$ together with the carbon atoms to which they are attached, form an optionally substituted, non-aromatic 5 membered ring. In further or additional embodiments, $R^x$ and $R^{x'}$ together with the carbon atoms to which they are attached, form an optionally substituted, non-aromatic 6 membered ring. In further or additional embodiments, $R^y$ and $R^{y'}$ together with the carbon atoms to which they are attached, form an optionally substituted, non-aromatic 3-6 membered ring. In further or additional embodiments, $R^y$ and $R^{y'}$ together with the carbon atoms to which they are attached, form an optionally substituted, non-aromatic 3 membered ring. In further or additional embodiments, $R^y$ and $R^{y'}$ together with the carbon atoms to which they are attached, form an optionally substituted, non-aromatic 4 membered ring. In further or additional embodiments, $R^y$ and $R^{y'}$ together with the carbon atoms to which they are attached, form an optionally substituted, non-aromatic 5 membered ring. In further or additional embodiments, $R^y$ and $R^{y'}$ together with the carbon atoms to which they are attached, form an optionally substituted, non-aromatic 6 membered ring. In further or additional embodiments, $R^x$ and $R^y$ together with the carbon atoms to which they are attached, form an optionally substituted, non-aromatic 3-6 membered ring. In further or additional embodiments, $R^x$ and $R^y$ together with the carbon atoms to which they are attached, form an optionally substituted, non-aromatic 3 membered ring. In further or additional embodiments, $R^x$ and $R^y$ together with the carbon atoms to which they are attached, form an optionally substituted, non-aromatic 4 membered ring. In further or additional embodiments, $R^x$ and $R^y$ together with the carbon atoms to which they are attached, form an optionally substituted, non-aromatic 5 membered ring. In further or additional embodiments, $R^x$ and $R^y$ together with the carbon atoms to which they are attached, form an optionally substituted, non-aromatic 6 membered ring.

In some embodiments, $R^b$, $R^c$, $R^d$, $R^e$ and $R^f$ are each independently H, F, Cl, Br, I, $CF_3$, CN, alkyl, cycloalkyl, cyclopropylmethyl, $NH_2$, NHR', NR'R'', OH, OR', SH, SR', C(O)R', $CO_2H$, COOR', $CONH_2$, CONHR', CONR'R'', $SO_3H$, $S(O)_2R'$, $S(O)_2NH_2$, $S(O)_2NHR'$, $S(O)_2NR'R''$, aryl, heterocyclyl or heteroaryl; wherein R' is methyl, ethyl, n-propyl, i-propyl, n-butyl, i-butyl, s-butyl, t-butyl, cyclopropyl, cyclobutyl, cyclopentyl, cyclohexyl, phenyl or cyclopropylmethyl; R'' is methyl, ethyl, n-propyl, i-propyl, n-butyl, i-butyl, s-butyl, t-butyl, cyclopropyl, cyclobutyl, cyclopentyl, cyclohexyl, phenyl or cyclopropylmethyl; or R' and R'' together with the nitrogen atom to which they are attached form an optionally substituted, saturated or unsaturated 4-, 5- or 6-membered heterocyclic ring. In further or additional embodiments, at least one of $R^b$, $R^c$, $R^d$, $R^e$ and $R^f$ is not H. In further or additional embodiments, two of $R^b$, $R^c$, $R^d$, $R^e$ and $R^f$ are not H. In further or additional embodiments, three of $R^b$, $R^c$, $R^d$, $R^e$ and $R^f$ are not H. In further or additional embodiments, at least one of $R^b$, $R^c$, $R^d$, $R^e$ and $R^f$ is H. In further or additional embodiments, at least one of $R^b$, $R^c$, $R^d$, $R^e$ and $R^f$ is H and at least one is not H. In further or additional embodiments, $R^b$, $R^c$, $R^d$, $R^e$ and $R^f$ are each independently H, Cl, $CF_3$, alkyl, cycloalkyl, cyclopropylmethyl, $NH_2$, NHR', NR'R'', OR' or $CO_2H$.

In further or additional embodiments, $R^d$ is not H. In further or additional embodiments, $R^d$ is alkyl, cycloalkyl or cyclopropylmethyl. In further or additional embodiments, $R^d$ is alkyl. In further or additional embodiments, $R^d$ is methyl or ethyl. In further or additional embodiments, $R^d$ is cycloalkyl. In further or additional embodiments, $R^d$ is cyproyl, cyclobutyl or cyclopentyl.

In some embodiments, $R^b$ and $R^c$, or $R^c$ and $R^d$, or $R^d$ and $R^e$, or $R^e$ and $R^f$ together with the two carbon atoms to which they are attached, form an optionally substituted, aromatic or non-aromatic, 5-, 6- or 7-membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S; and wherein the optional substituents are each independently F, Cl, Br, I, $CF_3$, CN, alkyl, cycloalkyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl or heteroaryl.

In some embodiments, $R^b$ and $R^c$ together with the two carbon atoms to which they are attached, form an optionally substituted, aromatic or non-aromatic, 5-, 6- or 7-membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S; and wherein the optional substituents are each independently F, Cl, Br, I, $CF_3$, CN, alkyl, cycloalkyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl or heteroaryl.

In some embodiments, $R^b$ and $R^c$ together with the two carbon atoms to which they are attached, form an optionally substituted, aromatic or non-aromatic, 5-, 6- or 7-membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S.

In some embodiments, $R^b$ and $R^c$ together with the two carbon atoms to which they are attached, form an optionally substituted, aromatic or non-aromatic, 5-, 6- or 7-membered ring, optionally comprising 1 or 2 heteroatoms selected from O, N and S. In some embodiments, $R^b$ and $R^c$ together with the two carbon atoms to which they are attached, form an optionally substituted, aromatic or non-aromatic, 5-, 6- or 7-membered ring. In some embodiments, $R^b$ and $R^c$ together with the two carbon atoms to which they are attached, form an optionally substituted, aromatic or non-aromatic, 5-membered ring. In some embodiments, $R^b$ and $R^c$ together with the two carbon atoms to which they are attached, form an optionally substituted, aromatic or non-aromatic, 6-membered ring. In some embodiments, $R^b$ and $R^c$ together with the two carbon atoms to which they are attached, form an optionally substituted, aromatic or non-aromatic, 7-membered ring. In some embodiments, $R^b$ and $R^c$ together with the two carbon atoms to which they are attached, form a substituted, aromatic or non-aromatic, 5-, 6- or 7-membered ring. In some embodiments, $R^b$ and $R^c$ together with the two carbon atoms to which they are attached, form a substituted, aromatic, 5-, 6- or 7-membered ring. In some embodiments, $R^b$ and $R^c$ together with the two carbon atoms to which they are attached, form a substituted, aromatic, 5-membered ring. In some embodiments, $R^b$ and $R^c$ together with the two carbon atoms to which they are attached, form a substituted, aromatic, 6-membered ring. In some embodiments, $R^b$ and $R^c$ together with the two carbon atoms to which they are attached, form a substituted, aromatic, 7-membered ring. In some embodiments, $R^b$ and $R^c$ together with the two carbon atoms to which they are attached, form a substituted, non-aromatic, 5-, 6- or 7-membered ring. In some embodiments, $R^b$ and $R^c$ together with the two carbon atoms to which they are attached, form a substituted, non-aromatic, 5-membered ring. In some embodiments, $R^b$ and $R^c$ together with the two carbon atoms to which they are attached, form a substituted, non-aromatic, 6-membered ring. In some embodiments, $R^b$ and $R^c$ together with the two carbon atoms to which they are attached, form a substituted, non-aromatic, 7-membered ring. In further or additional embodiments, $R^b$ and $R^c$, together with the two carbon atoms to which they are attached, form an optionally substituted, aromatic or non-aromatic, 6-membered ring, comprising 1 heteroatom selected from O, N and S. In further or additional embodiments, $R^b$ and $R^c$, together with the two carbon atoms to which they are attached, form an optionally substituted, aromatic or non-aromatic, 5-, 6- or 7-membered ring, comprising 1 oxygen atom. In further or additional embodiments, $R^b$ and $R^c$, together with the two carbon atoms to which they are attached, form an optionally substituted, aromatic or non-aromatic, 6-membered ring, comprising 1 sulfur atom. In further or additional embodiments, $R^b$ and $R^c$, together with the two carbon atoms to which they are attached, form an optionally substituted, aromatic or non-aromatic, 6-membered ring, comprising 1 nitrogen atom. In further or additional embodiments, $R^b$ and $R^c$, together with the two carbon atoms to which they are attached, form an optionally substituted, aromatic or non-aromatic, 6-membered ring, comprising 2 heteroatoms selected from O, N and S. In further or additional embodiments, $R^b$ and $R^c$, together with the two carbon atoms to which they are attached, form an optionally substituted, aromatic or non-aromatic, 6-membered ring, optionally comprising 1 or 2 heteroatoms selected from O, N and S. In further or additional embodiments, $R^b$ and $R^c$, together with the two carbon atoms to which they are attached, form an optionally substituted, aromatic or non-aromatic, 5-, 6- or 7-membered ring, optionally comprising 1 or 2 heteroatoms selected from O, N and S. In further or additional embodiments, $R^b$ and $R^c$, together with the two carbon atoms to which they are attached, form an optionally substituted, aromatic or non-aromatic, 6-membered ring, optionally comprising 1 or 2 heteroatoms selected from O, N and S. In further or additional embodiments, $R^b$ and $R^c$, together with the two carbon atoms to which they are attached, form an optionally substituted, aromatic or non-aromatic, 5-, 6- or 7-membered ring, optionally comprising 1 nitrogen atom. In further or additional embodiments, $R^b$ and $R^c$, together with the two carbon atoms to which they are attached, form an optionally substituted, aromatic or non-aromatic, 6-membered ring, optionally comprising 1 nitrogen atom. In some embodiments, $R^c$ and $R^d$ together with the two carbon atoms to which they are attached, form an optionally substituted, aromatic or non-aromatic, 5-, 6- or 7-membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S; and wherein the optional substituents are each independently F, Cl, Br, I, $CF_3$, CN, alkyl, cycloalkyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl or heteroaryl.

In further or additional embodiments, $R^c$ and $R^d$, together with the two carbon atoms to which they are attached, form an optionally substituted, aromatic or non-aromatic, 5-, 6- or 7-membered ring, optionally comprising 1 or 2 heteroatoms selected from O, N and S. In further or additional embodiments, $R^c$ and $R^d$, together with the two carbon atoms to which they are attached, form an optionally substituted, aromatic or non-aromatic, 6-membered ring, optionally comprising 1 or 2 heteroatoms selected from O, N and S.

Another aspect of the invention provides for a compound of formula (II-A), (II-B), (II-C), (II-D), (II-E), (II-F), (II-G), (II-H), (II-I) or (II-J), or a metabolite, pharmaceutically acceptable salt, solvate, polymorph, ester, tautomer or prodrug thereof:

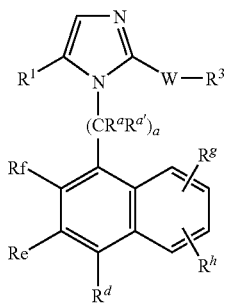
(II-A)
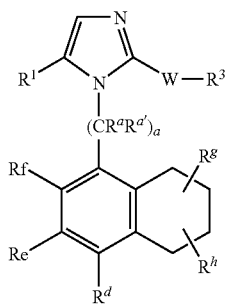
(II-B)
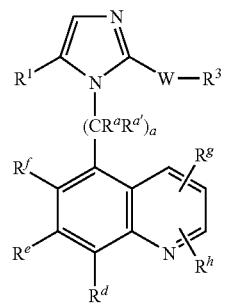
(II-C)
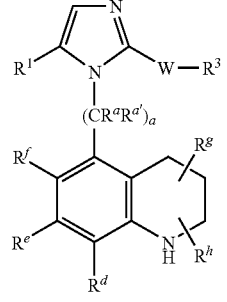
(II-D)
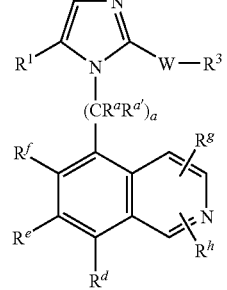
(II-E)
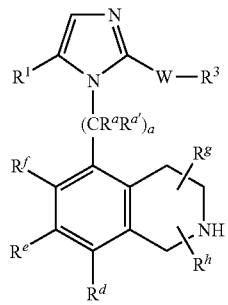
(II-F)
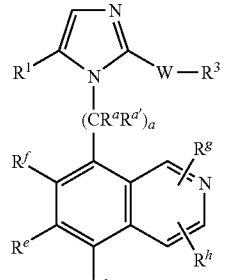
(II-G)
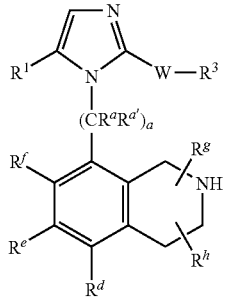
(II-H)
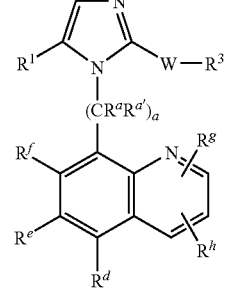
(II-I)
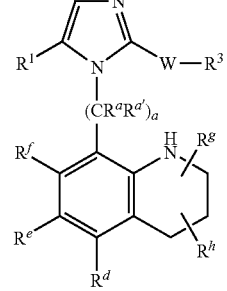
(II-J)
wherein:
W is O, S, S(O), S(O)$_2$, NH, N(optionally substituted alkyl), CH$_2$, CH$_2$O, CH$_2$S or CH$_2$NH;

R¹ is H, F, Cl, Br, I, CH₂F, CF₂H, CF₃, CN, OH, NO₂, NH₂, NH(alkyl) or N(alkyl)(alkyl), SO₂CH₃, SO₂NH₂, SO₂NHCH₃, CO₂-alkyl, optionally substituted alkyl, optionally substituted alkenyl, optionally substituted alkoxy, optionally substituted S-alkyl, optionally substituted cycloalkyl, optionally substituted heterocycle, optionally substituted aryl or optionally substituted heteroaryl;

a is 0, 1 or 2;

$R^a$ is H or optionally substituted $C_{1-3}$ alkyl;

$R^{a'}$ is H or optionally substituted $C_{1-3}$ alkyl; or $R^a$ and $R^{a'}$ together with the carbon atom to which they are attached form a 3-, 4-, 5- or 6-membered ring, optionally comprising 1 or 2 heteroatoms selected from O, N and S;

$R^d$, $R^e$, $R^f$, $R^g$ and $R^h$ are each independently H, F, Cl, Br, I, CF₃, CN, alkyl, cycloalkyl, cyclopropylmethyl, NH₂, NHR', NR'R", OH, OR', SH, SR', C(O)R', CO₂H, COOR', CONH₂, CONHR', CONR'R", SO₃H, S(O)₂R', S(O)₂NH₂, S(O)₂NHR', S(O)₂NR'R", aryl, heterocyclyl or heteroaryl;

wherein
R' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;

R" is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or R' and R" together with the nitrogen atom to which they are attached form an optionally substituted, saturated or unsaturated 4-, 5- or 6-membered heterocyclic ring;

$R^3$ is —$(CR^xR^{x'})_x$—$(CR^yR^{y'})_y$—$(CR^zR^{z'})_z$-A; wherein x is 0 or 1;
y is 0 or 1;
z is 0 or 1;

$R^x$, $R^{x'}$, $R^y$, $R^{y'}$, $R^z$ and $R^{z'}$ are each independently H, F, Cl, Br, or optionally substituted $C_{1-3}$ alkyl; or $R^x$ and $R^{x'}$, or $R^y$ and $R^{y'}$, or $R^z$ and $R^{z'}$, or $R^x$ and $R^y$, or $R^y$ and $R^z$, or $R^x$ and $R^z$ together with the carbon atoms to which they are attached, form an optionally substituted, aromatic or non-aromatic, 3-7 membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S;

A is H, C(O)O—B¹ or C(O)NH—B²; wherein

B¹ is H, optionally substituted $C_{1-6}$ alkyl or a pharmaceutically acceptable cation;

B² is H or optionally substituted $C_{1-6}$ alkyl; and wherein all alkyl, alkylene, cycloalkyl, heterocyclyl, aryl and heteroaryl moieties may be optionally further substituted.

In some embodiments, the invention provides for compounds of formula (II-A), (II-B), (II-C), (II-D), (II-E), (II-F), (II-G), (II-H), (II-I) or (II-J). In further or additional embodiments, the invention provides for metabolites of a compound of formula (II-A), (II-B), (II-C), (II-D), (II-E), (II-F), (II-G), (II-H), (II-I) or (II-J). In further or additional embodiments, the invention provides for pharmaceutically acceptable salts of compounds of formula (II-A), (II-B), (II-C), (II-D), (II-E), (II-F), (II-G), (II-H), (II-I) or (II-J). In further or additional embodiments, the invention provides for pharmaceutically acceptable solvates of compounds of formula (II-A), (II-B), (II-C), (II-D), (II-E), (II-F), (II-G), (II-H), (II-I) or (II-J). In further or additional embodiments, the invention provides for pharmaceutically acceptable polymorphs of compounds of formula (II-A), (II-B), (II-C), (II-D), (II-E), (II-F), (II-G), (II-H), (II-I) or (II-J). In further or additional embodiments, the invention provides for pharmaceutically acceptable esters of compounds of formula (II-A), (II-B), (II-C), (II-D), (II-E), (II-F), (II-G), (II-H), (II-I) or (II-J). In further or additional embodiments, the invention provides for pharmaceutically acceptable tautomers of compounds of formula (II-A), (II-B), (II-C), (II-D), (II-E), (II-F), (II-G), (II-H), (II-I) or (II-J). In further or additional embodiments, the invention provides for pharmaceutically acceptable prodrugs of compounds of formula (II-A), (II-B), (II-C), (II-D), (II-E), (II-F), (II-G), (II-H), (II-I) or (II-J).

In some embodiments, the invention provides for compounds of formula (II-A). In some embodiments, the invention provides for compounds of formula (II-B). In some embodiments, the invention provides for compounds of formula (II-C). In some embodiments, the invention provides for compounds of formula (II-D). In some embodiments, the invention provides for compounds of formula (II-E). In some embodiments, the invention provides for compounds of formula (II-F). In some embodiments, the invention provides for compounds of formula (II-G). In some embodiments, the invention provides for compounds of formula (II-H). In some embodiments, the invention provides for compounds of formula (II-I). In some embodiments, the invention provides for compounds of formula (II-J).

In further or additional embodiments, $R^d$, $R^e$, $R^f$, $R^g$ and $R^h$ are each independently H, Cl, CF₃, alkyl, cycloalkyl, cyclopropylmethyl, NH₂, NHR', NR'R", OR' or CO₂H. In some embodiments, at least of one of $R^d$, $R^e$, $R^f$, $R^g$ and $R^h$ is not H. In further or additional embodiments, two of $R^d$, $R^e$, $R^f$, $R^g$ and $R^h$ are not H. In further or additional embodiments, three of $R^d$, $R^e$, $R^f$, $R^g$ and $R^h$ are not H. In further or additional embodiments, at least of one of $R^d$, $R^e$, $R^f$, $R^g$ and $R^h$ is H. In further or additional embodiments, at least of one of $R^d$, $R^e$, $R^f$, $R^g$ and $R^h$ is H and at least one is not H. In further or additional embodiments, $R^d$ is not H. In further or additional embodiments, $R^d$ is optionally substituted alkyl, cycloalkyl or cyclopropylmethyl. In further or additional embodiments, $R^d$ is substituted alkyl, cycloalkyl or cyclopropylmethyl. In further or additional embodiments, $R^d$ is alkyl, cycloalkyl or cyclopropylmethyl. In further or additional embodiments, $R^d$ is alkyl. In further or additional embodiments, $R^d$ is methyl or ethyl. In further or additional embodiments, $R^d$ is cycloalkyl. In further or additional embodiments, $R^d$ is cyproyl, cyclobutyl or cyclopentyl.

Another aspect of the invention provides for a compound of formula (IIK), (IIL), (IIM), (IIN), (IIO) or (IIP), or a metabolite, pharmaceutically acceptable salt, solvate, polymorph, ester, tautomer or prodrug thereof:

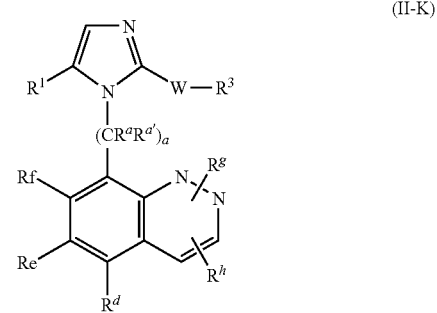

(II-K)

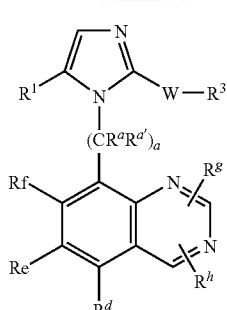
(II-L)

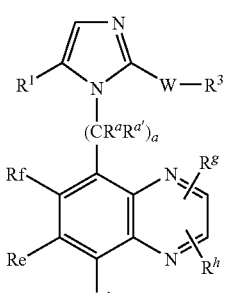
(II-M)

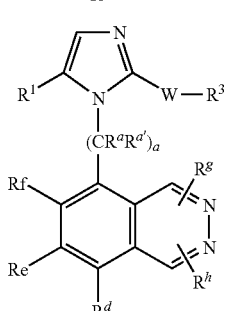
(II-N)

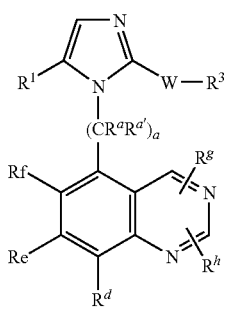
(II-O)

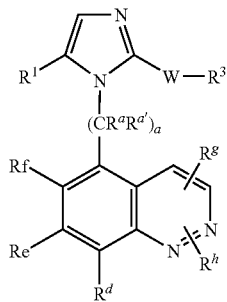
(II-P)

wherein:
$R^g$ and $R^h$ are each independently H, F, Cl, Br, I, $CF_3$, CN, alkyl, cycloalkyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl or heteroaryl; wherein R' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;

R" is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or R' and R" together with the nitrogen atom to which they are attached form an optionally substituted, saturated or unsaturated 4-, 5- or 6-membered heterocyclic ring.

In some embodiments, the invention provides compounds of formula (II-K), (II-L), (II-M), (II-N), (II-O) or (II-P). In some embodiments, the invention provides for metabolites of compounds of formula (II-K), (II-L), (II-M), (II-N), (II-O) or (II-P). In some embodiments, the invention provides for pharmaceutically acceptable salts of compounds of formula (II-K), (II-L), (II-M), (II-N), (II-O) or (II-P). In some embodiments, the invention provides for pharmaceutically acceptable solvates of compounds of formula (II-K), (II-L), (II-M), (II-N), (II-O) or (II-P). In some embodiments, the invention provides for pharmaceutically acceptable polymorphs of compounds of formula (II-K), (II-L), (II-M), (II-N), (II-O) or (II-P). In some embodiments, the invention provides for pharmaceutically acceptable esters of compounds of formula (II-K), (II-L), (II-M), (II-N), (II-O) or (II-P). In some embodiments, the invention provides for pharmaceutically acceptable tautomers of compounds of formula (II-K), (II-L), (II-M), (II-N), (II-O) or (II-P). In some embodiments, the invention provides for pharmaceutically acceptable prodrugs of compounds of formula (II-K), (II-L), (II-M), (II-N), (II-O) or (II-P). In some embodiments, the invention provides compounds of formula (II-K). In some embodiments, the invention provides compounds of formula (II-L). In some embodiments, the invention provides compounds of formula (II-M). In some embodiments, the invention provides compounds of formula (II-N). In some embodiments, the invention provides compounds of formula (II-O). In some embodiments, the invention provides compounds of formula (II-P).

In other embodiments, the invention provides compounds of formula (II-Q), or a metabolite, pharmaceutically acceptable salt, solvate, polymorph, ester, tautomer or prodrug thereof:

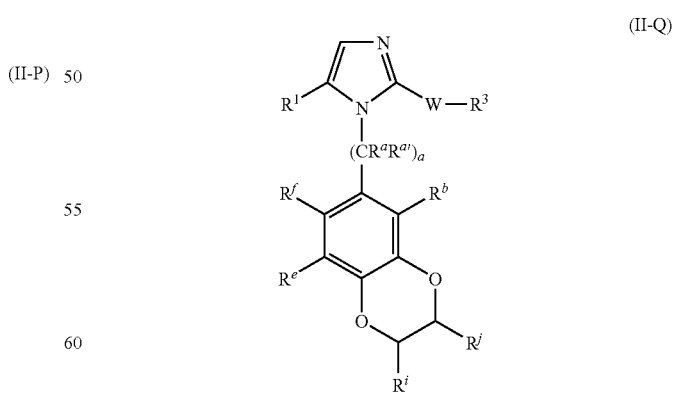
(II-Q)

wherein:
$R^i$ and $R^j$ are each independently H, F, Cl, Br, I, $CF_3$, CN, alkyl, cycloalkyl, cyclopropylmethyl, $NH_2$, NHR', NR'R", OH, OR', SH, SR', C(O)R', $CO_2H$, COOR', CONH$_2$, CONHR', CONR'R", SO$_3$H, S(O)$_2$R', S(O)$_2$NH$_2$, S(O)$_2$NHR', S(O)$_2$NR'R", aryl, heterocyclyl or heteroaryl; wherein R' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;

R" is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or R' and R" together with the nitrogen atom to which they are attached form an optionally substituted, saturated or unsaturated 4-, 5- or 6-membered heterocyclic ring.

In further or additional embodiments, W is O or S. In further or additional embodiments, W is S. In further or additional embodiments, R$^1$ is H, F, Cl, Br, CH$_2$F, CF$_2$H, CF$_3$, NH$_2$, CH$_3$ or optionally substituted phenyl. In further or additional embodiments, a is 0. In further or additional embodiments, R$^a$ is H and R$^{a'}$ is H. In further or additional embodiments, W is O or S; R$^1$ is H, F, Cl, Br, CH$_2$F, CF$_2$H, CF$_3$, NH$_2$, CH$_3$ or optionally substituted phenyl; and a is 0.

Another aspect of the invention provides a method for decreasing uric acid levels in one or more tissues or organs of a subject in need of decreased uric acid levels, comprising administering to the subject a uric acid level decreasing amount of a compound disclosed herein or a metabolite, pharmaceutically acceptable salt, solvate, polymorph, ester, tautomer or prodrug thereof. In some embodiments, the subject has a disorder characterized by an abnormally high content of uric acid in one or more tissues or organs of the subject.

In further or additional embodiments, the disorder is characterized by overproduction of uric acid, low excretion of uric acid, tumor lysis, a blood disorder or a combination thereof. In further or additional embodiments, the blood disorder is polycythemia or myeloid metaplasia. In further or additional embodiments, the subject in need of decreased serum uric acid levels is suffering from gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis. In further or additional embodiments, the uric acid levels are decreased by at least about 1% in one or more tissues or organs of the subject. In further or additional embodiments, the uric acid levels are decreased by at least about 2% in one or more tissues or organs of the subject. In further or additional embodiments, the uric acid levels are decreased by at least about 5% in one or more tissues or organs of the subject. In further or additional embodiments, the uric acid levels are decreased by at least about 10% in one or more tissues or organs of the subject. In further or additional embodiments, the uric acid levels are decreased by at least about 12% in one or more tissues or organs of the subject. In further or additional embodiments, the uric acid levels are decreased by at least about 15% in one or more tissues or organs of the subject. In further or additional embodiments, the uric acid levels are decreased by at least about 20% in one or more tissues or organs of the subject. In further or additional embodiments, the uric acid levels are decreased by at least about 25% in one or more tissues or organs of the subject. In further or additional embodiments, the uric acid levels are decreased by at least about 30% in one or more tissues or organs of the subject. In further or additional embodiments, the uric acid levels are decreased by at least about 40% in one or more tissues or organs of the subject. In further or additional embodiments, the uric acid levels are decreased by at least about 50% in one or more tissues or organs of the subject. In further or additional embodiments, the uric acid levels are decreased by at least about 60% in one or more tissues or organs of the subject. In further or additional embodiments, the uric acid levels are decreased by at least about 70% in one or more tissues or organs of the subject. In further or additional embodiments, the uric acid levels are decreased by at least about 75% in one or more tissues or organs of the subject.

In further or additional embodiments, the tissue or organ is blood. In further or additional embodiments, the blood uric acid level is decreased by at least about 0.5 mg/dL. In further or additional embodiments, the blood uric acid level is decreased by at least about 1 mg/dL. In further or additional embodiments, the blood uric acid level is decreased by at least about 2 mg/dL.

In further or additional embodiments, one or more metabolites of a compound disclosed herein is administered. In further or additional embodiments, one or more pharmaceutically acceptable salts of a compound disclosed herein is administered. In further or additional embodiments, one or more pharmaceutically acceptable solvates of a compound disclosed herein is administered. In further or additional embodiments, one or more pharmaceutically acceptable polymorphs of a compound disclosed herein is administered. In further or additional embodiments, one or more pharmaceutically acceptable of a esters compound of formula (II) is administered. In further or additional embodiments, one or more pharmaceutically acceptable tautomers of a compound disclosed herein is administered. In further or additional embodiments, one or more pharmaceutically acceptable prodrugs of a compound disclosed herein is administered.

Yet another aspect of the invention provides a method for reducing uric acid production, increasing uric acid excretion or both in a subject, comprising administering to the subject a compound disclosed herein or a metabolite, pharmaceutically acceptable salt, solvate, polymorph, ester, tautomer or prodrug thereof.

Another aspect of the invention provides a method for treating or preventing hyperuricemia in a subject comprising administering to the subject an effective amount of a compound disclosed herein, or a metabolite, pharmaceutically acceptable salt, solvate, polymorph, ester, tautomer or prodrug thereof, wherein said amount is effective in lowering the level of uric acid.

Another aspect of the invention provides a method of treating a subject suffering from a condition characterized by abnormal tissue or organ levels of uric acid comprising administering to the subject an effective amount of a compound disclosed herein or a metabolite, pharmaceutically acceptable salt, solvate, polymorph, ester, tautomer or prodrug thereof. In some embodiments, the condition is characterized by low tissue levels of uric acid. In further or additional embodiments, the condition is characterized by high tissue levels of uric acid. In further or additional embodiments, the condition is selected from gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis. In further or additional embodiments, the condition is gout. In further or additional embodiments, the condition is joint inflammation. In further or additional embodiments, the joint inflammation is caused by deposits of uric acid crystals in the joint. In further or additional embodiments, the uric acid crystals are deposited in the joint fluid (synovial fluid) or joint lining (synovial lining). In other embodiments, the method further comprises administering an agent effective for the treatment of the condition. In further or additional embodiments, the agent is effective in reducing tissue levels of uric acid. In further or additional embodiments, the agent is a nonsteroidal anti-inflammatory drugs (NSAIDs), colchicine, a corticosteroid, adrenocorticotropic hormone (ACTH), probenecid, sulfinpyrazone or allopurinol. In further or additional embodiments, the agent is allopurinol.

Yet another aspect of the invention provides a method for preventing a condition characterized by abnormal tissue levels of uric acid in a subject at increased risk of developing the condition, comprising administering to the subject an effective amount of a compound disclosed herein or a metabolite, pharmaceutically acceptable salt, solvate, polymorph, ester, tautomer or prodrug thereof. In some embodiments, the condition is selected from gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis.

Another aspect of the invention provides a method for treating gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosisin a subject comprising administering to the subject an effective amount of a compound disclosed herein or a metabolite, pharmaceutically acceptable salt, solvate, polymorph, ester, tautomer or prodrug thereof.

Another aspect of the invention provides a method for treating gout in a subject comprising administering to the subject an effective amount of a compound disclosed herein or a metabolite, pharmaceutically acceptable salt, solvate, polymorph, ester, tautomer or prodrug thereof. In some embodiments, the method further comprises administering an agent effective for the treatment of the gout. In further or additional embodiments, the agent is allopurinol.

Another aspect of the invention provides a method for preventing the formation or reducing the size of tophi/tophus in a subject, comprising administering to the subject an effective amount of a compound disclosed herein or a metabolite, pharmaceutically acceptable salt, solvate, polymorph, ester, tautomer or prodrug thereof.

Another aspect of the invention provides a method for decreasing uric acid levels in one or more tissues or organs of a subject comprising administering to the subject a uric acid level decreasing amount of a compound disclosed herein or a metabolite, pharmaceutically acceptable salt, solvate, polymorph, ester, tautomer or prodrug thereof, wherein the reduction in uric acid levels results in a reduction in hypertension or cardiovascular events.

Another aspect of the invention provides a method for treating hypoxanthine-guanine phosphoribosyltransferase (HPRT) deficiency in a subject comprising administering to the subject a compound disclosed herein or a metabolite, pharmaceutically acceptable salt, solvate, polymorph, ester, tautomer or prodrug thereof.

Other aspects of the invention provide a pharmaceutical composition useful for decreasing uric acid levels comprising:
i) a sufficient amount of a compound disclosed herein or a metabolite, pharmaceutically acceptable salt, solvate, polymorph, ester, tautomer or prodrug thereof, to decrease uric acid levels; and
ii) optionally one or more pharmaceutically acceptable carriers.

Other aspects of the invention provide a pharmaceutical composition useful for reducing hypertension or cardiovascular events comprising:
i) a sufficient amount of a compound disclosed herein or a metabolite, pharmaceutically acceptable salt, solvate, polymorph, ester, tautomer or prodrug thereof to decrease uric acid levels; and
ii) optionally one or more pharmaceutically acceptable carriers.

Other aspects of the invention provide a pharmaceutical composition comprising:
i) a compound disclosed herein or a metabolite, pharmaceutically acceptable salt, solvate, polymorph, ester, tautomer or prodrug thereof;
ii) allopurinol; and
iii) optionally one or more pharmaceutically acceptable carriers.

Other aspects of the invention provide a pharmaceutical composition useful in the treatment of edema and hypertension which also maintains uric acid levels at pretreatment levels or causes a decrease in uric acid levels comprising:
i) an antihypertensive agent;
ii) a uric acid level maintaining or lowering amount of a compound of the formula (II) or a metabolite, pharmaceutically acceptable salt, solvate, polymorph, ester, tautomer or prodrug thereof; and
iii) optionally one or more pharmaceutically acceptable carriers.

Other aspects of the invention provide a pharmaceutical composition useful in the treatment of cancer which also maintains uric acid levels at pretreatment levels or causes a decrease in uric acid levels comprising:
i) an anticancer agent;
ii) a uric acid level maintaining or lowering amount of a compound of the formula (II) or a metabolite, pharmaceutically acceptable salt, solvate, polymorph, ester, tautomer or prodrug thereof; and
iii) optionally one or more pharmaceutically acceptable carriers.

Other aspects of the invention provide a pharmaceutical composition useful for reducing the side effects of chemotherapy in a cancer patient, comprising:
i) a uric acid level maintaining or lowering amount of a compound of the formula (II) or a metabolite, pharmaceutically acceptable salt, solvate, polymorph, ester, tautomer or prodrug thereof; and
ii) optionally one or more pharmaceutically acceptable carriers;
wherein said side effects are related to elevated uric acid levels.

The present invention provides methods for modulating the content of uric acid in a subject comprising administrating to the subject an effective content-modulating amount of a compound disclosed herein. The invention also provides pharmaceutical compositions and methods for treating disorders of uric acid metabolism and resulting ailments in a subject, such as gout, gouty arthritis, inflammatory arthritis, kidney disease, nephrolithiasis (kidney stones), joint inflammation, deposition of urate crystals in joints, urolithiasis (formation of calculus in the urinary tract), deposition of urate crystals in renal parenchyma, Lesch-Nyhan syndrome, and/or Kelley-Seegmiller syndrome.

Disclosed herein, in certain embodiments, is a compound having the following structure:

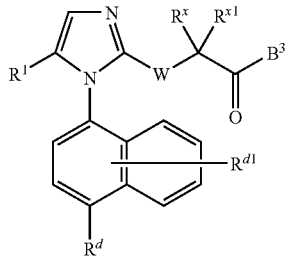

or a metabolite, pharmaceutically acceptable salt, solvate, polymorph, ester, tautomer or prodrug thereof,
wherein:
W is O or S;
$R^1$ is H, F, Cl, Br, I, —$CH_2F$, —$CF_2H$, —$CF_3$, —CN, —OH, —$NO_2$, —$NH_2$, —NH($C_{1-4}$alkyl), —N($C_{1-4}$alkyl)($C_{1-4}$alkyl), —$SO_2CH_3$, —$SO_2NH_2$, —$SO_2NHCH_3$, —$CO_2$—$C_{1-4}$alkyl, $C_{1-4}$alkyl, $C_{1-4}$alkenyl, $C_{1-4}$alkoxy, $C_{1-4}$S-alkyl, $C_{3-6}$cycloalkyl, optionally substituted $C_{1-6}$heterocycloalkyl, optionally substituted phenyl, or optionally substituted 5 or 6 membered heteroaryl;
$R^d$ is F, Cl, Br, I, $CF_3$, aryl, heteroaryl, CN, $NO_2$, $NH_2$, NHR', OH, OR', SH, SR', C(O)R', $CO_2H$, COOR', $CONH_2$, CONHR', CONR'R", $SO_3H$, $SO_3R'$, $S(O)_2R'$, $S(O)_2NH_2$, $S(O)_2NHR'$, or $S(O)_2NR'R"$;
$R^{d1}$ is zero to four substituents independently selected from optionally substituted alkyl, optionally substituted alkenyl, optionally substituted alkynyl, optionally substituted heteroalkyl, optionally substituted heteroalkenyl, optionally substituted heteroalkynyl, optionally substituted cycloalkyl, optionally substituted cycloalkenyl, optionally substituted heterocyclyl, optionally substituted aryl, optionally substituted heteroaryl, halo, CN, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, or $S(O)_2NR'R"$;
each R' is independently methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;
each R" is independently methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or
R' and R" are together with the atom to which they are attached form an optionally substituted, saturated or unsaturated 4-, 5- or 6-membered ring;
$R^x$ and $R^{x'}$ are each independently H, optionally substituted alkyl, optionally substituted alkenyl, optionally substituted alkynyl, optionally substituted heteroalkyl, optionally substituted heteroalkenyl, optionally substituted heteroalkynyl, optionally substituted cycloalkyl, optionally substituted cycloalkenyl, optionally substituted heterocyclyl, optionally substituted aryl, optionally substituted heteroaryl, halo, CN, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2$ NHR', or $S(O)_2NR'R"$; or
$R^x$ and $R^{x'}$ together with the carbon atom to which they are attached, form an optionally substituted non-aromatic 3-7 membered ring, optionally comprising 1 or 2 heteroatoms selected from O, N and S;
$B^3$ is $OB^1$, $NB^2_2$, or an amino acid residue or an alkyl ester thereof;
$B^1$ is H, optionally substituted $C_{1-6}$ alkyl or a pharmaceutically acceptable cation; and
each $B^2$ is independently H or optionally substituted alkyl.
In some embodiments, W is S. In some embodiments, W is O. In some embodiments, $B^3$ is $OB^1$. In some embodiments, $B^1$ is an alkali earth metal cation or an alkaline earth metal cation. In some embodiments, $B^3$ is $NB^2_2$. The compound disclosed herein wherein $B^3$ is an amino acid residue or lower alkyl ester thereof. In some embodiments, $R^x$ and $R^{x'}$ are independently H, F, $CF_3$, or methyl. In some embodiments, $R^x$ is F and $R^{x1}$ is F. In some embodiments, $R^1$ is H, F, Cl, Br, $CH_2F$, $CF_2H$, $CF_3$, $NH_2$, or $CH_3$. In some embodiments, $R^1$ is Br. In some embodiments, $R^d$ is H, F, Cl, Br, I, $CF_3$, or CN.

Disclosed herein, in certain embodiments, is a compound having the following structure:

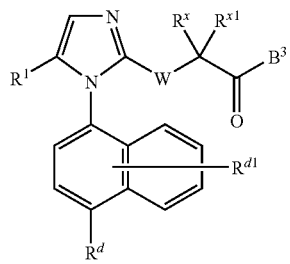

or a metabolite, pharmaceutically acceptable salt, solvate, polymorph, ester, tautomer or prodrug thereof,
wherein:
W is O or S;
$R^1$ is H, F, Cl, Br, I, —$CH_2F$, —$CF_2H$, —$CF_3$, —CN, —OH, —$NO_2$, —$NH_2$, —NH($C_{1-4}$alkyl), —N($C_{1-4}$alkyl)($C_{1-4}$alkyl), —$SO_2CH_3$, —$SO_2NH_2$, —$SO_2NHCH_3$, —$CO_2$—$C_{1-4}$alkyl, $C_{1-4}$alkyl, $C_{1-4}$alkenyl, $C_{1-4}$alkoxy, $C_{1-4}$S-alkyl, $C_{3-6}$cycloalkyl, optionally substituted $C_{1-6}$heterocycloalkyl, optionally substituted phenyl, or optionally substituted 5 or 6 membered heteroaryl;
$R^d$ is H, optionally substituted alkyl, optionally substituted alkenyl, optionally substituted alkynyl, optionally substituted heteroalkyl, optionally substituted heteroalkenyl, optionally substituted heteroalkynyl, optionally substituted cycloalkyl, optionally substituted cycloalkenyl, optionally substituted heterocyclyl, optionally substituted aryl, optionally substituted heteroaryl, halo, CN, $NO_2$, $NH_2$, NHR', NR'R", OH, OR', SH, SR', C(O)R', $CO_2H$, COOR', $CONH_2$, CONHR', CONR'R", $SO_3H$, $SO_3R'$, $S(O)_2R'$, $S(O)_2NH_2$, $S(O)_2NHR'$, or $S(O)_2NR'R"$;
$R^{d1}$ is zero to four substituents independently selected from optionally substituted alkyl, optionally substituted alkenyl, optionally substituted alkynyl, optionally substituted heteroalkyl, optionally substituted heteroalkenyl, optionally substituted heteroalkynyl, optionally substituted cycloalkyl, optionally substituted cycloalkenyl, optionally substituted heterocyclyl, optionally substituted aryl, optionally substituted heteroaryl, halo, CN, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, or $S(O)_2NR'R"$;

each R' is independently methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;

each R" is independently methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or R' and R" are together with the atom to which they are attached form an optionally substituted, saturated or unsaturated 4-, 5- or 6-membered ring;

$R^x$ is F, Cl, Br, I, or $C_1$-$C_3$ fluoroalkyl;

$R^{x'}$ is independently H, optionally substituted alkyl, optionally substituted alkenyl, optionally substituted alkynyl, optionally substituted heteroalkyl, optionally substituted heteroalkenyl, optionally substituted heteroalkynyl, optionally substituted cycloalkyl, optionally substituted cycloalkenyl, optionally substituted heterocyclyl, optionally substituted aryl, optionally substituted heteroaryl, halo, CN, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, or $S(O)_2NR'R''$; and $B^3$ is $OB^1$, $NB^2_2$, or an amino acid residue or an alkyl ester thereof;

$B^1$ is H, optionally substituted $C_{1-6}$ alkyl or a pharmaceutically acceptable cation; and each $B^2$ is independently H or optionally substituted alkyl.

In some embodiments, W is S. In some embodiments, W is O. In some embodiments, $B^3$ is $OB^1$. In some embodiments, $B^1$ is an alkali earth metal cation or an alkaline earth metal cation. In some embodiments, $B^3$ is $NB^2_2$. The compound disclosed herein wherein $B^3$ is an amino acid residue or lower alkyl ester thereof. In some embodiments, $R^x$ and $R^{x'}$ are independently H, F, methyl, or $CF_3$. In some embodiments, $R^x$ is F and $R^{x1}$ is F. In some embodiments, $R^1$ is H, F, Cl, Br, $CH_2F$, $CF_2H$, $CF_3$, $NH_2$, or $CH_3$. In some embodiments, $R^1$ is Br. In some embodiments, $R^d$ is F, Cl, Br, I, $CF_3$, or CN.

Disclosed herein, in certain embodiments, is a compound having the following structure:

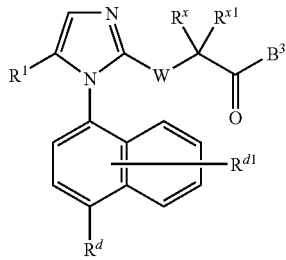

or a metabolite, pharmaceutically acceptable salt, solvate, polymorph, ester, tautomer or prodrug thereof, wherein:

W is O or S;

$R^1$ is halo or haloalkyl;

$R^d$ is H;

$R^{d1}$ is zero to four substituents independently selected from optionally substituted alkyl, optionally substituted alkenyl, optionally substituted alkynyl, optionally substituted heteroalkyl, optionally substituted heteroalkenyl, optionally substituted heteroalkynyl, optionally substituted cycloalkyl, optionally substituted cycloalkenyl, optionally substituted heterocyclyl, optionally substituted aryl, optionally substituted heteroaryl, halo, CN, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, or $S(O)_2NR'R''$;

each R' is independently methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;

each R" is independently methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or R' and R" are together with the atom to which they are attached form an optionally substituted, saturated or unsaturated 4-, 5- or 6-membered ring;

$R^x$ and $R^{x'}$ are each independently H, optionally substituted alkyl, optionally substituted alkenyl, optionally substituted alkynyl, optionally substituted heteroalkyl, optionally substituted heteroalkenyl, optionally substituted heteroalkynyl, optionally substituted cycloalkyl, optionally substituted cycloalkenyl, optionally substituted heterocyclyl, optionally substituted aryl, optionally substituted heteroaryl, halo, CN, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, or $S(O)_2NR'R''$; or $R^x$ and $R^{x'}$ together with the carbon atom to which they are attached, form an optionally substituted non-aromatic 3-7 membered ring, optionally comprising 1 or 2 heteroatoms selected from O, N and S;

$B^3$ is $OB^1$, $NB^2_2$, or an amino acid residue or an alkyl ester thereof;

$B^1$ is H, optionally substituted $C_{1-6}$ alkyl or a pharmaceutically acceptable cation; and each $B^2$ is independently H or optionally substituted alkyl.

In some embodiments, W is S. In some embodiments, W is O. In some embodiments, $B^3$ is $OB^1$. In some embodiments, $B^1$ is an alkali earth metal cation or an alkaline earth metal cation. In some embodiments, $B^3$ is $NB^2_2$. The compound disclosed herein wherein $B^3$ is an amino acid residue or lower alkyl ester thereof. In some embodiments, $R^x$ and $R^{x1}$ are independently H, F, $CF_3$, or methyl. In some embodiments, $R^x$ is methyl and $R^{x1}$ is methyl.

Disclosed herein, in certain embodiments, is a method of treating gout comprising administering to an individual in need thereof a therapeutically effective amount of a compound disclosed herein.

Disclosed herein, in certain embodiments, is a method of treating hyperuricemia in an individual with comprising administering to an individual in need thereof a therapeutically effective amount of a compound disclosed herein.

Disclosed herein, in certain embodiments, is a pharmaceutical composition comprising a therapeutically effective amount of a compound disclosed herein and a pharmaceutically acceptable excipient. In some embodiments, the therapeutically effective amount of the compound is an amount therapeutically effective for treating gout.

Pharmaceutically acceptable salts of any compound described herein include benzathine, chloroprocaine, choline, diethanolamine, ethylenediamine, meglumine, procaine, aluminum, calcium, lithium, magnesium, potassium, sodium, zinc, benethamine, clemizole, diethyliunine, piperazine, tromethamine, barium, and bismuth salts. In some embodiments, $B^1$ of any compound described herein is a benzathine, chloroprocaine, choline, diethanolamine, ethylenediamine, meglumine, procaine, aluminum, calcium, lithium, magnesium, potassium, sodium, zinc, benethamine, clemizole, diethyliunine, piperazine, tromethamine, barium, or bismuth cation.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
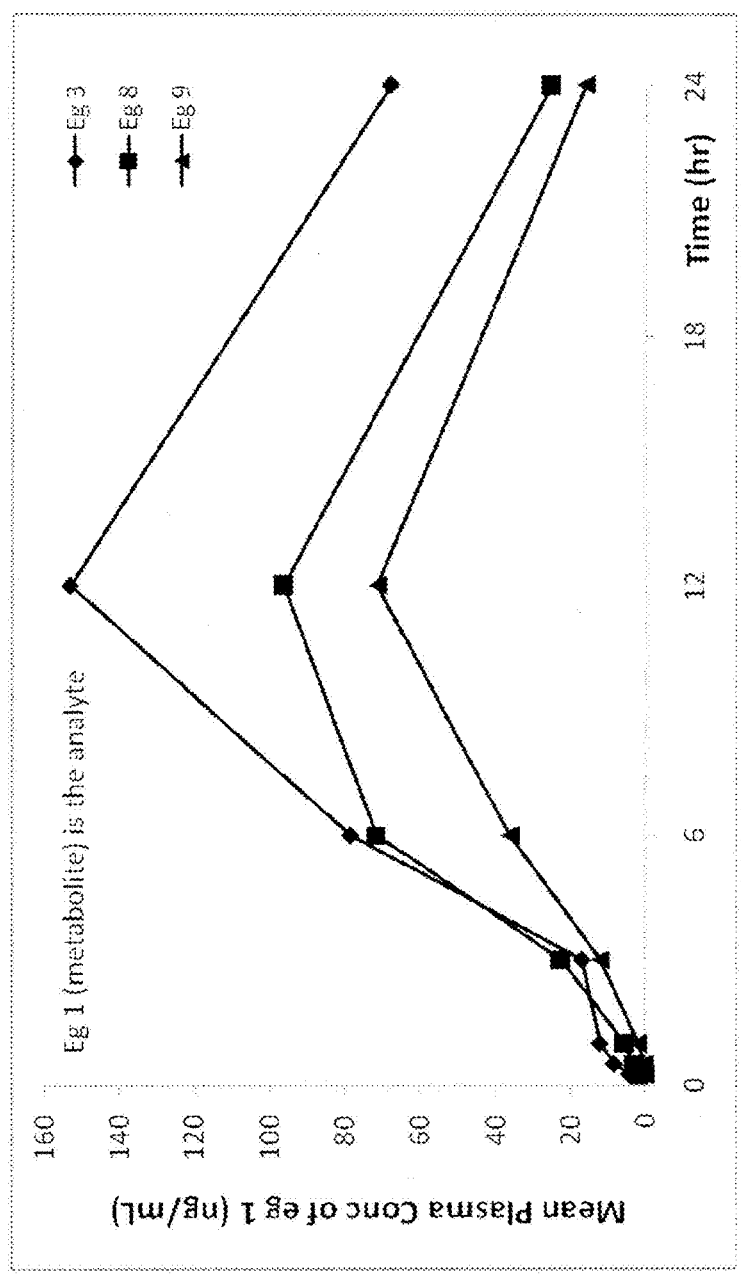
FIG. 1 shows a graph of mean plasma concentration of 2-(5-Bromo-1-(4-cyanonaphthalen-1-yl)-1H-imidazol-2-ylthio)acetic acid (Eg. 1) at various time points (0.25, 0.5, 1, 3, 6, 12 and 24 hr) post dosing, as released by in vivo metabolism of 2-(2-(5-Bromo-1-(4-cyanonaphthalen-1-yl)-1H-imidazol-2-ylthio)acetamido)acetic acid (Eg. 3), (2S)-2-(2-(5-bromo-1-(4-cyanonaphthalen-1-yl)-1H-imidazol-2-ylthio)acetamido)propanoic acid (Eg. 8) and (2S)-2-(2-(5-bromo-1-(4-cyanonaphthalen-1-yl)-1H-imidazol-2-ylthio)acetamido)-3-methylbutanoic acid (Eg. 9), after PO dosing to male rats (3 mg/kg).

The novel features of the invention are set forth with particularity in the appended claims. A better understanding of the features and advantages of the present invention will be obtained by reference to the following detailed description that sets forth illustrative embodiments, in which the principles of the invention are utilized.

While preferred embodiments of the present invention have been shown and described herein, such embodiments are provided by way of example only. Various alternatives to the embodiments of the invention described herein may be employed in practicing the invention. It is intended that the following claims define the scope of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference for the purposes stated herein.

Methods: Aberrant Uric Acid Levels

The present invention also provides methods useful for diseases or diseases related to aberrant uric acid levels. The method includes administering an effective amount of a composition as described herein to a subject with aberrant levels of uric acid so as to restore uric acid levels to acceptable levels or non-aberrant levels. The present invention also provides methods useful for decreasing uric acid levels in one or more tissues or organs of a subject in need of decreased uric acid levels, comprising administering to the subject a uric acid level decreasing amount of a composition as described herein. The present invention also provides methods useful for reducing uric acid production, increasing uric acid excretion or both in a subject, comprising administering to the subject an effective amount of a composition as described herein. The present invention also provides methods useful for treating or preventing hyperuricemia in a subject comprising administering to the subject an effective amount of a composition as described herein. The present invention also provides methods useful for treating a subject suffering from a condition characterized by abnormal tissue or organ levels of uric acid comprising administering to the subject an effective amount of a composition as described herein The present invention also provides methods useful for treating a subject suffering from gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis, comprising administering to the subject an effective amount of a composition as described herein. The present invention also provides methods useful for preventing a condition characterized by abnormal tissue levels of uric acid in a subject at increased risk of developing the condition, comprising administering to the subject an effective amount of a composition as described herein. The present invention also provides methods useful for treating gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosisin a subject comprising administering to the subject an effective amount of a composition as described herein. The present invention also provides methods useful for treating gout in a subject comprising administering to the subject an effective amount of a composition as described herein. The present invention also provides methods useful for preventing the formation or reducing the size of tophi/tophus in a subject, comprising administering to the subject an effective amount of a composition as described herein.

Certain Chemical Terminology

Unless defined otherwise, all technical and scientific terms used herein have the same meaning as is commonly understood by one of skill in the art to which the claimed subject matter belongs. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

Definition of standard chemistry terms are found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, are employed.

Where substituent groups are specified by their conventional chemical formulas, written from left to right, they equally encompass the chemically identical substituents that would result from writing the structure from right to left. As a non-limiting example, —$CH_2O$— is equivalent to —$OCH_2$—.

Unless otherwise noted, the use of general chemical terms, such as though not limited to "alkyl," "amine," "aryl," are equivalent to their optionally substituted forms. For example, "alkyl," as used herein, includes optionally substituted alkyl.

In some embodiments, the compounds presented herein possess one or more stereocenters. In some embodiments, each center exists in the R or S configuration, or combinations thereof. In some embodiments, the compounds presented herein possess one or more double bonds. In some embodiments, each double bond exists in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Techniques for inverting or leaving unchanged a particular stereocenter, and those for resolving mixtures of stereoisomers are found, for example, Furniss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, Acc. Chem. Res. 1990, 23, 128.

The terms "moiety", "chemical moiety", "group" and "chemical group", as used herein refer to a specific segment or functional group of a molecule. Chemical moieties are often recognized chemical entities embedded in or appended to a molecule.

The term "reactant," as used herein, refers to a nucleophile or electrophile used to create covalent linkages.

The term "bond" or "single bond" refers to a chemical bond between two atoms, or two moieties when the atoms joined by the bond are considered to be part of larger substructure.

The term "optional" or "optionally" means that the subsequently described event or circumstance may or may not occur, and that the description includes instances where the event or circumstance occurs and instances in which it does not. For example, "optionally substituted alkyl" means either "alkyl" or "substituted alkyl". Further, an optionally substituted group means un-substituted (e.g., —$CH_2CH_3$), fully substituted (e.g., —$CF_2CF_3$), mono-substituted (e.g., —$CH_2CH_2F$) or substituted at a level anywhere in-between fully substituted and mono-substituted (e.g., —$CH_2CHF_2$, —$CH_2CF_3$, —$CF_2CH_3$, —$CFHCHF_2$, etc). With respect to any group containing one or more substituents, such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like). "Substituted" groups are optionally substituted with, by way of non-limiting example, alkyl, alkenyl, alkynyl, heteroalkyl, heteroalkenyl, heteroalkynyl, cycloalkyl, cycloalkenyl, heterocyclyl, aryl, alkylheteroaryl, alkylcycloalkyl, alkylcycloalkenyl, alkylheterocyclyl, alkylaryl, cycloalkylalkyl, cycloalkenylalkyl, heterocyclylalkyl, arylalkyl, heteroarylalkyl, heteroarylalkyl, heteroalkylheterocyclyl, heteroalkylaryl, cycloheteroalkylheteroalkyl, cycloalkenylheteroalkyl, heterocyclylheteroalkyl, arylheteroalkyl, heteroarylheteroalkyl, heteroarylheteroalkyl, halo, CN, $No_2$, $NR_2$, OR, SR, C(O)R, $CO_2R$, $CONR_2$, $SO_3R$, $S(O)_2R$, $S(O)_2NR_2$, or the like, wherein each R is independently alkyl, alkenyl, alkynyl, heteroalkyl, heteroalkenyl, heteroalkynyl, cycloalkyl, cycloalkenyl, heterocyclyl, aryl, heteroaryl, or the like, or wherein two R groups on the same atom, taken together, form a 3-10 membered heterocyclic ring.

As used herein, $C_1$-$C_x$ includes $C_1$-$C_2$, $C_1$-$C_3$ . . . $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The term "lower" as used herein in combination with terms such as alkyl, alkenyl or alkynyl, (i.e. "lower alkyl", "lower alkenyl" or "lower alkynyl") refers to an optionally substituted straight-chain, or optionally substituted branched-chain saturated hydrocarbon monoradical having from one to about six carbon atoms, more preferably one to three carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl.

The term "hydrocarbon" as used herein, alone or in combination, refers to a compound or chemical group containing only carbon and hydrogen atoms.

The terms "heteroatom" or "hetero" as used herein, alone or in combination, refer to an atom other than carbon or hydrogen. Heteroatoms include, but are not limited to, oxygen, nitrogen, sulfur, phosphorous, silicon, selenium and tin, but are not limited to these atoms. Where two or more heteroatoms are present, in some embodiments, the two or more heteroatoms are the same as each another. Where two or more heteroatoms are present, in some embodiments, the two or more heteroatoms are different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that: in some embodiments, the alkyl group consists of 1 carbon atom; in some embodiments, 2 carbon atoms; in some embodiments, 3 carbon atoms; in some embodiments, 4 carbon atoms; in some embodiments, 5 carbon atoms; in some embodiments, 6 carbon atoms. The present definition also covers the occurrence of the term "alkyl" where no numerical range is designated. In certain instances, "alkyl" groups described herein include linear and branched alkyl groups, saturated and unsaturated alkyl groups, and cyclic and acyclic alkyl groups.

The term "alkylene" as used herein, alone or in combination, refers to a diradical derived from the above-defined monoradical, alkyl. Examples include, but are not limited to methylene (—$CH_2$—), ethylene (—$CH_2CH_2$—), propylene (—$CH_2CH_2CH_2$—), isopropylene (—$CH(CH_3)CH_2$—) and the like.

The term "alkenyl" as used herein, alone or in combination, refers to an optionally substituted straight-chain, or optionally substituted branched-chain hydrocarbon monoradical having one or more carbon-carbon double-bonds and having from two to about ten carbon atoms, more preferably two to about six carbon atoms. The group includes either the cis or trans conformation about the double bond(s), and should be understood to include both isomers. Examples include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" or "$C_{2-6}$ alkenyl", means that: in some embodiments, the alkenyl group consists of 2 carbon atoms; in some embodiments, 3 carbon atoms; in some embodiments, 4 carbon atoms; in some embodiments, 5 carbon atoms; in some embodiments, 6 carbon atoms. The present definition also covers the occurrence of the term "alkenyl" where no numerical range is designated.

The term "alkenylene" as used herein, alone or in combination, refers to a diradical derived from the above-defined monoradical alkenyl. Examples include, but are not limited to ethenylene (—CH=CH—), the propenylene isomers (e.g., —$CH_2$CH=CH— and —C($CH_3$)=CH—) and the like.

The term "alkynyl" as used herein, alone or in combination, refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$ alkynyl", means: in some embodiments, the alkynyl group consists of 2 carbon atoms; in some embodiments, 3 carbon atoms; in some embodiments, 4 carbon atoms; in some embodiments, 5 carbon atoms; in some embodiments, 6 carbon atoms. The present definition also covers the occurrence of the term "alkynyl" where no numerical range is designated.

The term "alkynylene" as used herein, alone or in combination, refers to a diradical derived from the above-defined monoradical, alkynyl. Examples include, but are not limited to ethynylene (—C≡C—), propargylene (—$CH_2$—C≡C—) and the like.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The terms "heteroalkyl", "heteroalkenyl" and "heteroalkynyl" as used herein, alone or in combination, refer to optionally substituted alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof), or heteroatomic group such as though not limited to —O—O—, —S—S—, —O—S—, —S—O—, =N—N=, —N=N—, —N=N—NH—, —P(O)$_2$—, —O—P(O)$_2$—, —P(O)$_2$—O—, —S(O)—, —S(O)$_2$—, —Sn$H_2$— and the like.

The terms "haloalkyl", "haloalkenyl" and "haloalkynyl" as used herein, alone or in combination, refer to optionally substituted alkyl, alkenyl and alkynyl groups respectively, as defined above, in which one or more hydrogen atoms is replaced by fluorine, chlorine, bromine or iodine atoms, or combinations thereof. In some embodiments, two or more hydrogen atoms are replaced with halogen atoms that are the same as each another (e.g. difluoromethyl); in other embodiments, two or more hydrogen atoms are replaced with halogen atoms that are not all the same as each other (e.g. 1-chloro-1-fluoro-1-iodoethyl). Non-limiting examples of haloalkyl groups are fluoromethyl and bromoethyl. A non-limiting example of a haloalkenyl group is bromoethenyl. A non-limiting example of a haloalkynyl group is chloroethynyl.

The term "perhalo" as used herein, alone or in combination, refers to groups in which all of the hydrogen atoms are replaced by fluorines, chlorines, bromines, iodines, or combinations thereof. Thus, as a non-limiting example, the term "perhaloalkyl" refers to an alkyl group, as defined herein, in which all of the H atoms have been replaced by fluorines, chlorines, bromines or iodines, or combinations thereof. A non-limiting example of a perhaloalkyl group is bromo,chloro,fluoromethyl. A non-limiting example of a perhaloalkenyl group is trichloroethenyl. A non-limiting example of a perhaloalkynyl group is tribromopropynyl.

The term "carbon chain" as used herein, alone or in combination, refers to any alkyl, alkenyl, alkynyl, heteroalkyl, heteroalkenyl or heteroalkynyl group, which is linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. In some embodiments, rings are optionally substituted. In some embodiments, rings form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "fused" as used herein, alone or in combination, refers to cyclic structures in which two or more rings share one or more bonds.

The term "cycloalkyl" as used herein, alone or in combination, refers to an optionally substituted, saturated, hydrocarbon monoradical ring, containing from three to about fifteen ring carbon atoms or from three to about ten ring carbon atoms. In some embodiments, the compound includes additional, non-ring carbon atoms as substituents (e.g. methylcyclopropyl). Whenever it appears herein, a numerical range such as "$C_3$-$C_6$ cycloalkyl" or "$C_{3-6}$ cycloalkyl", means: in some embodiments, the cycloalkyl group consists of 3 carbon atoms (e.g., cyclopropyl); in some embodiments, 4 carbon atoms (e.g., cyclobutyl); in some embodiments, 5 carbon atoms (e.g., cyclopentyl); in some embodiments, 6 carbon atoms (e.g., cyclohepty). The present definition also covers the occurrence of the term "cycloalkyl" where no numerical range is designated. Further, the term includes fused, non-fused, bridged and spiro radicals. A fused cycloalkyl contains from two to four fused rings where the ring of attachment is a cycloalkyl ring, and the other individual rings are alicyclic, heterocyclic, aromatic, heteroaromatic or any combination thereof. Examples include, but are not limited to cyclopropyl, cyclopentyl, cyclohexyl, decalinyl, and bicyclo[2.2.1]heptyl and adamantyl ring systems. Illustrative examples include, but are not limited to the following moieties:

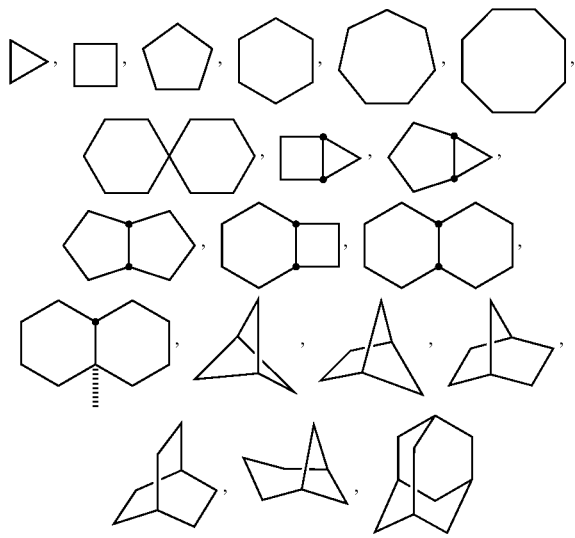

and the like.

The term "cycloalkenyl" as used herein, alone or in combination, refers to an optionally substituted hydrocarbon non-aromatic, monoradical ring, having one or more carbon-carbon double-bonds and from three to about twenty ring carbon atoms, three to about twelve ring carbon atoms, or from three to about ten ring carbon atoms. The term includes fused, non-fused, bridged and spiro radicals. A fused cycloalkenyl contains from two to four fused rings where the ring of attachment is a cycloalkenyl ring, and the other individual rings are alicyclic, heterocyclic, aromatic, heteroaromatic or any combination thereof. In some embodiments, fused ring systems are fused across a bond that is a carbon-carbon single bond or a carbon-carbon double bond. Examples of cycloalkenyls include, but are not limited to cyclohexenyl, cyclopentadienyl and bicyclo[2.2.1]hept-2-ene ring systems. Illustrative examples include, but are not limited to the following moieties:

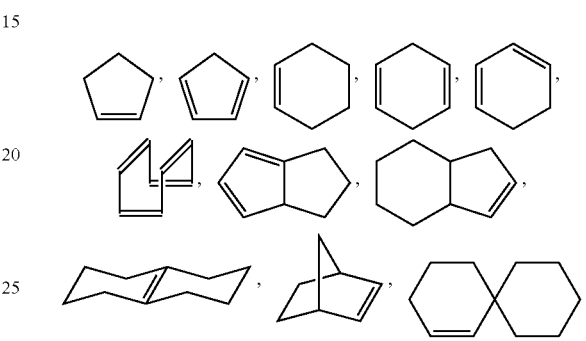

and the like.

The terms "alicyclyl" or "alicyclic" as used herein, alone or in combination, refer to an optionally substituted, saturated, partially unsaturated, or fully unsaturated nonaromatic hydrocarbon ring systems containing from three to about twenty ring carbon atoms, three to about twelve ring carbon atoms, or from three to about ten ring carbon atoms. Thus, the terms collectively include cycloalkyl and cycloalkenyl groups.

The terms "non-aromatic heterocyclyl" and "heteroalicyclyl" as used herein, alone or in combination, refer to optionally substituted, saturated, partially unsaturated, or fully unsaturated nonaromatic ring monoradicals containing from three to about twenty ring atoms, where one or more of the ring atoms are an atom other than carbon, independently selected from among oxygen, nitrogen, sulfur, phosphorous, silicon, selenium and tin but are not limited to these atoms. Where two or more heteroatoms are present in the ring, in some embodiments, the two or more heteroatoms are the same as each another; in some embodiments, some or all of the two or more heteroatoms are different from the others. The terms include fused, non-fused, bridged and spiro radicals. A fused non-aromatic heterocyclic radical contains from two to four fused rings where the attaching ring is a non-aromatic heterocycle, and the other individual rings are alicyclic, heterocyclic, aromatic, heteroaromatic or any combination thereof. Fused ring systems are fused across a single bond or a double bond, as well as across bonds that are carbon-carbon, carbon-hetero atom or hetero atom-hetero atom. The terms also include radicals having from three to about twelve skeletal ring atoms, as well as those having from three to about ten skeletal ring atoms. In some embodiments, attachment of a non-aromatic heterocyclic subunit to its parent molecule is via a heteroatom; in some embodiments, via a carbon atom. In some embodiments, additional substitution is via a heteroatom or a carbon atom. As a non-limiting example, an imidazolidine non-aromatic heterocycle is attached to a parent molecule via either of its N atoms (imidazolidin-1-yl or imidazolidin-3-yl) or any of its carbon atoms (imidazolidin-2-yl, imidazolidin-4-yl or imidazolidin-5-yl). In certain embodiments, non-aromatic heterocycles contain one or more carbonyl or thiocarbonyl groups such as, for example, oxo- and thio-containing groups. Examples include, but are not limited to pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Illustrative examples of heterocycloalkyl groups, also referred to as non-aromatic heterocycles, include:

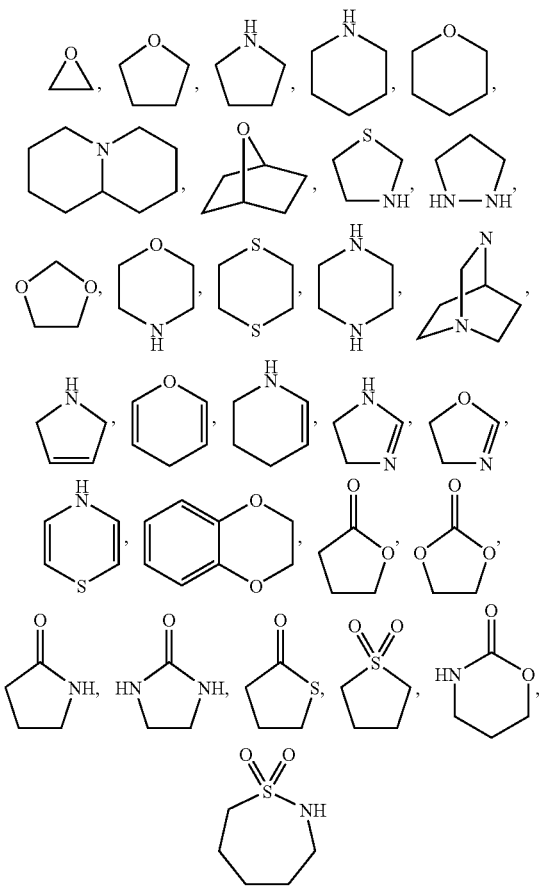

and the like. The terms also include all ring forms of the carbohydrates, including but not limited to the monosaccharides, the disaccharides and the oligosaccharides.

The term "aromatic" as used herein, refers to a planar, cyclic or polycyclic, ring moiety having a delocalized π-electron system containing 4n+2 π electrons, where n is an integer. In some embodiments, aromatic rings are formed by five atoms; in some embodiments, six atoms; in some embodiments, seven atoms; in some embodiments, eight atoms; in some embodiments, nine atoms; in some embodiments, more than nine atoms. Aromatics are optionally substituted and are monocyclic or fused-ring polycyclic. The term aromatic encompasses both all carbon containing rings (e.g., phenyl) and those rings containing one or more heteroatoms (e.g., pyridine).

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings, where the ring of attachment is an aryl ring, and the other individual rings are alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "arylene" as used herein, alone or in combination, refers to a diradical derived from the above-defined monoradical, aryl. Examples include, but are not limited to 1, 2-phenylene, 1,3-phenylene, 1,4-phenylene, 1,2-naphthylene and the like.

The term "heteroaryl" as used herein, alone or in combination, refers to optionally substituted aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of the group does not contain two adjacent O or S atoms. Where two or more heteroatoms are present in the ring, in some embodiments, the two or more heteroatoms are the same as each another; in some embodiments, some or all of the two or more heteroatoms are be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. In some embodiments, bonding to a heteroaryl group is via a carbon atom; in some embodiments, via a heteroatom. Thus, as a non-limiting example, an imidiazole group is attached to a parent molecule via any of its carbon atoms (imidazol-2-yl, imidazol-4-yl or imidazol-5-yl), or its nitrogen atoms (imidazol-1-yl or imidazol-3-yl). Further, in some embodiments, a heteroaryl group is substituted via any or all of its carbon atoms, and/or any or all of its heteroatoms. A fused heteroaryl radical contains from two to four fused rings, where the ring of attachment is a heteroaromatic ring. In some embodiments, the other individual rings are alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide. Illustrative examples of heteroaryl groups include the following moieties:

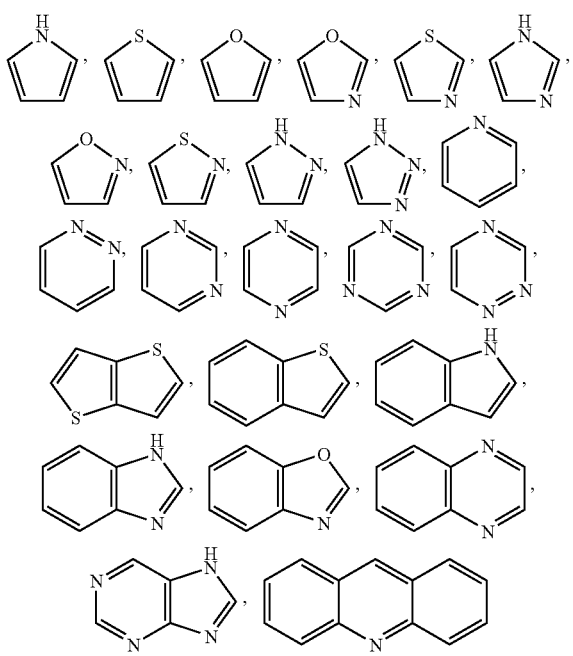

and the like.

The term "heteroarylene" as used herein, alone or in combination, refers to a diradical derived from the above-defined monoradical heteroaryl. Examples include, but are not limited to pyridinyl and pyrimidinyl.

The term "heterocyclyl" as used herein, alone or in combination, refers collectively to heteroalicyclyl and heteroaryl groups. Herein, whenever the number of carbon atoms in a heterocycle is indicated (e.g., $C_1$-$C_6$ heterocycle), at least one non-carbon atom (the heteroatom) must be present in the ring. Designations such as "$C_1$-$C_6$ heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, in some embodiments, those two or more heteroatoms are the same; in some embodiments, they are different from one another. In some embodiments, heterocycles are substituted. Non-aromatic heterocyclic groups include groups having only three atoms in the ring, while aromatic heterocyclic groups must have at least five atoms in the ring. In some embodiments, bonding (i.e. attachment to a parent molecule or further substitution) to a heterocycle is via a heteroatom; in some embodiments, via a carbon atom.

The term "carbocyclyl" as used herein, alone or in combination, refers collectively to alicyclyl and aryl groups; i.e. all carbon, covalently closed ring structures. In some embodiments, the carbocyclyl is saturated, partially unsaturated, fully unsaturated or aromatic. In some embodiments, carbocyclic rings are formed by three, carbon atoms; in some embodiments, four carbon atoms; in some embodiments, five carbon atoms; in some embodiments, six carbon atoms; in some embodiment, seven carbon atoms; in some embodiments, eight carbon atoms; in some embodiments, nine carbon atoms; in some embodiments, more than nine carbon atoms. Carbocycles are optionally substituted. The term distinguishes carbocyclic from heterocyclic rings in which the ring backbone contains at least one atom which is different from carbon.

The terms "halogen", "halo" or "halide" as used herein, alone or in combination refer to fluoro, chloro, bromo and iodo.

The term "hydroxy" as used herein, alone or in combination, refers to the monoradical —OH.

The term "cyano" as used herein, alone or in combination, refers to the monoradical —CN.

The term "cyanomethyl" as used herein, alone or in combination, refers to the monoradical —$CH_2CN$.

The term "nitro" as used herein, alone or in combination, refers to the monoradical —$NO_2$.

The term "oxy" as used herein, alone or in combination, refers to the diradical —O—.

The term "oxo" as used herein, alone or in combination, refers to the diradical =O.

The term "carbonyl" as used herein, alone or in combination, refers to the diradical —C(=O)—, which is also written as —C(O)—.

The terms "carboxy" or "carboxyl" as used herein, alone or in combination, refer to the moiety —C(O)OH, which is alternatively written as —COOH.

The term "alkoxy" as used herein, alone or in combination, refers to an alkyl ether radical, —O-alkyl, including the groups —O-aliphatic and —O-carbocyclyl, wherein the alkyl, aliphatic and carbocyclyl groups are optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tert-butoxy and the like.

The term "sulfinyl" as used herein, alone or in combination, refers to the diradical —S(=O)—.

The term "sulfonyl" as used herein, alone or in combination, refers to the diradical —S(=O)$_2$—.

The terms "sulfonamide", "sulfonamido" and "sulfonamidyl" as used herein, alone or in combination, refer to the diradical groups —S(=O)$_2$—NH— and —NH—S(=O)$_2$—.

The terms "sulfamide", "sulfamido" and "sulfamidyl" as used herein, alone or in combination, refer to the diradical group —NH—S(=O)$_2$—NH—.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

Certain Pharmaceutical Terminology

The term "subject", "patient" or "individual" as used herein in reference to individuals suffering from a disease, and encompasses mammals and non-mammals. Mammals are any member of the Mammalian class, including but not limited to humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the subject is a mammal. In preferred embodiments, the subject is a human. None of the terms should be construed as requiring the supervision od a medical profesisonal (e.g., a physician, nurse, physician's assistant, orderly, hospice worker, etc.).

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disease being treated. Also, a therapeutic benefit is achieved with the eradication or amelioration of one or more of the physiological symptoms associated with the underlying disease such that an improvement is observed in the patient, notwithstanding that, in some embodiments, the patient is still afflicted with the underlying disease. For prophylactic benefit, the compositions are administered to a patient at risk of developing a particular disease, or to a patient reporting one or more of the physiological symptoms of a disease, even if a diagnosis of the disease has not been made.

The terms "administer," "administering", "administration," and the like, as used herein, refer to the methods that are used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. In preferred embodiments, the compounds and compositions described herein are administered orally.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. In some embodiments, the result is a reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. In some embodiments, the "effective" amount differs from one individual to another. In some embodiments, an appropriate "effective" amount is determined using any suitable technique (e.g., a dose escalation study).

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of a compound disclosed herein, and is relatively nontoxic (i.e., when the material is administered to an individual it does not cause undesirable biological effects nor does it interact in a deleterious manner with any of the components of the composition in which it is contained).

The term "prodrug" as used herein, refers to a drug precursor that, following administration to a subject and subsequent absorption, is converted to an active, or a more active species via some process, such as conversion by a metabolic pathway. Thus, the term encompasses any derivative of a compound, which, upon administration to a recipient, is capable of providing, either directly or indirectly, a compound of this invention or a pharmaceutically active metabolite or residue thereof. Some prodrugs have a chemical group present on the prodrug that renders it less active and/or confers solubility or some other property to the drug. Once the chemical group has been cleaved and/or modified from the prodrug the active drug is generated. Particularly favored derivatives or prodrugs are those that increase the bioavailability of the compounds of this invention when such compounds are administered to a patient (e.g. by allowing an orally administered compound to be more readily absorbed into the blood) or which enhance delivery of the parent compound to a biological compartment (e.g. the brain or lymphatic system).

The term "pharmaceutically acceptable salt" as used herein, refers to salts that retain the biological effectiveness of the free acids and bases of the specified compound and that are not biologically or otherwise undesirable. In some embodiments, a compound disclosed herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free base form with a suitable organic or inorganic acid, and isolating the salt thus formed.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, excipients and the like.

The term "carrier" as used herein, refers to relatively nontoxic chemical compounds or agents that facilitate the incorporation of a compound into cells or tissues.

The terms "pharmaceutical combination", "administering an additional therapy", "administering an additional therapeutic agent" and the like, as used herein, refer to a pharmaceutical therapy resulting from the mixing or combining of more than one active ingredient and includes both fixed and non-fixed combinations of a compound or composition disclosed herein. The term "fixed combination" means that at least one of a compound disclosed herein, and at least one co-agent, are both administered to a patient simultaneously in the form of a single entity or dosage. The term "non-fixed combination" means that at least one of a compound disclosed herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments, a compound disclosed herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent(s) are administered in a single composition. In some embodiments, compounds of the invention and the other agent(s) are admixed in the composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. In some embodiments, enzymes produce structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism is found in *The Pharmacological Basis of Therapeutics*, 9th Edition, McGraw-Hill (1996).

Compounds

Disclosed herein, in certain embodiments, is a compound of formula (I):

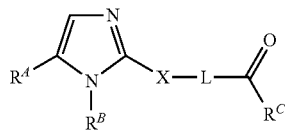

wherein
X is O or S;
L is —$(CR^xR^{x'})_x$—$(CR^yR^{y'})_y$—$(CR^zR^{z'})_z$—; wherein
x is 0 or 1;
y is 0 or 1;
z is 0 or 1;
$R^x$, $R^{x'}$, $R^y$, $R^{y'}$, $R^z$ and $R^{z'}$ are each independently H, F, Cl, Br, I or optionally substituted $C_{1-3}$ alkyl; or
$R^x$ and $R^{x'}$, or $R^y$ and $R^{y'}$, or $R^z$ and $R^{z'}$, or $R^x$ and $R^y$, or $R^y$ and $R^z$, or $R^x$ and $R^z$ together with the carbon atoms to which they are attached, form an optionally substituted, aromatic or non-aromatic, 3-7 membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S;
$R^A$ is H, Cl, Br, I, $NH_2$, methyl, ethyl, n-propyl, i-propyl, optionally substituted methyl, optionally substituted ethyl, optionally substituted n-propyl, optionally substituted i-propyl, $CF_3$, $CHF_2$ or $CH_2F$;

$R^B$ is

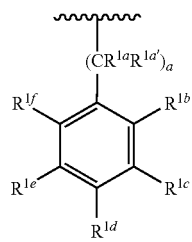

a is 0, 1 or 2;
$R^{1a}$ is H or optionally substituted $C_{1-3}$ alkyl;
$R^{1a'}$ is H or optionally substituted $C_{1-3}$ alkyl; or
$R^{1a}$ and $R^{1a'}$ together with the carbon atom to which they are attached form an optionally substituted 3-, 4-, 5- or 6-membered ring, optionally comprising 1 or 2 heteroatoms selected from O, N and S;
$R^{1b}$, $R^{1c}$, $R^{1d}$, $R^{1e}$ and $R^{1f}$ are each independently H, F, Cl, Br, I, $CF_3$, CN, alkyl, cycloalkyl, cyclopropylmethyl, $NH_2$, NHR', NR'R", OH, OR', SH, SR', C(O)R', $CO_2H$, COOR', $CONH_2$, CONHR', CONR'R"$SO_3H$, $S(O)_2R'$, $S(O)_2NH_2$, $S(O)_2NHR'$, $S(O)_2NR'R"$ aryl, heterocyclyl or heteroaryl; or
$R^{1b}$ and $R^{1c}$, or $R^{1c}$ and $R^{1d}$, or $R^{1d}$ and $R^{1e}$, or $R^{1e}$ and $R^{1f}$ together with the two carbon atoms to which they are attached, form an optionally substituted, aromatic or non-aromatic, 5-, 6- or 7-membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S; and wherein the optional substituents are each independently H, F, Cl, Br, I, $CF_3$, CN, alkyl, cycloalkyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl or heteroaryl;
wherein
R' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;
R" is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or
R' and R" together with the nitrogen atom to which they are attached form an optionally substituted, saturated or unsaturated 4-, 5- or 6-membered heterocyclic ring;
$R^C$ is an amino acid, a dipeptide, a tripeptide, a tetrapeptide, a polypeptide, a lipid, a phospholipid, a glycoside, a nucleoside, a nucleotide, an oligonucleotide, polyethylene glycol, $OR^{2a}$, $SR^{3a}$, $NR^{4a}R^{4b}$, or a combination thereof, wherein;
$R^{2a}$ is substituted $C_1$-$C_4$ alkyl, optionally substituted $C_5$-$C_{10}$ alkyl, optionally substituted heteroalkyl, optionally substituted cycloalkyl, optionally substituted heterocycloalkyl, optionally substituted aryl or optionally substituted heteroaryl; or
$R^{2a}$ is a pharmaceutically acceptable cation; or
$R^{2a}$ is —$[C(R^{5a})(R^{5b})]_mR^{5c}$;
$R^{3a}$ is hydrogen, optionally substituted $C_1$-$C_{10}$ alkyl, optionally substituted heteroalkyl, optionally substituted cycloalkyl, optionally substituted heterocycloalkyl, optionally substituted aryl, optionally substituted heteroaryl; or $R^{3a}$ is —$[C(R^{5a})(R^{5b})]_n R^{5c}$;

$R^{4a}$ is hydrogen, optionally substituted alkyl, optionally substituted heteroalkyl, optionally substituted cycloalkyl or optionally substituted heterocycloalkyl; and $R^{4b}$ is hydrogen, optionally substituted alkyl, optionally substituted heteroalkyl, optionally substituted cycloalkyl or optionally substituted heterocycloalkyl; or $R^{4b}$ is —$[C(R^{5a})(R^{5b})]_n R^{5c}$, wherein $R^{5a}$ and $R^{5b}$ are each independently hydrogen, halogen, cyano, nitro, an amino acid, a dipeptide, a tripeptide, a tetrapeptide, a polypeptide, a lipid, a phospholipid, a glycoside, a nucleoside, a nucleotide, an oligonucleotide, polyethylene glycol, -L-OH, -L-SH, -L-NH$_2$, substituted -L-C$_1$-C$_3$ alkyl, optionally substituted -L-C$_4$-C$_9$ alkyl, optionally substituted L-C$_2$-C$_5$ alkenyl, optionally substituted L-C$_2$-C$_5$ alkynyl, optionally substituted L-C$_2$-C$_5$ heteroalkyl, optionally substituted -L-C$_3$-C$_7$ cycloalkyl, optionally substituted L-C$_3$-C$_7$ cycloalkenyl, optionally substituted -L-C$_3$-C$_7$ heterocycloalkyl, optionally substituted -L-C$_1$-C$_4$ haloalkyl, optionally substituted -L-C$_1$-C$_4$ alkoxy, optionally substituted -L-C$_1$-C$_4$ alkylamine, optionally substituted -L-di-(C$_1$-C$_4$)alkylamine, optionally substituted -L-C$_5$-C$_7$ aryl, optionally substituted -L-C$_5$-C$_7$ heteroaryl,

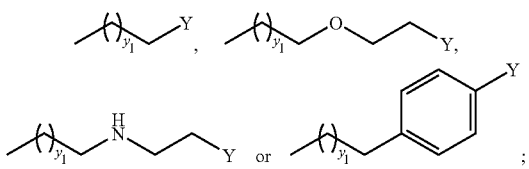

$R^{5c}$ is hydrogen, halogen, cyano, nitro, an amino acid, a dipeptide, a tripeptide, a tetrapeptide, a polypeptide, a lipid, a phospholipid, a glycoside, a nucleoside, a nucleotide, an oligonucleotide, polyethylene glycol, -L-OH, -L-SH, -L-NH$_2$, substituted -L-C$_1$-C$_3$ alkyl, optionally substituted -L-C$_4$-C$_9$ alkyl, optionally substituted L-C$_2$-C$_5$ alkenyl, optionally substituted L-C$_2$-C$_5$ alkynyl, optionally substituted L-C$_2$-C$_5$ heteroalkyl, optionally substituted -L-C$_3$-C$_7$ cycloalkyl, optionally substituted L-C$_3$-C$_7$ cycloalkenyl, optionally substituted -L-C$_3$-C$_7$ heterocycloalkyl, optionally substituted -L-C$_1$-C$_4$ haloalkyl, optionally substituted -L-C$_1$-C$_4$ alkoxy, optionally substituted -L-C$_1$-C$_4$alkylamine, optionally substituted -L-di(C$_1$-C$_4$)alkylamine, optionally substituted -L-C$_5$-C$_7$ aryl, optionally substituted -L-C$_5$-C$_7$ heteroaryl,

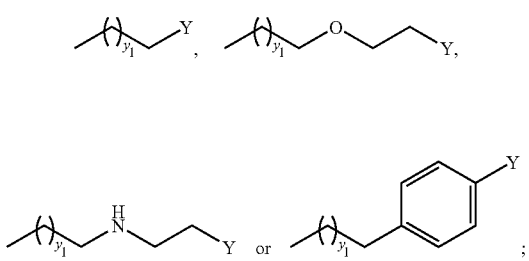

wherein L is a bond, —C(O)—, —S(O), or —S(O)$_2$;

$y_1$ is 0, 1, 2 or 3;

Y is OH, OMe, COOH, SO$_3$H, OSO$_3$H, OS(O)$_2$NH$_2$, P(O)(OH)$_2$, OP(O)(OH)$_2$, OP(O)(OH)(O—C$_{1-4}$ alkyl) or NY$^2$Y$^3$Y$^4$; wherein Y$^2$ and Y$^3$ are each independently hydrogen or methyl; or Y$^2$ and Y$^3$ are taken together with the nitrogen to which they are attached form a five or six membered ring that optionally contains an oxygen atom or a second nitrogen atom; and Y$^4$ is an electron pair or an oxygen atom;

m is 1, 2, 3, 4;

n is 0, 1, 2, 3, 4, 5, 6, 7, 8, 9 or 10;

or a metabolite, pharmaceutically acceptable salt, solvate, ester, tautomer or prodrug thereof In some embodiments, X is O. In some embodiments, X is S.

In some embodiments, x is 1, y is 0 and z is 0.

In some embodiments, X is S, x is 1, y is 0 and z is 0.

In some embodiments, $R^x$ and $R^{x'}$ are H, F or methyl. In some embodiments, $R^x$ and $R^{x'}$ are both H. In some embodiments, $R^x$ and $R^{x'}$ are both F. In some embodiments, $R^x$ and $R^{x'}$ are both methyl.

In some embodiments, x is 1, y is 0, z is 0, $R^x$ is H and $R^{x'}$ is H.

In some embodiments, x is 1, y is 0, z is 0, $R^x$ is F and $R^{x'}$ is F.

In some embodiments, x is 1, y is 0, z is 0, $R^x$ is methyl and $R^{x'}$ is methyl.

In some embodiments, X is S, x is 1, y is 0, z is 0 and $R^x$ and $R^{x'}$ are either both H or both F.

In some embodiments, $R^x$ and $R^{x'}$, or $R^y$ and $R^{y'}$, or $R^z$ and $R^{z'}$, or $R^x$ and $R^y$, or $R^y$ and $R^z$, or $R^x$ and $R^z$ together with the carbon atoms to which they are attached, form an optionally substituted, aromatic or non-aromatic, 3-7 membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S. In some embodiments, $R^x$ and $R^{x'}$, or $R^y$ and $R^{y'}$, or $R^z$ and $R^{z'}$, or $R^x$ and $R^y$, or $R^y$ and $R^z$, or $R^x$ and $R^z$ together with the carbon atoms to which they are attached, form an optionally substituted, aromatic or non-aromatic, 3-7 membered ring. In some embodiments, $R^x$ and $R^{x'}$ together with the carbon atoms to which they are attached, form an optionally substituted, aromatic or non-aromatic, 3-7 membered ring. In some embodiments, $R^x$ and $R^y$ together with the carbon atoms to which they are attached, form an optionally substituted, aromatic or non-aromatic, 3-7 membered ring.

In some embodiments, $R^4$ is H. In some embodiments, $R^4$ is Br.

In some embodiments, a is 0.

In some embodiments, $R^{1b}$, $R^{1c}$, $R^{1d}$, $R^{1e}$ and $R^{1f}$ are each independently H, F, Cl, Br, I, CF$_3$, CN, alkyl, cycloalkyl, cyclopropylmethyl, NH$_2$, NHR', NR'R'', OH, OR', SH, SR', C(O)R', CO$_2$H, COOR', CONH$_2$, CONHR', CONR'R''SO$_3$H, S(O)$_2$R', S(O)$_2$NH$_2$, S(O)$_2$NHR', S(O)$_2$NR'R'' aryl, heterocyclyl or heteroaryl.

In some embodiments, $R^{1b}$ and $R^{1c}$, or $R^{1c}$ and $R^{1d}$, or $R^{1d}$ and $R^{1e}$, or $R^{1e}$ and $R^{1f}$ together with the two carbon atoms to which they are attached, form an optionally substituted, aromatic or non-aromatic, 5-, 6- or 7-membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S. In some embodiments, $R^{1b}$ and $R^{1c}$ together with the two carbon atoms to which they are attached, form an optionally substituted, aromatic or non-aromatic, 5-, 6- or 7-membered ring. In some embodiments, $R^{1b}$ and $R^{1c}$ together with the two carbon atoms to which they are attached, form an optionally substituted, aromatic 5-, 6- or 7-membered ring. In some embodiments, $R^{1b}$ and $R^{1c}$ together with the two carbon atoms to which they are attached, form an optionally substituted, aromatic 6-membered ring.

In some embodiments, $R^B$ is

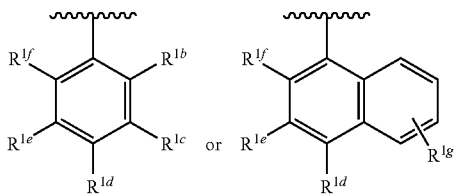

wherein
$R^{1g}$ is H, F, Cl, Br, I, $CF_3$, CN, alkyl, cycloalkyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl or heteroaryl;
wherein
R' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;
R" is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or
R' and R" together with the nitrogen atom to which they are attached form an optionally substituted, saturated or unsaturated 4-, 5- or 6-membered heterocyclic ring.

In some embodiments, $R^B$ is

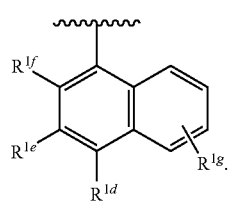

In some embodiments, $R^{1e}$, $R^{1f}$ and $R^{1g}$ are H.
In some embodiments, $R^{1d}$ is CN, alkyl or cycloalkyl.
In some embodiments, $R^{1e}$, $R^{1f}$ and $R^{1g}$ are H and $R^{1d}$ is CN, alkyl or cycloalkyl. In some embodiments, $R^{1e}$, $R^{1f}$ and $R^{1g}$ are H and $R^{1d}$ is CN or cyclopropyl.

In some embodiments, $R^B$ is

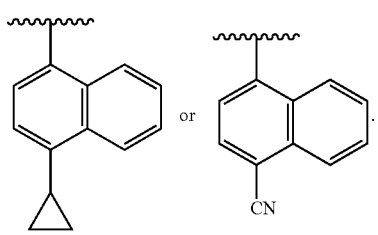 [SMILES: *c1ccc(C2CC2)c2ccccc12 ; "or" ; *c1ccc(C#N)c2ccccc12 ; "."]

In some embodiments, X is S, x is 1, y is 0, z is 0 and $R^x$ and $R^{x'}$ are either both H or both F.

In some embodiments, $R^C$ is an amino acid, a dipeptide, a tripeptide. In some embodiments, $R^C$ is an amino acid or a dipeptide. In some embodiments, $R^C$ is glycine, alanine or valine. In some embodiments, $R^C$ is a dipeptide comprising glycine, alanine or valine.

Disclosed herein, in certain embodiments, is a compound of Formula (I-A):

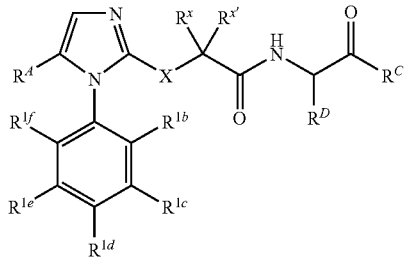

(I-A)

wherein
X is O or S;
$R^A$ is H, Cl, Br, I, $NH_2$, methyl, ethyl, n-propyl, i-propyl, optionally substituted methyl, optionally substituted ethyl, optionally substituted n-propyl, optionally substituted i-propyl, $CF_3$, $CHF_2$ or $CH_2F$;
$R^{1b}$, $R^{1c}$, $R^{1d}$, $R^{1e}$ and $R^{1f}$ are each independently H, F, Cl, Br, I, $CF_3$, CN, alkyl, cycloalkyl, cyclopropylmethyl, $NH_2$, NHR', NR'R", OH, OR', SH, SR', C(O)R', $CO_2H$, COOR', $CONH_2$, CONHR', CONR'R"$SO_3H$, $S(O)_2R'$, $S(O)_2NH_2$, $S(O)_2NHR'$, $S(O)_2NR'R"$ aryl, heterocyclyl or heteroaryl; or
$R^{1b}$ and $R^{1c}$, or $R^{1c}$ and $R^{1d}$, or $R^{1d}$ and $R^{1e}$, or $R^{1e}$ and $R^{1f}$ together with the two carbon atoms to which they are attached, form an optionally substituted, aromatic or non-aromatic, 5-, 6- or 7-membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S; and wherein the optional substituents are each independently H, F, Cl, Br, I, $CF_3$, CN, alkyl, cycloalkyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl or heteroaryl;
wherein
R' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;
R" is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or
R' and R" together with the nitrogen atom to which they are attached form an optionally substituted, saturated or unsaturated 4-, 5- or 6-membered heterocyclic ring;
$R^C$ is an amino acid, a dipeptide, a tripeptide, a tetrapeptide, a polypeptide, a lipid, a phospholipid, a glycoside, a nucleoside, a nucleotide, an oligonucleotide, polyethylene glycol, $OR^{2a}$, $SR^{3a}$, $NR^{4a}R^{4b}$, or a combination thereof, wherein;
$R^{2a}$ is substituted hydrogen, optionally substituted $C_1$-$C_{10}$ alkyl, optionally substituted heteroalkyl, optionally substituted cycloalkyl, optionally substituted heterocycloalkyl, optionally substituted aryl or optionally substituted heteroaryl; or $R^{2a}$ is a pharmaceutically acceptable cation; or $R^{2a}$ is —[C($R^{5a}$)($R^{5b}$)]$_m$$R^{5c}$;

$R^{3a}$ is hydrogen, optionally substituted $C_1$-$C_{10}$ alkyl, optionally substituted heteroalkyl, optionally substituted cycloalkyl, optionally substituted heterocycloalkyl, optionally substituted aryl, optionally substituted heteroaryl; or $R^{3a}$ is —[C($R^{5a}$)($R^{5b}$)]$_n$$R^{5c}$;

$R^{4a}$ is hydrogen, optionally substituted alkyl, optionally substituted heteroalkyl, optionally substituted cycloalkyl or optionally substituted heterocycloalkyl; and $R^{4b}$ is hydrogen, optionally substituted alkyl, optionally substituted heteroalkyl, optionally substituted cycloalkyl or optionally substituted heterocycloalkyl; or $R^{4b}$ is —[C($R^{5a}$)($R^{5b}$)]$_n$$R^{5c}$, wherein $R^{5a}$ and $R^{5b}$ are each independently hydrogen, halogen, cyano, nitro, an amino acid, a dipeptide, a tripeptide, a tetrapeptide, a polypeptide, a lipid, a phospholipid, a glycoside, a nucleoside, a nucleotide, an oligonucleotide, polyethylene glycol, -L-OH, -L-SH, -L-NH$_2$, substituted -L-$C_1$-$C_3$ alkyl, optionally substituted -L-$C_4$-$C_9$ alkyl, optionally substituted L-$C_2$-$C_5$ alkenyl, optionally substituted L-$C_2$-$C_5$ alkynyl, optionally substituted L-$C_2$-$C_5$ heteroalkyl, optionally substituted -L-$C_3$-$C_7$ cycloalkyl, optionally substituted L-$C_3$-$C_7$ cycloalkenyl, optionally substituted -L-$C_3$-$C_7$ heterocycloalkyl, optionally substituted -L-$C_1$-$C_4$ haloalkyl, optionally substituted -L-$C_1$-$C_4$ alkoxy, optionally substituted -L-$C_1$-$C_4$ alkylamine, optionally substituted -L-di-($C_1$-$C_4$)alkylamine, optionally substituted -L-$C_5$-$C_7$ aryl, optionally substituted -L-$C_5$-$C_7$ heteroaryl,

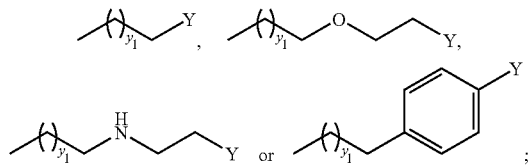

$R^{5c}$ is hydrogen, halogen, cyano, nitro, an amino acid, a dipeptide, a tripeptide, a tetrapeptide, a polypeptide, a lipid, a phospholipid, a glycoside, a nucleoside, a nucleotide, an oligonucleotide, polyethylene glycol, -L-OH, -L-SH, -L-NH$_2$, substituted -L-$C_1$-$C_3$ alkyl, optionally substituted -L-$C_4$-$C_9$ alkyl, optionally substituted L-$C_2$-$C_5$ alkenyl, optionally substituted L-$C_2$-$C_5$ alkynyl, optionally substituted L-$C_2$-$C_5$ heteroalkyl, optionally substituted -L-$C_3$-$C_7$ cycloalkyl, optionally substituted L-$C_3$-$C_7$ cycloalkenyl, optionally substituted -L-$C_3$-$C_7$ heterocycloalkyl, optionally substituted -L-$C_1$-$C_4$ haloalkyl, optionally substituted -L-$C_1$-$C_4$ alkoxy, optionally substituted -L-$C_1$-$C_4$alkylamine, optionally substituted -L-di($C_1$-$C_4$)alkylamine, optionally substituted -L-$C_5$-$C_7$ aryl, optionally substituted -L-$C_5$-$C_7$ heteroaryl,

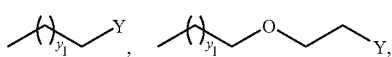 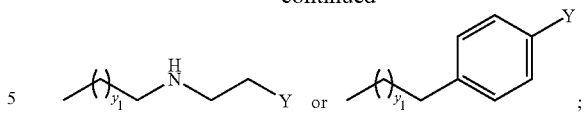

wherein L is a bond, —C(O)—, —S(O), or —S(O)$_2$;

$y_1$ is 0, 1, 2 or 3;

Y is OH, OMe, COOH, SO$_3$H, OSO$_3$H, OS(O)$_2$NH$_2$, P(O)(OH)$_2$, OP(O)(OH)$_2$, OP(O)(O)(OH)(O—$C_{1-4}$ alkyl) or NY$^2$Y$^3$Y$^4$; wherein Y$^2$ and Y$^3$ are each independently hydrogen or methyl; or Y$^2$ and Y$^3$ are taken together with the nitrogen to which they are attached form a five or six membered ring that optionally contains an oxygen atom or a second nitrogen atom; and Y$^4$ is an electron pair or an oxygen atom;

m is 1, 2, 3, 4;

n is 0, 1, 2, 3, 4, 5, 6, 7, 8, 9 or 10;

$R^D$ is a natural or unnatural amino acid residue;

or a metabolite, pharmaceutically acceptable salt, solvate, ester, tautomer or prodrug thereof.

Disclosed herein are compounds of formula (II), or a metabolite, pharmaceutically acceptable salt, solvate, polymorph, ester, tautomer or prodrug thereof:

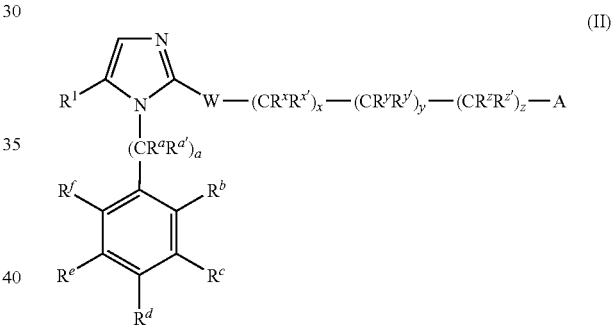

wherein:

W is O, S, S(O), S(O)$_2$, NH, N(optionally substituted alkyl), CH$_2$, CH$_2$O, CH$_2$S or CH$_2$NH;

$R^1$ is H, F, Cl, Br, I, CH$_2$F, CF$_2$H, CF$_3$, CN, OH, NO$_2$, NH$_2$, NH(alkyl) or N(alkyl)(alkyl), SO$_2$CH$_3$, SO$_2$NH$_2$, SO$_2$NHCH$_3$, CO$_2$-alkyl, optionally substituted alkyl, optionally substituted alkenyl, optionally substituted alkoxy, optionally substituted S-alkyl, optionally substituted cycloalkyl, optionally substituted heterocycle, optionally substituted aryl or optionally substituted heteroaryl;

a is 0, 1 or 2;

$R^a$ is H or optionally substituted $C_{1-3}$ alkyl;

$R^{a'}$ is H or optionally substituted $C_{1-3}$ alkyl; or $R^a$ and $R^{a'}$ together with the carbon atom to which they are attached form an optionally substituted, 3-, 4-, 5- or 6-membered ring, optionally comprising 1 or 2 heteroatoms selected from O, N and S;

$R^b$, $R^c$, $R^d$, $R^e$ and $R^f$ are each independently H, F, Cl, Br, I, CF$_3$, CN, alkyl, cycloalkyl, cyclopropylmethyl, NH$_2$, NHR', NR'R", OH, OR', SH, SR', C(O)R', CO$_2$H, COOR', CONH$_2$, CONHR', CONR'R", SO$_3$H, S(O)$_2$R', S(O)$_2$NH$_2$, S(O)$_2$NHR', S(O)$_2$NR'R", aryl, heterocyclyl or heteroaryl;

wherein
- R' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;
- R" is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or
- R' and R" together with the nitrogen atom to which they are attached form an optionally substituted, saturated or unsaturated 4-, 5- or 6-membered heterocyclic ring; or
- $R^b$ and $R^c$, or $R^c$ and $R^d$, or $R^d$ and $R^e$, or $R^e$ and $R^f$ together with the two carbon atoms to which they are attached, form an optionally substituted, aromatic or non-aromatic, 5-, 6- or 7-membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S; and wherein the optional substituents are each independently F, Cl, Br, I, $CF_3$, CN, alkyl, cycloalkyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl or heteroaryl;
- x is 0 or 1;
- y is 0 or 1;
- z is 0 or 1;
- $R^x$, $R^{x'}$, $R^y$, $R^{y'}$, $R^z$ and $R^{z'}$ are each independently H, F, Cl, Br, or optionally substituted $C_{1-3}$ alkyl; or
- $R^x$ and $R^{x'}$, or $R^y$ and $R^{y'}$, or $R^z$ and $R^{z'}$, or $R^x$ and $R^y$, or $R^y$ and $R^z$, or $R^x$ and $R^z$ together with the carbon atoms to which they are attached, form an optionally substituted, aromatic or non-aromatic, 3-7 membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S;
- A is H, C(O)O—$B^1$ or C(O)NH—$B^2$; wherein
  - $B^1$ is H, optionally substituted $C_{1-6}$ alkyl or a pharmaceutically acceptable cation;
  - $B^2$ is H or optionally substituted $C_{1-6}$ alkyl; and wherein all alkyl, alkylene, cycloalkyl, heterocyclyl, aryl and heteroaryl moieties may be optionally further substituted.

Another aspect of the invention provides for a compound of formula (II-A), (II-B), (II-C), (II-D), (II-E), (II-F), (II-G), (II-H), (II-I) or (II-J), or a metabolite, pharmaceutically acceptable salt, solvate, polymorph, ester, tautomer or prodrug thereof:

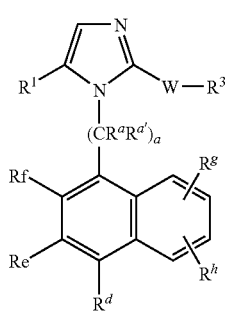

(II-A)

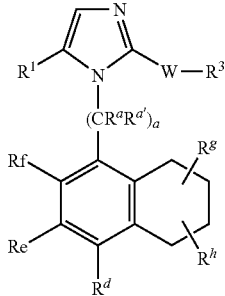

(II-B)

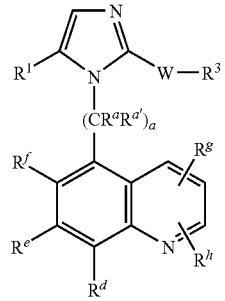

(II-C)

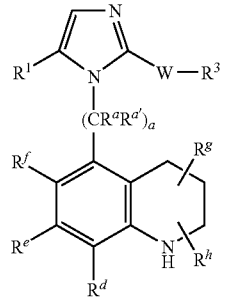

(II-D)

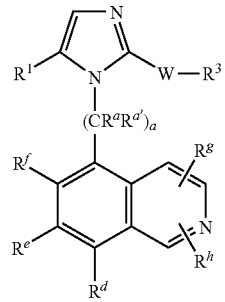

(II-E)

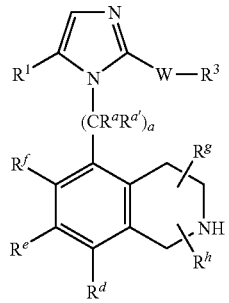

(II-F)

-continued

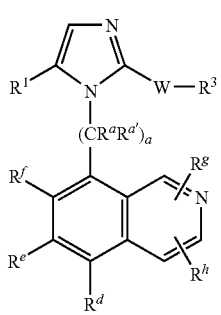
(II-G)

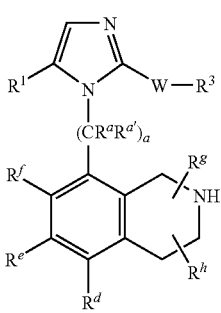
(II-H)

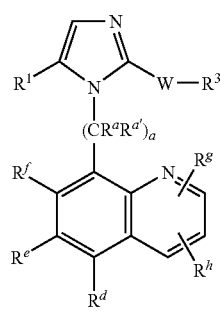
(II-I)

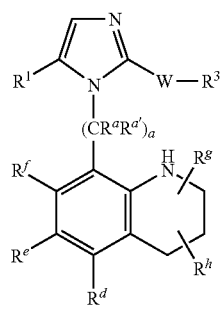
(II-J)

wherein:

W is O, S, S(O), S(O)$_2$, NH, N(optionally substituted alkyl), CH$_2$, CH$_2$O, CH$_2$S or CH$_2$NH;

R$^1$ is H, F, Cl, Br, I, CH$_2$F, CF$_2$H, CF$_3$, CN, OH, NO$_2$, NH$_2$, NH(alkyl) or N(alkyl)(alkyl), SO$_2$CH$_3$, SO$_2$NH$_2$, SO$_2$NHCH$_3$, CO$_2$-alkyl, optionally substituted alkyl, optionally substituted alkenyl, optionally substituted alkoxy, optionally substituted S-alkyl, optionally substituted cycloalkyl, optionally substituted heterocycle, optionally substituted aryl or optionally substituted heteroaryl;

a is 0, 1 or 2;

R$^a$ is H or optionally substituted C$_{1-3}$ alkyl;

R$^{a'}$ is H or optionally substituted C$_{1-3}$ alkyl; or

R$^a$ and R$^{a'}$ together with the carbon atom to which they are attached form a 3-, 4-, 5- or 6-membered ring, optionally comprising 1 or 2 heteroatoms selected from O, N and S;

R$^d$, R$^e$, R$^f$, R$^g$ and R$^h$ are each independently H, F, Cl, Br, I, CF$_3$, CN, alkyl, cycloalkyl, cyclopropylmethyl, NH$_2$, NHR', NR'R'', OH, OR', SH, SR', C(O)R', CO$_2$H, COOR', CONH$_2$, CONHR', CONR'R'', SO$_3$H, S(O)$_2$R', S(O)$_2$NH$_2$, S(O)$_2$NHR', S(O)$_2$NR'R'', aryl, heterocyclyl or heteroaryl;

wherein

R' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;

R'' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or R' and R'' together with the nitrogen atom to which they are attached form an optionally substituted, saturated or unsaturated 4-, 5- or 6-membered heterocyclic ring;

R$^3$ is —(CR$^x$R$^{x'}$)$_x$—(CR$^y$R$^{y'}$)$_y$—(CR$^z$R$^{z'}$)$_z$-A; wherein x is 0 or 1;

y is 0 or 1;

z is 0 or 1;

R$^x$, R$^{x'}$, R$^y$, R$^{y'}$, R$^z$ and R$^{z'}$ are each independently H, F, Cl, Br, or optionally substituted C$_{1-3}$ alkyl; or R$^x$ and R$^{x'}$, or R$^y$ and R$^{y'}$, or R$^z$ and R$^{z'}$, or R$^x$ and R$^y$, or R$^y$ and R$^z$, or R$^x$ and R$^z$ together with the carbon atoms to which they are attached, form an optionally substituted, aromatic or non-aromatic, 3-7 membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S;

A is H, C(O)O—B$^1$ or C(O)NH—B$^2$; wherein

B$^1$ is H, optionally substituted C$_{1-6}$ alkyl or a pharmaceutically acceptable cation;

B$^2$ is H or optionally substituted C$_{1-6}$ alkyl; and wherein all alkyl, alkylene, cycloalkyl, heterocyclyl, aryl and heteroaryl moieties may be optionally further substituted.

Another aspect of the invention provides for a compound of formula (IIK), (IIL), (IIM), (IIN), (IIO) or (IIP), or a metabolite, pharmaceutically acceptable salt, solvate, polymorph, ester, tautomer or prodrug thereof:

(II-K)

-continued

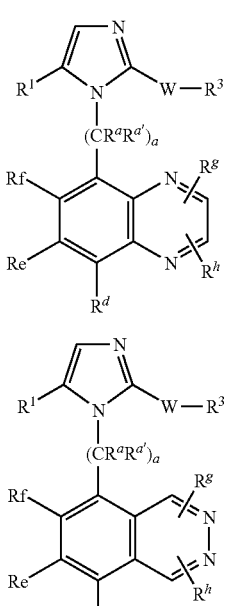
(II-L)

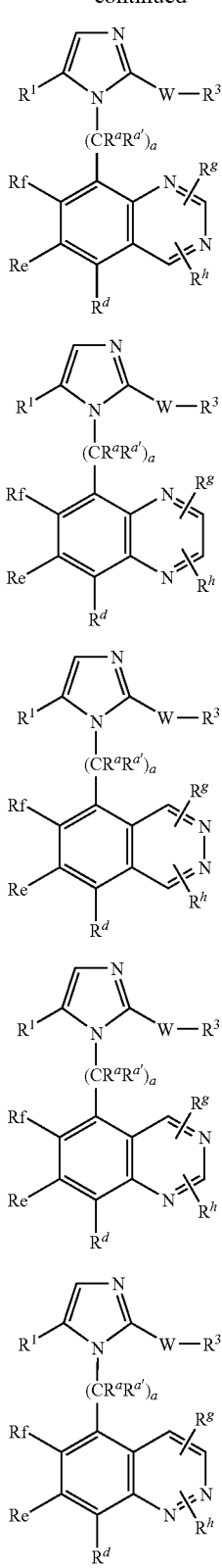
(II-M)

(II-N)

(II-O)

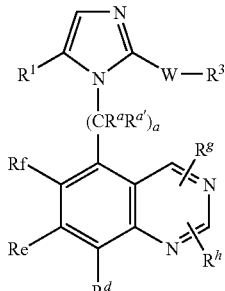
(II-P)

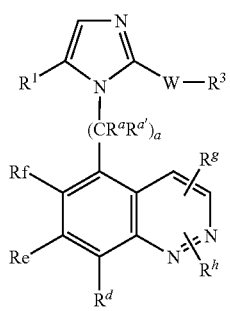

wherein:
R$^g$ and R$^h$ are each independently H, F, Cl, Br, I, CF$_3$, CN, alkyl, cycloalkyl, cyclopropylmethyl, NH$_2$, NHR', NR'R", OH, OR', SH, SR', C(O)R', CO$_2$H, COOR', CONH$_2$, CONHR', CONR'R", SO$_3$H, S(O)$_2$R', S(O)$_2$NH$_2$, S(O)$_2$NHR', S(O)$_2$NR'R", aryl, heterocyclyl or heteroaryl; wherein
R' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;
R" is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or
R' and R" together with the nitrogen atom to which they are attached form an optionally substituted, saturated or unsaturated 4-, 5- or 6-membered heterocyclic ring.

In other embodiments, the invention provides compounds of formula (II-Q), or a metabolite, pharmaceutically acceptable salt, solvate, polymorph, ester, tautomer or prodrug thereof:

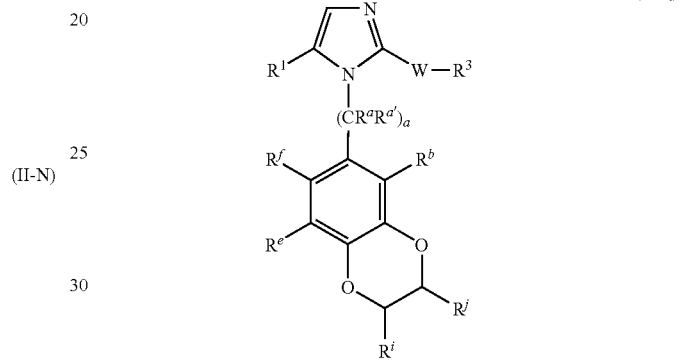
(II-Q)

wherein:
R$^i$ and R$^j$ are each independently H, F, Cl, Br, I, CF$_3$, CN, alkyl, cycloalkyl, cyclopropylmethyl, NH$_2$, NHR', NR'R", OH, OR', SH, SR', C(O)R', CO$_2$H, COOR', CONH$_2$, CONHR', CONR'R", SO$_3$H, S(O)$_2$R', S(O)$_2$NH$_2$, S(O)$_2$NHR', S(O)$_2$NR'R", aryl, heterocyclyl or heteroaryl; wherein
R' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;
R" is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or
R' and R" together with the nitrogen atom to which they are attached form an optionally substituted, saturated or unsaturated 4-, 5- or 6-membered heterocyclic ring.

Disclosed herein, in certain embodiments, is a compound having the following structure:

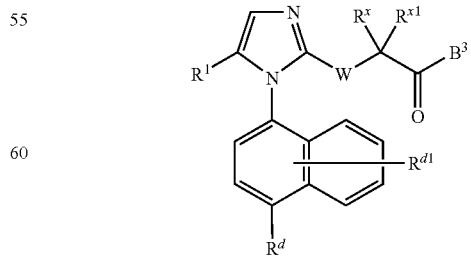

or a metabolite, pharmaceutically acceptable salt, solvate, polymorph, ester, tautomer or prodrug thereof, wherein:
  W is O or S;
  R¹ is H, F, Cl, Br, I, —CH₂F, —CF₂H, —CF₃, —CN, —OH, —NO₂, —NH₂, —NH($C_{1-4}$alkyl), —N($C_{1-4}$alkyl)($C_{1-4}$alkyl), —SO₂CH₃, —SO₂NH₂, —SO₂NHCH₃, —CO₂—$C_{1-4}$alkyl, $C_{1-4}$alkyl, $C_{1-4}$alkenyl, $C_{1-4}$alkoxy, $C_{1-4}$S-alkyl, $C_{3-6}$cycloalkyl, optionally substituted $C_{1-6}$heterocycloalkyl, optionally substituted phenyl, or optionally substituted 5 or 6 membered heteroaryl;
  $R^d$ is F, Cl, Br, I, CF₃, aryl, heteroaryl, CN, NO₂, NH₂, NHR', OH, OR', SH, SR', C(O)R', CO₂H, COOR', CONH₂, CONHR', CONR'R", SO₃H, SO₃R', S(O)₂R', S(O)₂NH₂, S(O)₂NHR', or S(O)₂NR'R";
  $R^{d1}$ is zero to four substituents independently selected from optionally substituted alkyl, optionally substituted alkenyl, optionally substituted alkynyl, optionally substituted heteroalkyl, optionally substituted heteroalkenyl, optionally substituted heteroalkynyl, optionally substituted cycloalkyl, optionally substituted cycloalkenyl, optionally substituted heterocyclyl, optionally substituted aryl, optionally substituted heteroaryl, halo, CN, NH₂, NHR', NR'R", OH, OR', SH, SR', C(O)R', CO₂H, COOR', CONH₂, CONHR', CONR'R", SO₃H, S(O)₂R', S(O)₂NH₂, S(O)₂NHR', or S(O)₂NR'R";
  each R' is independently methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;
  each R" is independently methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or
  R' and R" are together with the atom to which they are attached form an optionally substituted, saturated or unsaturated 4-, 5- or 6-membered ring;
  $R^x$ and $R^{x'}$ are each independently H, optionally substituted alkyl, optionally substituted alkenyl, optionally substituted alkynyl, optionally substituted heteroalkyl, optionally substituted heteroalkenyl, optionally substituted heteroalkynyl, optionally substituted cycloalkyl, optionally substituted cycloalkenyl, optionally substituted heterocyclyl, optionally substituted aryl, optionally substituted heteroaryl, halo, CN, NH₂, NHR', NR'R", OH, OR', SH, SR', C(O)R', CO₂H, COOR', CONH₂, CONHR', CONR'R", SO₃H, S(O)₂R', S(O)₂NH₂, S(O)₂NHR', or S(O)₂NR'R"; or
  $R^x$ and $R^{x'}$ together with the carbon atom to which they are attached, form an optionally substituted non-aromatic 3-7 membered ring, optionally comprising 1 or 2 heteroatoms selected from O, N and S;
  B³ is OB¹, NB²₂, or an amino acid residue or an alkyl ester thereof;
  B¹ is H, optionally substituted $C_{1-6}$ alkyl or a pharmaceutically acceptable cation; and
  each B² is independently H or optionally substituted alkyl.
In some embodiments, W is S. In some embodiments, W is O. In some embodiments, B³ is OB¹. In some embodiments, B¹ is an alkali earth metal cation or an alkaline earth metal cation. In some embodiments, B³ is NB²₂. The compound disclosed herein wherein B³ is an amino acid residue or lower alkyl ester thereof. In some embodiments, $R^x$ and $R^{x'}$ are independently H, F, CF₃, or methyl. In some embodiments, $R^x$ is F and $R^{x'}$ is F. In some embodiments, R¹ is H, F, Cl, Br, CH₂F, CF₂H, CF₃, NH₂, or CH₃. In some embodiments, R¹ is Br. In some embodiments, $R^d$ is H, F, Cl, Br, I, CF₃, or CN.

Disclosed herein, in certain embodiments, is a compound having the following structure:

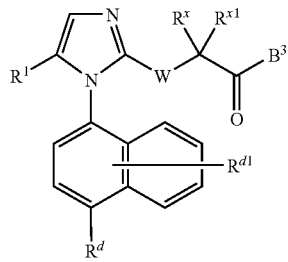

or a metabolite, pharmaceutically acceptable salt, solvate, polymorph, ester, tautomer or prodrug thereof,
wherein:
  W is O or S;
  R¹ is H, F, Cl, Br, I, —CH₂F, —CF₂H, —CF₃, —CN, —OH, —NO₂, —NH₂, —NH($C_{1-4}$alkyl), —N($C_{1-4}$alkyl)($C_{1-4}$alkyl), —SO₂CH₃, —SO₂NH₂, —SO₂NHCH₃, —CO₂—$C_{1-4}$alkyl, $C_{1-4}$alkyl, $C_{1-4}$alkenyl, $C_{1-4}$alkoxy, $C_{1-4}$S-alkyl, $C_{3-6}$cycloalkyl, optionally substituted $C_{1-6}$heterocycloalkyl, optionally substituted phenyl, or optionally substituted 5 or 6 membered heteroaryl;
  $R^d$ is H, optionally substituted alkyl, optionally substituted alkenyl, optionally substituted alkynyl, optionally substituted heteroalkyl, optionally substituted heteroalkenyl, optionally substituted heteroalkynyl, optionally substituted cycloalkyl, optionally substituted cycloalkenyl, optionally substituted heterocyclyl, optionally substituted aryl, optionally substituted heteroaryl, halo, CN, NO₂, NH₂, NHR', NR'R", OH, OR', SH, SR', C(O)R', CO₂H, COOR', CONH₂, CONHR', CONR'R", SO₃H, SO₃R', S(O)₂R', S(O)₂NH₂, S(O)₂NHR', or S(O)₂NR'R";
  $R^{d1}$ is zero to four substituents independently selected from optionally substituted alkyl, optionally substituted alkenyl, optionally substituted alkynyl, optionally substituted heteroalkyl, optionally substituted heteroalkenyl, optionally substituted heteroalkynyl, optionally substituted cycloalkyl, optionally substituted cycloalkenyl, optionally substituted heterocyclyl, optionally substituted aryl, optionally substituted heteroaryl, halo, CN, NH₂, NHR', NR'R", OH, OR', SH, SR', C(O)R', CO₂H, COOR', CONH₂, CONHR', CONR'R", SO₃H, S(O)₂R', S(O)₂NH₂, S(O)₂NHR', or S(O)₂NR'R";
  each R' is independently methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;
  each R" is independently methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or
  R' and R" are together with the atom to which they are attached form an optionally substituted, saturated or unsaturated 4-, 5- or 6-membered ring;
  $R^x$ is F, Cl, Br, I, or $C_1$-$C_3$ fluoroalkyl;
  $R^{x'}$ is independently H, optionally substituted alkyl, optionally substituted alkenyl, optionally substituted alkynyl, optionally substituted heteroalkyl, optionally substituted heteroalkenyl, optionally substituted heteroalkynyl, optionally substituted cycloalkyl, optionally substituted cycloalkenyl, optionally substituted heterocyclyl, optionally substituted aryl, optionally substituted heteroaryl, halo, CN, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, or $S(O)_2NR'R"$; and $B^3$ is $OB^1$, $NB^2_2$, or an amino acid residue or an alkyl ester thereof;

$B^1$ is H, optionally substituted $C_{1-6}$ alkyl or a pharmaceutically acceptable cation; and each $B^2$ is independently H or optionally substituted alkyl.

In some embodiments, W is S. In some embodiments, W is O. In some embodiments, $B^3$ is $OB^1$. In some embodiments, $B^1$ is an alkali earth metal cation or an alkaline earth metal cation. In some embodiments, $B^3$ is $NB^2_2$. The compound disclosed herein wherein $B^3$ is an amino acid residue or lower alkyl ester thereof. In some embodiments, $R^x$ and $R^{x'}$ are independently H, F, methyl, or $CF_3$. In some embodiments, $R^x$ is F and $R^{x1}$ is F. In some embodiments, $R^1$ is H, F, Cl, Br, $CH_2F$, $CF_2H$, $CF_3$, $NH_2$, or $CH_3$. In some embodiments, $R^1$ is Br. In some embodiments, $R^d$ is F, Cl, Br, I, $CF_3$, or CN.

Disclosed herein, in certain embodiments, is a compound having the following structure:

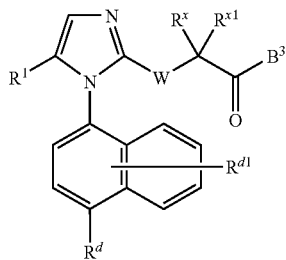

or a metabolite, pharmaceutically acceptable salt, solvate, polymorph, ester, tautomer or prodrug thereof,
wherein:
W is O or S;
$R^1$ is halo or haloalkyl;
$R^d$ is H;
$R^{d1}$ is zero to four substituents independently selected from optionally substituted alkyl, optionally substituted alkenyl, optionally substituted alkynyl, optionally substituted heteroalkyl, optionally substituted heteroalkenyl, optionally substituted heteroalkynyl, optionally substituted cycloalkyl, optionally substituted cycloalkenyl, optionally substituted heterocyclyl, optionally substituted aryl, optionally substituted heteroaryl, halo, CN, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)2NHR'$, or $S(O)_2NR'R"$;
each R' is independently methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;
each R" is independently methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl; or
R' and R" are together with the atom to which they are attached form an optionally substituted, saturated or unsaturated 4-, 5- or 6-membered ring;
$R^x$ and $R^{x'}$ are each independently H, optionally substituted alkyl, optionally substituted alkenyl, optionally substituted alkynyl, optionally substituted heteroalkyl, optionally substituted heteroalkenyl, optionally substituted heteroalkynyl, optionally substituted cycloalkyl, optionally substituted cycloalkenyl, optionally substituted heterocyclyl, optionally substituted aryl, optionally substituted heteroaryl, halo, CN, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, or $S(O)_2NR'R"$; or $R^x$ and $R^{x'}$ together with the carbon atom to which they are attached, form an optionally substituted non-aromatic 3-7 membered ring, optionally comprising 1 or 2 heteroatoms selected from O, N and S;

$B^3$ is $OB^1$, $NB^2_2$, or an amino acid residue or an alkyl ester thereof;

$B^1$ is H, optionally substituted $C_{1-6}$ alkyl or a pharmaceutically acceptable cation; and each $B^2$ is independently H or optionally substituted alkyl.

In some embodiments, W is S. In some embodiments, W is O. In some embodiments, $B^3$ is $OB^1$. In some embodiments, $B^1$ is an alkali earth metal cation or an alkaline earth metal cation. In some embodiments, $B^3$ is $NB^2_2$. The compound disclosed herein wherein $B^3$ is an amino acid residue or lower alkyl ester thereof. In some embodiments, $R^x$ and $R^{x1}$ are independently H, F, $CF_3$, or methyl. In some embodiments, $R^x$ is methyl and $R^{x1}$ is methyl.

Synthetic Procedures

In another aspect, methods for synthesizing a compound disclosed herein are provided. A compound disclosed herein is prepared by any of the methods described below. The procedures and examples below are intended to illustrate those methods. Neither the procedures nor the examples should be construed as limiting the invention in any way. A compound disclosed herein is also synthesized using standard synthetic techniques or using such methods in combination with methods described herein.

In some embodiments, the starting materials used for the synthesis of the compounds as described herein are obtained from commercial sources, such as Aldrich Chemical Co. (Milwaukee, Wis.), Sigma Chemical Co. (St. Louis, Mo.). In some embodiments, the starting materials are synthesized.

A compound disclosed herein, and other related compounds having different substituents is synthesized using any suitable technique, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999) (all of which are incorporated by reference for such disclosures). The various moieties found in the formulae as provided herein are obtained using any suitable method. The following synthetic methods serve as a guide for synthesizing a compound disclosed herein.

Formation of Covalent Linkages by Reaction of an Electrophile with a Nucleophile In some embodiments, a compound disclosed herein is modified using various electrophiles or nucleophiles to form new functional groups or substituents. The table below entitled "Examples of Covalent Linkages and Precursors Thereof" lists selected examples of covalent linkages and precursor functional groups. Precursor functional groups are shown as electrophilic groups and nucleophilic groups.

| Examples of Covalent Linkages and Precursors Thereof | | |
|---|---|---|
| Covalent Linkage Product | Electrophile | Nucleophile |
| Carboxamides | Activated esters | Amines/anilines |
| Carboxamides | Acyl azides | Amines/anilines |
| Carboxamides | Acyl halides | Amines/anilines |
| Esters | Acyl halides | Alcohols/phenols |
| Esters | Acyl nitriles | Alcohols/phenols |
| Carboxamides | Acyl nitriles | Amines/anilines |
| Imines | Aldehydes | Amines/anilines |
| Hydrazones | Aldehydes or ketones | Hydrazines |
| Oximes | Aldehydes or ketones | Hydroxylamines |
| Alkyl amines | Alkyl halides | Amines/anilines |
| Esters | Alkyl halides | Carboxylic acids |
| Thioethers | Alkyl halides | Thiols |
| Ethers | Alkyl halides | Alcohols/phenols |
| Thioethers | Alkyl sulfonates | Thiols |
| Esters | Alkyl sulfonates | Carboxylic acids |
| Ethers | Alkyl sulfonates | Alcohols/phenols |
| Esters | Anhydrides | Alcohols/phenols |
| Carboxamides | Anhydrides | Amines/anilines |
| Thiophenols | Aryl halides | Thiols |
| Aryl amines | Aryl halides | Amines |
| Thioethers | Aziridines | Thiols |
| Boronate esters | Boronates | Glycols |
| Carboxamides | Carboxylic acids | Amines/anilines |
| Esters | Carboxylic acids | Alcohols |
| Hydrazines | Hydrazides | Carboxylic acids |
| N-acylureas or Anhydrides | Carbodiimides | Carboxylic acids |
| Esters | Diazoalkanes | Carboxylic acids |
| Thioethers | Epoxides | Thiols |
| Thioethers | Haloacetamides | Thiols |
| Ammotriazines | Halotriazines | Amines/anilines |
| Triazinyl ethers | Halotriazines | Alcohols/phenols |
| Amidines | Imido esters | Amines/anilines |
| Ureas | Isocyanates | Amines/anilines |
| Urethanes | Isocyanates | Alcohols/phenols |
| Thioureas | Isothiocyanates | Amines/anilines |
| Thioethers | Maleimides | Thiols |
| Phosphite esters | Phosphoramidites | Alcohols |
| Silyl ethers | Silyl halides | Alcohols |
| Alkyl amines | Sulfonate esters | Amines/anilines |
| Thioethers | Sulfonate esters | Thiols |
| Esters | Sulfonate esters | Carboxylic acids |
| Ethers | Sulfonate esters | Alcohols |
| Sulfonamides | Sulfonyl halides | Amines/anilines |
| Sulfonate esters | Sulfonyl halides | Phenols/alcohols |

Use of Protecting Groups

In some embodiments, it is necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. It is preferred that each protective group be removable by a different means. Protective groups that are cleaved under totally disparate reaction conditions fulfill the requirement of differential removal. In some embodiments, protective groups are removed by acid, base, hydrogenolysis, or combinations thereof. In some embodiments, groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. In some embodiments, carboxylic acid and hydroxy reactive moieties are blocked with base labile groups such as, but not limited to, methyl, ethyl, and acetyl in the presence of amines blocked with acid labile groups such as t-butyl carbamate or with carbamates that are both acid and base stable but hydrolytically removable.

In some embodiments, carboxylic acid and hydroxy reactive moieties are blocked with hydrolytically removable protective groups such as the benzyl group. In some embodiments, amine groups capable of hydrogen bonding with acids are blocked with base labile groups such as Fmoc. In some embodiments, carboxylic acid reactive moieties are protected by conversion to simple ester compounds as exemplified herein. In some embodiments, carboxylic acid reactive moieties are blocked with oxidatively-removable protective groups such as 2,4-dimethoxybenzyl, while co-existing amino groups are blocked with fluoride labile silyl carbamates.

In some embodiments, allyl blocking groups are used in the presence of acid- and base-protecting groups since the former are stable. In some embodiments, allyl blocking groups are subsequently removed by metal or pi-acid catalysts. For example, an allyl-blocked carboxylic acid is deprotected with a Pd-catalyzed reaction in the presence of acid labile t-butyl carbamate or base-labile acetate amine protecting groups.

In some embodiments, the protecting group is a resin to which a compound or intermediate is attached. In certain instances, as long as the residue is attached to the resin, the functional group is blocked and cannot react. Once released from the resin, the functional group is available to react.

In some embodiments, the protecting group is:

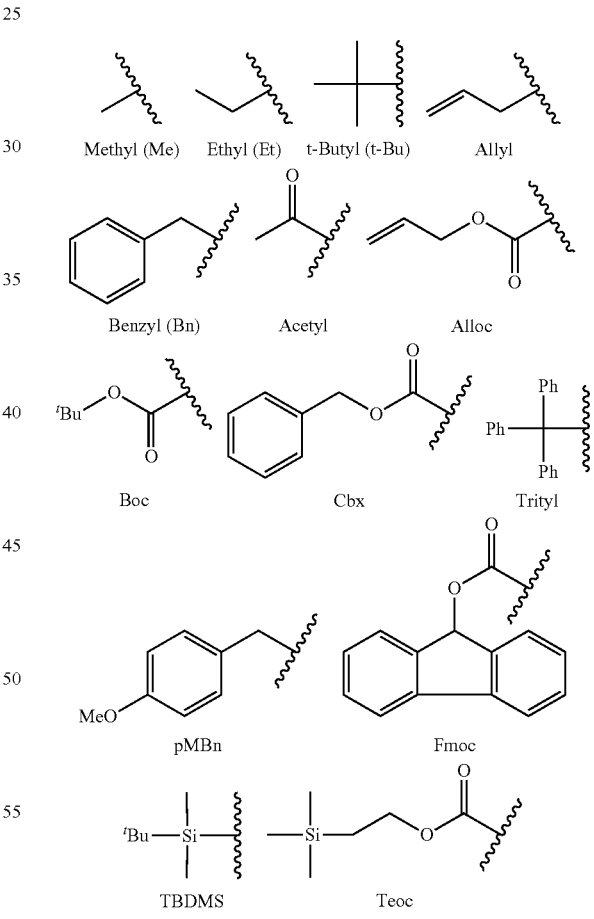

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosures.

Further Forms
Isomers

In some embodiments, a compound disclosed herein exists as geometric isomers. In some embodiments, a compound disclosed herein possesses one or more double bonds. The compounds presented herein include all cis, trans, syn, anti, entgegen (E), and zusammen (Z) isomers as well as the corresponding mixtures thereof.

In some embodiments, compounds disclosed herein exist as tautomers. A compound disclosed herein includes all possible tautomers within the formulas described herein. In some embodiments, a compound disclosed herein possesses one or more chiral centers. In some embodiments, each center exists in the R or S configuration. A compound disclosed herein includes all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein.

In some embodiments, a compound disclosed herein is prepared as their individual stereoisomers by reacting a racemic mixture of the compound with an optically active resolving agent to form a pair of diastereoisomeric compounds, separating the diastereomers and recovering the optically pure enantiomers. In some embodiments, resolution of enantiomers is carried out using covalent diastereomeric derivatives of a compound disclosed herein. In some embodiments, resolution of enantiomers is carried out using dissociable complexes (e.g., crystalline diastereomeric salts). In certain instances, diastereomers have distinct physical properties (e.g., melting points, boiling points, solubilities, reactivity, etc.). In some embodiments, diastereomers are separated by taking advantage of these dissimilarities. In some embodiments, diastereomers are separated by chiral chromatography, or preferably, by separation/resolution techniques based upon differences in solubility. The optically pure enantiomer is then recovered, along with the resolving agent, by any practical means that would not result in racemization.

Labeled Compounds

In some embodiments, a compound disclosed herein exists in its isotopically-labeled forms. The invention provides for methods of treating diseases by administering such isotopically-labeled compounds. The invention further provides for methods of treating diseases by administering such isotopically-labeled compounds as pharmaceutical compositions. Thus, compounds of formula I also include isotopically-labeled compounds, which are identical to those recited herein, but for the fact that one or more atoms are replaced by an atom having an atomic mass or mass number different from the atomic mass or mass number usually found in nature. Isotopes for use with a method or compound disclosed herein include, but are not limited to, include isotopes of hydrogen, carbon, nitrogen, oxygen, phosphorous, sulfur, fluorine and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. A compound disclosed herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability. In some embodiments, substitution with heavy isotopes (e.g., deuterium, i.e., $^2H$) is utilized with a method or compound disclosed herein. In certain instances, substitution with heavy isotopes affords certain therapeutic advantages resulting from greater metabolic stability, for example increased in vivo half-life or reduced dosage requirements. In some embodiments, a compound, pharmaceutically acceptable salt, ester, prodrug, solvate, hydrate or derivative thereof is isotopically labeled by substituting a readily available isotopically labeled reagent for a non-isotopically labeled reagent in any procedure disclosed herein.

In some embodiments, a compound described herein is labeled by other means, including, but not limited to, the use of chromophores or fluorescent moieties, bioluminescent labels, or chemiluminescent labels.

Metabolites

In some embodiments, a compound disclosed herein exists as a metabolite. The invention provides for methods of treating diseases by administering such metabolites. The invention further provides for methods of treating diseases by administering such metabolites as pharmaceutical compositions.

In some embodiments, a compound disclosed herein is metabolized by a variety of metabolic mechanisms, such as hydrolysis, oxidation, glycolysis, phosphorylation, alkylation, dehalogenation, or combinations thereof.

Pharmaceutically Acceptable Salts

In some embodiments, a compound disclosed herein exists as a pharmaceutically acceptable salt. The invention provides for methods of treating diseases by administering such pharmaceutically acceptable salts. The invention further provides for methods of treating diseases by administering such pharmaceutically acceptable salts as pharmaceutical compositions.

In some embodiments, a compound disclosed herein possesses an acidic or basic group. In some embodiments, a compound disclosed herein that possesses an acidic or basic group reacts with any of a number of inorganic or organic bases, and inorganic and organic acids, to form a pharmaceutically acceptable salt. In some embodiments, a salt is prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of a compound disclosed herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, a compound disclosed herein is optionally prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. Other acids, such as oxalic, while not in themselves pharmaceutically acceptable, are optionally employed in the preparation of salts useful as intermediates in obtaining the compounds of the invention and their pharmaceutically acceptable acid addition salts.

In some embodiments, a compound disclosed herein which comprises a free acid group reacts with a suitable base, such as the hydroxide, carbonate, bicarbonate, sulfate, of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, $N^+(C_{1-4}\text{ alkyl})_4$, and the like. Representative organic amines useful for the formation of base addition salts include ethylamine, diethylamine, ethylenediamine, ethanolamine, diethanolamine, piperazine and the like. It should be understood that a compound disclosed herein also includes the quaternization of any basic nitrogen-containing groups they contain. In some embodiments, water or oil-soluble or dispersible products are obtained by such quaternization. A compound disclosed herein is optionally prepared as pharmaceutically acceptable salts formed when an acidic proton present in the parent compound either is replaced by a metal ion, for example an alkali metal ion, an alkaline earth ion, or an aluminum ion; or coordinates with an organic base. In some embodiments, base addition salts are also prepared by reacting the free acid form of a compound disclosed herein with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like. In addition, the salt forms of the disclosed compounds are optionally prepared using salts of the starting materials or intermediates.

Solvates

In some embodiments, a compound disclosed herein exists as a solvate. The invention provides for methods of treating diseases by administering such solvates. The invention further provides for methods of treating diseases by administering such solvates as pharmaceutical compositions.

In certain instances, solvates contain either stoichiometric or non-stoichiometric amounts of a solvent. In some embodiments, a solvate is formed during the process of crystallization with pharmaceutically acceptable solvents such as water, ethanol, and the like. Hydrates are formed when the solvent is water, or alcoholates are formed when the solvent is alcohol. In some embodiments, a solvate of a compound disclosed herein is prepared or formed during the processes described herein. By way of example only, hydrates of a compound disclosed herein are conveniently prepared by recrystallization from an aqueous/organic solvent mixture, using organic solvents including, but not limited to, dioxane, tetrahydrofuran or methanol. In some embodiments, a compound provided herein exists in unsolvated as well as solvated forms. In general, the solvated forms are considered equivalent to the unsolvated forms for the purposes of the compounds and methods provided herein.

Polymorphs

In some embodiments, a compound disclosed herein exists as a polymorph. The invention provides for methods of treating diseases by administering such polymorphs. The invention further provides for methods of treating diseases by administering such polymorphs as pharmaceutical compositions.

Thus, a compound disclosed herein includes all crystalline forms, known as polymorphs. Polymorphs include the different crystal packing arrangements of the same elemental composition of a compound. In certain instances, polymorphs have different X-ray diffraction patterns, infrared spectra, melting points, density, hardness, crystal shape, optical and electrical properties, stability, and solubility. In certain instances, varying the recrystallization solvent, rate of crystallization, storage temperature, or a combination thereof results in a single crystal form dominating.

Prodrugs

In some embodiments, a compound disclosed herein exists as a prodrug. The invention provides for methods of treating diseases by administering such prodrugs. The invention further provides for methods of treating diseases by administering such prodrugs as pharmaceutical compositions.

As used herein, a "prodrugs" is a drug precursor that, following administration to a subject and subsequent absorption, is converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated.

In certain instances, prodrugs are useful as they easier to administer than the parent drug. In certain instances, a prodrug is bioavailable by oral administration whereas the parent is not. In some embodiments, a prodrug has improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug is a short peptide (polyamino acid) bonded to an acid group where the peptide is metabolized to reveal the active moiety.

Various forms of prodrugs include those found, for example in Bundgaard, "Design and Application of Prodrugs" in *A Textbook of Drug Design and Development*, Krosgaard-Larsen and Bundgaard, Ed., 1991, Chapter 5, 113-191, which is incorporated herein by reference for such disclosures.

In some embodiments, prodrugs are designed as reversible drug derivatives, for use as modifiers to enhance drug transport to site-specific tissues. The design of prodrugs to date has been to increase the effective water solubility of the therapeutic compound for targeting to regions where water is the principal solvent.

Additionally, prodrug derivatives of a compound disclosed herein are prepared by methods such as those described in Saulnier et al., *Bioorganic and Medicinal Chemistry Letters*, 1994, 4, 1985). By way of example only, appropriate prodrugs are prepared by reacting a non-derivatized compound with a suitable carbamylating agent, such as, but not limited to, 1,1-acyloxyalkylcarbanochloridate, para-nitrophenyl carbonate, or the like. Prodrug forms of a compound disclosed herein, wherein the prodrug is metabolized in vivo to produce a derivative as set forth herein, are included within the scope of the claims. In some embodiments, some of the herein-described compounds are prodrugs for another derivative or active compound.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound of the present invention.

Pharmaceutically acceptable prodrugs of a compound disclosed herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy or carboxylic groups are converted into prodrugs. For instance, free carboxyl groups are derivatized as amides or alkyl esters. In some embodiments, a prodrug moiety incorporates groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

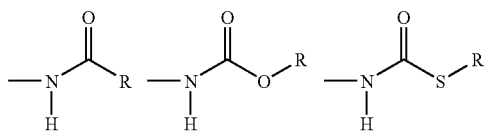

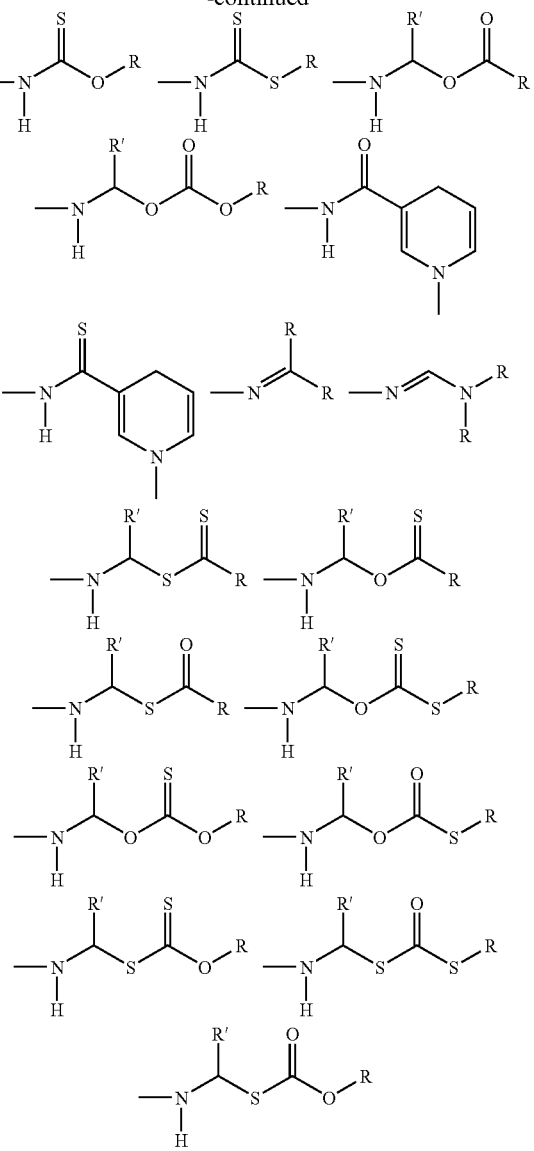

as well as sulfonamides and phosphonamides.

In certain instances, sites on any aromatic ring portions are susceptible to various metabolic reactions. In some embodiments, incorporation of appropriate substituents on the aromatic ring structures reduces, minimizes or eliminates this metabolic pathway.

Pharmacokinetics

In some embodiments, a compound described herein has an in vivo half life of about 2 hours to about 10 hours. In some embodiments, a compound described herein has an in vivo half life of about 2 hours to about 9 hours. In some embodiments, a compound described herein has an in vivo half life of about 2 hours to about 8 hours. In some embodiments, a compound described herein has an in vivo half life of about 2 hours to about 7 hours. In some embodiments, a compound described herein has an in vivo half life of about 2 hours to about 6 hours. In some embodiments, a compound described herein has an in vivo half life of about 2 hours to about 5 hours. In some embodiments, a compound described herein has an in vivo half life of about 2 hours to about 4 hours. In some embodiments, a compound described herein has an in vivo half life of about 2 hours to about 3 hours.

In some embodiments, a compound described herein has an in vivo half life of about 2 hours, about 3 hours, about 4 hours, about 5 hours, about 6 hours, about 7 hours, about 8 hours, about 9 hours, about 10 hours, about 12 hours, about 24 hours, about 2 days, about 3 days, about 4 days, about 5 days, about 6 days, or about 7 days.

In some embodiments, a compound disclosed herein has an in vivo half life of about 2.1 hours, about 2.2 hours, about 2.3 hours, about 2.4 hours, about 2.5 hours, about 2.6 hours, about 2.7 hours, about 2.8 hours, about 2.9 hours, about 3.1 hours, about 3.2 hours, about 3.3 hours, about 3.4 hours, about 3.5 hours, about 3.6 hours, about 3.7 hours, about 3.8 hours, about 3.9 hours.

Pharmaceutical Compositions

Described herein are pharmaceutical compositions. Further described herein are uses of a compound disclosed herein in the preparation of medicaments for the treatment of disorders related to aberrant uric acid levels in a tissue. In some embodiments, the pharmaceutical compositions comprise an effective amount of a compound disclosed herein, or a pharmaceutically acceptable salt, pharmaceutically acceptable N-oxide, pharmaceutically active metabolite, pharmaceutically acceptable prodrug, or pharmaceutically acceptable solvate thereof. In some embodiments, the pharmaceutical compositions comprise an effective amount of a compound disclosed herein, or a metabolite, pharmaceutically acceptable salt, ester, prodrug, solvate, hydrate or derivative thereof and at least one pharmaceutically acceptable carrier.

In some embodiments the pharmaceutical compositions are for the treatment of a disease disclosed herein.

In some embodiments the pharmaceutical compositions are for the treatment of diseases in a mammal. In some embodiments the pharmaceutical compositions are for the treatment of diseases in a human.

Formulations

A compound or composition described herein is administered either alone or in combination with pharmaceutically acceptable carriers, excipients or diluents, in a pharmaceutical composition, according to standard pharmaceutical practice. Administration of a compound or composition described herein is effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration. In some embodiments, the most suitable route depends upon the condition and disease of the recipient. By way of example only, a compound disclosed herein is administered locally to the area in need of treatment by local infusion during surgery, topical application (e.g., as a cream or ointment), injection (e.g., directly into the site of a diseased tissue or organ), catheter, or implant.

In some embodiments, a formulation suitable for oral administration is presented as discrete units such as capsules, cachets or tablets each containing a predetermined amount of a compound or composition disclosed herein; as a powder or granules; as a solution or a suspension in an aqueous liquid or a non-aqueous liquid; or as an oil-in-water liquid emulsion or a water-in-oil liquid emulsion. In some embodiments, a compound or composition disclosed herein is presented as a bolus, electuary or paste.

Pharmaceutical preparations for oral administration include tablets, solutions, suspension, push-fit capsules made of gelatin, as well as soft, sealed capsules made of gelatin and a plasticizer, such as glycerol or sorbitol. In some embodiments, dye or pigment is added to an oral dosage form for identification or to characterize different doses.

In some embodiments, a tablet is made by compression or molding, optionally with one or more accessory ingredients. In some embodiments, a compressed tablet is prepared by compressing in a suitable machine a compound or composition disclosed herein in a free-flowing form such as a powder or granules, optionally mixed with binders, inert diluents, or lubricating, surface active or dispersing agents. In some embodiments, a molded tablet is made by molding in a suitable machine a mixture of the powdered compound moistened with an inert liquid diluent. In some embodiments, a tablet disclosed herein is coated or scored. In some embodiments, a tablet disclosed herein is formulated so as to provide slow or controlled release of a compound or composition disclosed herein therein. In some embodiments, a tablet disclosed herein further comprises an excipient. In some embodiments, a tablet disclosed herein further comprises inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. In some embodiments, a composition comprising a compound disclosed herein further comprises a sweetening agent, flavoring agent, coloring agent, or preserving agents.

In some embodiments, a compound or composition disclosed herein is formulated as a hard gelatin capsule. In some embodiments, a compound or composition disclosed herein is mixed with an inert solid diluent, for example, calcium carbonate, calcium phosphate or kaolin.

In some embodiments, a push-fit capsule contains a compound or composition disclosed herein in admixture with a filler (e.g., lactose, binders such as starches, and/or lubricants such as talc or magnesium stearate and, optionally, stabilizers).

In some embodiments, a soft capsule comprises a compound or composition disclosed herein dissolved or suspended in suitable liquids, such as fatty oils, liquid paraffin, or liquid polyethylene glycols. In some embodiments, a stabilizer is added. In some embodiments, a compound or composition disclosed herein is mixed with a water soluble carrier such as polyethyleneglycol or an oil medium, for example peanut oil, liquid paraffin, or olive oil.

In some embodiments, a dragee core is provided with suitable coatings. In some embodiments, concentrated sugar solutions are used. In some embodiments, the sugar solution comprises gum arabic, talc, polyvinyl pyrrolidone, carbopol gel, polyethylene glycol, and/or titanium dioxide, lacquer solutions, and suitable organic solvents or solvent mixtures.

In some embodiments, a compound or composition disclosed herein is formulated as an aqueous suspension. In some embodiments, a compound or composition disclosed herein further comprises a suspending agent, for example sodium carboxymethylcellulose, methylcellulose, hydroxypropylmethyl-cellulose, sodium alginate, polyvinyl-pyrrolidone, gum tragacanth and gum acacia; or a dispersing or wetting agent (e.g., a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. In some embodiments, a compound or composition disclosed herein further comprises a preservative, for example ethyl, or n-propyl p-hydroxybenzoate; a coloring agent; a flavoring agents; a sweetening agent, such as sucrose, saccharin or aspartame; or combinations thereof.

In some embodiments, a compound or composition disclosed herein is formulated as an oily suspension. In some embodiments, an oily suspension is formulated by suspending a compound or composition disclosed herein in a vegetable oil, for example arachis oil, olive oil, sesame oil or coconut oil, or in mineral oil such as liquid paraffin. In some embodiments, a composition or compound disclosed herein further comprises a thickening agent, for example beeswax, hard paraffin or cetyl alcohol. In some embodiments, a composition or compound disclosed herein further comprises a sweetening agent, a flavoring agent, or a combination thereof. In some embodiments, a composition or compound disclosed herein further comprises an anti-oxidant such as butylated hydroxyanisol or alpha-tocopherol.

In some embodiments, a compound or composition disclosed herein is formulated as an oil-in-water emulsion. In some embodiments, the oily phase is a vegetable oil, for example olive oil or arachis oil, or a mineral oil, for example liquid paraffin or mixtures of these. In some embodiments, an oil-in-water emulsion comprises an emulsifying agent. In some embodiments, the emulsifying agent is a naturally-occurring phosphatides, for example soy bean lecithin, and esters or partial esters derived from fatty acids and hexitol anhydrides, for example sorbitan monooleate, and condensation products of the the partial esters with ethylene oxide, for example polyoxyethylene sorbitan monooleate. In some embodiments, a composition disclosed herein further comprises a sweetening agent, flavoring agent, preservative, or antioxidant.

In some embodiments, a composition or compound disclosed herein is formulated as a syrup or elixir. In some embodiments, a syrup or elixir further comprises a sweetening agent, for example glycerol, propylene glycol, sorbitol or sucrose. In some embodiments, a syrup or elixir further comprises a demulcent, a preservative, a flavoring agent, a coloring agent, and antioxidant, or a combination thereof.

In some embodiments, a compound or composition disclosed herein is formulated for parenteral administration (e.g., by bolus injection or continuous infusion). In some embodiments, a formulation for parenteral administration comprises suspending agents (fatty oils such as sesame oil, or synthetic fatty acid esters, such as ethyl oleate or triglycerides, or liposomes), thickening agents (e.g., sodium carboxymethyl cellulose, sorbitol, or dextran), stabilizing agents, dispersing agents, or combinations thereof. In some embodiments, a formulation for parenteral administration further comprises an antioxidant, buffer, bacteriostat, solute which render the formulation isotonic with blood, or a combination thereof. In some embodiments, a formulation for injection further comprises a preservative.

In some embodiments, a formulation for parenteral administration is an aqueous solution. In some embodiments, a formulation for parenteral administration comprises water, Ringer's solution, or isotonic sodium chloride solution.

In some embodiments, a formulation for parenteral administration is in the form of an oil-in-water micro-emulsion where a compound or composition disclosed herein is dissolved in the oily phase. In some embodiments, the oily phase comprises a mixture of soybean oil and lecithin. In some embodiments, the oily phase is introduced into a water and glycerol mixture and processed to form a microemulsion.

In some embodiments, a formulation for parenteral administration is administered into a patient's blood-stream by local bolus injection. In some embodiments, a continuous intravenous delivery device is utilized. An example of such a device is the Deltec CADD-PLUS™ model 5400 intravenous pump.

In some embodiments, a formulation for parenteral administration is presented in unit-dose or multi-dose containers, for example sealed ampoules and vials. In some embodiments, a formulation for parenteral administration is stored in powder form or in a freeze-dried (lyophilized) condition requiring only the addition of the sterile liquid carrier, for example, saline or sterile pyrogen-free water, prior to use. In some embodiments, a formulation for parenteral administration extemporaneous injection solutions and suspensions are prepared from sterile powders, granules and tablets of the kind previously described.

In some embodiments, a compound or composition disclosed herein is formulated as a depot preparation. In some embodiments, a depot preparation is administered by implantation (for example subcutaneously or intramuscularly) or by intramuscular injection. In some embodiments, a compound or composition disclosed herein is formulated with any suitable polymeric or hydrophobic material (e.g., emulsion in an acceptable oil), ion exchange resin. In some embodiments, a compound disclosed herein is formulated as a sparingly soluble derivatives, for example, as a sparingly soluble salt.

In some embodiments, a compound or composition disclosed herein is formulated for buccal or sublingual administration. In some embodiments, a compound or composition disclosed herein is in the form of a tablet, lozenge, pastille, or gel. In some embodiments, formulation for buccal or sublingual administration further comprises a flavoring agent (e.g., sucrose, acacia, or tragacanth).

In some embodiments, a compound or composition disclosed herein is formulated for rectal administration (e.g., as a suppository or retention enema). In some embodiments, a compound or composition disclosed herein is formulated as a suppository. In some embodiments, a rectal formulation comprises a non-irritating excipient which is solid at ordinary temperatures but liquid at the rectal temperature. In some embodiments, a rectal formulation comprises cocoa butter, glycerinated gelatin, hydrogenated vegetable oils, mixtures of polyethylene glycols of various molecular weights and fatty acid esters of polyethylene glycol.

In some embodiments, a compound or composition disclosed herein is administered topically, that is by non-systemic administration. In some embodiments, a compound or composition disclosed herein is administered to the epidermis or the buccal cavity. In some embodiments, a compound or composition disclosed herein is formulated as a gel, liniment, lotion, cream, ointment, paste, or solution (e.g., as drops suitable for administration to the eye, ear or nose). In some embodiments, compound disclosed herein comprises from about 0.001% to 10% w/w of a topical formulation. In some embodiments, compound disclosed herein comprises from about 1% to 2% by weight of a topical formulation. In some embodiments, compound disclosed herein comprises about 10% w/w of a topical formulation; preferably, less than 5% w/w; more preferably from 0.1% to 1% w/w.

In some embodiments, a pharmaceutical formulation for administration by inhalation is delivered from an insufflator, nebulizer pressurized packs or other means of delivering an aerosol spray. In some embodiments, a pressurized pack comprises a suitable propellant (e.g., dichlorodifluoromethane, trichlorofluoromethane, dichlorotetrafluoroethane, or carbon dioxide). In some embodiments, a device for administering an inhalable formulation comprises a meter. In some embodiments, a pharmaceutical formulation for administration by inhalation is in the form of a dry powder composition, for example a powder mix of the compound and a suitable powder base such as lactose or starch. In some embodiments, the powder composition is presented in unit dosage form, in for example, capsules, cartridges, gelatin or blister packs from which the powder is administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Doses

Disclosed herein, in certain embodiments, are methods of treating a disorder characterized by aberrant levels of uric acid is a tissue. In some embodiments, the method involves administration of a composition or formulation disclosed herein in an effective amount. In some embodiments, the method involves administration of a composition or formulation disclosed herein in a therapeutically effective amount.

The effective amount of a compound, composition, or formulation disclosed herein will firstly be dependent on the mammal being treated. In the instances where the compound, composition, or formulation disclosed herein is administered to a human, the daily dosage will normally be determined by the prescribing physician with the dosage generally varying according to the age, sex, diet, weight, general health and response of the individual patient, the severity of the patient's symptoms, the precise indication or condition being treated, the severity of the indication or condition being treated, time of administration, route of administration, the disposition of the composition, rate of excretion, drug combination, and the discretion of the prescribing physician. In some embodiments, treatment is initiated with smaller dosages which are less than the optimum dose; thereafter, the dosage is increased by small amounts until the optimum effect under the circumstances is reached. In some embodiments, the total daily dosage is divided and administered in portions. The amount and frequency of administration of the compound, composition, or formulation disclosed herein, and if applicable other therapeutic agents and/or therapies, will be regulated according to the judgment of the attending clinician.

In some embodiments, the dosage is between about 0.001 mg/kg of body weight to about 100 mg/kg of body weight per day (administered in single or divided doses), more preferably at least about 0.1 mg/kg of body weight per day. In some embodiments, the dosage is from about 0.01 mg/kg of body weight per day to about 7000 mg/kg of body weight per day of compound, and preferably includes, e.g., from about 0.05 mg/kg of body weight per day to about 2500 mg/kg of body weight per day. In some embodiments, the dosage is from about 0.1 mg/kg of body weight per day to 1000 mg/kg of body weight per day, from about 1 mg/kg of body weight per day to about 500 mg/kg of body weight per day, from about 1 mg/kg of body weight per day to about 250 mg/kg of body weight per day, from about 1 mg/kg of body weight per day to about 100 mg/kg of body weight per day, from about 1 mg/kg of body weight per day to about 50 mg/kg of body weight per day, from about 1 mg/kg of body weight per day to about 20 mg/kg of body weight per day, from about 1 mg/kg of body weight per day to about 10 mg/kg of body weight per day according to the particular application. In some embodiments, the dosage is from about 1 mg/kg of body weight to about 5 mg/kg of body weight. In some embodiments, the dosage is from about 2 mg/kg of body weight to about 4 mg/kg of body weight. In some embodiments, the dosage is about 3 mg/kg of body weight. In some instances, dosage levels below the lower limit of the aforementioned range may be more than adequate, while in other cases still larger doses may be employed without causing any harmful side effect, e.g. by dividing such larger doses into several small doses for administration throughout the day. The amount administered will vary depending on the particular $IC_{50}$ value of the compound used. In combinational applications in which the compound is not the sole therapy, it may be possible to administer lesser amounts of compound and still have therapeutic or prophylactic effect.

In certain embodiments, a dose of any compound described herein (e.g., a compound of Formula (I) or Formula (II)) that is effective for reducing uric acid levels in the blood/serum of an individual displaying aberrant uric acid levels is at least 100 mg of a compound disclosed herein, at least 200 mg of a compound disclosed herein, at least 300 mg of a compound disclosed herein, at least 400 mg of a compound disclosed herein, at least 500 mg of a compound disclosed herein, at least 600 mg of a compound disclosed herein, least 700 mg of a compound disclosed herein, at least 800 mg of a compound disclosed herein, at least 900 mg of a compound disclosed herein, or at least 1 g of a compound disclosed herein.

In certain embodiments, a dose of a compound described herein is administered to an individual in need thereof once a day, twice a day, three times a day, four times a day or any other frequency based on the judgement of an attending physician. In some embodiments, a dose is administered before a meal. In some instances a dose is administered after a meal. In some embodiments, a dose is administered without food.

In the case wherein the individual's condition does not improve, upon the doctor's discretion a compound disclosed herein is optionally administered chronically, that is, for an extended period of time, including throughout the duration of the individual's life in order to ameliorate or otherwise control or limit the symptoms of the individual's disease or condition.

In the case wherein the individual's status does improve, upon the doctor's discretion a compound disclosed herein is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the individual's disease has occurred, a maintenance dose is administered if necessary. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms.

Combination Therapies

In some embodiments, a compound or composition disclosed herein is administered as a sole therapy. In some embodiments, a compound or composition disclosed herein is administered in combination with an additional active agent.

In some embodiments, the therapeutic effectiveness of a compound disclosed herein is enhanced by administration of an adjuvant. In some embodiments, the benefit experienced by an individual is increased by administering a compound or composition disclosed herein with another therapeutic agent. In some embodiments, the therapeutic effectiveness of a compound disclosed herein is enhanced by administration of physiotherapy, psychotherapy, radiation therapy, application of compresses to a diseased area, rest, altered diet, and the like.

By way of example only, in a treatment for gout the therapeutic effectiveness of a compound disclosed herein is increased by also providing the patient with another therapeutic agent for gout. Or, by way of example only, if one of the side effects experienced by a patient upon receiving one of a compound disclosed herein is nausea, then an anti-nausea agent is administered in combination with the compound.

In some embodiments, a compound disclosed herein is not administered in the same pharmaceutical composition as the additional therapeutic agent. In some embodiments, a compound disclosed herein is administered by a different route than the additional therapeutic agent. For example, a compound or composition disclosed herein is administered orally, while the additional therapeutic agent is administered intravenously.

In some embodiments, a compound or composition disclosed herein and an additional therapeutic agent (or additional therapy) are administered concurrently (e.g., simultaneously, essentially simultaneously or within the same treatment protocol), sequentially or dosed separately.

The particular choice of compound and other therapeutic agent will depend upon the diagnosis of the attending physicians and their judgment of the condition of the individual and the appropriate treatment protocol. In some embodiments, the additional agent is a URAT 1 inhibitor, a xanthine oxidase inhibitor, a xanthine dehydrogenase, a xanthine oxidoreductase inhibitor, a purine nucleoside phosphorylase (PNP) inhibitor, a uric acid transporter inhibitor, a glucose transporter (GLUT) inhibitor, a GLUT-9 inhibitor, a solute carrier family 2 (facilitated glucose transporter), member 9 (SLC2A9) inhibitor, an organic anion transporter (OAT) inhibitor, an OAT-4 inhibitor, or combinations thereof. In certain instances, URAT 1 is an ion exchanger that mediates urate transportation. In certain instances, URAT I mediates urate transportation in the proximal tubule. In certain instances, URAT I exchanges urate in a proximal tubule for lactate and nicotinate. In certain instances, xanthine oxidase oxidizes hypoxanthine to xanthine, and further to uric acid. In certain instances, xanthine dehydrogenase catalyzes the conversion of xanthine, $NAD^+$, and $H_2O$ into urate, NADH, and $H^+$. In some embodiments, the additional agent is allopurinol, febuxostat (2-(3-cyano-4-isobutoxyphenyl)-4-methyl-1,3-thiazole-5-carboxylic acid), FYX-051 (4-(5-pyridin-4-yl-1H-[1,2,4]triazol-3-yl)pyridine-2-carbonitrile), probenecid, sulfinpyrazone, benzbromarone, acetaminophen, steroids, nonsteroidal anti-inflammatory drugs (NSAIDs), adrenocorticotropic hormone (ACTH), colchicine, a glucorticoid, an androgen, a cox-2 inhibitor, a PPAR agonist, naproxen, sevelamer, sibutmaine, troglitazone, proglitazone, another uric acid lowering agent, losartan, fibric acid, benziodarone, salicylate, anlodipine, vitamin C, or combinations thereof.

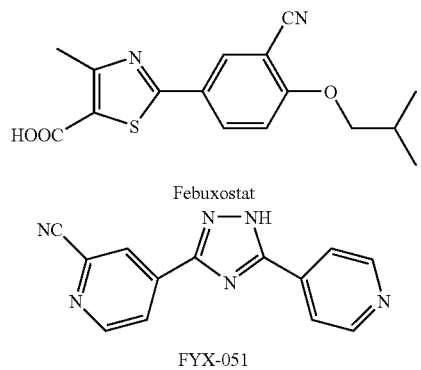

Diseases

Described herein are methods of treating a disease in an individual suffering from the disease comprising administering to the individual an effective amount of a composition comprising a compound disclosed herein or a pharmaceutically acceptable salt, solvate, polymorph, ester, tautomer or prodrug thereof.

Also described herein are methods of preventing or delaying onset of a disease in an individual at risk for developing the disease comprising administering to the individual an effective amount to prevent or delay onset of the disease, of a composition comprising a compound disclosed herein or a pharmaceutically acceptable salt, solvate, polymorph, ester, tautomer or prodrug thereof Further described herein are methods for the prophylaxis or treatment of any disease or disorder in which aberrant levels of uric acid plays a role including, without limitation: hyperuricemia, gout, gouty arthritis, inflammatory arthritis, kidney disease, nephrolithiasis (kidney stones), joint inflammation, deposition of urate crystals in joints, urolithiasis (formation of calculus in the urinary tract), deposition of urate crystals in renal parenchyma, Lesch-Nyhan syndrome, Kelley-Seegmiller syndrome, gout flare, tophaceous gout, kidney failure, or combinations thereof in a human or other mammal. The methods disclosed herein extend to such a use and to the use of the compounds for the manufacture of a medicament for treating such diseases or disorders. Further, the methods disclosed herein extend to the administration to a human an effective amount of a compound disclosed herein for treating any such disease or disorder.

Individuals that are able to be treated with a compound described herein, or a pharmaceutically acceptable salt, ester, prodrug, solvate, hydrate or derivative of the compound, according to the methods of this invention include, for example, individuals that have been diagnosed as having gout, gouty arthritis, inflammatory arthritis, kidney disease, nephrolithiasis (kidney stones), joint inflammation, deposition of urate crystals in joints, urolithiasis (formation of calculus in the urinary tract), deposition of urate crystals in renal parenchyma, Lesch-Nyhan syndrome, Kelley-Seegmiller syndrome, gout flare, tophaceous gout, kidney failure, or combinations thereof.

In some embodiments, an individual having an aberrant uric acid level is administered an amount of at least one compound disclosed herein sufficient to modulate the aberrant uric acid level (e.g., to a medically-acceptable level). In some embodiments, an individual treated with a compound disclosed herein displays aberrant uric acid levels wherein the uric acid levels in blood exceed a medically-accepted range (i.e., hyperuricemia). In some embodiments, an individual treated with a compound disclosed herein displays aberrant uric acid levels wherein uric acid levels in the blood exceed 360 μmol/L (6 mg/dL) for a female individual or 400 μmol/L (6.8 mg/dL) for a male individual. In some embodiments, an individual treated with a compound disclosed herein displays aberrant uric acid levels wherein uric acid levels in urine exceed a medically-accepted range (i.e., hyperuricosuria). In some embodiments, an individual treated with a compound disclosed herein displays aberrant uric acid levels wherein uric acid levels in urine exceed 800 mg/day (in a male individual) and greater than 750 mg/day (in a female individual).

In some embodiments, an individual treated with a compound disclosed herein (1) displays aberrant uric acid levels, and (2) suffers from a cardiovascular disease. In some embodiments, an individual treated with a compound disclosed herein (1) displays aberrant uric acid levels, and (2) suffers from an aneurysm; angina; atherosclerosis; a stroke; cerebrovascular disease; congestive heart failure; coronary artery disease; and/or a myocardial infarction. In some embodiments, an individual treated with a compound disclosed herein (1) displays aberrant uric acid levels, and (2) displays (a) c-reactive protein (CRP) levels above about 3.0 mg/L; (b) homocysteine levels above about 15.9 mmol/L; (c) LDL levels above about 160 mg/dL; (d) HDL levels below about 40 mg/dL; and/or (e) serum creatinine levels above about 1.5 mg/dL.

In some embodiments, an individual treated with a compound disclosed herein (1) displays aberrant uric acid levels, and (2) suffers from diabetes. In some embodiments, an individual treated with a compound disclosed herein (1) displays aberrant uric acid levels, and (2) suffers from Type I diabetes. In some embodiments, an individual treated with a compound disclosed herein (1) displays aberrant uric acid levels, and (2) suffers from Type II diabetes. In some embodiments, an individual treated with a compound disclosed herein (1) displays aberrant uric acid levels, and (2) suffers from a loss of beta cells of the islets of Langerhans in the pancreas. In some embodiments, an individual treated with a compound disclosed herein (1) displays aberrant uric acid levels, and (2) suffers from insulin resistance and/or reduced insulin sensitivity. In some embodiments, an individual treated with a compound disclosed herein (1) displays aberrant uric acid levels, and (2) displays (a) a fasting plasma glucose level ≧126 mg/dL; (b) a plasma glucose level ≧200 mg/dL two hours after a glucose tolerance test; and/or (c) symptoms of hyperglycemia and casual plasma glucose levels ≧200 mg/dL (11.1 mmol/l).

In some embodiments, an individual treated with a compound disclosed herein (1) displays aberrant uric acid levels, and (2) suffers from metabolic syndrome. In some embodiments, an individual treated with a compound disclosed herein (1) displays aberrant uric acid levels, and (2) suffers from (a) diabetes mellitus, impaired glucose tolerance, impaired fasting glucose and/or insulin resistance, (b) at least two of (i) blood pressure: ≧140/90 mmHg; (ii) dyslipidaemia: triglycerides (TG): ≧1.695 mmol/L and high-density lipoprotein cholesterol (HDL-C) ≦0.9 mmol/L (male), ≦1.0 mmol/L (female); (iii) central obesity: waist:hip ratio >0.90 (male); >0.85 (female), and/or body mass index >30 kg/m2; and (iv) microalbuminuria: urinary albumin excretion ratio ≧20 mg/min or albumin:creatinine ratio ≧30 mg/g. In some embodiments, an individual treated with a compound disclosed herein (1) displays aberrant uric acid levels, and (2) suffers from insulin resistance (i.e., the top 25% of the fasting insulin values among non-diabetic individuals) and (b) at least two of (i) central obesity: waist circumference ≧94 cm (male), ≧80 cm (female); (ii) dyslipidaemia: TG ≧2.0 mmol/L and/or HDL-C <1.0 mmol/L or treated for dyslipidaemia; (iii) hypertension: blood pressure ≧140/90 mmHg or antihypertensive medication; and (iv) fasting plasma glucose ≧6.1 mmol/L. In some embodiments, an individual treated with a compound disclosed herein (1) displays aberrant uric acid levels, and (2) displays at least three of (a) elevated waist circumference: Men ≧40 inches (men) and ≧35 inches (women); (b) elevated triglycerides: ≧150 mg/dL; (c) reduced HDL: <40 mg/dL (men) and <50 mg/dL (women); (d) elevated blood pressure: ≧130/85 mm Hg or use of medication for hypertension; and (e) elevated fasting glucose: ≧100 mg/dL (5.6 mmol/L) or use of medication for hyperglycemia.

In some embodiments, an individual treated with a compound disclosed herein (1) displays aberrant uric acid levels, and (2) suffers from kidney disease or kidney failure. In some embodiments, an individual treated with a compound disclosed herein (1) displays aberrant uric acid levels, and (2) displays oliguria (decreased urine production. In some embodiments, an individual treated with a compound disclosed herein (1) displays aberrant uric acid levels, and (2) produces less than 400 mL per day of urine (adults), produces less than 0.5 mL/kg/h of urine (children), or produces less than 1 mL/kg/h of urine (infants).

Uric Acid

Disclosed herein, in certain embodiments, is a method of reducing uric acid levels in the tissue of an individual in need thereof In some embodiments, the method reduces uric acid levels in the blood/serum of an individual in need thereof. In some embodiments, a compound disclosed herein reduces uric acid levels in an individual in need thereof by about 110 μmol/L to about 140 μmol/L from the uric acid levels in the blood/serum of the individual prior to administration of the compound. In some embodiments, a compound disclosed herein reduces uric acid levels in an individual in need thereof by about 120 μmol/L to about 130 μmol/L from the uric acid levels in the blood/serum of the individual prior to administration of the compound. In some embodiments, a compound disclosed herein reduces uric acid levels in an individual in need thereof by about 125 μmol/L to about 135 μmol/L from the uric acid levels in the blood/serum of the individual prior to administration of the compound.

In some embodiments, the method reduces uric acid levels in the blood/serum of an individual in need thereof. In some embodiments, a compound disclosed herein reduces uric acid levels in an individual in need thereof by about 25 μmol/L, about 30 about μmol/L, about 40 μmol/L, about 50 μmol/L, about 60 μmol/L, about 70 μmol/L, about 75 μmol/L, about 80 μmol/L, about 85 μmol/L, about 90 μmol/L, about 95 μmol/L, about 100 μmol/L, about 105 μmol/L, about 110 μmol/L, about 115 μmol/L, about 120 μmol/L, about 125 μmol/L, about 130 μmol/L, about 135 μmol/L, about 140 μmol/L, about 145 μmol/L, about 150 μmol/L, about 155 μmol/L, about 160 μmol/L, about 165 μmol/L, about 170 μmol/L, about 175 μmol/L, about 180 μmol/L, about 185 μmol/L, about 190 μmol/L, about 195 μmol/L, about 200 μmol/L, about 205 μmol/L, about 210 μmol/L, about 215 μmol/L, about 220 μmol/L, about 225 μmol/L, about 230 μmol/L, about 235 μmol/L, about 240 μmol/L, about 245 μmol/L, or about 250 μmol/L, compared to the uric acid levels in the blood/serum of the individual prior to administration of the compound.

In certain instances, purines (i.e., adenine, guanine), derived from food or tissue turnover (cellular nucleotides undergo continuous turnover), are catabolized in humans to their final oxidation product, uric acid. In certain instances, guanine is oxidized to xanthine, which is turn is further oxidized to uric acid by the action of xanthine oxidase; adenosine is converted to inosine which is further oxidized to hypoxanthine. In certain instances, xanthine oxidase oxidizes hypoxanthine to xanthine, and further to uric acid. In certain instances, as part of the reverse process, the enzyme hypoxanthine-guanine phosphoribosyltransferase (HGPRT) salvages guanine and hypoxanthine.

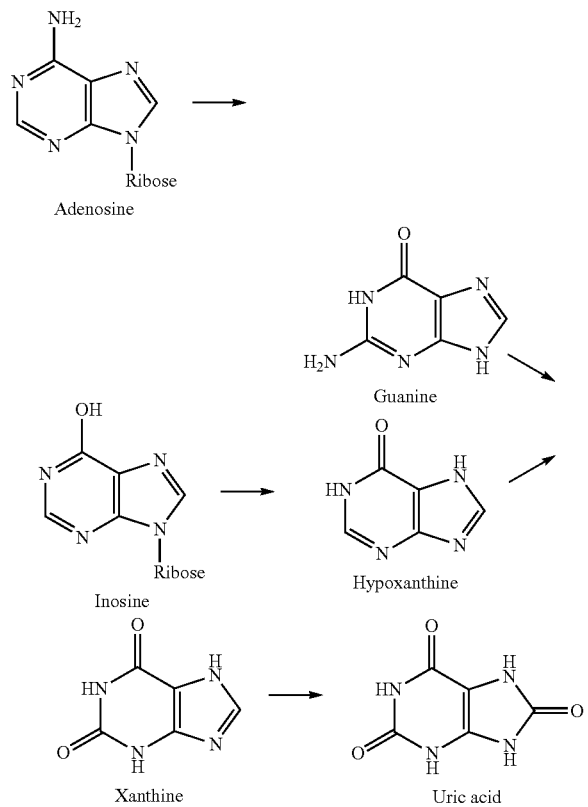

In certain instances, the keto form of uric acid is in equilibrium with the enol form which loses a proton at physiological pH to form urate. In certain instances, (e.g., under serum conditions (pH 7.40, 37° C.)), about 98% of uric acid is ionized as the monosodium urate salt. In certain instances, urate is a strong reducing agent and potent antioxidant. In humans, about half the antioxidant capacity of plasma comes from uric acid.

One of the peculiar characteristics of the uric acid transport system is that, although the net activity of tubular function is reabsorption of uric acid, the molecule is both secreted and reabsorbed during its passage through the nephron. In certain instances, reabsorption dominates in the S1 and S3 segments of the proximal tubule and secretion dominates in the S2 segment. In certain instances, the bidirectional transport results in drugs that inhibit uric acid transport decreasing, rather than increasing, the excretion of uric acid, compromising their therapeutic usefulness. In certain instances, normal uric acid levels in human adults (5.1+/−0.93 mg/dL) are close to the limits of urate solubility (~7 mg/dL at 37° C.), which creates a delicate physiologic urate balance. In certain instances, the normal uric acid range for females is approximately 1 mg/dL below the male range.

Hyperuricemia

In certain instances, hyperuricemia is characterized by higher than normal blood levels of uric acid, sustained over long periods of time. In certain instances, increased blood urate levels may be due to enhanced uric acid production (~10-20%) and/or reduced renal excretion (~80-90%) of uric acid. In certain instances, causes of hyperuricemia may include:

Obesity/weight gain

Excessive alcohol use

Excessive dietary purine intake (foods such as shellfish, fish roe, scallops, peas lentils, beans and red meat, particularly offal—brains, kidneys, tripe, liver)

Certain medications, including low-dose aspirin, diuretics, niacin, cyclosporine, pyrazinamide, ethambutol, some high blood pressure drugs and some cancer chemotherapeutics, immunosuppressive and cytotoxic agents Specific disease states, particularly those associated with a high cell turnover rate (such as malignancy, leukemia, lymphoma or psoriasis), and also including high blood pressure, hemoglobin diseases, hemolytic anemia, sickle cell anemia, various nephropathies, myeloproliferative and lymphoproliferative diseases, hyperparathyroidism, renal disease, conditions associated with insulin resistance and diabetes mellitus, and in transplant recipients, and possibly heart disease Inherited enzyme defects Abnormal kidney function (e.g. increased ATP turn over, reduced glomerular urate filtration)

Exposure to lead (plumbism or "saturnine gout")

In certain instances, hyperuricemia may be asymptomatic, though is associated with the following conditions: gout, gouty arthritis, uric acid stones in the urinary tract (urolithi-

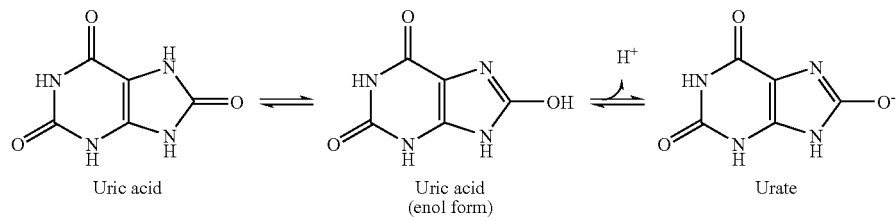

In certain instances, most uric acid dissolves in blood and passes to the kidneys, where it is excreted by glomerular filtration and tubular secretion. In certain instances, a substantial fraction of uric acid is reabsorbed by the renal tubules.

asis), deposits of uric acid in the soft tissue (tophi), deposits of uric acid in the kidneys (uric acid nephropathy), and impaired kidney function, possibly leading to chronic and acute renal failure.

Gout

Prevalence

The incidence of gout has increased over the past two decades and, in the United States, affects as much as 2.7% of the population aged 20 years and older, totaling over 5.1 million American adults. Gout is more common in men than women, (3.8% or 3.4 million men vs. 1.6% or 1.7 million women), typically affecting men in their 40's and 50's (although gout attacks can occur after puberty which sees an increase in uric acid levels). An increase in prevalence of gout from 2.9 to 5.2 per 1000 in the time period 1990 to 1999 was observed, with most of the increase occurring in those over the age of 65. Gout attacks are more common in women after menopause. In certain instances, gout is one of the most common forms of arthritis, accounting for approximately 5% of all arthritis cases. In certain instances, kidney failure and urolithiasis occur in 10-18% of individuals with gout and are common sources of morbidity and mortality from the disease.

Leading Causes

In most cases, gout is associated with hyperuricemia. In certain instances, individuals suffering from gout excrete approximately 40% less uric acid than nongouty individuals for any given plasma urate concentration. In certain instances, urate levels increase until the saturation point is reached. In certain instances, precipitation of urate crystals occurs when the saturation point is reached. In certain instances, these hardened, crystallized deposits (tophi) form in the joints and skin, causing joint inflammation (arthritis). In certain instances, deposits are be made in the joint fluid (synovial fluid) and/or joint lining (synovial lining). Common areas for these deposits are the large toe, feet, ankles and hands (less common areas include the ears and eyes). In certain instances, the skin around an affected joint becomes red and shiny with the affected area being tender and painful to touch. In certain instances, gout attacks increase in frequency. In certain instances, untreated acute gout attacks lead to permanent joint damage and disability. In certain instances, tissue deposition of urate leads to: acute inflammatory arthritis, chronic arthritis, deposition of urate crystals in renal parenchyma and urolithiasis. In certain instances, the incidence of gouty arthritis increases 5 fold in individuals with serum urate levels of 7 to 8.9 mg/dL and up to 50 fold in individuals with levels >9 mg/dL (530 µmol/L). In certain instances, individuals with gout develop renal insufficiency and end stage renal disease (i.e., "gouty nephropathy"). In certain instances, gouty nephropathy is characterized by a chronic interstitial nephropathy, which is promoted by medullary deposition of monosodium urate.

In certain instances, gout includes painful attacks of acute, monarticular, inflammatory arthritis, deposition of urate crystals in joints, deposition of urate crystals in renal parenchyma, urolithiasis (formation of calculus in the urinary tract), and nephrolithiasis (formation of kidney stones). In certain instances, secondary gout occurs in individuals with cancer, particularly leukemia, and those with other blood diseases (e.g. polycythemia, myeloid metaplasia, etc).

Symptoms

In certain instances, attacks of gout develop very quickly, frequently the first attack occurring at night. In certain instances, symptoms include sudden, severe joint pain and extreme tenderness in the joint area, joint swelling and shiny red or purple skin around the joint. In certain instances, the attacks are infrequent lasting 5-10 days, with no symptoms between episodes. In certain instances, attacks become more frequent and last longer, especially if the disease is not controlled. In certain instances, episodes damage the affected joint(s) resulting in stiffness, swelling, limited motion and/or persistent mild to moderate pain.

Treatment

In certain instances, gout is treated by lowering the production of uric acid. In certain instances, gout is treated by increasing the excretion of uric acid. In certain instances, gout is treated by URAT 1, xanthine oxidase, xanthine dehydrogenase, xanthine oxidoreductase, a purine nucleoside phosphorylase (PNP) inhibitor, a uric acid transporter (URAT) inhibitor, a glucose transporter (GLUT) inhibitor, a GLUT-9 inhibitor, a solute carrier family 2 (facilitated glucose transporter), member 9 (SLC2A9) inhibitor, an organic anion transporter (OAT) inhibitor, an OAT-4 inhibitor, or combinations thereof. In general, the goals of gout treatment are to i) reduce the pain, swelling and duration of an acute attack, and ii) prevent future attacks and joint damage. In certain instances, gout attacks are treated successfully using a combination of treatments. In certain instances, gout is one of the most treatable forms of arthritis.

i) Treating the gout attack. In certain instances, the pain and swelling associated with an acute attack of gout can be addressed with medications such as acetaminophen, steroids, nonsteroidal anti-inflammatory drugs (NSAIDs), adrenocorticotropic hormone (ACTH) or colchicine. In certain instances, proper medication controls gout within 12 to 24 hours and treatment is stopped after a few days. In certain instances, medication is used in conjunction with rest, increased fluid intake, ice-packs, elevation and/or protection of the affected area/s. In certain instances, the aforementioned treatments do not prevent recurrent attacks and they do not affect the underlying diseases of abnormal uric acid metabolism.

ii) Preventing future attacks. In certain instances, reducing serum uric acid levels below the saturation level is the goal for preventing further gout attacks. In some cases, this is achieved by decreasing uric acid production (e.g. allopurinol), or increasing uric acid excretion with uricosuric agents (e.g. probenecid, sulfinpyrazone, benzbromarone).

In certain instances, allopurinol inhibits uric acid formation, resulting in a reduction in both the serum and urinary uric acid levels and becomes fully effective after 2 to 3 months.

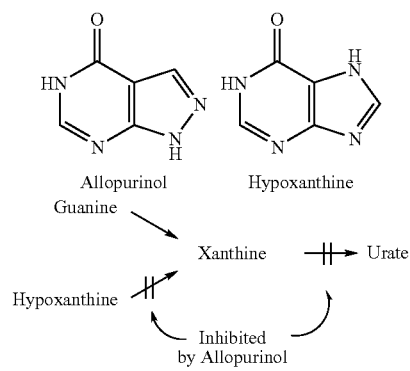

In certain instances, allopurinol is a structural analogue of hypoxanthine, (differing only in the transposition of the carbon and nitrogen atoms at positions 7 and 8), which inhibits the action of xanthine oxidase, the enzyme responsible for the conversion of hypoxanthine to xanthine, and xanthine to uric acid. In certain instances, it is metabolized to the corresponding xanthine analogue, alloxanthine (oxypurinol), which is also an inhibitor of xanthine oxidase. In certain instances, alloxanthine, though more potent in inhibiting xanthine oxidase, is less pharmaceutically acceptable due to low oral bioavailability. In certain instances, fatal reactions due to hypersensitivity, bone marrow suppression, hepatitis, and vasculitis have been reported with Allopurinol. In certain instances, the incidence of side effects may total 20% of all individuals treated with the drug. Treatment for diseases of uric acid metabolism has not evolved significantly in the following two decades since the introduction of allopurinol.

In certain instances, uricosuric agents (e.g., probenecid, sulfinpyrazone, and benzbromarone) increase uric acid excretion. In certain instances, probenecid causes an increase in uric acid secretion by the renal tubules and, when used chronically, mobilizes body stores of urate. In certain instances, 25-50% of individuals treated with probenecid fail to achieve reduction of serum uric acid levels <6 mg/dL. In certain instances, insensitivity to probenecid results from drug intolerance, concomitant salicylate ingestion, and renal impairment. In certain instances, one-third of the individuals develop intolerance to probenecid. In certain instances, administration of uricosuric agents also results in urinary calculus, gastrointestinal obstruction, jaundice and anemia.

Plumbism or "Saturnine Gout"

In certain instances, excessive exposure to lead (lead poisoning or plumbism) results in "saturnine gout," a lead-induced hyperuricemia that results from lead inhibition of tubular urate transport causing decreased renal excretion of uric acid. In certain instances, more than 50% of individuals suffering from lead nephropathy suffer from gout. In certain instances, acute attacks of saturnine gout occur in the knee more frequently than the big toe. In certain instances, renal disease is more frequent and more severe in saturnine gout than in primary gout. In certain instances, treatment consists of excluding the individual from further exposure to lead, the use of chelating agents to remove lead, and control of acute gouty arthritis and hyperuricaemia. In certain instances, saturnine gout is characterized by less frequent attacks than primary gout. In certain instances, lead-associated gout occurs in pre-menopausal women, an uncommon occurrence in non lead-associated gout.

Lesch-Nyhan Syndrome

In certain instances, Lesch-Nyhan syndrome (LNS or Nyhan's syndrome) affects about one in 100,000 live births. In certain instances, LNS is caused by a genetic deficiency of the enzyme hypoxanthine-guanine phosphoribosyltransferase (HGPRT). In certain instances, LNS is an X-linked recessive disease. In certain instances, LNS is present at birth in baby boys. In certain instances, the disease leads to severe gout, poor muscle control, and moderate mental retardation, which appear in the first year of life. In certain instances, the disease also results in self-mutilating behaviors (e.g., lip and finger biting, head banging) beginning in the second year of life. In certain instances, the disease also results in gout-like swelling in the joints and severe kidney problems. In certain instances, the disease leads neurological symptoms include facial grimacing, involuntary writhing, and repetitive movements of the arms and legs similar to those seen in Huntington's disease. The prognosis for individuals with LNS is poor. In certain instances, the life expectancy of an untreated individual with LNS is less than about 5 years. In certain instances, the life expectancy of a treated individual with LNS is greater than about 40 years of age.

Hyperuricemia and Other Diseases

In certain instances, hyperuricemia is found in individuals with cardiovascular disease (CVD) and/or renal disease. In certain instances, hyperuricemia is found in individuals with prehypertension, hypertension, increased proximal sodium reabsorption, microalbuminuria, proteinuria, kidney disease, obesity, hypertriglyceridemia, low high-density lipoprotein cholesterol, hyperinsulinemia, hyperleptinemia, hypoadiponectinemia, peripheral, carotid and coronary artery disease, atherosclerosis, congestive heart failure, stroke, tumor lysis syndrome, endothelial dysfunction, oxidative stress, elevated renin levels, elevated endothelin levels, and/or elevated C-reactive protein levels. In certain instances, hyperuricemia is found in individuals with obesity (e.g., central obesity), high blood pressure, hyperlipidemia, and/or impaired fasting glucose. In certain instances, hyperuricemia is found in individuals with metabolic syndrome. In certain instances, gouty arthritis is indicative of an increased risk of acute myocardial infarction. In some embodiments, administration of a compound described herein to an individual are useful for decreasing the likelihood of a clinical event associated with a disease or condition linked to hyperuricemia, including, but not limited to, prehypertension, hypertension, increased proximal sodium reabsorption, microalbuminuria, proteinuria, kidney disease, obesity, hypertriglyceridemia, low high-density lipoprotein cholesterol, hyperinsulinemia, hyperleptinemia, hypoadiponectinemia, peripheral, carotid and coronary artery disease, atherosclerosis, congestive heart failure, stroke, tumor lysis syndrome, endothelial dysfunction, oxidative stress, elevated renin levels, elevated endothelin levels, and/or elevated C-reactive protein levels.

In some embodiments, a compound described herein is administered to an individual suffering from a disease or condition requiring treatment with a diuretic. In some embodiments, a compound described herein are administered to an individual suffering from a disease or condition requiring treatment with a diuretic, wherein the diuretic causes renal retention of urate. In some embodiments, the disease or condition is congestive heart failure or essential hypertension.

In some embodiments, administration of a compound described herein to an individual is useful for improving motility or improving quality of life.

In some embodiments, administration of a compound described herein to an individual is useful for treating or decreasing the side effects of cancer treatment.

In some embodiments, administration of a compound described herein to an individual is useful for decreasing kidney toxicity of cis-platin.

EXAMPLES

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

I Chemical Syntheses

Example 1A 2-(5-Bromo-1-(4-cyanonaphthalen-1-yl)-1H-imidazol-2-ylthio)acetic acid

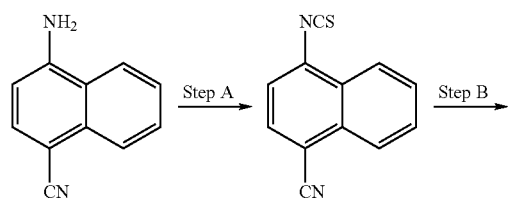

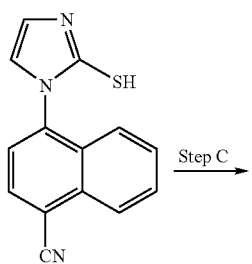

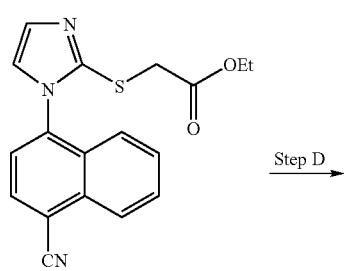

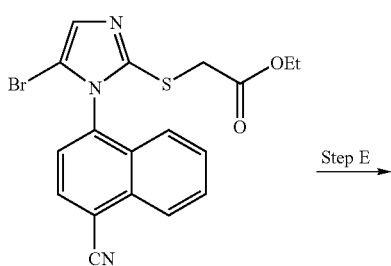

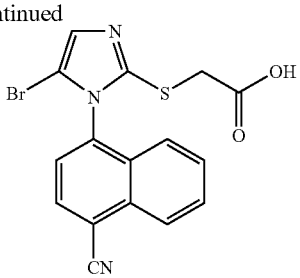

Step A: 4-Isothiocyanato-1-naphthonitrile

Thiophosgene (9.1 mL, 118.9 mmol) was added to a stirring slurry of 4-amino-1-naphthalenecarbonitrile (10 g, 59.45 mmol) in dichloromethane (200mL) and saturated aqueous NaHCO₃ solution (200 mL) at 0° C., and the mixture stirred for 3 days at room temp. The layers were separated and the organic layer concentrated to provide 4-isothiocyanato-1-naphthonitrile as a tan solid (11.64 g, 93%).

Step B: 4-(2-Mercapto-1H-imidazol-1-yl)-1-naphthonitrile

Aminoacetaldehyde dimethyl acetal (5.98 mL, 55.36 mmol) was added to a stirring slurry of 4-isothiocyanato-1-naphthonitrile (11.64 g, 55.36 mmol) in dioxane (55 mL), and stirring continued for 1 h (sizeable exotherm observed). HCl was added (4.8 mL, 58.13 mmol) and the mixture heated to 105° C. for 18 h. The mixture was then concentrated, methanol added (100 mL), concentrated again, more methanol added (100 mL) and sonicated. Filtration provided 4-(2-mercapto-1H-imidazol-1-yl)-1-naphthonitrile as a tan solid (8.33 g, 60%).

Step C: Ethyl 2-(1-(4-cyanonaphthalen-1-yl)-1H-imidazol-2-ylthio)acetate

Triethylamine (4.92 mL, 35.32 mmol), followed by ethyl bromoacetate (3.74 mL, 33.72 mmol) were added to a stirring slurry of 4-(2-mercapto-1H-imidazol-1-yl)-1-naphthonitrile (8.07 g, 32.11 mmol) in dichloromethane (60 mL) and stirring continued for 3 h. The mixture was washed with aqueous HCl solution (0.2M 100 mL), 50% saturated sodium chloride solution (50 mL), dried over sodium sulfate, filtered, and concentrated. Hexanes (100 mL) were added and the mixture concentrated to provide ethyl 2-(1-(4-cyanonaphthalen-1-yl)-1H-imidazol-2-ylthio)acetate as a light-tan solid (10.47 g, 97%).

Step D: Ethyl 2-(5-bromo-1-(4-cyanonaphthalen-1-yl)-1H-imidazol-2-ylthio)acetate N-bromosuccinimide (5.48 g, 30.82 mmol) was added in three portions to a solution of ethyl 2-(1-(4-cyanonaphthalen-1-yl)-1H-imidazol-2-ylthio)acetate (10.40 g, 30.82 mmol) in dichloromethane (150 mL) at 0° C. and then stirred at room temperature for 18 h. The mixture was washed with water (2×50 mL), saturated aqueous sodium chloride solution (50 mL), dried over sodium sulfate, filtered and concentrated. Purification by column chromatography (0-50% EtOAc/hexanes) provided ethyl 2-(5-bromo-1-(4-cyanonaphthalen-1-yl)-1H-imidazol-2-ylthio)acetate as an off-white solid (9.18 g, 71.5%).

Step E: 2-(5-Bromo-1-(4-cyanonaphthalen-1-yl)-1H-imidazol-2-ylthio)acetic acid

Aqueous lithium hydroxide solution (1M, 44 mL, 44.00 mmol) was added to a solution of ethyl 2-(5-bromo-1-(4-cyanonaphthalen-1-yl)-1H-imidazol-2-ylthio)acetate (9.14 g, 21.96 mmol) in THF (60 mL), ethanol (24 mL) and water (20 mL), and stirred for 4 h. After concentrating, the residue was acidified with aqueous HCl solution (1N, 50 mL), diluted with water (100 mL) and filtered to afford 2-(5-bromo-1-(4- cyanonaphthalen-1-yl)-1H-imidazol-2-ylthio)acetic acid as an off-white solid (8.52 g, 100%).

Example 1B

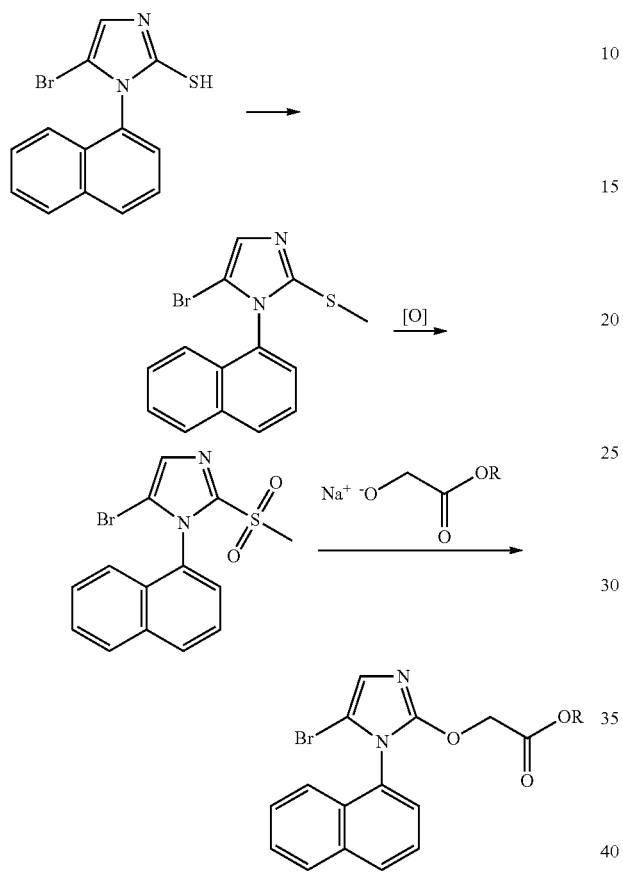

Step 1: The thioimidazole compound is dissolved in DMF (0.5 M final concentration), cooled to 0° C. and potassium carbonate (1 equivalent) is added. After stirring for 5 min, methyl iodide (1.0 equivalent) is added and the reaction allowed to stir until thin-layer chromatography shows no starting material remains. The reaction mixture is then concentrated under reduced pressure and the residue extracted between sat. NaHCO$_3$ and ethyl acetate. The crude product is used in Step 2.

Step 2: The methylthioether compound is dissolved absolute ethanol (0.2 M final concentration). Ammonium molybdate tetrahydrate ((NH$_4$)$_6$Mo$_7$O$_{24}$·4H$_2$O) 0.3 equivalents) and hydrogen peroxide (10 equivalents of 30% aqueous solution) are added and the reaction mixture is stirred at room temperature until no starting material remains. The reaction mixture is then concentrated under reduced pressure and the residue is extracted between water and ethyl acetate. The combined organic extracts are dried and purified by chromatography to give the methylsulfone product.

Step 3: The methylsulfone compound is dissolved in DMF (0.5 M final concentration), cooled to 0° C. and sodium hydride (1 equivalent) is added. After stirring for 5 min, methyl glycolate (1.0 equivalent) is added and the reaction allowed to stir until thin-layer chromatography shows no starting material remains. The reaction mixture is quenched with sat. NaHCO$_3$, the resulting mixture is concentrated under reduced pressure. The residue is extracted with ethyl acetate and the combined organic extracts are dried, concentrated and purified by chromatography.

Similar synthetic methods are optionally utilized to prepare other compounds having various naphthyl and/or imidazolyl substituents.

Example 2

Ethyl 2-(2-(5-bromo-1-(4-cyanonaphthalen-1-yl)-1H-imidazol-2-ylthio)acetamido)acetate

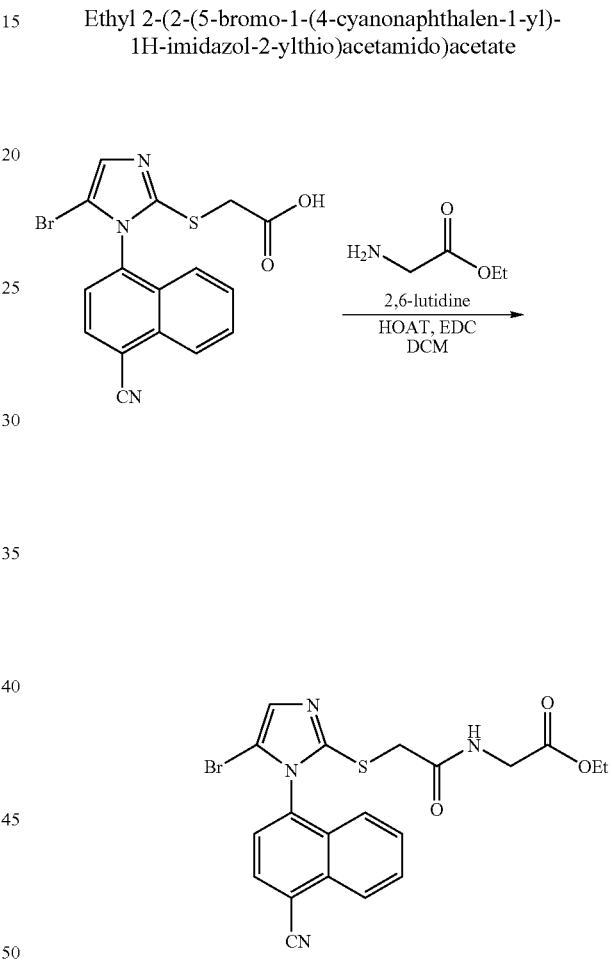

Glycine ethyl ester hydrochloride (76 mg, 0.541 mmol, 1.2 equiv.), 1-ethyl-3-(3-dimethylaminopropyl)carbodiimide hydrochloride (130 mg, 0.676 mmol, 1.5 equiv.), 1-hydroxy-7-azabenzotriazole (92 mg, 0.676 mmol, 1.5 equiv.) and 2,6-lutidine (0.16 mL, 1.35 mmol, 3.0 equiv) were added to a solution of 2-(5-bromo-1-(4-cyanonaphthalen-1-yl)-1H-imidazol-2-ylthio)acetic acid (175 mg, 0.451 mmol) in dichloromethane (2.25 mL) and stirred at room temperature for 18 hours. The crude product was purified by SGC (0-100% ethyl acetate/hexanes) to afford the title compound containing some 1-hydroxy-7-azabenzotriazole. The impure product was dissolved in ethyl acetate (50 mL), washed with aqueous HCl solution (0.1M, 2×30 mL), saturated aqueous NaHCO$_3$ solution (30 mL), and saturated sodium chloride solution (30 mL). The organics were dried over sodium sulfate, filtered, and concentrated to afford ethyl 2-(2-(5-bromo-1-(4-cyanonaphthalen-1-yl)-1H-imidazol-2-ylthio)acetamido)acetate as a yellow oil (199 mg, 93%).

Example 3

2-(2-(5-Bromo-1-(4-cyanonaphthalen-1-yl)-1H-imidazol-2-ylthio)acetamido)acetic acid

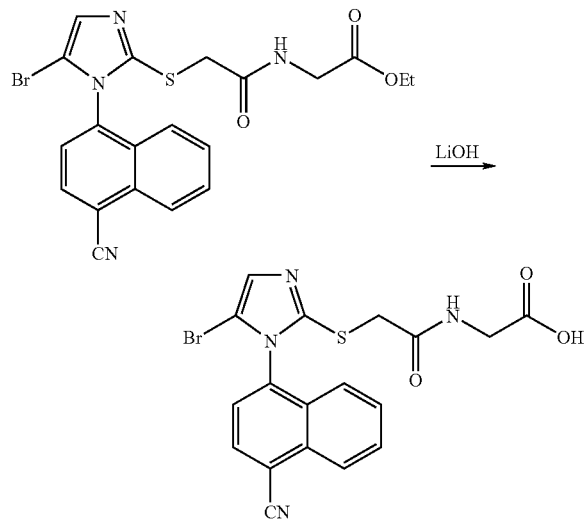

Aqueous lithium hydroxide solution (1M, 0.47 mL, 0.473 mmol) was added to a solution of ethyl 2-(2-(5-bromo-1-(4-cyanonaphthalen-1-yl)-1H-imidazol-2-ylthio)acetamido)acetae (112 mg, 0.237 mmol) in 3:1, THF/water (0.95 mL) and stirred for 18 h at room temperature. After concentrating, the crude reaction mixture was acidified with aqueous HCl solution (1M 1.2 mL), diluted with water (10 mL), stirred to break up solids, and filtered to afford 2-(2-(5-bromo-1-(4-cyanonaphthalen-1-yl)-1H-imidazol-2-ylthio)acetamido)acetic acid as an off-white solid (99 mg, 94%).

Example 4

Ethyl 3-(2-(5-bromo-1-(4-cyanonaphthalen-1-yl)-1H-imidazol-2-ylthio)acetamido)propanoate

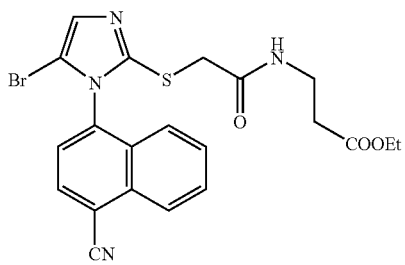 [SMILES: CCOC(=O)CCNC(=O)CSc1ncc(Br)n1-c1ccc(C#N)c2ccccc12]

Ethyl 3-(2-(5-bromo-1-(4-cyanonaphthalen-1-yl)-1H-imidazol-2-ylthio)acetamido)propanoate was prepared by coupling 2-(5-bromo-1-(4-cyanonaphthalen-1-yl)-1H-imidazol-2-ylthio)-acetic acid with β-alanine ethyl ester according to the procedure described in example 2.

Example 5

(2S)-Ethyl 2-(2-(5-bromo-1-(4-cyanonaphthalen-1-yl)-1H-imidazol-2-ylthio)acetamido)propanoate

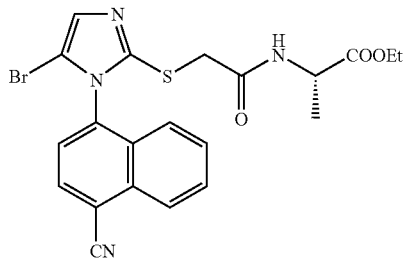 [SMILES: CCOC(=O)[C@H](C)NC(=O)CSc1ncc(Br)n1-c1ccc(C#N)c2ccccc12]

(2S)-ethyl 2-(2-(5-bromo-1-(4-cyanonaphthalen-1-yl)-1H-imidazol-2-ylthio)acetamido)propanoate was prepared by coupling 2-(5-bromo-1-(4-cyanonaphthalen-1-yl)-1H-imidazol-2-ylthio)-acetic acid with alanine ethyl ester according to the procedure described in example 2.

Example 6

(2S)-Ethyl 2-(2-(5-bromo-1-(4-cyanonaphthalen-1-yl)-1H-imidazol-2-ylthio)acetamido)-3-methylbutanoate

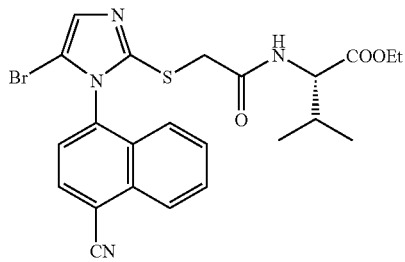

(2S)-ethyl 2-(2-(5-bromo-1-(4-cyanonaphthalen-1-yl)-1H-imidazol-2-ylthio)acetamido-3-methylbutanoate was prepared by coupling 2-(5-bromo-1-(4-cyanonaphthalen-1-yl)-1H-imidazol-2-ylthio)-acetic acid with valnine ethyl ester according to the procedure described in example 2.

Example 7

3-(2-(5-bromo-1-(4-cyanonaphthalen-1-yl)-1H-imidazol-2-ylthio)acetamido)propanoic acid

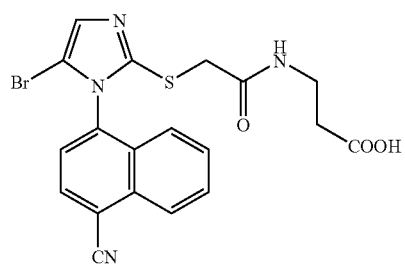

3-(2-(5-bromo-1-(4-cyanonaphthalen-1-yl)-1H-imidazol-2-ylthio)acetamido)propanoic acid was prepared by hydrolysis of ethyl 3-(2-(5-bromo-1-(4-cyanonaphthalen-1-yl)-1H-imidazol-2-ylthio)acetamido)propanoate (prepared as described herein), according to the procedure described in example 3.

Example 8

(2S)-2-(2-(5-bromo-1-(4-cyanonaphthalen-1-yl)-1H-imidazol-2-ylthio)acetamido)propanoic acid

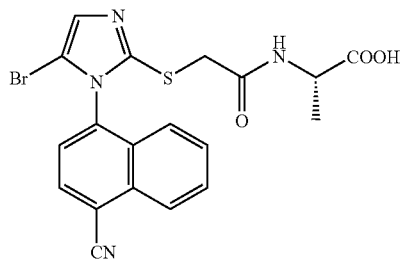

(2S)-2-(2-(5-bromo-1-(4-cyanonaphthalen-1-yl)-1H-imidazol-2-ylthio)acetamido)propanoic acid was prepared by hydrolysis of (2S)-ethyl 2-(2-(5-bromo-1-(4-cyanonaphthalen-1-yl)-1H-imidazol-2-ylthio)acetamido) propanoate (prepared as described herein), according to the procedure described in example 3.

Example 9

(2S)-2-(2-(5-bromo-1-(4-cyanonaphthalen-1-yl)-1H-imidazol-2-ylthio)acetamido)-3-methylbutanoic acid

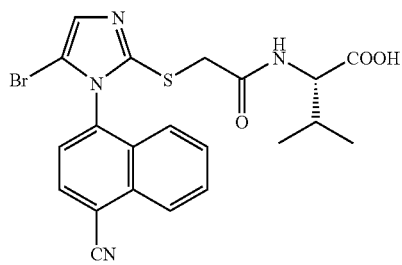 [SMILES: CCOC(=O)[C@@H](NC(=O)CSc1ncc(Br)n1-c1ccc(C#N)c2ccccc12)C(C)C]

(2S)-2-(2-(5-bromo-1-(4-cyanonaphthalen-1-yl)-1H-imidazol-2-ylthio)acetamido)-3-methylbutanoic acid was prepared by hydrolysis of (2S)-ethyl 2-(2-(5-bromo-1-(4-cyanonaphthalen-1-yl)-1H-imidazol-2-ylthio)acetamido)-3-methylbutanoate (prepared as described herein), according to the procedure described in example 3.

Example 10

2-(5-Bromo-1-(4-cyanonaphthalen-1-yl)-1H-imidazol-2-ylthio)-2,2-difluoroacetic acid

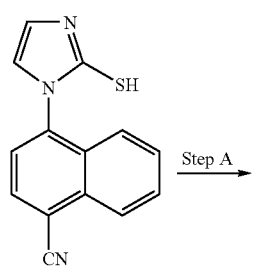

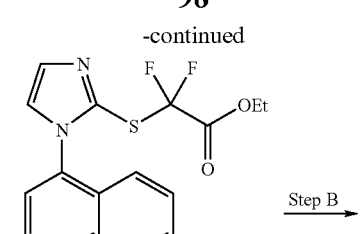

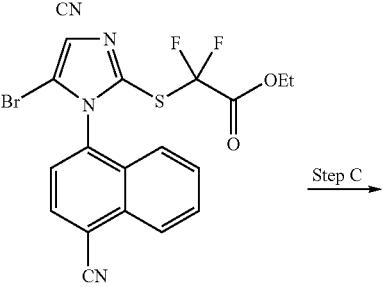

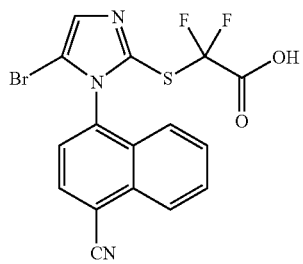

Step A: Ethyl 2-(1-(4-cyanonaphthalen-1-yl)-1H-imidazol-2-ylthio)-2,2-difluoroacetate Triethylamine (1.1 eq), followed by ethyl 2-bromo-2,2-difluoroacetate (1.05 eq) were added to a stirring slurry of 4-(2-mercapto-1H-imidazol-1-yl)-1-naphthonitrile (prepared as described herein, 1 eq) in dichloromethane and stirring continued for 3 h. The mixture was washed with aqueous HCl solution (0.2M), 50% saturated sodium chloride solution, dried over sodium sulfate, filtered, and concentrated. Hexanes were added and the mixture concentrated to provide ethyl 2-(1-(4-cyanonaphthalen-1-yl)-1H-imidazol-2-ylthio)-2,2-difluoroacetate.

Step B: Ethyl 2-(5-bromo-1-(4-cyanonaphthalen-1-yl)-1H-imidazol-2-ylthio)-2,2-difluoroacetate N-bromosuccinimide (1 eq) was added in three portions to a solution of ethyl 2-(1-(4-cyanonaphthalen-1-yl)-1H-imidazol-2-ylthio)-2,2-difluoroacetate (1 eq) in dichloromethane at 0° C. and then stirred at room temperature for 18 h. The mixture was washed twice with water and once with saturated aqueous sodium chloride solution, dried over sodium sulfate, filtered and concentrated. Purification by column chromatography (0-50% ethyl actetae/hexanes) provided ethyl 2-(5-bromo-1-(4-cyanonaphthalen-1-yl)-1H-imidazol-2-ylthio)-2,2-difluoroacetate.

Step C: 2-(5-Bromo-1-(4-cyanonaphthalen-1-yl)-1H-imidazol-2-ylthio)-2,2-difluoroacetic acid Aqueous lithium hydroxide solution (1M, 2 eq) was added to a solution of ethyl 2-(5-bromo-1-(4-cyanonaphthalen-1-yl)-1H-imidazol-2-ylthio)-2,2-difluoroacetate (1 eq) in THF, ethanol and water, and stirred for 4 h. After concentrating, the residue was acidified with aqueous HCl solution (1N), diluted with water and filtered to afford 2-(5-bromo-1-(4-cyanonaphthalen-1-yl)-1H-imidazol-2-ylthio)-2,2-difluoroacetic acid.

Example 11

*t*Butyl 2-(2-(5-bromo-1-(4-cyanonaphthalen-1-yl)-1H-imidazol-2-ylthio)-2,2-difluoroacetamido)acetate

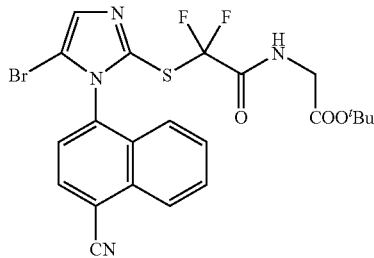

*t*Butyl 2-(2-(5-bromo-1-(4-cyanonaphthalen-1-yl)-1H-imidazol-2-ylthio)-2,2-difluoroacetamido)acetate was prepared by coupling 2-(5-bromo-1-(4-cyanonaphthalen-1-yl)-1H-imidazol-2-ylthio)-2,2-difluoroacetic acid with glycine *t*butyl ester according to the procedure described in example 2.

Example 12

(2S)-*t*Butyl 2-(2-(5-bromo-1-(4-cyanonaphthalen-1-yl)-1H-imidazol-2-ylthio)-2,2-difluoroacetamido) propanoate

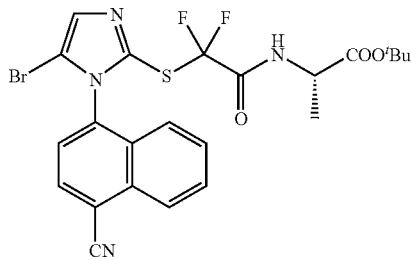

(2S)-*t*Butyl 2-(2-(5-bromo-1-(4-cyanonaphthalen-1-yl)-1H-imidazol-2-ylthio)-2,2-difluoroacetamido)propanoate was prepared by coupling 2-(5-bromo-1-(4-cyanonaphthalen-1-yl)-1H-imidazol-2-ylthio)-2,2-difluoroacetic acid with alanine *t*butyl ester according to the procedure described in example 2.

Example 13

(2S)-*t*Butyl 2-(2-(5-bromo-1-(4-cyanonaphthalen-1-yl)-1H-imidazol-2-ylthio)-2,2-difluoroacetamido)-3-methylbutanoate

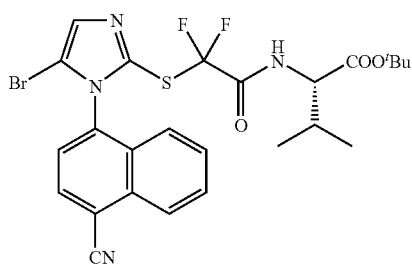

(2S)-*t*Butyl 2-(2-(5-bromo-1-(4-cyanonaphthalen-1-yl)-1H-imidazol-2-ylthio)-2,2-difluoroacetamido)-3-methylbutanoate was prepared by coupling 2-(5-bromo-1-(4-cyanonaphthalen-1-yl)-1H-imidazol-2-ylthio)-2,2-difluoroacetic acid with valine *t*butyl ester according to the procedure described in example 2.

Example 14

2-(2-(5-Bromo-1-(4-cyanonaphthalen-1-yl)-1H-imidazol-2-ylthio)-2,2-difluoroacetamido)acetic acid

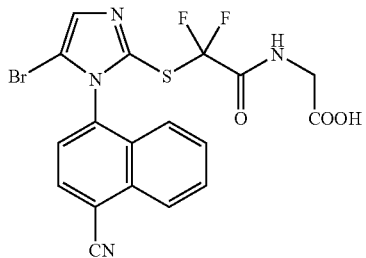 [SMILES: N#Cc1ccc(-n2c(Br)cnc2SC(F)(F)C(=O)NCC(=O)O)c2ccccc12]

2-(2-(5-Bromo-1-(4-cyanonaphthalen-1-yl)-1H-imidazol-2-ylthio)-2,2-difluoroacetamido)acetic acid was prepared by hydrolysis of ethyl 2-(2-(5-bromo-1-(4-cyanonaphthalen-1-yl)-1H-imidazol-2-ylthio)-2,2-difluoroacetamido) acetate (prepared as described herein), according to the procedure described in example 3.

Example 15

(2S)-2-(2-(5-Bromo-1-(4-cyanonaphthalen-1-yl)-1H-imidazol-2-ylthio)-2,2-difluoroacetamido)propanoic acid

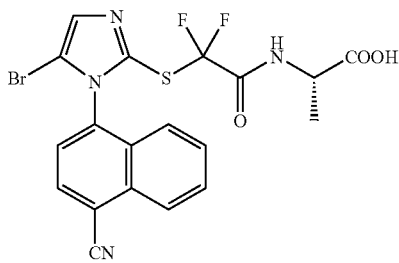 [SMILES: C[C@H](NC(=O)C(F)(F)Sc1ncc(Br)n1-c1ccc(C#N)c2ccccc12)C(=O)O]

(2S)-2-(2-(5-Bromo-1-(4-cyanonaphthalen-1-yl)-1H-imidazol-2-ylthio)-2,2-difluoroacetamido)propanoic acid was prepared by hydrolysis of (2S)-ethyl 2-(2-(5-bromo-1-(4-cyanonaphthalen-1-yl)-1H-imidazol-2-ylthio)-2,2-difluoroacetamido)propanoate (prepared as described herein), according to the procedure described in example 3.

Example 16

(2S)-2-(2-(5-Bromo-1-(4-cyanonaphthalen-1-yl)-1H-imidazol-2-ylthio)-2,2-difluoroacetamido)-3-methylbutanoic acid

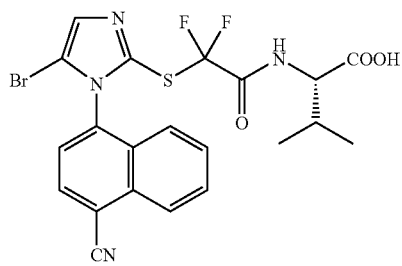 [SMILES: CC(C)[C@H](NC(=O)C(F)(F)Sc1ncc(Br)n1-c1ccc(C#N)c2ccccc12)C(=O)O]

(2S)-2-(2-(5-Bromo-1-(4-cyanonaphthalen-1-yl)-1H-imidazol-2-ylthio)-2,2-difluoroacetamido)-3-methylbutanoic acid was prepared by hydrolysis of (2S)-Ethyl 2-(2-(5-bromo-1-(4-cyanonaphthalen-1-yl)-1H-imidazol-2-ylthio)-2,2-difluoroacetamido)-3-methylbutanoate (prepared as described herein), according to the procedure described in example 3.

Example 17

2-(2-(2-(5-Bromo-1-(4-cyanonaphthalen-1-yl)-1H-imidazol-2-ylthio)acetamido)acetamido)acetic acid 2-(2-(2-(5-bromo-1-(4-cyanonaphthalen-1-yl)-1H-imidazol-2-ylthio)acetamido)acetamido)acetic acid is prepared via either of the two routes shown below. In the first, 2-(2-(5-bromo-1-(4-cyanonaphthalen-1-yl)-1H-imidazol-2-ylthio)acetamido)acetic acid (see eg 3) is coupled with glycine ethyl ester and then hydrolyzed to the acid. In the second, 2-(5-bromo-1-(4-cyanonaphthalen-1-yl)-1H-imidazol-2-ylthio)acetic acid (see eg 1) is coupled with NH$_2$-Gly-Gly-OEt, which is then hydrolyzed to the acid.

Eg 17: Route 1

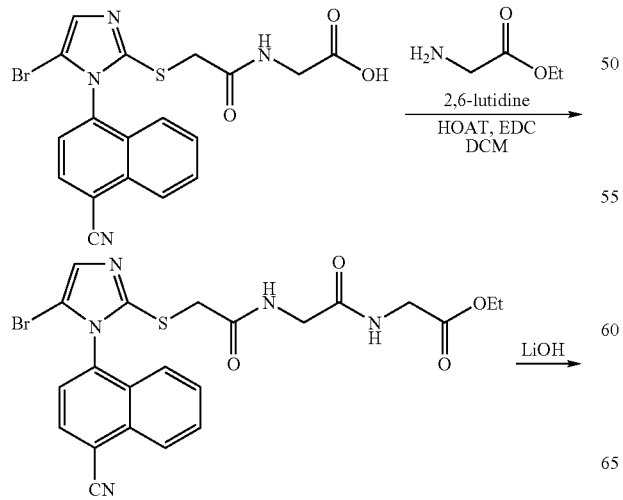

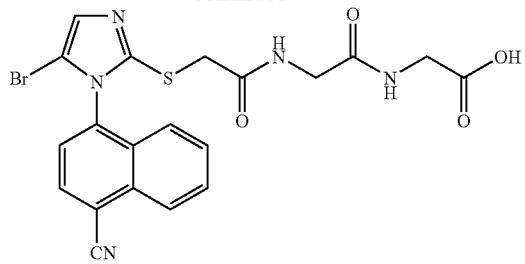

Eg 17: Route 2

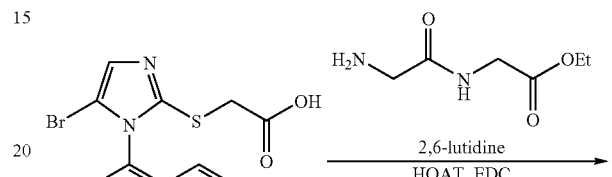

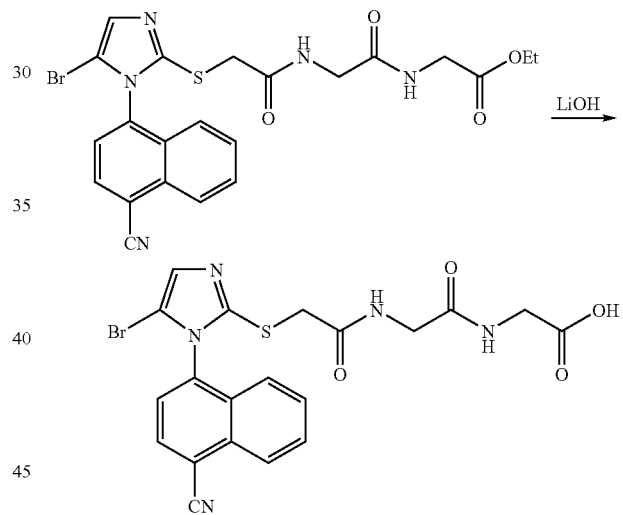

Example 18

2-(2-(2-(5-Bromo-1-(4-cyanonaphthalen-1-yl)-1H-imidazol-2-ylthio)-2,2-difluoroacetamido)acetamido)acetic acid 2-(2-(2-(5-bromo-1-(4-cyanonaphthalen-1-yl)-1H-imidazol-2-ylthio)-2,2-difluoroacetamido)acetamido)acetic acid is prepared via either of the two routes shown below. In the first, 2-(2-(5-bromo-1-(4-cyanonaphthalen-1-yl)-1H-imidazol-2-ylthio)-2,2-difluoroacetamido)acetic acid (see eg 14) is coupled with glycine ethyl ester and then hydrolyzed to the acid. In the second, (see eg 10), 2-(5-bromo-1-(4-cyanonaphthalen-1-yl)-1H-imidazol-2-ylthio)-2,2-difluoroacetic acid is coupled with NH$_2$-Gly-Gly-OEt, which is then hydrolyzed to the acid.

Eg 18: Route 1

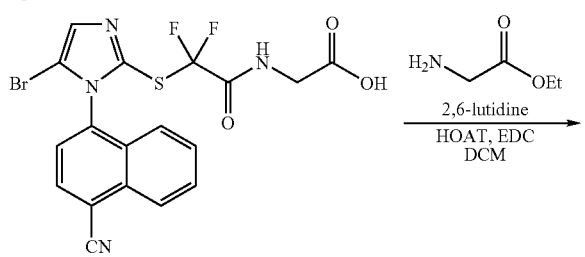

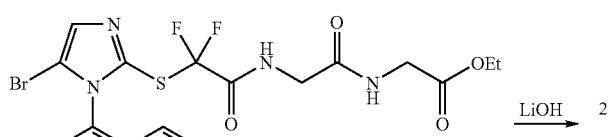

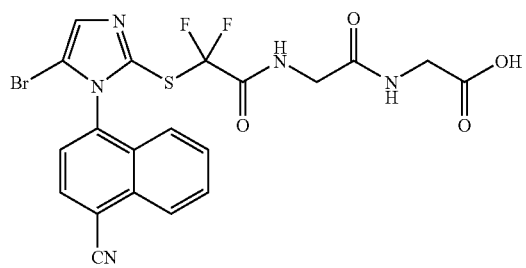

Eg 18: Route 2

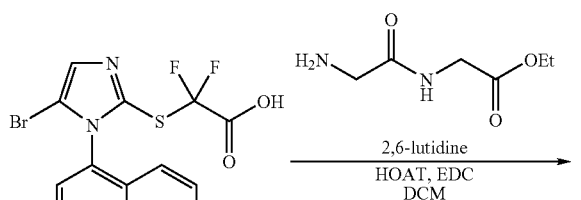

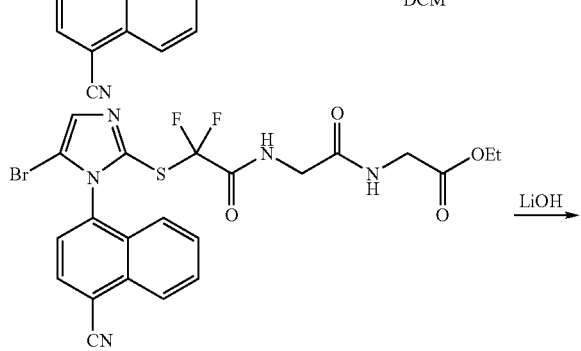

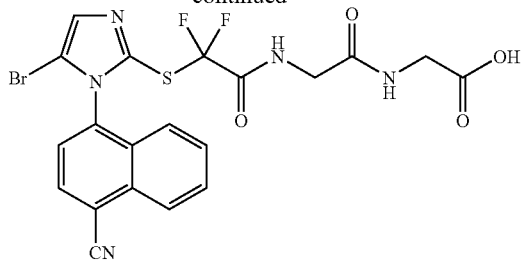

Examples 19-35

The following compounds are prepared by coupling 2-(5-Bromo-1-(4-cyanonaphthalen-1-yl)-1H-imidazol-2-ylthio) acetic acid with an amino acid or amino acid derivative.

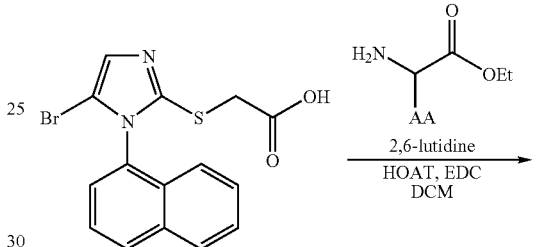

AA = Amino acid residue

Amino acid ester hydrochloride ($NH_2$—CH(AA)-COOEt·HCl; 1.2 equiv.), 1-ethyl-3-(3-dimethylaminopropyl)carbodiimide hydrochloride (1.5 equiv.), 1-hydroxy-7-azabenzotriazole (1.5 equiv.) and 2,6-lutidine (3.0 equiv) are added to a solution of 2-(5-bromo-1-(4-cyanonaphthalen-1-yl)-1H-imidazol-2-ylthio)acetic acid (1.0 equiv.) in dichloromethane and stirred at room temperature for 18 hours. The crude product is purified by SGC (0-100% ethyl acetate/hexanes). If any starting material remains, the product is further purified by dissolving in ethyl acetate (50 mL), washing with aqueous HCl solution (0.1M, 2×30 mL), saturated aqueous $NaHCO_3$ solution (30 mL), and saturated sodium chloride solution (30 mL). Combined organics are dried (sodium sulfate), filtered and concentrated.

| Eg | Compound Structure | Compound Name |
|---|---|---|
| 19 | 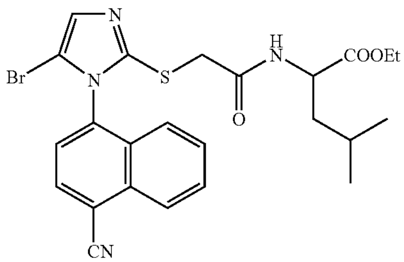 [SMILES: CCOC(=O)C(CC(C)C)NC(=O)CSc1ncc(Br)n1-c1ccc(C#N)c2ccccc12] | Ethyl 2-(2-(5-bromo-1-(4-cyanonaphthalen-1-yl)-1H-imidazol-2-ylthio)acetamido)-4-methylpentanoate |
| 20 | 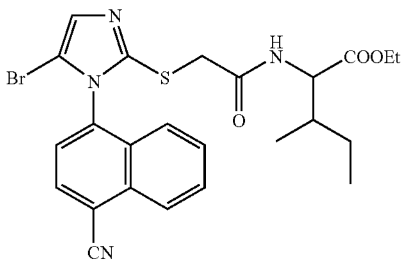 [SMILES: CCOC(=O)C(NC(=O)CSc1ncc(Br)n1-c1ccc(C#N)c2ccccc12)C(C)CC] | Ethyl 2-(2-(5-bromo-1-(4-cyanonaphthalen-1-yl)-1H-imidazol-2-ylthio)acetamido)-3-methylpentanoate |
| 21 | 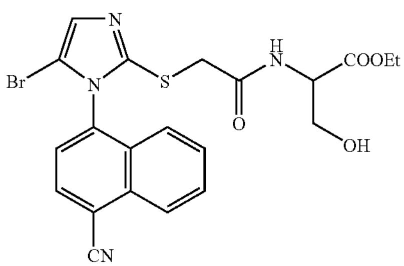 [SMILES: CCOC(=O)C(CO)NC(=O)CSc1ncc(Br)n1-c1ccc(C#N)c2ccccc12] | Ethyl 2-(2-(5-bromo-1-(4-cyanonaphthalen-1-yl)-1H-imidazol-2-ylthio)acetamido)-3-hydroxypropanoate |
| 22 | 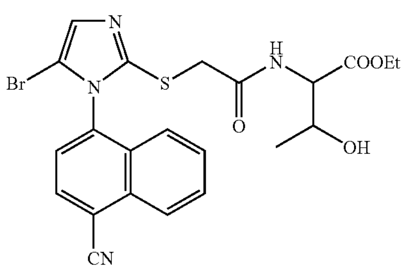 [SMILES: CCOC(=O)C(NC(=O)CSc1ncc(Br)n1-c1ccc(C#N)c2ccccc12)C(C)O] | Ethyl 2-(2-(5-bromo-1-(4-cyanonaphthalen-1-yl)-1H-imidazol-2-ylthio)acetamido)-3-hydroxybutanoate |
| 23 | 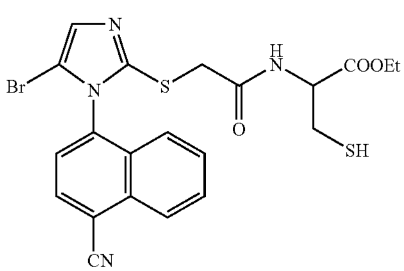 [SMILES: CCOC(=O)C(CS)NC(=O)CSc1ncc(Br)n1-c1ccc(C#N)c2ccccc12] | Ethyl 2-(2-(5-bromo-1-(4-cyanonaphthalen-1-yl)-1H-imidazol-2-ylthio)acetamido)-3-mercaptopropanoate |
| 24 | 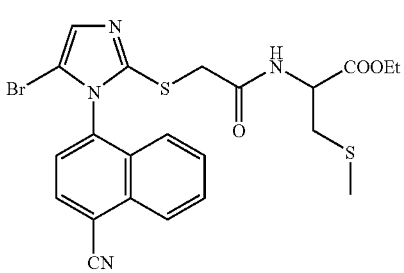 [SMILES: CCOC(=O)C(CSC)NC(=O)CSc1ncc(Br)n1-c1ccc(C#N)c2ccccc12] | Ethyl 2-(2-(5-bromo-1-(4-cyanonaphthalen-1-yl)-1H-imidazol-2-ylthio)acetamido)-3-(methythio)propanoate |

| Eg | Compound Structure | Compound Name |
|---|---|---|
| 25 | 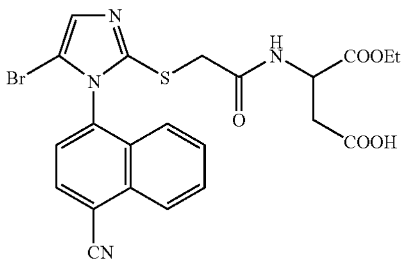 [SMILES: CCOC(=O)C(CC(=O)O)NC(=O)CSc1ncc(Br)n1-c1ccc(C#N)c2ccccc12] | 3-(2-(5-bromo-1-(4-cyanonaphthalen-1-yl)-1H-imidazol-2-ylthio)acetamido)-4-ethoxy-4-oxobutanoic acid |
| 26 | 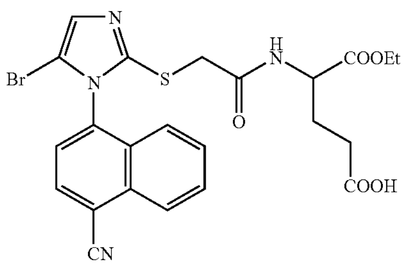 [SMILES: CCOC(=O)C(CCC(=O)O)NC(=O)CSc1ncc(Br)n1-c1ccc(C#N)c2ccccc12] | 4-(2-(5-bromo-1-(4-cyanonaphthalen-1-yl)-1H-imidazol-2-ylthio)acetamido)-5-ethoxy-5-oxopentanoic acid |
| 27 | 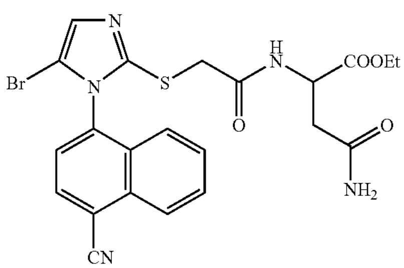 [SMILES: CCOC(=O)C(CC(N)=O)NC(=O)CSc1ncc(Br)n1-c1ccc(C#N)c2ccccc12] | Ethyl 4-amino-2-(2-(5-bromo-1-(4-cyanonaphthalen-1-yl)-1H-imidazol-2-ylthio)acetamido)-4-oxobutanoate |
| 28 | 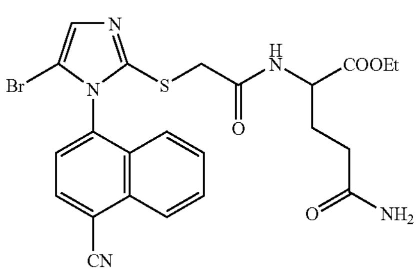 [SMILES: CCOC(=O)C(CCC(N)=O)NC(=O)CSc1ncc(Br)n1-c1ccc(C#N)c2ccccc12] | Ethyl 5-amino-2-(2-(5-bromo-1-(4-cyanonaphthalen-1-yl)-1H-imidazol-2-ylthio)acetamido)-5-oxopentanoate |
| 29 | 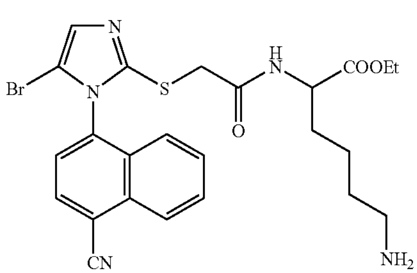 | Ethyl 6-amino-2-(2-(5-bromo-1-(4-cyanonaphthalen-1-yl)-1H-imidazol-2-ylthio)acetamido)hexanoate |

-continued

| Eg | Compound Structure | Compound Name |
|---|---|---|
| 30 | 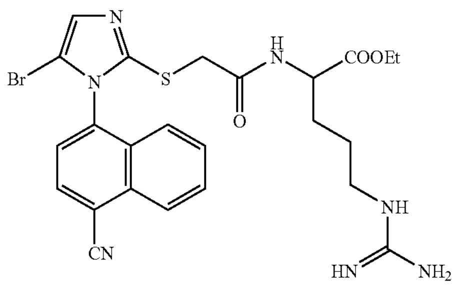 [SMILES: CCOC(=O)C(CCCNC(=N)N)NC(=O)CSc1ncc(Br)n1-c1ccc(C#N)c2ccccc12] | Ethyl 2-(2-(5-bromo-1-(4-cyanonaphthalen-1-yl)-1H-imidazol-2-ylthio)acetamido)-5-guanidinopentanoate |
| 31 | 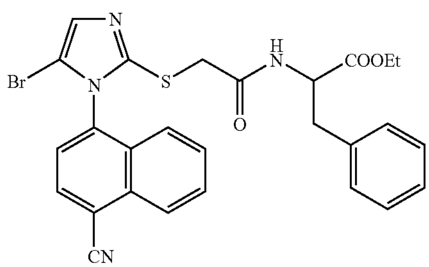 [SMILES: CCOC(=O)C(Cc1ccccc1)NC(=O)CSc1ncc(Br)n1-c1ccc(C#N)c2ccccc12] | Ethyl 2-(2-(5-bromo-1-(4-cyanonaphthalen-1-yl)-1H-imidazol-2-ylthio)acetamido)-3-phenylpropanoate |
| 32 | 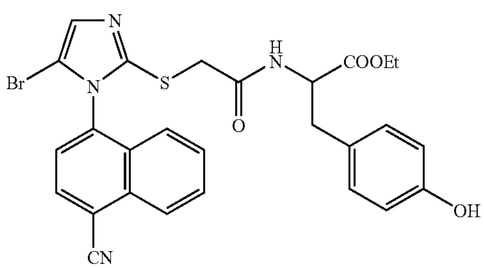 | Ethyl 2-(2-(5-bromo-1-(4-cyanonaphthalen-1-yl)-1H-imidazol-2-ylthio)acetamido)-3-(4-hydroxyphenyl)propanoate |
| 33 | 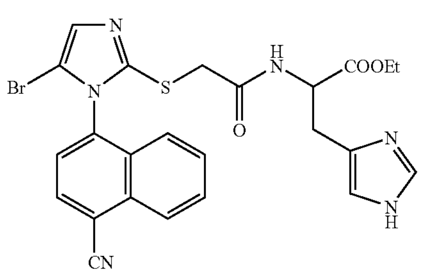 [SMILES: CCOC(=O)C(Cc1c[nH]cn1)NC(=O)CSc1ncc(Br)n1-c1ccc(C#N)c2ccccc12] | Ethyl 2-(2-(5-bromo-1-(4-cyanonaphthalen-1-yl)-1H-imidazol-2-ylthio)acetamido)-3-(1H-imidazol-4-yl)propanoate |
| 34 | 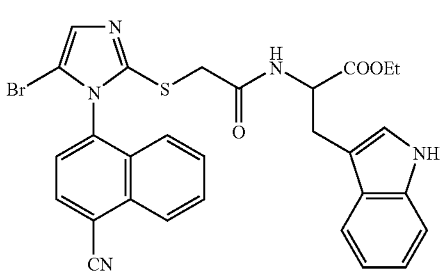 [SMILES: CCOC(=O)C(Cc1c[nH]c2ccccc12)NC(=O)CSc1ncc(Br)n1-c1ccc(C#N)c2ccccc12] | Ethyl 2-(2-(5-bromo-1-(4-cyanonaphthalen-1-yl)-1H-imidazol-2-ylthio)acetamido)-3-(1H-indol-3-yl)propanoate |

| Eg | Compound Structure | Compound Name |
|---|---|---|
| 35 | 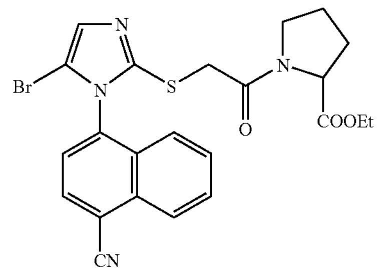 [SMILES: CCOC(=O)C1CCCN1C(=O)CSc1ncc(Br)n1-c1ccc(C#N)c2ccccc12] | Ethyl 1-(2-(5-bromo-1-(4-cyanonaphthalen-1-yl)-1H-imidazol-2-ylthio)acetyl)pyrrolidine-2-carboxylate |

Examples 36-52

The following compounds are prepared by hydrolysis of the compounds described in examples 19-35.

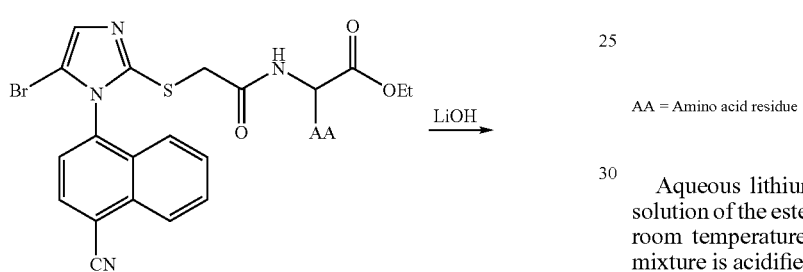

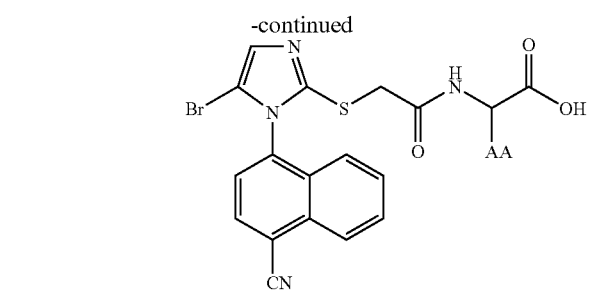

AA = Amino acid residue

Aqueous lithium hydroxide solution (1M) is added to a solution of the ester in THF/water (3/1), and stirred for 18 h at room temperature. After concentrating, the crude reaction mixture is acidified with aqueous HCl solution (1M), diluted with water, stirred to break up solids, and the solid isolated by filtration to provide the acid.

| Eg | Compound Structure | Compound Name |
|---|---|---|
| 36 | 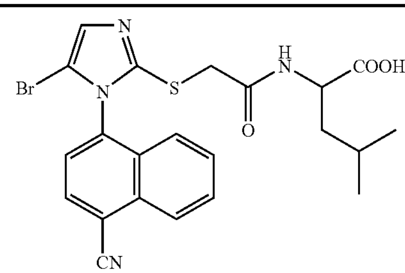 | 2-(2-(5-bromo-1-(4-cyanonaphthalen-1-yl)-1H-imidazol-2-ylthio)acetamido)-4-methylpentanoic acid |
| 37 | 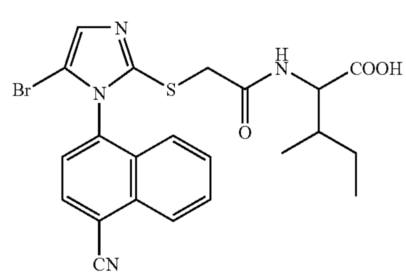 [SMILES: CCC(C)C(NC(=O)CSc1ncc(Br)n1-c1ccc(C#N)c2ccccc12)C(=O)O] | 2-(2-(5-bromo-1-(4-cyanonaphthalen-1-yl)-1H-imidazol-2-ylthio)acetamido)-3-methylpentanoic acid |

-continued

| Eg | Compound Structure | Compound Name |
|---|---|---|
| 38 | 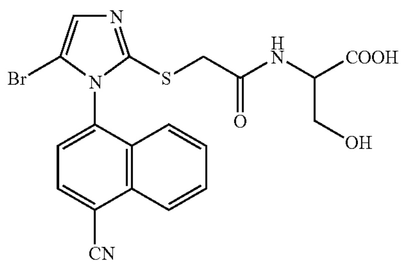 [SMILES: N#Cc1ccc(-n2c(Br)cnc2SCC(=O)NC(CO)C(=O)O)c2ccccc12] | 2-(2-(5-bromo-1-(4-cyanonaphthalen-1-yl)-1H-imidazol-2-ylthio)acetamido)-3-hydroxypropanoic acid |
| 39 | 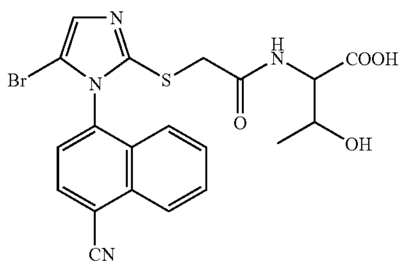 [SMILES: CC(O)C(NC(=O)CSc1ncc(Br)n1-c1ccc(C#N)c2ccccc12)C(=O)O] | 2-(2-(5-bromo-1-(4-cyanonaphthalen-1-yl)-1H-imidazol-2-ylthio)acetamido)-3-hydroxybutanoic acid |
| 40 | 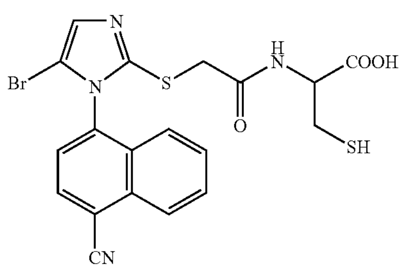 [SMILES: N#Cc1ccc(-n2c(Br)cnc2SCC(=O)NC(CS)C(=O)O)c2ccccc12] | 2-(2-(5-bromo-1-(4-cyanonaphthalen-1-yl)-1H-imidazol-2-ylthio)acetamido)-3-mercaptopropanoic acid |
| 41 | 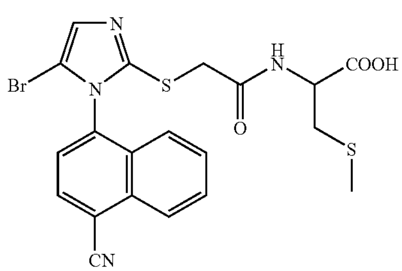 [SMILES: CSCC(NC(=O)CSc1ncc(Br)n1-c1ccc(C#N)c2ccccc12)C(=O)O] | 2-(2-(5-bromo-1-(4-cyanonaphthalen-1-yl)-1H-imidazol-2-ylthio)acetamido)-3-(methylthio)propanoic acid |
| 42 | 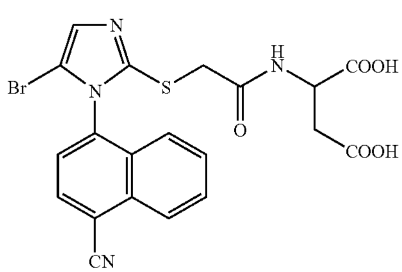 [SMILES: N#Cc1ccc(-n2c(Br)cnc2SCC(=O)NC(CC(=O)O)C(=O)O)c2ccccc12] | 2-(2-(5-bromo-1-(4-cyanonaphthalen-1-yl)-1H-imidazol-2-ylthio)acetamido)succinic acid |
| 43 | 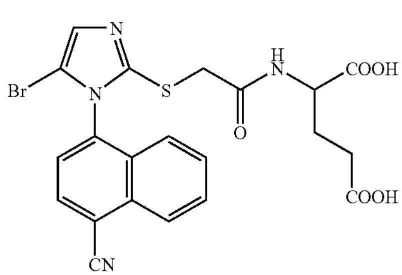 [SMILES: N#Cc1ccc(-n2c(Br)cnc2SCC(=O)NC(CCC(=O)O)C(=O)O)c2ccccc12] | 2-(2-(5-bromo-1-(4-cyanonaphthalen-1-yl)-1H-imidazol-2-ylthio)acetamido)pentanedioic acid |

-continued

| Eg | Compound Structure | Compound Name |
|---|---|---|
| 44 | 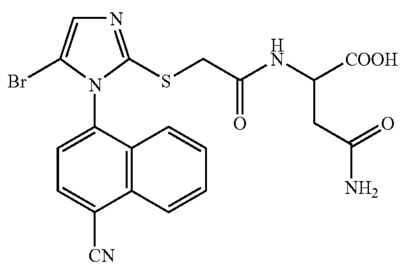 [SMILES: N#Cc1ccc(-n2c(Br)cnc2SCC(=O)NC(CC(N)=O)C(=O)O)c2ccccc12] | 4-amino-2-(2-(5-bromo-1-(4-cyanonaphthalen-1-yl)-1H-imidazol-2-ylthio)acetamido)-4-oxobutanoic acid |
| 45 | 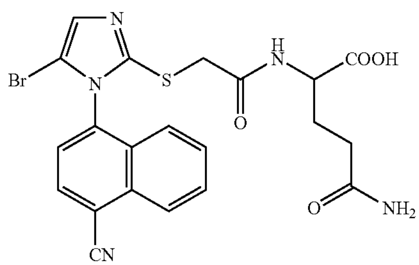 | 5-amino-2-(2-(5-bromo-1-(4-cyanonaphthalen-1-yl)-1H-imidazol-2-ylthio)acetamido)-5-oxopentanoic acid |
| 46 | 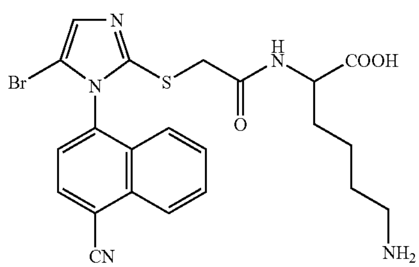 [SMILES: N#Cc1ccc(-n2c(Br)cnc2SCC(=O)NC(CCCCN)C(=O)O)c2ccccc12] | 6-amino-2-(2-(5-bromo-1-(4-cyanonaphthalen-1-yl)-1H-imidazol-2-ylthio)acetamido)hexanoic acid |
| 47 | 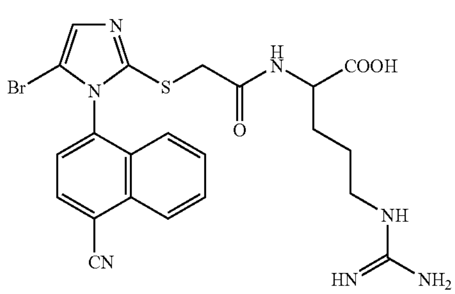 [SMILES: N#Cc1ccc(-n2c(Br)cnc2SCC(=O)NC(CCCNC(=N)N)C(=O)O)c2ccccc12] | 2-(2-(5-bromo-1-(4-cyanonaphthalen-1-yl)-1H-imidazol-2-ylthio)acetamido)-5-guanidinopentanoic acid |
| 48 | 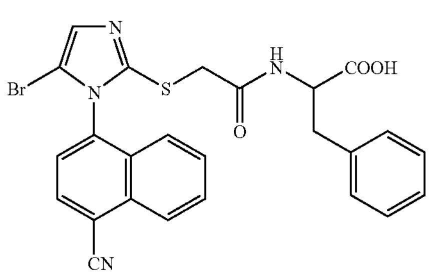 [SMILES: N#Cc1ccc(-n2c(Br)cnc2SCC(=O)NC(Cc2ccccc2)C(=O)O)c2ccccc12] | 2-(2-(5-bromo-1-(4-cyanonaphthalen-1-yl)-1H-imidazol-2-ylthio)acetamido)-3-phenylpropanoic acid |

-continued

| Eg | Compound Structure | Compound Name |
|---|---|---|
| 49 | 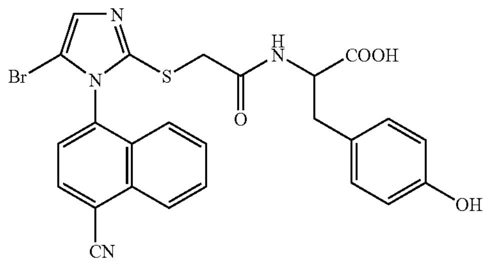 [SMILES: N#Cc1ccc(-n2c(Br)cnc2SCC(=O)NC(Cc2ccc(O)cc2)C(=O)O)c2ccccc12] | 2-(2-(5-bromo-1-(4-cyanonaphthalen-1-yl)-1H-imidazol-2-ylthio)acetamido)-3-(4-hydroxyphenyl)propanoic acid |
| 50 | 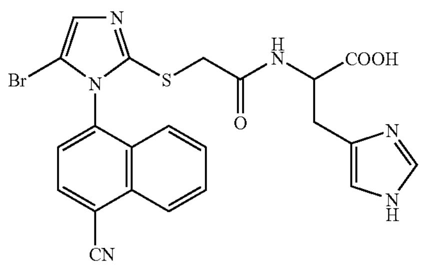 [SMILES: N#Cc1ccc(-n2c(Br)cnc2SCC(=O)NC(Cc2c[nH]cn2)C(=O)O)c2ccccc12] | 2-(2-(5-bromo-1-(4-cyanonaphthalen-1-yl)-1H-imidazol-2-ylthio)acetamido)-3-(1H-imidazol-4-yl)propanoic acid |
| 51 | 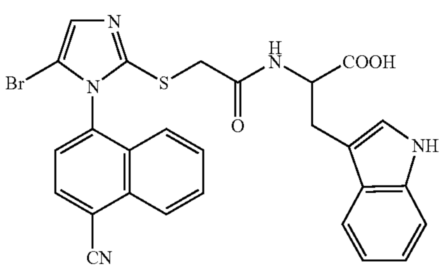 [SMILES: N#Cc1ccc(-n2c(Br)cnc2SCC(=O)NC(Cc2c[nH]c3ccccc23)C(=O)O)c2ccccc12] | 2-(2-(5-bromo-1-(4-cyanonaphthalen-1-yl)-1H-imidazol-2-ylthio)acetamido)-3-(1H-indol-3-yl)propanoic acid |
| 52 | 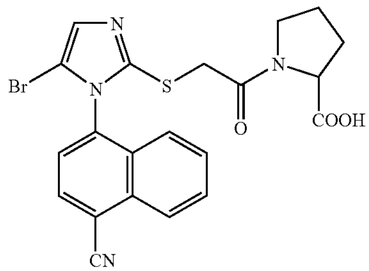 [SMILES: N#Cc1ccc(-n2c(Br)cnc2SCC(=O)N2CCCC2C(=O)O)c2ccccc12] | 1-(2-(5-bromo-1-(4-cyanonaphthalen-1-yl)-1H-imidazol-2-ylthio)acetyl)pyrrolidine-2-carboxylic acid |

Examples 53-69

The following compounds are prepared by coupling 2-(5-bromo-1-(4-cyanonaphthalen-1-yl)-1H-imidazol-2-ylthio)-2,2-difluoroacetic acid with an amino acid or amino acid derivative.

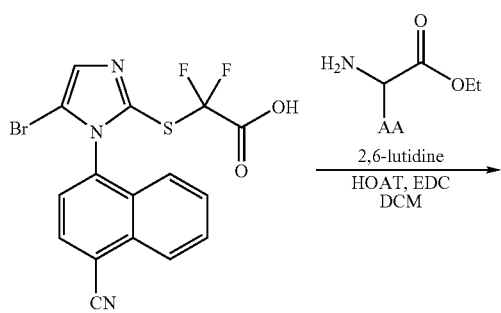

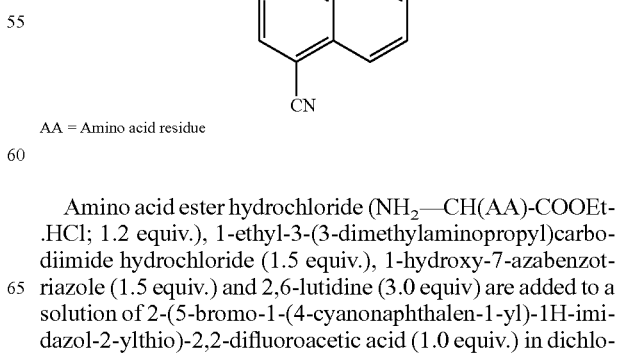

AA = Amino acid residue

Amino acid ester hydrochloride (NH₂—CH(AA)-COOEt-.HCl; 1.2 equiv.), 1-ethyl-3-(3-dimethylaminopropyl)carbodiimide hydrochloride (1.5 equiv.), 1-hydroxy-7-azabenzotriazole (1.5 equiv.) and 2,6-lutidine (3.0 equiv) are added to a solution of 2-(5-bromo-1-(4-cyanonaphthalen-1-yl)-1H-imidazol-2-ylthio)-2,2-difluoroacetic acid (1.0 equiv.) in dichloromethane and stirred at room temperature for 18 hours. The crude product is purified by SGC (0-100% ethyl acetate/hexanes). If any starting material remains, the product is further purified by dissolving in ethyl acetate (50 mL), washing with aqueous HCl solution (0.1M, 2×30 mL), saturated aqueous NaHCO$_3$ solution (30 mL), and saturated sodium chloride solution (30 mL). Combined organics are dried (sodium sulfate), filtered and concentrated.

| Eg | Compound Structure | Compound Name |
|---|---|---|
| 53 | 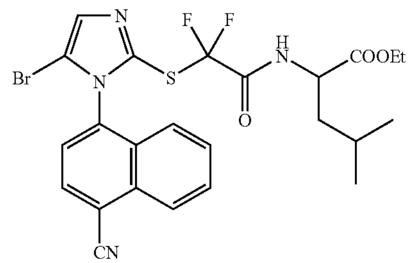 [SMILES: CCOC(=O)C(CC(C)C)NC(=O)C(F)(F)Sc1ncc(Br)n1-c1ccc(C#N)c2ccccc12] | Ethyl 2-(2-(5-bromo-1-(4-cyanonaphthalen-1-yl)-1H-imidazol-2-ylthio)-2,2-difluoroacetamido)-4-methylpentanoate |
| 54 | 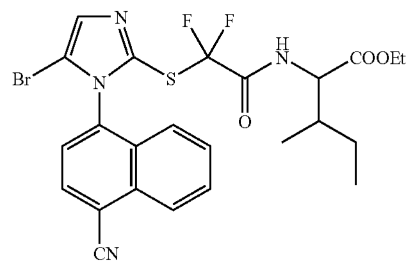 [SMILES: CCOC(=O)C(NC(=O)C(F)(F)Sc1ncc(Br)n1-c1ccc(C#N)c2ccccc12)C(C)CC] | Ethyl 2-(2-(5-bromo-1-(4-cyanonaphthalen-1-yl)-1H-imidazol-2-ylthio)-2,2-difluoroacetamido)-3-methylpentanoate |
| 55 | 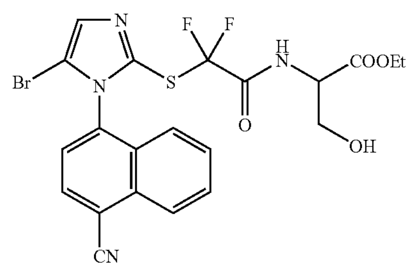 [SMILES: CCOC(=O)C(CO)NC(=O)C(F)(F)Sc1ncc(Br)n1-c1ccc(C#N)c2ccccc12] | Ethyl 2-(2-(5-bromo-1-(4-cyanonaphthalen-1-yl)-1H-imidazol-2-ylthio)-2,2-difluoroacetamido)-3-hydroxypropanoate |
| 56 | 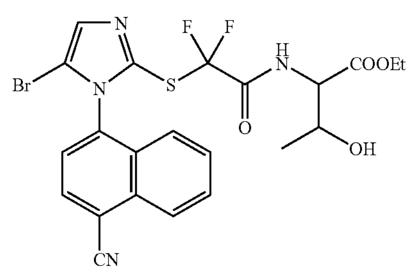 [SMILES: CCOC(=O)C(NC(=O)C(F)(F)Sc1ncc(Br)n1-c1ccc(C#N)c2ccccc12)C(C)O] | Ethyl 2-(2-(5-bromo-1-(4-cyanonaphthalen-1-yl)-1H-imidazol-2-ylthio)-2,2-difluoroacetamido)-3-hydroxybutanoate |
| 57 | 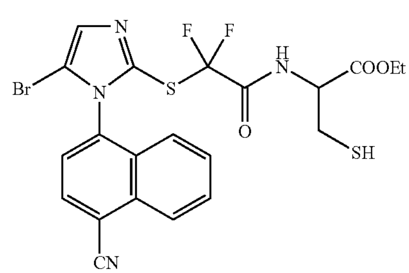 [SMILES: CCOC(=O)C(CS)NC(=O)C(F)(F)Sc1ncc(Br)n1-c1ccc(C#N)c2ccccc12] | Ethyl 2-(2-(5-bromo-1-(4-cyanonaphthalen-1-yl)-1H-imidazol-2-ylthio)-2,2-difluoroacetamido)-3-mercaptopropanoate |

-continued

| Eg | Compound Structure | Compound Name |
|---|---|---|
| 58 | 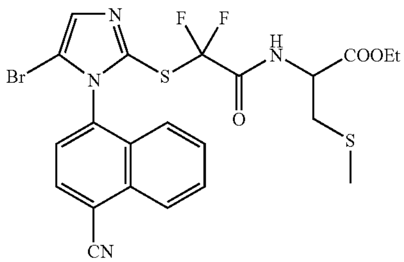 [SMILES: CCOC(=O)C(CSC)NC(=O)C(F)(F)Sc1ncc(Br)n1-c1ccc(C#N)c2ccccc12] | Ethyl 2-(2-(5-bromo-1-(4-cyanonaphthalen-1-yl)-1H-imidazol-2-ylthio)-2,2-difluoroacetamido)-3-(methylthio)propanoate |
| 59 | 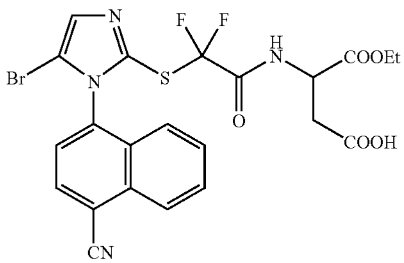 [SMILES: CCOC(=O)C(CC(=O)O)NC(=O)C(F)(F)Sc1ncc(Br)n1-c1ccc(C#N)c2ccccc12] | 3-(2-(5-bromo-1-(4-cyanonaphthalen-1-yl)-1H-imidazol-2-ylthio)-2,2-difluoroacetamido)-4-ethoxy-4-oxobutanoic acid |
| 60 | 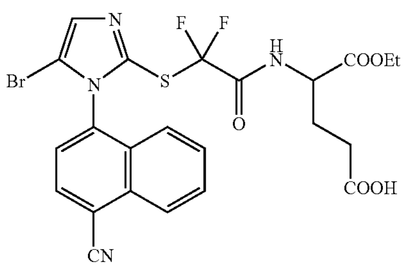 [SMILES: CCOC(=O)C(CCC(=O)O)NC(=O)C(F)(F)Sc1ncc(Br)n1-c1ccc(C#N)c2ccccc12] | 4-(2-(5-bromo-1-(4-cyanonaphthalen-1-yl)-1H-imidazol-2-ylthio)-2,2-difluoroacetamido)-5-ethoxy-5-oxopentanoic acid |
| 61 | 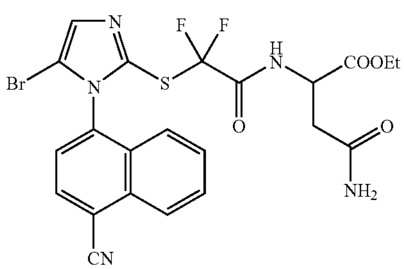 [SMILES: CCOC(=O)C(CC(N)=O)NC(=O)C(F)(F)Sc1ncc(Br)n1-c1ccc(C#N)c2ccccc12] | Ethyl 4-amino-2-(2-(5-bromo-1-(4-cyanonaphthalen-1-yl)-1H-imidazol-2-ylthio)-2,2-difluoroacetamido)-4-oxobutanoate |
| 62 | 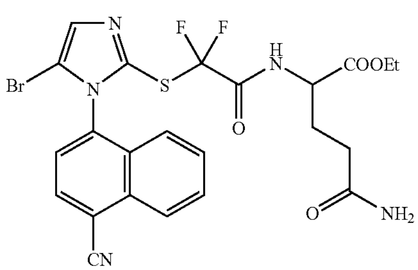 | Ethyl 5-amino-2-(2-(5-bromo-1-(4-cyanonaphthalen-1-yl)-1H-imidazol-2-ylthio)-2,2-difluoroacetamido)-5-oxopentanoate |
| 63 | 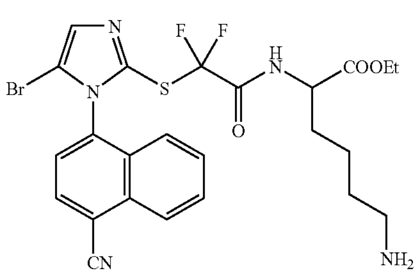 | Ethyl 6-amino-2-(2-(5-bromo-1-(4-cyanonaphthalen-1-yl)-1H-imidazol-2-ylthio)-2,2-difluoroacetamido)hexanoate |

-continued

| Eg | Compound Structure | Compound Name |
| --- | --- | --- |
| 64 | 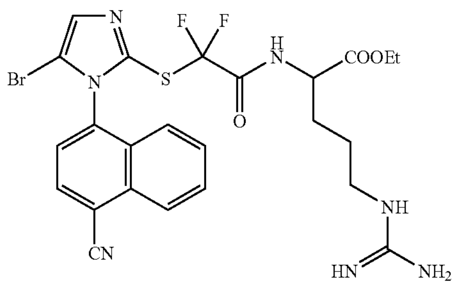 [SMILES: CCOC(=O)C(CCCNC(=N)N)NC(=O)C(F)(F)Sc1ncc(Br)n1-c1ccc(C#N)c2ccccc12] | Ethyl 2-(2-(5-bromo-1-(4-cyanonaphthalen-1-yl)-1H-imidazol-2-ylthio)-2,2-difluoroacetamido)-5-guanidinopentanoate |
| 65 | 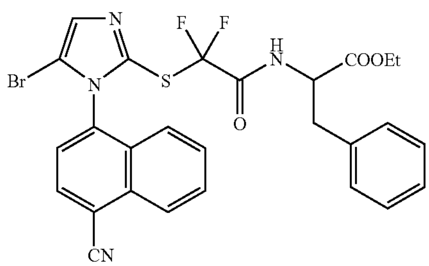 [SMILES: CCOC(=O)C(Cc1ccccc1)NC(=O)C(F)(F)Sc1ncc(Br)n1-c1ccc(C#N)c2ccccc12] | Ethyl 2-(2-(5-bromo-1-(4-cyanonaphthalen-1-yl)-1H-imidazol-2-ylthio)-2,2-difluoroacetamido)-3-phenylpropanoate |
| 66 | 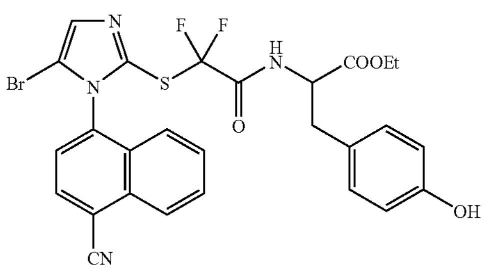 | Ethyl 2-(2-(5-bromo-1-(4-cyanonaphthalen-1-yl)-1H-imidazol-2-ylthio)-2,2-difluoroacetamido)-3-(4-hydroxyphenyl)propanoate |
| 67 | 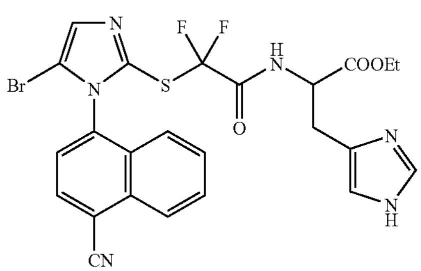 [SMILES: CCOC(=O)C(Cc1c[nH]cn1)NC(=O)C(F)(F)Sc1ncc(Br)n1-c1ccc(C#N)c2ccccc12] | Ethyl 2-(2-(5-bromo-1-(4-cyanonaphthalen-1-yl)-1H-imidazol-2-ylthio)-2,2-difluoroacetamido)-3-(1H-imidazol-4-yl)propanoate |
| 68 | 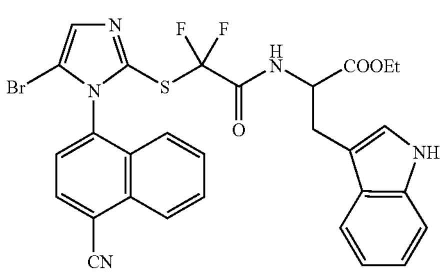 [SMILES: CCOC(=O)C(Cc1c[nH]c2ccccc12)NC(=O)C(F)(F)Sc1ncc(Br)n1-c1ccc(C#N)c2ccccc12] | Ethyl 2-(2-(5-bromo-1-(4-cyanonaphthalen-1-yl)-1H-imidazol-2-ylthio)-2,2-difluoroacetamido)-3-(1H-indol-3-yl)propanoate |

| Eg | Compound Structure | Compound Name |
|---|---|---|
| 69 | 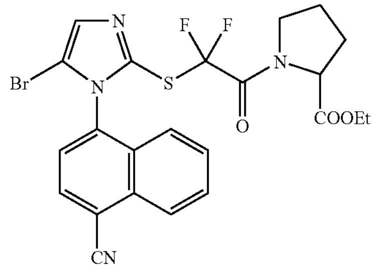 [SMILES: CCOC(=O)C1CCCN1C(=O)C(F)(F)Sc1ncc(Br)n1-c1ccc(C#N)c2ccccc12] | Ethyl 1-(2-(5-bromo-1-(4-cyanonaphthalen-1-yl)-1H-imidazol-2-ylthio)-2,2-difluoroacetyl)pyrrolidine-2-carboxylate |

Examples 70-87

The following compounds are prepared by hydrolysis of the compounds described in examples 53-69.

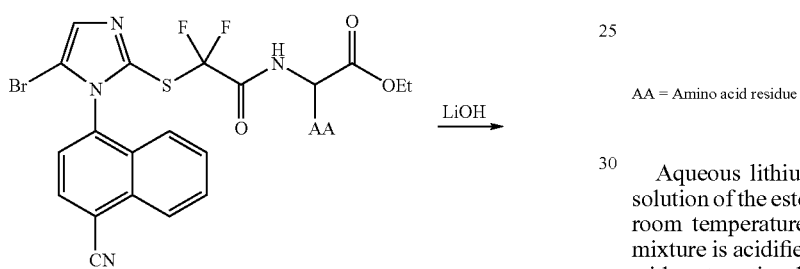

AA = Amino acid residue

Aqueous lithium hydroxide solution (1M) is added to a solution of the ester in THF/water (3/1), and stirred for 18 h at room temperature. After concentrating, the crude reaction mixture is acidified with aqueous HCl solution (1M), diluted with water, stirred to break up solids, and the solid isolated by filtration to provide the acid.

| Eg | Compound Structure | Compound Name |
|---|---|---|
| 70 | 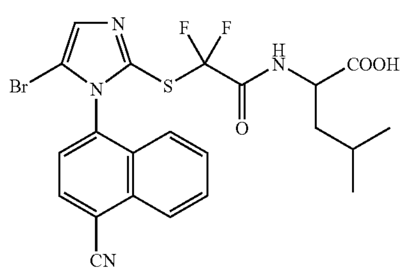 [SMILES: CC(C)CC(NC(=O)C(F)(F)Sc1ncc(Br)n1-c1ccc(C#N)c2ccccc12)C(=O)O] | 2-(2-(5-bromo-1-(4-cyanonaphthalen-1-yl)-1H-imidazol-2-ylthio)-2,2-difluoroacetamido)-3-methylpentanoic acid |
| 71 | 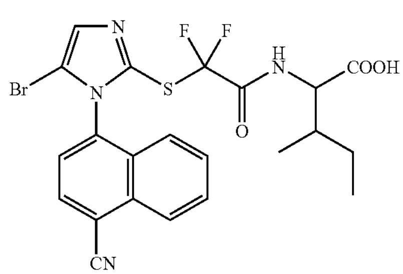 [SMILES: CCC(C)C(NC(=O)C(F)(F)Sc1ncc(Br)n1-c1ccc(C#N)c2ccccc12)C(=O)O] | 2-(2-(5-bromo-1-(4-cyanonaphthalen-1-yl)-1H-imidazol-2-ylthio)-2,2-difluoroacetamido)-3-methylpentanoic acid |

-continued

| Eg | Compound Structure | Compound Name |
|---|---|---|
| 72 | 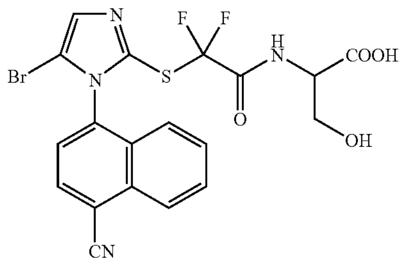 [SMILES: N#Cc1ccc(-n2c(Br)cnc2SC(F)(F)C(=O)NC(CO)C(=O)O)c2ccccc12] | 2-(2-(5-bromo-1-(4-cyanonaphthalen-1-yl)-1H-imidazol-2-ylthio)-2,2-difluoroacetamido)-3-hydroxypropanoic acid |
| 73 | 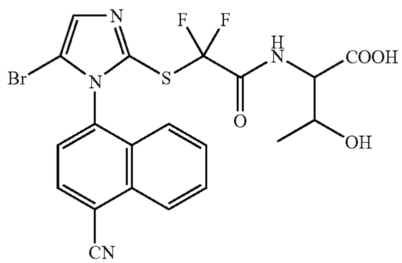 [SMILES: CC(O)C(NC(=O)C(F)(F)Sc1ncc(Br)n1-c1ccc(C#N)c2ccccc12)C(=O)O] | 2-(2-(5-bromo-1-(4-cyanonaphthalen-1-yl)-1H-imidazol-2-ylthio)-2,2-difluoroacetamido)-3-hydroxybutanoic acid |
| 74 | 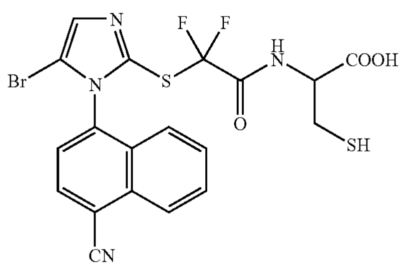 [SMILES: N#Cc1ccc(-n2c(Br)cnc2SC(F)(F)C(=O)NC(CS)C(=O)O)c2ccccc12] | 2-(2-(5-bromo-1-(4-cyanonaphthalen-1-yl)-1H-imidazol-2-ylthio)-2,2-difluoroacetamido)-3-mercaptopropanoic acid |
| 75 | 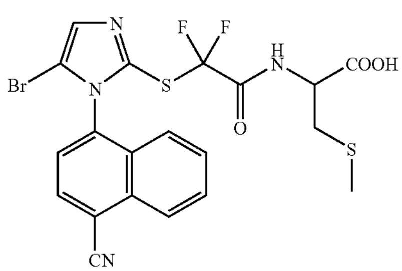 [SMILES: CSCC(NC(=O)C(F)(F)Sc1ncc(Br)n1-c1ccc(C#N)c2ccccc12)C(=O)O] | 2-(2-(5-bromo-1-(4-cyanonaphthalen-1-yl)-1H-imidazol-2-ylthio)-2,2-difluoroacetamido)-3-(methylthio)propanoic acid |
| 76 | 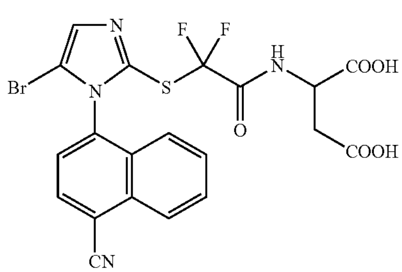 [SMILES: N#Cc1ccc(-n2c(Br)cnc2SC(F)(F)C(=O)NC(CC(=O)O)C(=O)O)c2ccccc12] | 2-(2-(5-bromo-1-(4-cyanonaphthalen-1-yl)-1H-imidazol-2-ylthio)-2,2-difluoroacetamido)succinic acid |
| 78 | 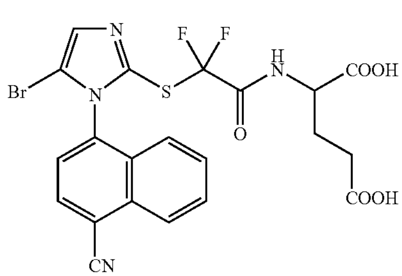 [SMILES: N#Cc1ccc(-n2c(Br)cnc2SC(F)(F)C(=O)NC(CCC(=O)O)C(=O)O)c2ccccc12] | 2-(2-(5-bromo-1-(4-cyanonaphthalen-1-yl)-1H-imidazol-2-ylthio)-2,2-difluoroacetamido)pentanedioic acid |

-continued

| Eg | Compound Structure | Compound Name |
|---|---|---|
| 79 | 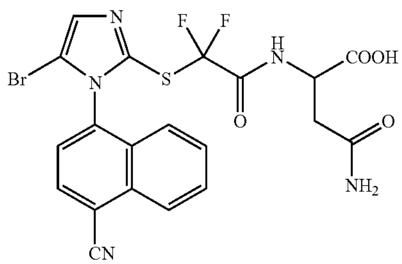 [SMILES: N#Cc1ccc(-n2c(Br)cnc2SC(F)(F)C(=O)NC(CC(N)=O)C(=O)O)c2ccccc12] | 4-amino-2-(2-(5-bromo-1-(4-cyanonaphthalen-1-yl)-1H-imidazol-2-ylthio)-2,2-difluoroacetamido)-4-oxobutanoic acid |
| 80 | 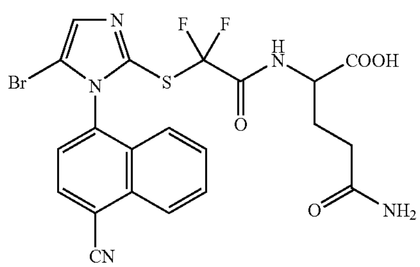 [SMILES: N#Cc1ccc(-n2c(Br)cnc2SC(F)(F)C(=O)NC(CCC(N)=O)C(=O)O)c2ccccc12] | 5-amino-2-(2-(5-bromo-1-(4-cyanonaphthalen-1-yl)-1H-imidazol-2-ylthio)-2,2-difluoroacetamido)-5-oxopentanoic acid |
| 81 | 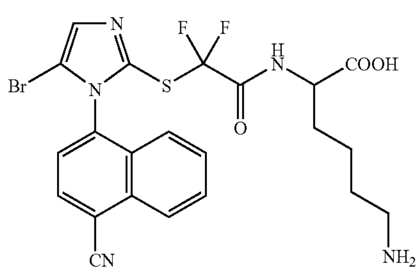 [SMILES: N#Cc1ccc(-n2c(Br)cnc2SC(F)(F)C(=O)NC(CCCCN)C(=O)O)c2ccccc12] | 6-amino-2-(2-(5-bromo-1-(4-cyanonaphthalen-1-yl)-1H-imidazol-2-ylthio)-2,2-difluoroacetamido)hexanoic acid |
| 82 | 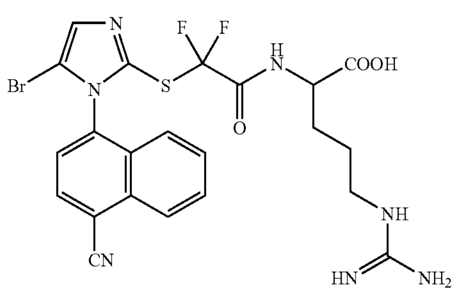 [SMILES: N#Cc1ccc(-n2c(Br)cnc2SC(F)(F)C(=O)NC(CCCNC(=N)N)C(=O)O)c2ccccc12] | 2-(2-(5-bromo-1-(4-cyanonaphthalen-1-yl)-1H-imidazol-2-ylthio)-2,2-difluoroacetamido)-5-guanidinopentanoic acid |
| 83 | 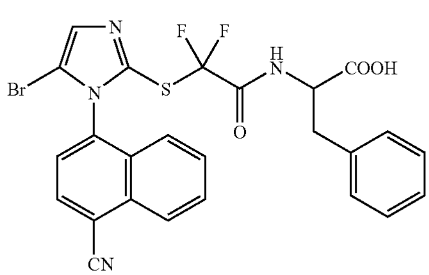 [SMILES: N#Cc1ccc(-n2c(Br)cnc2SC(F)(F)C(=O)NC(Cc2ccccc2)C(=O)O)c2ccccc12] | 2-(2-(5-bromo-1-(4-cyanonaphthalen-1-yl)-1H-imidazol-2-ylthio)-2,2-difluoroacetamido)-3-phenylpropanoic acid |

-continued

| Eg | Compound Structure | Compound Name |
|---|---|---|
| 84 | 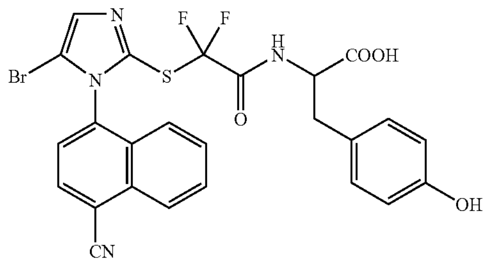 [SMILES: N#Cc1ccc(-n2c(Br)cnc2SC(F)(F)C(=O)NC(Cc2ccc(O)cc2)C(=O)O)c2ccccc12] | 2-(2-(5-bromo-1-(4-cyanonaphthalen-1-yl)-1H-imidazol-2-ylthio)-2,2-difluoroacetamido)-3-(4-hydroxyphenyl)propanoic acid |
| 85 | 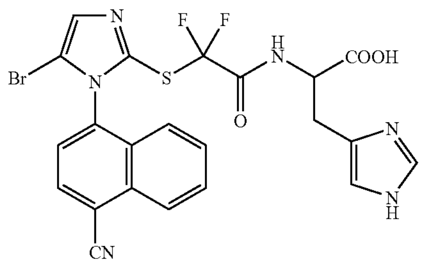 [SMILES: N#Cc1ccc(-n2c(Br)cnc2SC(F)(F)C(=O)NC(Cc2c[nH]cn2)C(=O)O)c2ccccc12] | 2-(2-(5-bromo-1-(4-cyanonaphthalen-1-yl)-1H-imidazol-2-ylthio)-2,2-difluoroacetamido)-3-(1H-imidazol-4-yl)propanoic acid |
| 86 | 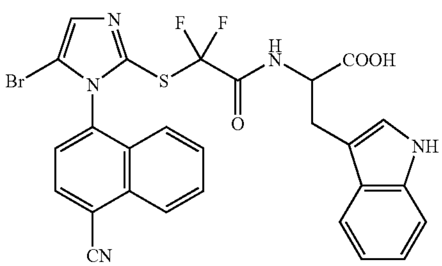 [SMILES: N#Cc1ccc(-n2c(Br)cnc2SC(F)(F)C(=O)NC(Cc2c[nH]c3ccccc23)C(=O)O)c2ccccc12] | 2-(2-(5-bromo-1-(4-cyanonaphthalen-1-yl)-1H-imidazol-2-ylthio)-2,2-difluoroacetamido)-3-(1H-indol-3-yl)propanoic acid |
| 87 | 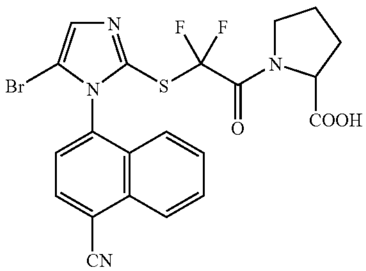 [SMILES: N#Cc1ccc(-n2c(Br)cnc2SC(F)(F)C(=O)N2CCCC2C(=O)O)c2ccccc12] | 1-(2-(5-bromo-1-(4-cyanonaphthalen-1-yl)-1H-imidazol-2-ylthio)-2,2-difluoroacetyl)pyrrolidine-2-carboxylic acid |

Example 88

Sodium 2-(5-bromo-1-(4-cyanonaphthalen-1-yl)-1H-imidazol-2-ylthio)acetate

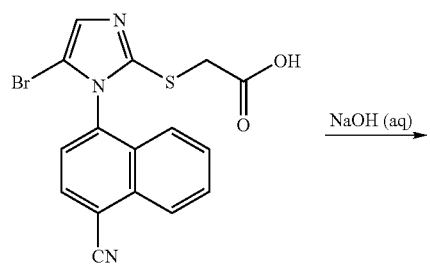

-continued

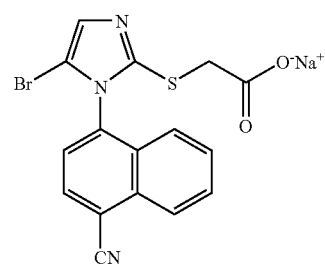

Aqueous sodium hydroxide solution (1M, 1 eq) is added dropwise over 5 mins to a solution of 2-(5-bromo-1-(4-cyanonaphthalen-1-yl)-1H-imidazol-2-ylthio)acetic acid (1 eq)

in ethanol at 10° C., and the mixture stirred for a further 10 mins at 10° C. Solvents are removed in vacuo to dryness to provide the sodium salt.

Example 89

Lithium 2-(5-bromo-1-(4-cyanonaphthalen-1-yl)-1H-imidazol-2-ylthio)acetate

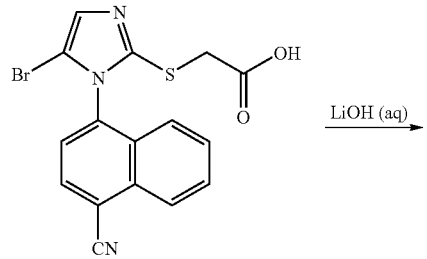

Aqueous lithium hydroxide solution (1M, 1 eq) is added dropwise over 5 mins to a solution of 2-(5-bromo-1-(4-cyanonaphthalen-1-yl)-1H-imidazol-2-ylthio)acetic acid (1 eq) in ethanol at 10° C., and the mixture stirred for a further 10 mins at 10° C. Solvents are removed in vacuo to dryness to provide the lithium salt.

Example 90

2-(5-Bromo-1-(4-cyanonaphthalen-1-yl)-1H-imidazol-2-ylthio)acetate salts

According to the methods described in examples 188 and 189, other pharmaceutically acceptable salts, such as the potassium, calcium or piperazine salts are prepared.

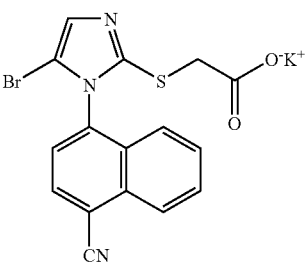

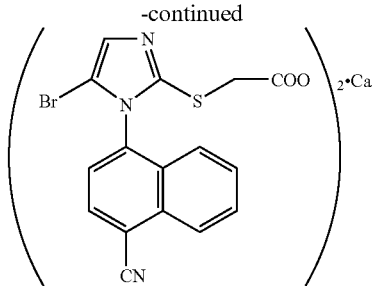

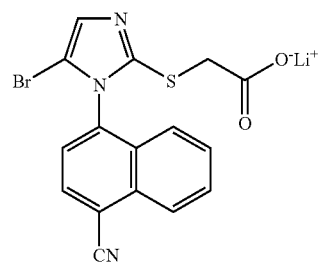

Example 91

Sodium 2-(5-bromo-1-(4-cyanonaphthalen-1-yl)-1H-imidazol-2-ylthio)-2,2-difluoroacetate

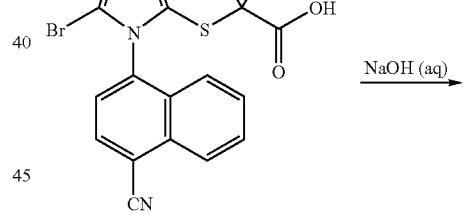

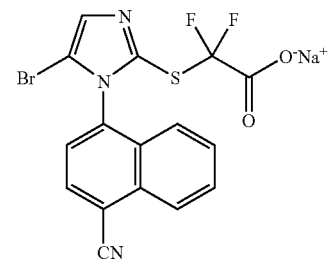

Aqueous sodium hydroxide solution (1M, 1 eq) is added dropwise over 5 mins to a solution of 2-(5-bromo-1-(4-cyanonaphthalen-1-yl)-1H-imidazol-2-ylthio)-2,2-difluoroacetic acid (1 eq) in ethanol at 10° C., and the mixture stirred for a further 10 mins at 10° C. Solvents are removed in vacuo to dryness to provide the sodium salt.

Example 92

Lithium 2-(5-bromo-1-(4-cyanonaphthalen-1-yl)-1H-imidazol-2-ylthio)-2,2-difluoroacetate

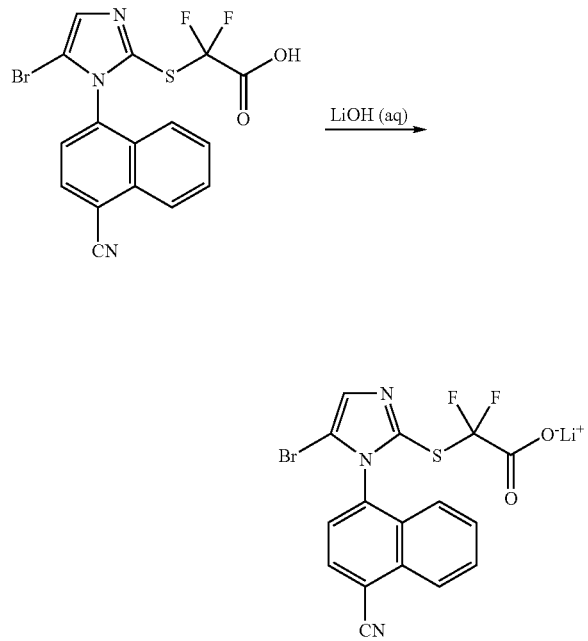

Aqueous lithium hydroxide solution (1M, 1 eq) is added dropwise over 5 mins to a solution of 2-(5-bromo-1-(4-cyanonaphthalen-1-yl)-1H-imidazol-2-ylthio)-2,2-difluoroacetic acid (1 eq) in ethanol at 10° C., and the mixture stirred for a further 10 mins at 10° C. Solvents are removed in vacuo to dryness to provide the lithium salt.

Example 93

2-(5-Bromo-1-(4-cyanonaphthalen-1-yl)-1H-imidazol-2-ylthio)-2,2-difluoroacetate salts According to the methods described in examples 91 and 92, other pharmaceutically acceptable salts, such as the potassium, calcium or piperazine salts are prepared.

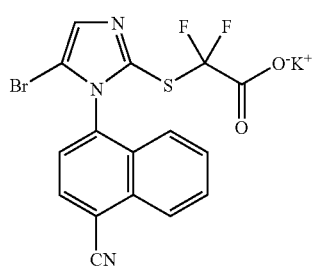

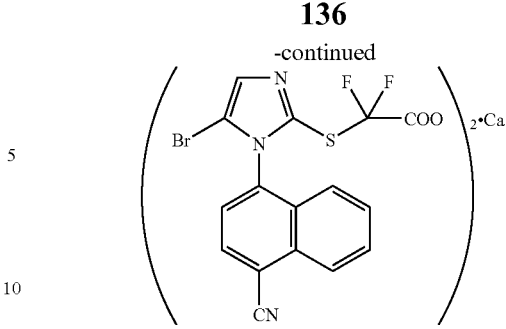

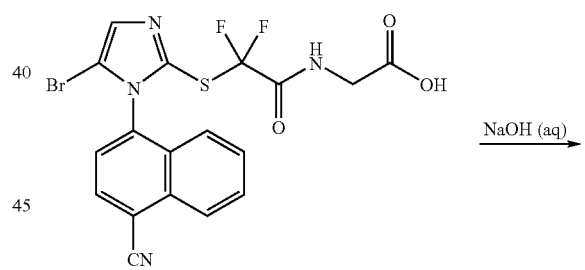

Example 94

Sodium 2-(2-(5-bromo-1-(4-cyanonaphthalen-1-yl)-1H-imidazol-2-ylthio)-2,2-dffluoroacetamido)acetate

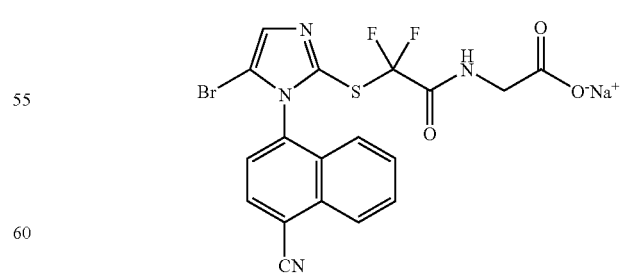

Aqueous sodium hydroxide solution (1M, 1 eq) is added dropwise over 5 mins to a solution of 2-(2-(5-bromo-1-(4-cyanonaphthalen-1-yl)-1H-imidazol-2-ylthio)-2,2-difluoroacetamido)acetic acid (1 eq) in ethanol at 10° C., and the mixture stirred for a further 10 mins at 10° C. Solvents are removed in vacuo to dryness to provide the sodium salt.

Example 95

Lithium 2-(2-(5-bromo-1-(4-cyanonaphthalen-1-yl)-1H-imidazol-2-ylthio)-2,2-difluoroacetamido)acetate

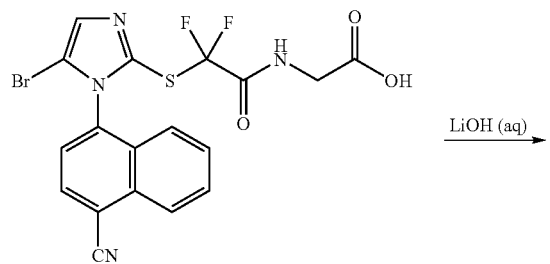

Aqueous lithium hydroxide solution (1M, 1 eq) is added dropwise over 5 mins to a solution of 2-(2-(5-bromo-1-(4-cyanonaphthalen-1-yl)-1H-imidazol-2-ylthio)-2,2-difluoroacetamido)acetic acid (1 eq) in ethanol at 10° C., and the mixture stirred for a further 10 mins at 10° C. Solvents are removed in vacuo to dryness to provide the lithium salt.

Example 96

2-(2-(5-Bromo-1-(4-cyanonaphthalen-1-yl)-1H-imidazol-2-ylthio)-2,2-difluoroacetamido)acetate salts According to the methods described in examples 94 and 95, other pharmaceutically acceptable salts, such as the potassium, calcium or piperazine salts are prepared.

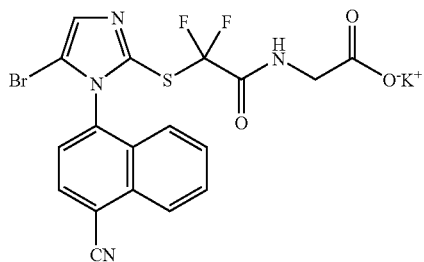

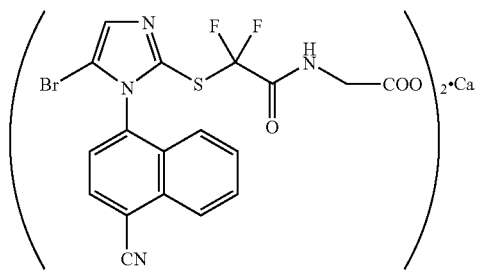

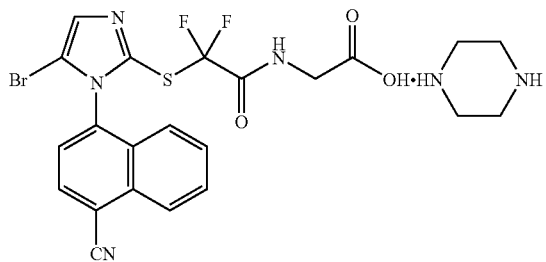

Example 97

Sodium 2-(2-(5-bromo-1-(4-cyclopropylnaphthalen-1-yl)-1H-imidazol-2-ylthio)-2,2-difluoroacetamido)acetate

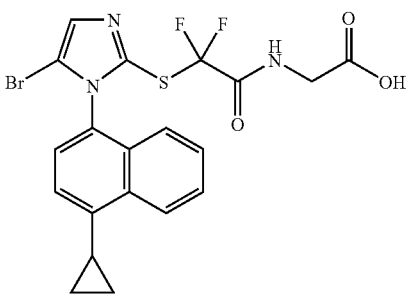

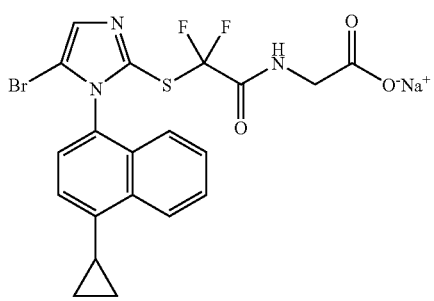

Aqueous sodium hydroxide solution (1M, 1 eq) is added dropwise over 5 mins to a solution of 2-(2-(5-bromo-1-(4-cyclopropylnaphthalen-1-yl)-1H-imidazol-2-ylthio)-2,2-difluoroacetamido)acetic acid (1 eq) in ethanol at 10° C., and the mixture stirred for a further 10 mins at 10° C. Solvents are removed in vacuo to dryness to provide the sodium salt.

Example 98

Lithium 2-(2-(5-bromo-1-(4-cyclopropylnaphthalen-1-yl)-1H-imidazol-2-ylthio)-2,2-difluoroacetamido)acetate

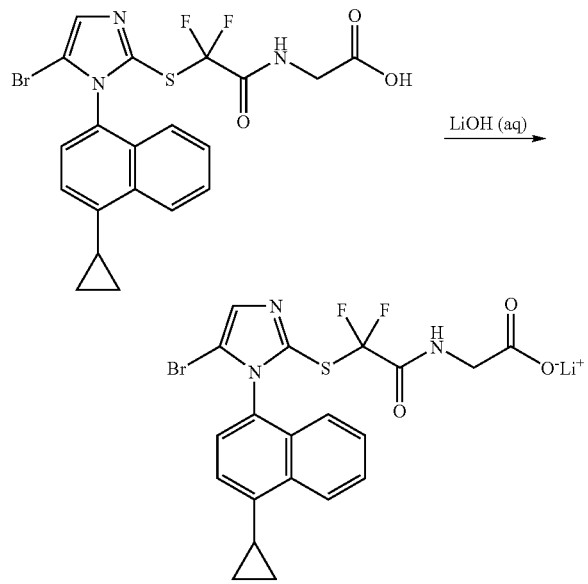

Aqueous lithium hydroxide solution (1M, 1 eq) is added dropwise over 5 mins to a solution of 2-(2-(5-bromo-1-(4-cyclopropylnaphthalen-1-yl)-1H-imidazol-2-ylthio)-2,2-difluoroacetamido)acetic acid (1 eq) in ethanol at 10° C., and the mixture stirred for a further 10 mins at 10° C. Solvents are removed in vacuo to dryness to provide the lithium salt.

Example 99

2-(2-(5-Bromo-1-(4-cyclopropylnaphthalen-1-yl)-1H-imidazol-2-ylthio)-2,2-difluoroacetamido)acetate salts According to the methods described in examples 97 and 98, other pharmaceutically acceptable salts, such as the potassium, calcium or piperazine salts are prepared.

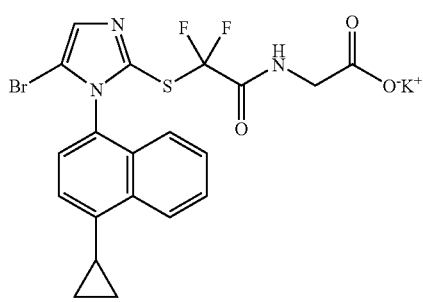

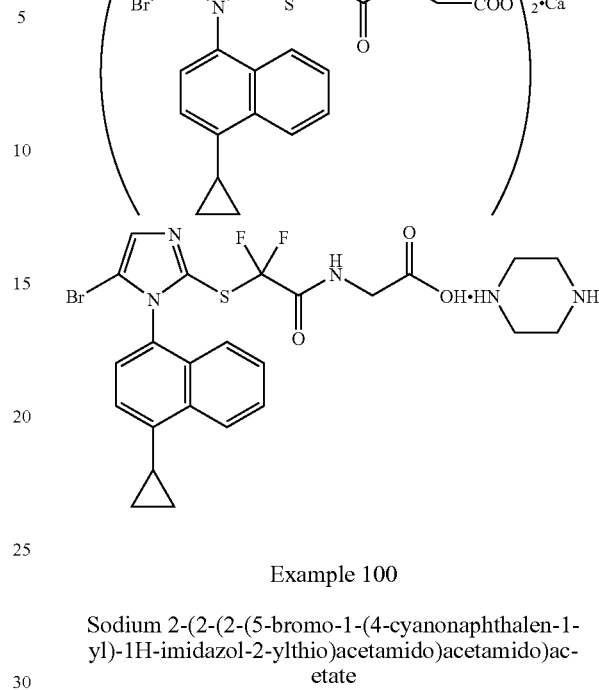

Example 100

Sodium 2-(2-(2-(5-bromo-1-(4-cyanonaphthalen-1-yl)-1H-imidazol-2-ylthio)acetamido)acetamido)acetate Aqueous sodium hydroxide solution (1M, 1 eq) is added dropwise over 5 mins to a solution of 2-(2-(2-(5-bromo-1-(4-cyanonaphthalen-1-yl)-1H-imidazol-2-ylthio)acetamido)acetic acid (1 eq) in ethanol at 10° C., and the mixture stirred for a further 10 mins at 10° C. Solvents are removed in vacuo to dryness to provide the sodium salt.

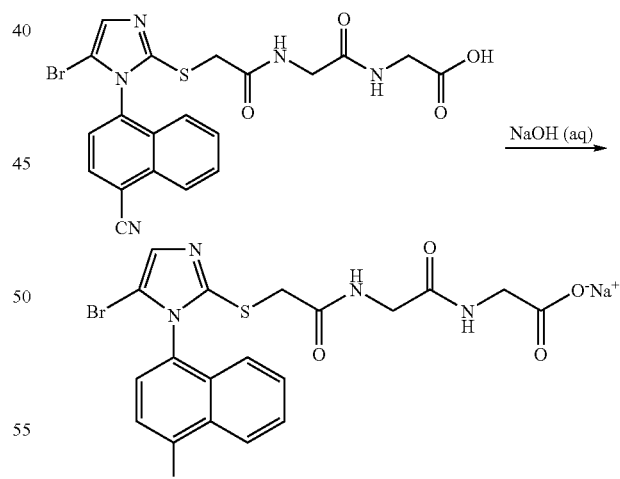

Example 101

Solubility of 2-(5-Bromo-1-(4-cyanonaphthalen-1-yl)-1H-imidazol-2-ylthio)acetic acid—free acid, sodium and piperazine salts To 1.00 mL (or 0.50 mL) of test solvent in an eppendorf vial, is added various weighed amounts of 2-(5-Bromo-1-(4- cyanonaphthalen-1-yl)-1H-imidazol-2-ylthio)acetic acid, (as the free acid, sodium and piperazine salts), and the weights recorded. When it appears the saturation point is being reached, addition is stopped, and the eppendorf vial is shaken at a constant speed of 1000 rpm at 22° C. for 24 hours. The tubes are then centrifuged for 5 minutes at 10-15,000 rpm, and checked for precipitation. Samples are diluted with acetonitrile/water, (1/1) (or iso-propyl alcohol for hexane) and analyzed by HPLC against known standards.

Example 102

Solubility of 2-(5-Bromo-1-(4-cyanonaphthalen-1-yl)-1H-imidazol-2-ylthio)-2,2-difluoroacetic acid—free acid, sodium and piperazine salts To 1.00 mL (or 0.50 mL) of test solvent in an eppendorf vial, is added various weighed amounts of 2-(5-Bromo-1-(4-cyanonaphthalen-1-yl)-1H-imidazol-2-ylthio)-2,2-difluoroacetic acid, (as the free acid, sodium and piperazine salts), and the weights recorded. When it appears the saturation point is being reached, addition is stopped, and the eppendorf vial is shaken at a constant speed of 1000 rpm at 22° C. for 24 hours. The tubes are then centrifuged for 5 minutes at 10-15,000 rpm, and checked for precipitation. Samples are diluted with acetonitrile/water, (1/1) (or iso-propyl alcohol for hexane) and analyzed by HPLC against known standards.

II Biological Evaluation

Example 103

Uric Acid Uptake Assay

Creation of Stable Cell Lines Expressing hURAT1 Transporter: Full-length human URAT1 gene (SLC22A12) was subcloned from plasmid pCMV6-XL5 (Origene) into eukaryotic expression plasmid pCMV6/Neo (Origene) using Not I restriction sites. Gene sequencing confirmed the sequence of hURAT1 as outlined in Genbank (Accession #NM_144585.2). HEK293 human embryonic kidney cells (ATCC# CRL-1573) were propagated in EMEM tissue culture medium as described by ATCC in an atmosphere of 5% $CO_2$ and 95% air. Transfections of HEK293 cells with the pCMV6/Neo/URAT1 construct were performed using L2000 transfection reagent (Invitrogen) as described by the manufacturer. After 24 h the transfected cells were split into 10 cm tissue culture plates and grown for 1 day after which the medium was replaced with fresh growth medium containing G418 (Gibco) at 0.5 mg/ml final concentration. Drug-resistant colonies were selected after approximately 8 days and then tested for $^{14}$C-uric acid transport activity. The HEK293/urat1 cells are plated on Poly-D-Lysine Coated 96-well Plates at a density of 75,000 cells per well.

Cells were grown overnight (20-26 hours) at 37° C. in an incubator. Plates were allowed to come to room temperature and media was washed out with one wash of 250 µl of Wash Buffer (125 mM Na Gluconate, 10 mM Hepes ph 7.3). Compound or vehicle is added in assay buffer with C14 Uric Acid for a final concentration of 40 µM Uric Acid with a specific activity of 54 mCi/mmol. Assay Buffer is 125 mM Sodium Gluconate, 4.8 mM Potassium Gluconate, 1.2 mM Potassium phosphate, monobasic, 1.2 mM magnesium sulfate, 1.3 mM Ca Gluconate, 5.6 mM Glucose, 25 mM HEPES, pH 7.3. Plates were incubated at room temperature for 10 minutes then washed 3 times with 50 µl Wash Buffer and 3 times with 250 µl Wash Buffer. Microscint 20 Scintillation Fluid was added and plates were incubated overnight at 45° C. to equilibrate. Plates are then read on the TopCount Plate Reader and an EC50 value generated. (See Enomoto et al, *Nature*, 2002, 417, 447-451 and Anzai et al, *J. Biol. Chem.*, 2004, 279, 45942-45950.).

Compounds prepared as described herein, were examined according to the procedure described above and $EC_{50}$ values generated. The table below summarizes the activity of the compounds in the Uric Acid Uptake Assay, wherein A represents an $EC_{50}$ from 1 nM to 1 µM; B represents an $EC_{50}$ from 1 µM to 30 µM; and C represents an $EC_{50}$ greater than 30 µM. (N/A means data not available).

| Structure | NMR Chemical Shifts | MS | Activity ($EC_{50}$) |
|---|---|---|---|
| 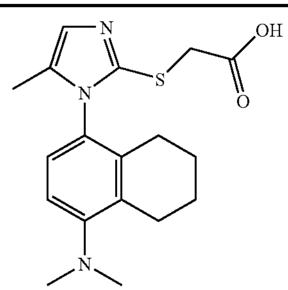 | $^1$H NMR (400 MHz, DMSO-$d_6$) δ ppm 1.67 (br. s., 4 H) 1.87 (s, 3 H) 2.07 (d, J = 16.79 Hz, 1 H) 2.23 (br. s., 1 H) 2.70 (s, 6 H) 2.73 (br. s., 2 H) 3.77 (br. s., 2 H) 6.88 (br. s., 1 H) 7.04 (s, 2 H) | Mass found: 346.09 (M + 1) | B |
| 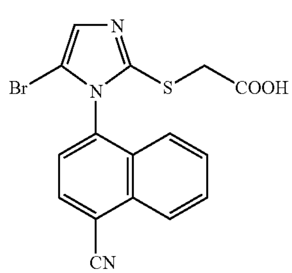 [SMILES: N#Cc1ccc(-n2c(Br)cnc2SCC(=O)O)c2ccccc12] | $^1$H NMR (DMSO-$d_6$, 400 MHz): δ 12.84 (bs, 1H), 8.46 (d, 1H), 8.32 (d, 1H), 7.98 (t, 1H), 7.87 (m, 2H), 7.46 (s, 1H), 7.30 (d, 1H). | msES + (387.91, 389.91) | A |

| Structure | NMR Chemical Shifts | MS | Activity (EC$_{50}$) |
|---|---|---|---|
| (5-bromo-1-(4-cyanonaphthalen-1-yl)imidazol-2-yl)thio-acetamide-glycine ethyl ester | ¹H NMR (DMSO-d$_6$, 400 MHz): δ 8.54 (t, 1H), 8.45 (d, 1H), 8.32 (d, 1H), 7.97 (dt, 1H), 7.90 (d, 1H), 7.84 (dt, 1H), 7.46 (s, 1H), 7.29 (d, 1H), 4.09 (q, 2H), 3.84 (s, 2H), 3.81 (d, 2H), 1.18 (t, 3H). | Ms ES + (472.87, 474.88) | A |
| (5-bromo-1-(4-cyanonaphthalen-1-yl)imidazol-2-yl)thio-acetamide-glycine | ¹H NMR (DMSO-d$_6$, 400 MHz): δ 12.61 (bs, 1H), 8.42 (d, 1H), 8.29 (d, 1H), 7.95 (dt, 1H), 7.88 (d, 1H) 7.82 (dt, 1H), 7.43 (s, 1H), 7.27 (d, 1H), 3.81 (d, 2H), 3.71 (d, 2H). | msES + (444.92, 446.93) | B |
| (5-bromo-1-(4-cyanonaphthalen-1-yl)imidazol-2-yl)thio-acetamide-β-alanine ethyl ester | ¹H NMR (DMSO-d$_6$, 400 MHz): δ 8.45 (d, 1H), 8.32 (d, 1H), 8.20 (t, 1H), 7.97 (dt, 1H), 7.90 (d, 1H) 7.85 (dt, 1H), 7.44 (s, 1H), 7.29 (d, 1H), 4.06 (q, 2H), 3.73 (s, 2H), 3.24 (q, 2H), 2.41 (t, 2H), 1.18 (t, 3H). | msES + (486.91, 488.92) | A |
| (5-bromo-1-(4-cyanonaphthalen-1-yl)imidazol-2-yl)thio-acetamide-alanine ethyl ester | ¹H NMR (DMSO-d$_6$, 400 MHz): δ 8.57 (d, 1H), 8.45 (dd, 1H), 8.32 (d, 1H), 7.97 (t, 1H) 7.90 (d. 1H), 7.84 (t, 1H), 7.46 (s, 1H), 7.29 (d, 1H), 4.18 (q, 1H), 4.07 (m, 2H), 3.81 (m, 2H), 1.24 (t, 3H), 1.16 (t, 3H). | msES + (486.91, 488.92) | A |
| (5-bromo-1-(4-cyanonaphthalen-1-yl)imidazol-2-yl)thio-acetamide-valine ethyl ester | ¹H NMR (DMSO-d$_6$, 400 MHz): δ 8.45 (m, 2H), 8.32 (d, 1H), 7.97 (t, 1H), 7.89 (dd, 1H), 7.84 (dt, 1H), 7.46 (s, 1H), 7.28 (dd, 1H), 4.10 (m, 3H), 3.86 (m, 2H), 2.02 (m, 1H), 1.18 (dt, 3H), 0.85 (m, 6H). | msES + (514.92, 516.93) | A |

| Structure | NMR Chemical Shifts | MS | Activity (EC$_{50}$) |
|---|---|---|---|
| (structure: 5-bromo-1-(4-cyanonaphthalen-1-yl)imidazol-2-yl-S-CH$_2$-C(O)NH-CH$_2$CH$_2$-COOH) | $^1$H NMR (DMSO-d$_6$, 400 MHz): δ 12.23 (bs, 1H), 8.42 (d, 1H), 8.29 (d, 1H), 8.17 (t, 1H), 7.95 (dt, 1H), 7.88 (d, 1H), 7.82 (dt, 1H), 7.42 (s, 1H), 7.26 (d, 1H), 3.71 (s, 2H), 3.19 (q, 2H), 2.32 (t, 2H). | msES + (458.96, 460.97) | B |
| (structure: alanine analog) | $^1$H NMR (DMSO-d$_6$, 400 MHz): δ 12.60 (bs, 1H), 8.42 (m, 2H), 8.29 (d, 1H), 7.95 (dt, 1H), 7.87 (dd, 1H), 7.82 (dt, 1H), 7.43 (s, 1H), 7.26 (d, 1H), 4.12 (q, 1H), 3.79 (m, 2H), 1.21 (m, 3H). | msES + (458.96, 460.97) | C |
| (structure: valine analog) | $^1$H NMR (DMSO-d$_6$, 400 MHz): δ 12.68 (bs, 1H), 8.42 (dd, 1H), 8.29 (m, 2H), 7.95 (dt, 1H), 7.87 (dd, 1H), 7.82 (dt, 1H), 7.43 (s, 1H), 7.26 (d, 1H), 4.08 (ddd, 1H), 3.87 (dd, 1H), 3.80 (dd, 1H), 2.01 (m, 1H), 0.82 (m, 6H). | msES + (486.97, 488.98) | B |
| (structure: difluoroacetic acid analog) | $^1$H NMR (DMSO-d$_6$, 400 MHz): δ 13.2 (bs, 1H), 8.46 (d, 1H), 8.31 (d, 1H), 7.96 (t, 1H), 7.87 (m, 2H), 7.70 (s, 1H), 7.23 (d, 1H). | msES + (423.89, 425.88) | A |
| (structure: difluoro-Gly-OtBu analog) | $^1$H NMR (DMSO-d$_6$, 400 MHz): δ 9.24 (dd, 1H), 8.45 (dd, 1H), 8.31 (d, 1H), 7.95 (m, 2H), 7.83 (t, 1H), 7.71 (s, 1H), 7.24 (dd, 1H), 4.16 (s, 2H), 1.35 (d, 9H). | msES + (537.10, 539.10) | N/A |

| Structure | NMR Chemical Shifts | MS | Activity (EC$_{50}$) |
|---|---|---|---|
| [Structure: 5-Bromo-imidazole-N-(4-cyanonaphthalen-1-yl), S-CF$_2$-C(O)NH-CH(CH$_3$)-COOtBu] | $^1$H NMR (DMSO-d$_6$, 400 MHz): δ 9.33 (dd, 1H), 8.47 (dd, 1H), 8.31 (d, 1H), 7.96 (m, 2H), 7.84 (t, 1H), 7.72 (s, 1H), 7.24 (dd, 1H), 4.06 (ddd, 1H), 1.27 (d, 9H), 1.25 (d, 3H). | msES+ (551.12, 552.12) | N/A |
| [Structure: analogous with valine-OtBu side chain] | $^1$H NMR (DMSO-d$_6$, 400 MHz): δ 9.18 (dd, 1H), 8.46 (dd, 1H), 8.31 (d, 1H), 7.94 (m, 2H), 7.82 (t, 1H), 7.70 (s, 1H), 7.24 (dd, 1H), 3.86 (ddd, 1H), 2.05 (m, 1H), 1.33 (d, 9H), 0.83 (m, 6H). | msES+ (579.15, 581.16) | N/A |
| [Structure: analogous with glycine-COOH side chain] | $^1$H NMR (DMSO-d$_6$, 400 MHz): δ 12.82 (bs, 1H), 9.32 (t, 1H), 8.46 (d, 1H), 8.31 (d, 1H), 7.95 (m, 2H), 7.84 (t, 1H), 7.72 (s, 1H), 7.24 (d, 1H), 3.72 (d, 1H). | msES+ (480.96, 482.96) | N/A |
| [Structure: analogous with alanine-COOH side chain] | $^1$H NMR (DMSO-d$_6$, 400 MHz): δ 12.79 (bs, 1H), 9.30 (t, 1H), 8.47 (dd, 1H), 8.31 (d, 1H), 7.93 (m, 2H), 7.84 (t, 1H), 7.72 (s, 1H), 7.24 (dd, 1H), 4.15 (ddd, 1H), 1.26 (d, 3H). | msES+ (495.06, 496.07) | N/A |
| [Structure: analogous with valine-COOH side chain] | $^1$H NMR (DMSO-d$_6$, 400 MHz): δ 12.95 (bs, 1H), 9.24 (dd, 1H), 8.53 (dt, 1H), 8.40 (dt, 1H), 8.01 (m, 2H), 7.79 (s, 1H), 7.30 (d, 1H), 4.03 (ddd, 1H), 2.15 (m, 1H), 0.89 (m, 6H). | msES+ (523.09, 525.10) | N/A |

Example 104

In Vitro Metabolic Stability

In vitro metabolic stability is assessed in rat and human liver microsomes (RLM/HLM). The incubation mixer contained the following: 1 uM test compound, 1 mg/mL HLM/RLM, 100 mM potassium phosphate buffer at pH 7.4, 1 mM NADPH and 5 mM MgCl$_2$. This mixture is preincubated for 3 min before the 30 minute incubation at 37° C. The reaction is initiated with the addition of NADPH and terminated by the addition of equal volume of acetonitrile with internal standard. Incubation samples without NADPH are used as control samples. After vortexing and centrifugation, the supernatant is injected onto LC-MS/MS for quantitation.

2-(5-Bromo-1-(4-cyanonaphthalen-1-yl)-1H-imidazol-2-ylthio)-2,2-difluoroacetic acid and 2-(5-Bromo-1-(4-cyanonaphthalen-1-yl)-1H-imidazol-2-ylthio)acetic acid are examined according to this procedure.

III In Vivo Testing

Example 105

PO Dosing in Rats

Compounds prepared as described in examples 1, 3, 7, 8, and 9 are administered PO to Male Sprague-Dawley Rats (250 grams; 3 animals per test group). The test compounds are dissolved in aqueous sodium hydroxide solution (0.2N), brought up to volume with phosphate buffered saline to a concentration of 0.6 mg/mL, and PO administered to the animals at a concentration of 3 mg/kg (5 mL/kg). Plasma samples are removed at 0.25, 0.5, 1, 3, 6, 12 and 24 hr after initial dose and analyzed for presence of compound and possible metabolite. Urine samples are also collected and analyzed for parent compound and/or metabolite.

Note that in some instances, 2-(5-Bromo-1-(4-cyanonaphthalen-1-yl)-1H-imidazol-2-ylthio)acetic acid (eg 1) is a possible in vivo metabolite of the compounds described in examples 2-9.

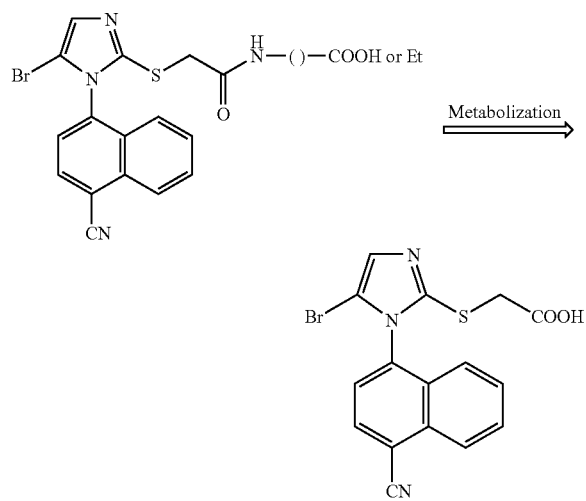

The plasma profiles of compounds 3, 8 and 9 are shown in the table below:

|    |         | Total Urinary |          | Urinary Distribution (%) |        |         |
|----|---------|-----|------------------|--------------------------|--------|---------|
|    |         | BA  | Excretion        |                          |        |         |
| Eg | Analyte | (%) | % of dose        | 0-6 h                    | 6-12 h | 12-24 h |
| Eg 1 | Eg 1 | 30 | 4.2 | 85* | 11* | 4* |
| Eg 3 | Eg 3 | nd | 7 | 74 | 20 | 7 |
|      | Eg 1 | nd | 12 | 15 | 38 | 47 |
| Eg 7 | Eg 7 | nd | 26 | 63 | 30 | 7 |
|      | Eg 1 | nd | 1 | 43 | 40 | 18 |
| Eg 8 | Eg 8 | nd | 8 | 63 | 32 | 5 |
|      | Eg 1 | nd | 10 | 8 | 46 | 47 |
| Eg 9 | Eg 9 | nd | 1 | 66 | 26 | 9 |
|      | Eg 1 | nd | 9 | 8 | 41 | 52 |

*Plasma Distribution

FIG. 1 shows a graph of mean plasma concentration of 2-(5-Bromo-1-(4-cyanonaphthalen-1-yl)-1H-imidazol-2-ylthio)acetic acid at various time points (0.25, 0.5, 1, 3, 6, 12 and 24 hr) post dosing, as released by in vivo metabolism of compounds 3, 8 and 9, after PO dosing to male rats (3 mg/kg).

Figure 2:
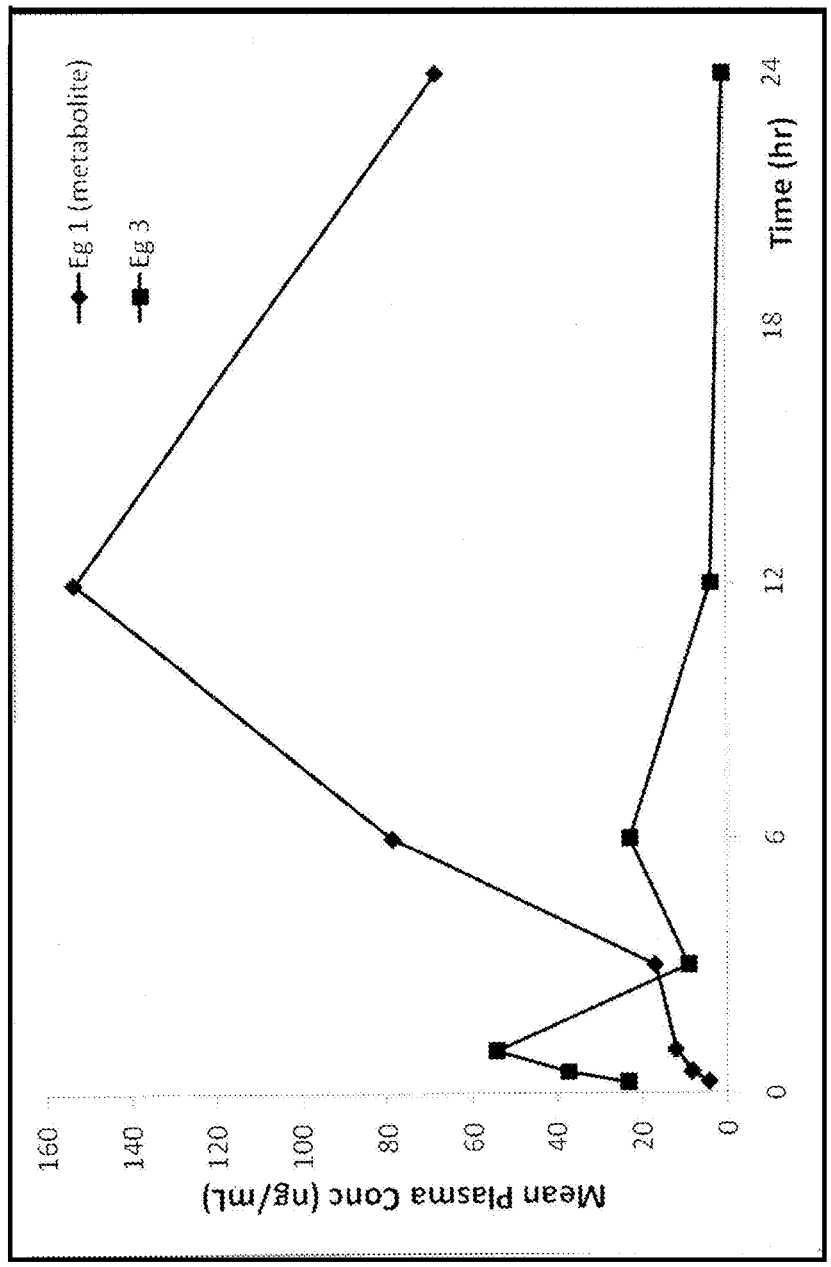
FIG. 2 shows a graph of mean plasma concentrations of 2-(2-(5-Bromo-1-(4-cyanonaphthalen-1-yl)-1H-imidazol-2-ylthio)acetamido)acetic acid (Eg. 3) and example 1 (2-(5-Bromo-1-(4-cyanonaphthalen-1-yl)-1H-imidazol-2-ylthio) acetic acid), at various time points (0.25, 0.5, 1, 3, 6, 12 and 24 hr) post PO dosing to male rats (3 mg/kg).

FIG. 2 shows a graph of mean plasma concentrations of example 3 and example 1 (2-(5-Bromo-1-(4-cyanonaphthalen-1-yl)-1H-imidazol-2-ylthio)acetic acid), at various time points (0.25, 0.5, 1, 3, 6, 12 and 24 hr) post PO dosing to male rats (3 mg/kg).

Figure 3:
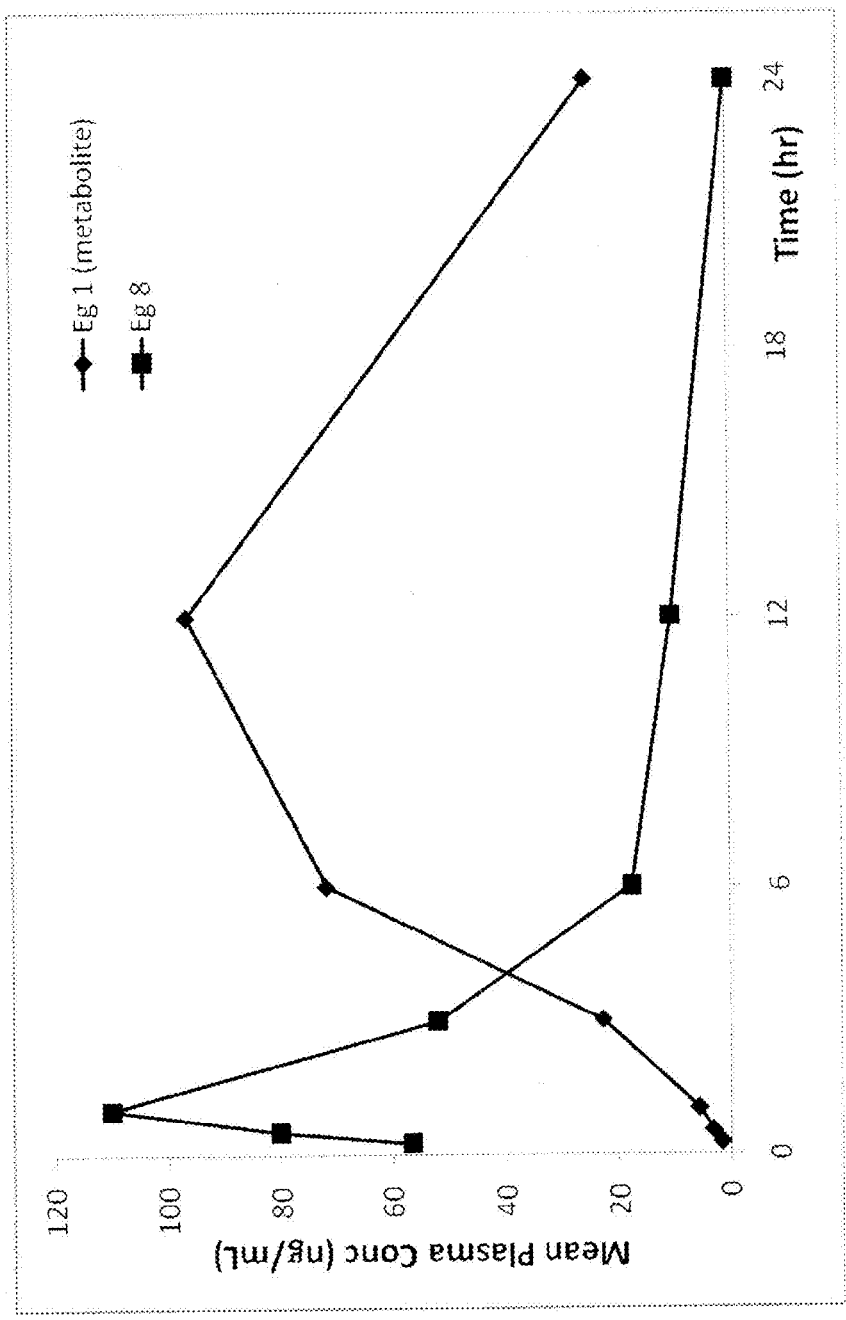
FIG. 3 shows a graph of mean plasma concentrations of (2S)-2-(2-(5-bromo-1-(4-cyanonaphthalen-1-yl)-iH-imidazol-2-ylthio)acetamido)propanoic acid (Eg. 8) and example 1 (2-(5-Bromo-1-(4-cyanonaphthalen-1-yl)-1H-imidazol-2-ylthio)acetic acid), at various time points (0.25, 0.5, 1, 3, 6, 12 and 24 hr) post PO dosing to male rats (3 mg/kg).

FIG. 3 shows a graph of mean plasma concentrations of example 8 and example 1 (2-(5-Bromo-1-(4-cyanonaphthalen-1-yl)-1H-imidazol-2-ylthio)acetic acid), at various time points (0.25, 0.5, 1, 3, 6, 12 and 24 hr) post PO dosing to male rats (3 mg/kg).

Figure 4:
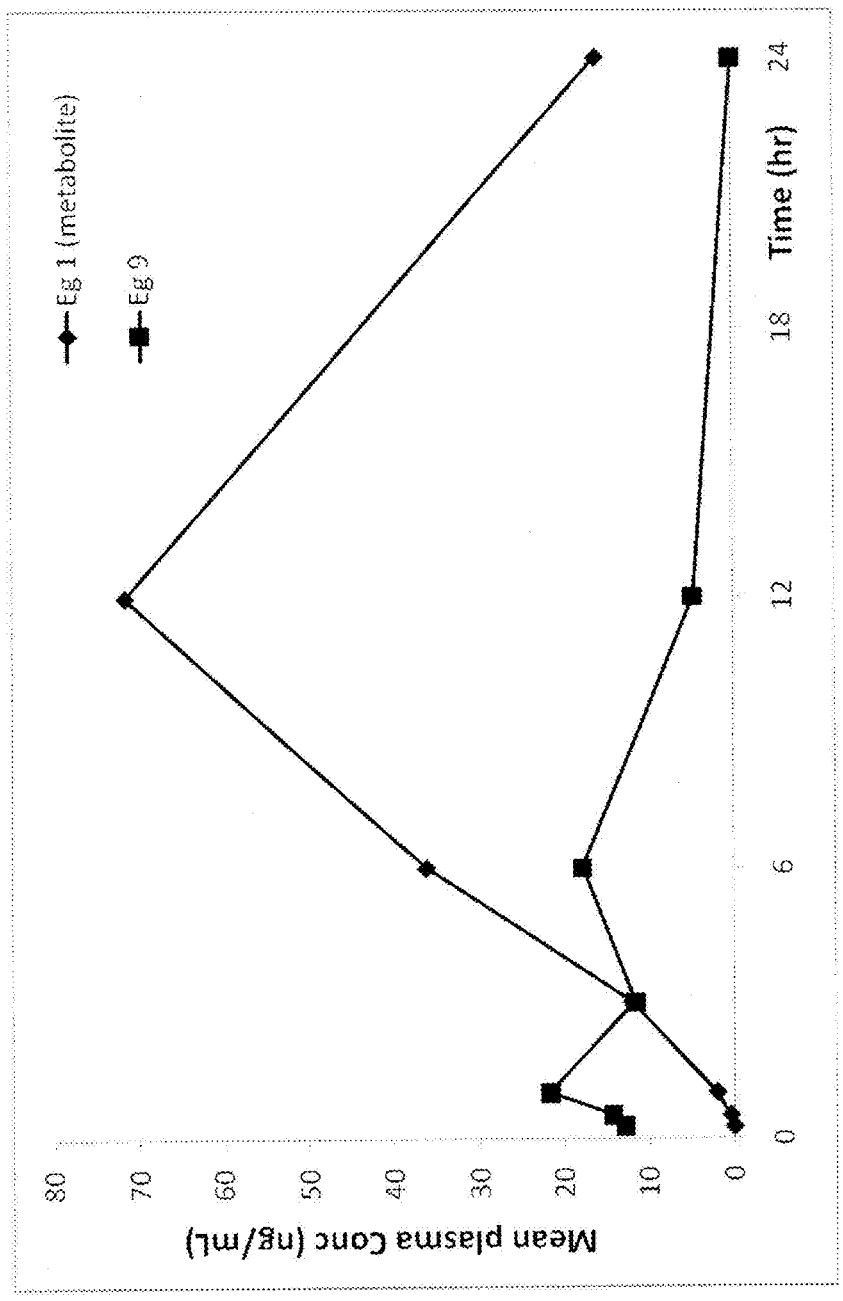
FIG. 4 shows a graph of mean plasma concentrations of (2S)-2-(2-(5-bromo-1-(4-cyanonaphthalen-1-yl)-1H-imidazol-2-ylthio)acetamido)-3-methylbutanoic acid (Eg. 9) and example 1 (2-(5-Bromo-1-(4-cyanonaphthalen-1-yl)-1H-imidazol-2-ylthio)acetic acid), at various time points (0.25, 0.5, 1, 3, 6, 12 and 24 hr) post PO dosing to male rats (3 mg/kg).

FIG. 4 shows a graph of mean plasma concentrations of example 9 and example 1 (2-(5-Bromo-1-(4-cyanonaphthalen-1-yl)-1H-imidazol-2-ylthio)acetic acid), at various time points (0.25, 0.5, 1, 3, 6, 12 and 24 hr) post PO dosing to male rats (3 mg/kg).

Example 106

In Vivo Uric Acid Lowering Activity

The uric acid lowering activity of the compounds described herein is determined in a multiple ascending dose, double-blind, placebo-controlled study in healthy adult male human volunteers, as follows.

The study is performed in compliance with the current version of the declaration of Helsinki and with the ICH note for guidance on good clinical practice (CPMP/ICH/135/95).

| Eg | Analyte | $t_{1/2}$ (hr) | Tmax (hr) | Cmax (ug/mL) | Clast (ug/mL) | AUC (hr * ug/mL) | | | | F (%) |
|----|---------|------|------|--------|--------|----------------|-----------|------------|-----------|------|
|    |         |      |      |        |        | t = 0_6        | t = _12   | t = 12_24  | t = 0_24  |      |
| Eg 3 | Eg 1 | 875  | 10   | 0.154  | 0.0681 | 0.180 (8%)     | 0.696 (32%) | 1.33 (60%) | 2.21     | 29   |
|      | Eg 3 | 3.49 | 0.833| 0.0566 | 0.000518 | 0.145 (58%) | 0.0798 (32%) | 0.0256 (10%) | 0.251 |      |
| Eg 8 | Eg 1 |      | 12   | 0.0965 | 0.0253 | 0.174 (12%)    | 0.505 (36%) | 0.731 (52%) | 1.41    | 19   |
|      | Eg 8 | 2.99 | 1    | 0.110  | 0.000371 | 0.339 (69%) | 0.0839 (17%) | 0.0652 (13%) | 0.488 |      |
| Eg 9 | Eg 1 |      | 12   | 0.0716 | 0.0160 | 0.0873 (9%)    | 0.323 (35%) | 0.526 (56%) | 0.936   | 13   |
|      | Eg 9 | 2.69 | 2.67 | 0.0258 | 0.00469 | 0.0915 (49%) | 0.0677 (36%) | 0.0282 (15%) | 0.187 |     |

The urinary excretion profile of compounds 1, 3, 7, 8 and 9 are shown in the table below:

16 healthy male individuals, aged 18-45 years inclusive, with a body mass index (BMI) within 18-30 kg/m² inclusive, having provided a written informed consent, non smokers for at least 6 months, not using any drug treatment for 2 weeks before screening (2 months for enzyme-inducing drugs) except occasional Acetaminophen. The individuals are confined at the clinical site beginning the day before dose administration until 72 hours after the final dose administration on Day 17 and returned for a follow-up visit on Day 21±1.

The study is performed using 2-(5-Bromo-1-(4-cyanonaphthalen-1-yl)-1H-imidazol-2-ylthio)-2,2-difluoroacetic acid, potassium salt or 2-(5-Bromo-1-(4-cyanonaphthalen-1-yl)-1H-imidazol-2-ylthio)acetic acid, potassium salt, supplied as 100-mg solid powder in size 2 gelatin capsules. Matching placebo capsules are supplied as size 2 gelatin capsules. Individuals are randomized to receive the same number of placebo capsules as administered to the active individuals.

Capsules (active or placebo) are administered orally with 240 mL water 30 min after a standard breakfast (morning dose) and dinner (evening dose) for 14 days.

16 individuals (8 individuals [6 active and 2 placebo] per dose group).

| | | |
|---|---|---|
| a. Group 1: | Placebo | |
| b. Group 2: | 300 mg (3 × 100-mg capsules) example 1 b.i.d. | |
| c. Group 3: | 500 mg (5 × 100-mg capsules) example 1 b.i.d. | |

Blood is collected from the individuals on days 0, 3, 7, 14 and at follow-up. Serum uric levels wearere measured using standard automated procedures.

Example 107

Human Clinical Trial Comparing Efficacy of 2-(5-Bromo-1-(4-cyanonaphthalen-1-yl)-1H-imidazol-2-ylthio)-2,2-difluoroacetic acid or 2-(5-Bromo-1-(4-cyanonaphthalen-1-yl)-1H-imidazol-2-ylthio)acetic acid versus Indomethacin Design
This is a double-blind, parallel-group, multicenter, randomized, 5-day study.
Endpoints
The primary efficacy endpoint is:
a. Individual assessment of pain.
The secondary efficacy endpoints are:
a. Tenderness of the study joint;
b. Swelling of the study joint; and
c. Proportion of individuals discontinuation due to lack of efficacy.
Treatment Regime
Individuals are randomized into two groups: a control group (n=100) and an experimental group (n=100).
The control group is administered Indomethacin (75 mg) sustained release capsule (2 times daily) for a total of two weeks.
The experimental group is administered 2-(5-Bromo-1-(4-cyanonaphthalen-1-yl)-1H-imidazol-2-ylthio)-2,2-difluoroacetic acid, potassium salt or 2-(5-Bromo-1-(4-cyanonaphthalen-1-yl)-1H-imidazol-2-ylthio)acetic acid, potassium salt supplied as 100-mg solid powder in size 2 gelatin capsules for a total of two weeks.
Inclusion Criteria
Male or Female
≧18 years of old
Diagnosed with gout according to the 1980 ARA Criteria for the Classification of Acute Arthritis of Primary Gout.

Experiencing an acute attack of clinically diagnosed gout <48 hours prior to randomization.

Score a sum of 5 across the 3 symptom questions for pain (0- to 4-Likert scale), tenderness (0- to 3-point scales), and swelling [0- to 3-point scales] with the pain score being at least moderate (i.e. 2, 3, or 4 on the 0- to 4-Likert scale).

Female individuals of childbearing potential must have a negative pregnancy test.

Female individuals of childbearing potential must be infertile or on contraception.
Stastical Methodology
The primary analysis is based on change from baseline in individual assessment of pain computed from the average of responses on Study Days 2 through 5 using an intention-to-treat approach. All individual efficacy variables (except endpoints defined as proportions) are assessed by ANCOVA (model to include terms for study site, stratum [monoarticular versus polyarticular acute gout], baseline covariate, and treatment group), pending no 2-factor interactions with treatment. The comparability of treatment groups is assessed by 95% confidence intervals for pairwise treatment difference. The 95% confidence interval for individual assessment of pain must fall entirely within the comparability bounds (i.e., ±0.5 Likert units). Endpoints defined as proportions are compared between groups using Fisher's exact test. Assumptions of normality and homogeneity are assessed by the Shapiro-Wilk statistic and Levene's test, respectively. If a significant interaction (p$\delta$0.050) is found, then the nature of the interaction is assessed and further exploratory analyses is performed.

Example 108

Human Clinical Trial Comparing Efficacy of 42-(5-Bromo-1-(4-cyanonaphthalen-1-yl)-1H-imidazol-2-ylthio)-2,2-difluoroacetic acid or 2-(5-Bromo-1-(4-cyanonaphthalen-1-yl)-1H-imidazol-2-ylthio)acetic acid in Individuals Treated for Hypertension Hypothesis
Thiazide-induced hyperuricemia decreases the efficacy of thiazides in controlling BP, leads to endothelial dysfunction, and increases the incidence of insulin resistance and impaired glucose tolerance.
Study Design
This study is a randomized, double-blind, placebo-controlled clinical trial of 8-week duration in which a total of 220 African American individuals with untreated stage I hypertension will be enrolled, randomized, and treated as follows:

The experimental group receives chlorthalidone (25 mg/day) and potassium chloride (40 mEq/day) for 4 weeks. They are then randomized to add-on a compound of 2-(5-Bromo-1-(4-cyanonaphthalen-1-yl)-1H-imidazol-2-ylthio)-2,2-difluoroacetic acid, potassium salt, or 2-(5-Bromo-1-(4-cyanonaphthalen-1-yl)-1H-imidazol-2-ylthio)acetic acid, potassium salt (300 mg/day) or placebo.

The dosage of 2-(5-Bromo-1-(4-cyanonaphthalen-1-yl)-1H-imidazol-2-ylthio)-2,2-difluoroacetic acid or 2-(5-Bromo-1-(4-cyanonaphthalen-1-yl)-1H-imidazol-2-ylthio) acetic acid will be adjusted to achieve serum uric acid levels between 4 and 5.5 mg/dL. All individuals will receive a low-sodium diet.
Endpoints
The primary endpoint is reduction in systolic BP.
The secondary endpoints measure changes in endothelial function, ambulatory blood pressure, body composition, systemic inflammation, metabolic parameters, oxidant stress, and renal hemodynamics.

Inclusion Criteria:
  African American (including black individuals born in the Caribbean, Africa, Canada, etc.)
    Male or Female
    18 years of age or older
    Untreated with any antihypertensive agent, with an average sitting clinic BP of between 140/90 and 159/99 mm Hg
    Random spot urine protein/creatinine ratio of less than 0.5 (approximates a 24-hour urinary protein excretion of 500 mg/day)
    Calculated MDRD GFR of greater than or equal to 60 ml/min/1.73/m^2
    No allopurinol or probenecid intake for at least one month prior to study entry
Exclusion Criteria
History of cancer or accelerated hypertension
Confirmed total white cell count of less than 2,500/mm^3, anemia, or thrombocytopenia
Known history of liver disease
Known secondary cause of hypertension
Known presence of diabetes or fasting blood glucose greater than or equal to 126 mg/dL
History of heart failure, acute myocardial infarction, or stroke or on a β-blocker or calcium channel blocker for cardiovascular indications other than for lowering blood pressure
Abnormal EKG requiring medical intervention
History of clinical or renal biopsy or evidence of renal parenchymal disease
Acute gout attack within 2 weeks of study entry
History of drug abuse in the last 2 years, including narcotics, cocaine, or alcohol (greater than 21 drinks/week)
Arm circumference of greater than 52 cm, which precludes measurement with a 'thigh' BP cuff
Pregnant or planning to become pregnant during the study, or breastfeeding
History of noncompliance, are unable to comply with the study requirements, or who are currently participating in another study
Not fasting prior to obtaining screening laboratory data. If a participant has clearly not fasted, we will exclude those individuals with casual blood glucose levels of greater than or equal to 200 mg/dL. In the event that a fasting blood sugar exceeds 126 mg/dL, it will be reconfirmed on a blood glucose measurement obtained on a subsequent day, per American Diabetes Association criteria.

Example 109

Human Clinical Trial for Hyperuricemia or Hyperuricosuria

Study Design
This study is a randomized, double-blind, placebo-controlled clinical trial of 4-week duration in which a total of 100 individuals with atherosclerosis will be enrolled, randomized, and treated as follows:
The experimental group receives 2-(5-Bromo-1-(4-cyanonaphthalen-1-yl)-1H-imidazol-2-ylthio)-2,2-difluoroacetic acid, potassium salt, or 2-(5-Bromo-1-(4-cyanonaphthalen-1-yl)-1H-imidazol-2-ylthio)acetic acid, potassium salt (300 mg/day). The control group will receive atorvastatin (80-mg daily).
Main Criteria for Inclusion
Male and female individuals
Between 30-75 years of age
At least one obstruction in a major cardiac vessel with at least a 20% luminal diameter narrowing by visual estimation.
A "target vessel" for IVUS interrogation with no more than 50% luminal narrowing throughout a segment that was a minimum of 30 mm in length (the "target segment"). The target vessel must not have undergone previous intervention, nor have been a candidate for intervention at the time of Baseline catheterization.
Low-density lipoprotein cholesterol (LDL-C) between 125 and 210 mg/dL following a 4- to 10-week washout period if the individual is taking antihyperlipidemic medication.
Uric acid levels in the blood exceed 360 μmol/L (6 mg/dL) for a female individual or 400 μmol/L (6.8 mg/dL) for a male individual; or uric acid levels in urine exceed 800 mg/day (in a male individual) and greater than 750 mg/day (in a female individual).
Endpoints
The primary efficacy parameter is restoration of uric acid levels to medically-acceptable levels.
The secondary endpoints are:
a. Change in TPV
b. Change in percent plaque PPV Example 110

2-(5-Bromo-1-(4-cyanonaphthalen-1-yl)-1H-imidazol-2-ylthio)-2,2-difluoroacetic acid or 2-(5-Bromo-1-(4-cyanonaphthalen-1-yl)-1H-imidazol-2-ylthio)acetic acid is administered to 12 healthy subjects as follows:
a. 100 mg, fasted state (4 subjects)
b. 100 mg, fed state (4 subjects)
c. 200 mg, fasted state (4 subjects)
The examples and embodiments described herein are for illustrative purposes only and various modifications or changes suggested to individuals skilled in the art are to be included within the spirit and purview of this application and scope of the appended claims.

What is claimed is:
1. A compound of formula (II), or a pharmaceutically acceptable salt, ester or tautomer thereof:

$$\text{(II)}$$

$$R^1-\text{imidazole}(CR^aR^{a'})_a\text{-phenyl}(R^b,R^c,R^d,R^e,R^f)\quad W-(CR^xR^{x'})_x-(CR^yR^{y'})_y-(CR^zR^{z'})_z-A$$

wherein:
W is O, S, S(O), S(O)$_2$, NH, N(optionally substituted alkyl), CH$_2$, CH$_2$O, CH$_2$S or CH$_2$NH;
R$^1$ is F, Cl, Br, I, CH$_2$F, CF$_2$H, CF$_3$, CN, OH, NO$_2$, NH$_2$, NH(alkyl) or N(alkyl)(alkyl), SO$_2$CH$_3$, SO$_2$NH$_2$, SO$_2$NHCH$_3$, CO$_2$-alkyl, optionally substituted alkyl, optionally substituted alkenyl, optionally substituted alkoxy, optionally substituted S-alkyl, optionally substituted cycloalkyl, or optionally substituted heterocycle,
a is 0, 1 or 2;
R$^a$ is H or optionally substituted C$_{1-3}$ alkyl;
R$^{a'}$ is H or optionally substituted C$_{1-3}$ alkyl; or $R^a$ and $R^{a'}$ together with the carbon atom to which they are attached form an optionally substituted, 3-, 4-, 5- or 6-membered ring, optionally comprising 1 or 2 heteroatoms selected from O, N and S;

$R^b$, $R^c$, $R^e$ and $R^f$ are each independently H, F, Cl, Br, I, $CF_3$, CN, alkyl, cycloalkyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl or heteroaryl;

$R^d$ is F, Cl, Br, I, $CF_3$, CN, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl or heteroaryl; wherein R' is methyl, ethyl, n-propyl, i-propyl, n-butyl, i-butyl, s-butyl, t-butyl, cyclopropyl, cyclobutyl, cyclopentyl, cyclohexyl, cyclopropylmethyl or phenyl;

R" is methyl, ethyl, n-propyl, i-propyl, n-butyl, s-butyl, t-butyl, cyclopropyl, cyclobutyl, cyclopentyl, cyclohexyl, cyclopropylmethyl or phenyl; or R' and R" together with the nitrogen atom to which they are attached form an optionally substituted, saturated or unsaturated 4-, 5- or 6-membered heterocyclic ring; or $R^b$ and $R^c$, or $R^c$ and $R^d$, or $R^d$ and $R^e$, or $R^e$ and $R^f$ together with the two carbon atoms to which they are attached, form an optionally substituted, aromatic or non-aromatic, 5-, 6- or 7-membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S; and wherein the optional substituents are each independently F, Cl, Br, I, $CF_3$, CN, alkyl, cycloalkyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl or heteroaryl;

x is 0 or 1;
y is 0 or 1;
z is 0 or 1;

$R^x$, $R^{x'}$, $R^y$, $R^{y'}$, $R^z$ and $R^{z'}$ are each independently H, F, Cl, Br, or optionally substituted $C_{1-3}$ alkyl; or $R^x$ and $R^{x'}$, or $R^y$ and $R^{y'}$, or $R^z$ and $R^{z'}$, or $R^x$ and $R^y$, or $R^y$ and $R^z$, or $R^x$ and $R^z$ together with the carbon atoms to which they are attached, form an optionally substituted, aromatic or non-aromatic, 3-7 membered ring, optionally comprising 1 or 2 heteroatoms selected from O, N and S, and wherein said ring may be optionally fused to 1 or 2 additional optionally substituted, aromatic or non-aromatic, 5-, 6- or 7-membered rings, optionally comprising 1 or 2 heteroatoms selected from O, N and S;

A is H, $C(O)O$—$B^1$ or $C(O)NH$—$B^2$; wherein $B^1$ is H, optionally substituted $C_{1-6}$ alkyl or a pharmaceutically acceptable cation;

$B^2$ is H or optionally substituted $C_{1-6}$ alkyl; and wherein all alkyl, alkylene, cycloalkyl, heterocyclyl, aryl and heteroaryl moieties may be optionally further substituted.

2. The compound of claim 1, wherein W is S.

3. The compound of claim 1, wherein $R^1$ is F, Cl, Br, $CH_2F$, $CF_2H$, $CF_3$, $NH_2$, or $CH_3$.

4. The compound of claim 1, wherein
W is S; and
$R^1$ is Br.

5. The compound of claim 1, wherein
a is 1;
$R^a$ is H; and
$R^{a'}$ is H.

6. The compound of claim 1, wherein A is $C(O)O$—$B^1$.

7. The compound of claim 1, wherein
A is $C(O)O$—$B^1$;
x is 1; and
$R^x$ and $R^{x'}$ are not H.

8. The compound of claim 1, wherein $R^x$ and $R^{x'}$ together with the carbon atoms to which they are attached, form an optionally substituted, non-aromatic 3 membered ring.

9. The compound of claim 1, wherein $R^b$, $R^c$, $R^e$ and $R^f$ are all H.

10. The compound of claim 1, wherein $R^b$ and $R^c$ together with the two carbon atoms to which they are attached, form an aromatic, 6-membered ring.

11. A method of treating gout in an individual, the method comprising administering to the individual a therapeutically effective amount of a compound of claim 1.

12. A method of treating hyperuricemia in an individual or reducing serum uric acid in an individual in need thereof, the method comprising administering to the individual a therapeutically effective amount of a compound of claim 1.

13. A pharmaceutical composition comprising a therapeutically effective amount of a compound of claim 1, and a pharmaceutically acceptable excipient.

* * * * *